US008968740B2

(12) United States Patent
Shipp et al.

(10) Patent No.: US 8,968,740 B2
(45) Date of Patent: Mar. 3, 2015

(54) COMPOSITIONS, KITS, AND METHODS FOR THE DIAGNOSIS, PROGNOSIS, MONITORING, TREATMENT AND MODULATION OF POST-TRANSPLANT LYMPHOPROLIFERATIVE DISORDERS AND HYPOXIA ASSOCIATED ANGIOGENESIS DISORDERS USING GALECTIN-1

(75) Inventors: Margaret A. Shipp, Wellesley, MA (US); Jing Ouyang, Chestnut Hill, MA (US); Kunihiko Takeyama, Tokyo (JP); Jeffery L. Kutok, Natick, MA (US); Scott J. Rodig, Westwood, MA (US); Gabriel Rabinovich, Ciudad De Buenos Aires (AR); Diego Omar Croci Russo, Provincia De Buenos Aires (AR); Mariana Salatino, Buenos Aires (AR)

(73) Assignees: Dana-Farber Cancer Institute, Inc., Boston, MA (US); The Brigham and Women's Hospital, Inc., Boston, MA (US); Consejo Nacional de Investigaciones Cientificas y Tecnicas (CONICET), Buenos Aires (AR); Fundacion Sales, Buenos Aires (AR)

( * ) Notice: Subject to any disclaimer, the term of this patent is extended or adjusted under 35 U.S.C. 154(b) by 0 days.

(21) Appl. No.: 13/509,466

(22) PCT Filed: Nov. 12, 2010

(86) PCT No.: PCT/US2010/056547
§ 371 (c)(1),
(2), (4) Date: Sep. 26, 2012

(87) PCT Pub. No.: WO2011/060272
PCT Pub. Date: May 19, 2011

(65) Prior Publication Data
US 2013/0011409 A1 Jan. 10, 2013

Related U.S. Application Data

(60) Provisional application No. 61/261,125, filed on Nov. 13, 2009, provisional application No. 61/283,159, filed on Nov. 30, 2009, provisional application No. 61/335,779, filed on Jan. 12, 2010.

(51) Int. Cl.
| | | |
|---|---|---|
| *A61K 39/395* | (2006.01) |
| *C12N 5/20* | (2006.01) |
| *C07K 16/18* | (2006.01) |
| *C07K 16/22* | (2006.01) |
| *A61K 39/00* | (2006.01) |

(52) U.S. Cl.
CPC ................ *C07K 16/18* (2013.01); *C07K 16/22* (2013.01); *A61K 2039/505* (2013.01); *C07K 2317/34* (2013.01); *C07K 2317/73* (2013.01); *C07K 2317/76* (2013.01)

USPC ... 424/152.1; 514/18.9; 514/13.3; 530/388.2; 530/391.3; 530/391.7; 424/178.1; 435/346

(58) Field of Classification Search
None
See application file for complete search history.

(56) References Cited

U.S. PATENT DOCUMENTS

| | | |
|---|---|---|
| 2003/0013681 A1 | 1/2003 | Chang et al. |
| 2003/0109464 A1 | 6/2003 | Huflejt et al. |
| 2009/0191182 A1 | 7/2009 | Shipp et al. |

FOREIGN PATENT DOCUMENTS

| | | |
|---|---|---|
| WO | WO-2006/108474 | 10/2006 |
| WO | WO2007001851 | * 1/2007 |
| WO | WO-2007/013807 | 2/2007 |
| WO | WO-2009/012384 | 1/2009 |

OTHER PUBLICATIONS

Le, Journal of Clinical Oncology, vol. 23, No. 35, pp. 8932-8941, 2005.*
Paul, Fundamental Immunology, 3rd Edition, 1993, pp. 292-295.*
Colman, Research in Immunology, vol. 145, p. 33-36, 1994.*
Bendig, Methods: A Companion to Methods in Enzymology, vol. 8, p. 83-93, 1995.*
Rudikoff, Proceedings of the National Academy of Sciences, U.S.A., vol. 79, p. 1979-1983, 1982.*
Baxevanis, Expert Opinion: Drug Discovery, vol. 3, No. 4, p. 441-452, 2008.*
Selvakumaran, Biochemical Pharmacology, vol. 75, p. 627-638, 2008.*
International Search Report dated Sep. 27, 2011, from PCT/US2010/056547.
Supplementary European Search Report dated May 23, 2013, from EP 10 83 0795.
Cornillot et al., "Production and characterization of a monoclonal antibody able to discriminate galectin-1 from galectin-2 and galectin-3," Glycobiology, 8:425-432 (1998).

(Continued)

*Primary Examiner* — Hong Sang
*Assistant Examiner* — Michael D Allen
(74) *Attorney, Agent, or Firm* — Foley Hoag LLP

(57) ABSTRACT

The present invention is based, in part, on the discovery that galectin-1 (Gal1) plays a role in viral-associated PTLD, e.g., EBV-associated PTLD and hypoxia associated angiogenesis disorders. Accordingly, the invention relates to compositions, kits, and methods for diagnosing, prognosing, monitoring, treating and modulating viral-associated PTLD, e.g., EBV-associated PTLD and hypoxia associated angiogenesis disorders.

14 Claims, 34 Drawing Sheets

(56) References Cited

OTHER PUBLICATIONS

Thijssen et al., "Galectin-1 is essential in tumor angiogenesis and is a target for antiangiogenesis therapy," PNAS, 103(43):15975-15980 (2006).
XP-002697576 "*Mus musculus* (house mouse) partial immunoglobulin lambda chain," Abstract.
Ouyang et al., "Expression and Targeted Inhibition of the Immunoregulatory Carbohydrate-Binding Lectin, Galectin 1, in EBV-Driven Post-Transplant Lymphoproliferative Disorders," Blood (ASH Annual Meeting Abstracts) 114(22) (2009) XP009169757.
Ouyang et al., "Viral induction and targeted inhibition of galectin-1 in Ebv+ posttransplant lymphoproliferative disorders," Blood, 117(16):4315-4322 (2011) XP-002697577.
Rubinstein et al., "Targeted inhibition of galectin-1 gene expression in tumor cells results in heightened T cell-mediated rejection: A potential mechanism of tumor-immune privilege," Cancer Cell, 5:241-251 (2004) XP-002397939.

\* cited by examiner

SEQUENCE LISTING

```
<160> NUMBER OF SEQ ID NOS: 35

<210> SEQ ID NO 1
<211> LENGTH: 408
<212> TYPE: DNA
<213> ORGANISM: Homo sapiens

<400> SEQUENCE: 1
atggcttgtg gtctggtcgc cagcaacctg aatctcaaac ctggagagtg ccttcgagtg      60
cgaggcgagg tggctcctga cgctaagagc ttcgtgctga acctgggcaa agacagcaac     120
aacctgtgcc tgcacttcaa ccctcgcttc aacgcccacg gcgacgccaa caccatcgtg     180
tgcaacagca aggacggcgg ggcctggggg accgagcagc gggaggctgt ctttcccttc     240
cagcctggaa gtgttgcaga ggtgtgcatc accttcgacc aggccaacct gaccgtcaag     300
ctgccagatg gatacgaatt caagttcccc aaccgcctca acctggaggc catcaactac     360
atggcagctg acggtgactt caagatcaaa tgtgtggcct tgactga                   408

<210> SEQ ID NO 2
<211> LENGTH: 135
<212> TYPE: PRT
<213> ORGANISM: Homo sapiens

<400> SEQUENCE: 2

Met Ala Cys Gly Leu Val Ala Ser Asn Leu Asn Leu Lys Pro Gly Glu
1               5                   10                  15

Cys Leu Arg Val Arg Gly Glu Val Ala Pro Asp Ala Lys Ser Phe Val
                20                  25                  30

Leu Asn Leu Gly Lys Asp Ser Asn Asn Leu Cys Leu His Phe Asn Pro
            35                  40                  45

Arg Phe Asn Ala His Gly Asp Ala Asn Thr Ile Val Cys Asn Ser Lys
        50                  55                  60

Asp Gly Gly Ala Trp Gly Thr Glu Gln Arg Glu Ala Val Phe Pro Phe
65                  70                  75                  80

Gln Pro Gly Ser Val Ala Glu Val Cys Ile Thr Phe Asp Gln Ala Asn
                85                  90                  95

Leu Thr Val Lys Leu Pro Asp Gly Tyr Glu Phe Lys Phe Pro Asn Arg
            100                 105                 110

Leu Asn Leu Glu Ala Ile Asn Tyr Met Ala Ala Asp Gly Asp Phe Lys
        115                 120                 125

Ile Lys Cys Val Ala Phe Asp
    130                 135

<210> SEQ ID NO 3
<211> LENGTH: 4071
<212> TYPE: DNA
<213> ORGANISM: Homo sapiens

<400> SEQUENCE: 3
atgcagagca aggtgctgct ggccgtcgcc ctgtggctct gcgtggagac ccgggccgcc      60
```

```
tctgtgggtt tgcctagtgt ttctcttgat ctgcccaggc tcagcataca aaaagacata    120
cttacaatta aggctaatac aactcttcaa attacttgca ggggacagag ggacttggac    180
tggctttggc ccaataatca gagtggcagt gagcaagggg tggaggtgac tgagtgcagc    240
gatggcctct tctgtaagac actcacaatt ccaaaagtga tcggaaatga cactggagcc    300
tacaagtgct tctaccggga aactgacttg gcctcggtca tttatgtcta tgttcaagat    360
tacagatctc catttattgc ttctgttagt gaccaacatg gagtcgtgta cattactgag    420
aacaaaaaca aaactgtggt gattccatgt ctcgggtcca tttcaaatct caacgtgtca    480
ctttgtgcaa gatacccaga aaagagattt gttcctgatg gtaacagaat tcctgggac    540 agcaagaagg gctttactat tcccagctac atgatcagct atgctggcat ggtcttctgt    600
gaagcaaaaa ttaatgatga agttaccag tctattatgt acatagttgt cgttgtaggg    660
tataggattt atgatgtggt tctgagtccg tctcatggaa ttgaactatc tgttggagaa    720
aagcttgtct taaattgtac agcaagaact gaactaaatg tggggattga cttcaactgg    780 gaatacccctt cttcgaagca tcagcataag aaacttgtaa accgagacct aaaaacccag    840
tctgggagtg agatgaagaa atttttgagc accttaacta tagatggtgt aacccggagt    900
gaccaaggat tgtacacctg tgcagcatcc agtgggctga tgaccaagaa gaacagcaca    960
tttgtcaggg tccatgaaaa accttttgtt gcttttggaa gtggcatgga atctctggtg   1020
gaagccacgt gggggagcg tgtcagaatc cctgcgaagt accttggtta cccaccccca   1080
gaaataaaat ggtataaaaa tggaatacc cttgagtcca atcacacaat taaagcgggg   1140
catgtactga cgattatgga agtgagtgaa agagacacag gaaattacac tgtcatcctt   1200
accaatccca tttcaaagga gaagcagagc catgtggtct ctctggttgt gtatgtccca   1260
ccccagattg tgagaaatc tctaatctct cctgtggatt cctaccagta cggcaccact   1320
caaacgctga catgtacggt ctatgccatt cctcccccgc atcacatcca ctggtattgg   1380
cagttggagg aagagtgcgc caacgagccc agccaagctg tctcagtgac aaacccatac   1440
ccttgtgaag aatggagaag tgtggaggac ttccagggag gaataaaaat gaagttaat   1500 aaaaatcaat ttgctctaat tgaaggaaaa aacaaaactg taagtaccct tgttatccaa   1560
gcggcaaatg tgtcagcttt gtacaaatgt gaagcggtca caaagtcgg gagaggagag   1620 agggtgatct ccttccacgt gaccaggggt cctgaaatta cttttgcaacc tgacatgcag   1680 cccactgagc aggagagcgt gtctttgtgg tgcactgcag acagatctac gtttgagaac   1740
ctcacatggt acaagcttgg cccacagcct ctgccaatcc atgtgggaga gttgcccaca   1800 cctgttttgca agaacttgga tactctttgg aaattgaatg ccaccatgtt ctctaatagc   1860
acaaatgaca ttttgatcat ggagcttaag aatgcatcct tgcaggacca aggagactat   1920
gtctgccttg ctcaagacag gaagaccaag aaaagacatt gcgtggtcag gcagctcaca   1980
gtcctagagc gtgtggcacc cacgatcaca ggaaacctgg agaatcagac acaagtatt   2040 ggggaaagca tcgaagtctc atgcacggca tctgggaatc cccctccaca gatcatgtgg   2100
tttaaagata atgagaccct tgtagaagac tcaggcattg tattgaagga tgggaaccgg   2160
aacctcacta tccgcagagt gaggaaggag gacgaaggcc tctacacctg ccaggcatgc   2220
agtgttcttg gctgtgcaaa agtggaggca ttttcataa tagaaggtgc ccaggaaaag   2280
acgaacttgg aaatcattat tctagtaggc acggcggtga ttgccatgtt cttctggcta   2340
cttcttgtca tcatcctacg gaccgttaag cgggccaatg gaggggaact gaagacaggc   2400
tacttgtcca tcgtcatgga tccagatgaa ctcccattgg atgaacattg tgaacgactg   2460
```

```
ccttatgatg ccagcaaatg ggaattcccc agagaccggc tgaagctagg taagcctctt    2520
ggccgtggtg cctttggcca agtgattgaa gcagatgcct ttggaattga caagacagca    2580
acttgcagga cagtagcagt caaaatgttg aaagaaggag caacacacag tgagcatcga    2640
gctctcatgt ctgaactcaa gatcctcatt catattggtc accatctcaa tgtggtcaac    2700
cttctaggtg cctgtaccaa gccaggaggg ccactcatgg tgattgtgga attctgcaaa    2760
tttggaaacc tgtccactta cctgaggagc aagagaaatg aatttgtccc ctacaagacc    2820 aaagggcac gattccgtca agggaaagac tacgttggag caatccctgt ggatctgaaa    2880
cggcgcttgg acagcatcac cagtagccag agctcagcca gctctggatt tgtggaggag    2940
aagtccctca gtgatgtaga agaagaggaa gctcctgaag atctgtataa ggacttcctg    3000
accttggagc atctcatctg ttacagcttc caagtggcta agggcatgga gttcttggca    3060
tcgcgaaagt gtatccacag ggacctggcg gcacgaaata tcctcttatc ggagaagaac    3120
gtggttaaaa tctgtgactt tggcttggcc cgggatattt ataaagatcc agattatgtc    3180
agaaaaggag atgctcgcct ccctttgaaa tggatggccc cagaaacaat ttttgacaga    3240
gtgtacacaa tccagagtga cgtctggtct tttggtgttt tgctgtggga aatattttcc    3300
ttaggtgctt ctccatatcc tggggtaaag attgatgaag aattttgtag gcgattgaaa    3360
gaaggaacta gaatgagggc ccctgattat actacaccag aaatgtacca gaccatgctg    3420
gactgctggc acggggagcc cagtcagaga cccacgtttt cagagttggt ggaacatttg    3480
ggaaatctct gcaagctaa tgctcagcag gatggcaaag actacattgt tcttccgata    3540
tcagagactt tgagcatgga agaggattct ggactctctc tgcctacctc acctgtttcc    3600
tgtatggagg aggaggaagt atgtgacccc aaattccatt atgacaacac agcaggaatc    3660
agtcagtatc tgcagaacag taagcgaaag agccggcctg tgagtgtaaa aacatttgaa    3720
gatatcccgt tagaagaacc agaagtaaaa gtaatcccag atgacaacca gacggacagt    3780
ggtatggttc ttgcctcaga agagctgaaa actttggaag acagaaccaa attatctcca    3840
tcttttggtg aatggtgcc cagcaaaagc agggagtctg tggcatctga aggctcaaac    3900
cagacaagcg gctaccagtc cggatatcac tccgatgaca cagacaccac cgtgtactcc    3960
agtgaggaag cagaactttt aaagctgata gagattggag tgcaaaccgg tagcacagcc    4020
cagattctcc agcctgactc ggggaccaca ctgagctctc tcctgtttta a              4071
```

<210> SEQ ID NO 4
<211> LENGTH: 1356
<212> TYPE: PRT
<213> ORGANISM: Homo sapiens

<400> SEQUENCE: 4

```
Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30

Arg Leu Ser Ile Gln Lys Asp Ile Leu Thr Ile Lys Ala Asn Thr Thr
        35                  40                  45

Leu Gln Ile Thr Cys Arg Gly Gln Arg Asp Leu Asp Trp Leu Trp Pro
    50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
```

```
                         85                  90                  95
Asp Thr Gly Ala Tyr Lys Cys Phe Tyr Arg Glu Thr Asp Leu Ala Ser
                100                 105                 110

Val Ile Tyr Val Tyr Val Gln Asp Tyr Arg Ser Pro Phe Ile Ala Ser
                115                 120                 125

Val Ser Asp Gln His Gly Val Val Tyr Ile Thr Glu Asn Lys Asn Lys
130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
                180                 185                 190

Ser Tyr Ala Gly Met Val Phe Cys Glu Ala Lys Ile Asn Asp Glu Ser
                195                 200                 205

Tyr Gln Ser Ile Met Tyr Ile Val Val Val Gly Tyr Arg Ile Tyr
                210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
                260                 265                 270

Val Asn Arg Asp Leu Lys Thr Gln Ser Gly Ser Glu Met Lys Lys Phe
                275                 280                 285

Leu Ser Thr Leu Thr Ile Asp Gly Val Thr Arg Ser Asp Gln Gly Leu
                290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
                340                 345                 350

Lys Tyr Leu Gly Tyr Pro Pro Pro Glu Ile Lys Trp Tyr Lys Asn Gly
                355                 360                 365

Ile Pro Leu Glu Ser Asn His Thr Ile Lys Ala Gly His Val Leu Thr
                370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
                420                 425                 430

Asp Ser Tyr Gln Tyr Gly Thr Thr Gln Thr Leu Thr Cys Thr Val Tyr
                435                 440                 445

Ala Ile Pro Pro Pro His His Ile His Trp Tyr Trp Gln Leu Glu Glu
                450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
                500                 505                 510
```

```
Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
    530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Arg His Cys Val Val
                645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
        675                 680                 685

Thr Ala Ser Gly Asn Pro Pro Pro Gln Ile Met Trp Phe Lys Asp Asn
    690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu Ile Ile Ile Leu
        755                 760                 765

Val Gly Thr Ala Val Ile Ala Met Phe Phe Trp Leu Leu Leu Val Ile
    770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
            820                 825                 830

Arg Leu Lys Leu Gly Lys Pro Leu Gly Arg Gly Ala Phe Gly Gln Val
        835                 840                 845

Ile Glu Ala Asp Ala Phe Gly Ile Asp Lys Thr Ala Thr Cys Arg Thr
    850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
            900                 905                 910

Met Val Ile Val Glu Phe Cys Lys Phe Gly Asn Leu Ser Thr Tyr Leu
        915                 920                 925
```

```
Arg Ser Lys Arg Asn Glu Phe Val Pro Tyr Lys Thr Lys Gly Ala Arg
930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
                965                 970                 975

Phe Val Glu Glu Lys Ser Leu Ser Asp Val Glu Glu Glu Ala Pro
            980                 985                 990

Glu Asp Leu Tyr Lys Asp Phe Leu Thr Leu Glu His Leu Ile Cys Tyr
        995                 1000                1005

Ser Phe Gln Val Ala Lys Gly Met Glu Phe Leu Ala Ser Arg Lys
    1010                1015                1020

Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
    1055                1060                1065

Leu Lys Trp Met Ala Pro Glu Thr Ile Phe Asp Arg Val Tyr Thr
    1070                1075                1080

Ile Gln Ser Asp Val Trp Ser Phe Gly Val Leu Leu Trp Glu Ile
    1085                1090                1095

Phe Ser Leu Gly Ala Ser Pro Tyr Pro Gly Val Lys Ile Asp Glu
    1100                1105                1110

Glu Phe Cys Arg Arg Leu Lys Glu Gly Thr Arg Met Arg Ala Pro
    1115                1120                1125

Asp Tyr Thr Thr Pro Glu Met Tyr Gln Thr Met Leu Asp Cys Trp
    1130                1135                1140

His Gly Glu Pro Ser Gln Arg Pro Thr Phe Ser Glu Leu Val Glu
    1145                1150                1155

His Leu Gly Asn Leu Leu Gln Ala Asn Ala Gln Gln Asp Gly Lys
    1160                1165                1170

Asp Tyr Ile Val Leu Pro Ile Ser Glu Thr Leu Ser Met Glu Glu
    1175                1180                1185

Asp Ser Gly Leu Ser Leu Pro Thr Ser Pro Val Ser Cys Met Glu
    1190                1195                1200

Glu Glu Glu Val Cys Asp Pro Lys Phe His Tyr Asp Asn Thr Ala
    1205                1210                1215

Gly Ile Ser Gln Tyr Leu Gln Asn Ser Lys Arg Lys Ser Arg Pro
    1220                1225                1230

Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val
    1250                1255                1260

Leu Ala Ser Glu Glu Leu Lys Thr Leu Glu Asp Arg Thr Lys Leu
    1265                1270                1275

Ser Pro Ser Phe Gly Gly Met Val Pro Ser Lys Ser Arg Glu Ser
    1280                1285                1290

Val Ala Ser Glu Gly Ser Asn Gln Thr Ser Gly Tyr Gln Ser Gly
    1295                1300                1305

Tyr His Ser Asp Asp Thr Asp Thr Thr Val Tyr Ser Ser Glu Glu
    1310                1315                1320

Ala Glu Leu Leu Lys Leu Ile Glu Ile Gly Val Gln Thr Gly Ser
```

```
                              1325                  1330                 1335
Thr Ala  Gln Ile Leu Gln Pro  Asp Ser Gly Thr Thr   Leu Ser Ser
         1340                 1345                  1350

Pro Pro  Val
         1355

<210> SEQ ID NO 5
<211> LENGTH: 19
<212> TYPE: DNA
<213> ORGANISM: Unknown
<220> FEATURE:
<223> OTHER INFORMATION: Description of Unknown: Exemplary
      Gal1 shRNA target sequence

<400> SEQUENCE: 5
gctgccagat ggatacgaa                                                      19

<210> SEQ ID NO 6
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(354)

<400> SEQUENCE: 6 gag gtt cag ctg cag cag tct gtg gca gag ttt gtg agg cca ggg gcc          48
Glu Val Gln Leu Gln Gln Ser Val Ala Glu Phe Val Arg Pro Gly Ala
1               5                   10                  15 tca gtc agg ttg tcc tgc aca gct tct ggc ttc aac att aaa aac acc          96
Ser Val Arg Leu Ser Cys Thr Ala Ser Gly Phe Asn Ile Lys Asn Thr
            20                  25                  30 tat ata cac tgg gtg agg cag agg cct gaa cag ggc ctg gag tgg att         144
Tyr Ile His Trp Val Arg Gln Arg Pro Glu Gln Gly Leu Glu Trp Ile
        35                  40                  45 gga aag att gat cct gcg aat ggt aat act aaa tat gtc ccg gag ttc         192
Gly Lys Ile Asp Pro Ala Asn Gly Asn Thr Lys Tyr Val Pro Glu Phe
    50                  55                  60 cag ggc aag gcc act atg act gcg gac aca tcc tcc aac aca gtc tac         240
Gln Gly Lys Ala Thr Met Thr Ala Asp Thr Ser Ser Asn Thr Val Tyr
65                  70                  75                  80 ctg cac ctc agc agc ctg aca tct gag gac act gcc atc tat tac tgt         288
Leu His Leu Ser Ser Leu Thr Ser Glu Asp Thr Ala Ile Tyr Tyr Cys
                85                  90                  95 gtc gat ggt tac tac ggc tgg tat ttc gct gtc tgg ggc aca ggg acc         336
Val Asp Gly Tyr Tyr Gly Trp Tyr Phe Ala Val Trp Gly Thr Gly Thr
            100                 105                 110 acg gtc acc gtc tcc tca                                                 354
Thr Val Thr Val Ser Ser
        115

<210> SEQ ID NO 7
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Gln Gln Ser Val Ala Glu Phe Val Arg Pro Gly Ala
```

```
  1               5                  10                 15
Ser Val Arg Leu Ser Cys Thr Ala Ser Gly Phe Asn Ile Lys Asn Thr
                20                  25                 30

Tyr Ile His Trp Val Arg Gln Arg Pro Glu Gln Gly Leu Glu Trp Ile
                35                  40                 45

Gly Lys Ile Asp Pro Ala Asn Gly Asn Thr Lys Tyr Val Pro Glu Phe
 50                  55                  60

Gln Gly Lys Ala Thr Met Thr Ala Asp Thr Ser Ser Asn Thr Val Tyr
 65                  70                  75                 80

Leu His Leu Ser Ser Leu Thr Ser Glu Asp Thr Ala Ile Tyr Tyr Cys
                 85                  90                 95

Val Asp Gly Tyr Tyr Gly Trp Tyr Phe Ala Val Trp Gly Thr Gly Thr
                100                 105                110

Thr Val Thr Val Ser Ser
                115
```

<210> SEQ ID NO 8
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(327)

<400> SEQUENCE: 8

```
cag gct gtt gtg act cag gaa tct gca ctc acc aca tca cct ggt gaa        48
Gln Ala Val Val Thr Gln Glu Ser Ala Leu Thr Thr Ser Pro Gly Glu
 1               5                  10                  15 aca gtc aca ctc act tgt cgc tca agc act ggg gct gtt aca act agt        96
Thr Val Thr Leu Thr Cys Arg Ser Ser Thr Gly Ala Val Thr Thr Ser
                20                  25                  30 aac tat gcc aac tgg gtc caa gaa aaa cca gat cat tta ttc act ggt       144
Asn Tyr Ala Asn Trp Val Gln Glu Lys Pro Asp His Leu Phe Thr Gly
             35                  40                  45 cta ata ggt gct acc aac aac cga gct cca ggt gtt cct gcc aga ttc       192
Leu Ile Gly Ala Thr Asn Asn Arg Ala Pro Gly Val Pro Ala Arg Phe
 50                  55                  60 tca ggc tcc ctg att gga gac aag gct gtc ctc acc atc aca ggg gca       240
Ser Gly Ser Leu Ile Gly Asp Lys Ala Val Leu Thr Ile Thr Gly Ala
 65                  70                  75                  80 caa act gag gat gag gca ata tat ttc tgt gct cta tgg tac aga aac       288
Gln Thr Glu Asp Glu Ala Ile Tyr Phe Cys Ala Leu Trp Tyr Arg Asn
                 85                  90                  95 cat ttt att ttc ggc agt gga acc aag gtc act gtc ctc                    327
His Phe Ile Phe Gly Ser Gly Thr Lys Val Thr Val Leu
                100                 105
```

<210> SEQ ID NO 9
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Gln Ala Val Val Thr Gln Glu Ser Ala Leu Thr Thr Ser Pro Gly Glu
 1               5                  10                  15
```

```
Thr Val Thr Leu Thr Cys Arg Ser Ser Thr Gly Ala Val Thr Thr Ser
             20                  25                  30

Asn Tyr Ala Asn Trp Val Gln Glu Lys Pro Asp His Leu Phe Thr Gly
         35                  40                  45

Leu Ile Gly Ala Thr Asn Asn Arg Ala Pro Gly Val Pro Ala Arg Phe
 50                  55                  60

Ser Gly Ser Leu Ile Gly Asp Lys Ala Val Leu Thr Ile Thr Gly Ala
 65                  70                  75                  80

Gln Thr Glu Asp Glu Ala Ile Tyr Phe Cys Ala Leu Trp Tyr Arg Asn
                 85                  90                  95

His Phe Ile Phe Gly Ser Gly Thr Lys Val Thr Val Leu
            100                 105
```

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer <400> SEQUENCE: 10
aagaaaggtt agtcatag                                                   18

<210> SEQ ID NO 11
<211> LENGTH: 16
<212> TYPE: DNA
<213> ORGANISM: Artificial Sequence
<220> FEATURE:
<223> OTHER INFORMATION: Description of Artificial Sequence: Synthetic
      primer <400> SEQUENCE: 11
tgtaaggcag tagtag                                                     16

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence: Synthetic
      primer <400> SEQUENCE: 12
gaagaattcg atggaacacg accttgag                                        28

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer <400> SEQUENCE: 13
gacagatcta ggttagtcat agtagcttag                                      30

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 14
gaattctgca gctatggggt cccta                                            25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
agatctgcga tctggtgggc attct                                            25

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, u, g, unknown or other

<400> SEQUENCE: 16
nnacacuuaa cuugacuaca a                                                21

<210> SEQ ID NO 17
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, u, g, unknown or other

<400> SEQUENCE: 17
nnacuaggaa cccaagauca a                                                21

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccaagcccac atctcctc                                                    18

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gaggctgcag ctggtttagt                                                  20

<210> SEQ ID NO 20
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tgaacctggg taaagaca                                                       18

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttggcctggt cgaaggtgat                                                     20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cggccggggg cattcgtatt                                                     20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tcgctctggt ccgtcttgcg                                                     20

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cctcctgaga ctccggggtc aga                                                 23

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctaggcggtc cgtgccctag c                                                   21

<210> SEQ ID NO 26
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
tgcccctgcc gggacttcat                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cagcagcatg gtgcagggct                                              20

<210> SEQ ID NO 28
<211> LENGTH: 13
<212> TYPE: DNA
<213> ORGANISM: Homo sapiens

<400> SEQUENCE: 28
ttggggaggc ccg                                                     13

<210> SEQ ID NO 29
<211> LENGTH: 13
<212> TYPE: DNA
<213> ORGANISM: Homo sapiens

<400> SEQUENCE: 29
cggggaaggc ccg                                                     13

<210> SEQ ID NO 30
<211> LENGTH: 13
<212> TYPE: DNA
<213> ORGANISM: Homo sapiens

<400> SEQUENCE: 30 caggggtgc cca                                                      13

<210> SEQ ID NO 31
<211> LENGTH: 13
<212> TYPE: DNA
<213> ORGANISM: Homo sapiens

<400> SEQUENCE: 31
ggaggatgtt ccc                                                     13

<210> SEQ ID NO 32
<211> LENGTH: 13
<212> TYPE: DNA
<213> ORGANISM: Homo sapiens

<400> SEQUENCE: 32
gtggggaccc ccc                                                     13

<210> SEQ ID NO 33
<211> LENGTH: 13
<212> TYPE: DNA
<213> ORGANISM: Homo sapiens
```

```
<400> SEQUENCE: 33
tgggggacac cca                                                     13

<210> SEQ ID NO 34
<211> LENGTH: 13
<212> TYPE: DNA
<213> ORGANISM: Homo sapiens

<400> SEQUENCE: 34 ggggggaaatt ccc                                                    13

<210> SEQ ID NO 35
<211> LENGTH: 13
<212> TYPE: DNA
<213> ORGANISM: Homo sapiens

<400> SEQUENCE: 35
tagggacttt ccc                                                     13
```

COMPOSITIONS, KITS, AND METHODS FOR THE DIAGNOSIS, PROGNOSIS, MONITORING, TREATMENT AND MODULATION OF POST-TRANSPLANT LYMPHOPROLIFERATIVE DISORDERS AND HYPOXIA ASSOCIATED ANGIOGENESIS DISORDERS USING GALECTIN-1

CROSS-REFERENCE TO RELATED APPLICATIONS

This application is the U.S. National Stage Application of International Application No. PCT/US2010/056547, filed on Nov. 12, 2010, which claims the benefit of priority to U.S. Provisional Application No. 61/335,779, filed on Jan. 12, 2010, U.S. Provisional Application No. 61/283,159, filed on Nov. 30, 2009, and U.S. Provisional Application No. 61/261,125, filed on Nov. 13, 2009; the entire contents of each of which application are expressly incorporated herein by reference.

BACKGROUND OF THE INVENTION

Post-transplant lymphoproliferative disorders (PTLD) are potentially fatal conditions associated with immunocompromised solid organ and stem cell transplantation that can have 70-80% mortality (Gottschalk et al. (2005) *Annu. Rev. Med.* 56, 29-44; Paya et al. (1999) *Transplantation* 68, 1517-1525). PTLD is often associated with viral infection, such that latent viral infection of the transplanted material can cause complications in the transplant subject. For example, Epstein-Barr virus (EBV)-associated PTLD derives from herpes virus exposure that establishes latent infection in a majority of healthy adults. Proliferation of EBV-infected B cells in PTLD is maintained by expression of EBV latent genes, such as latent membrane protein 1 (LMP1) and LMP2A, viral immune evasion strategies, and impaired host immune surveillance. The incidence of PTLD varies according to the organ transplanted, as well as the intensity and duration of immunosuppression. In renal transplant recipients PTLD occurs in 1-2% of patients, but the incidence is as high as 20% in small bowel transplant and 1%-10% in lung, heart, liver, and kidney transplant recipients (Gottschalk et al. (2005) *Annu. Rev. Med.* 56, 29-44; Paya et al. (1999) *Transplantation* 68, 1517-1525). Children and transplant recipients without previously established anti-EBV immunity are among those at greatest risk for development of a PTLD. There is no accepted standard of therapy for PTLD, and the progression of the disease in patients is often not responsive to currently available therapies. Management of early PTLD lesions is currently based on reduction or withdrawal of immunosuppression which increases the risk of graft rejection.

In addition, cancer cells adapt to low oxygen tension by promoting the expression of genes associated with anaerobic metabolism, invasion and angiogenesis (Pugh et al. (2003) *Nat Med* 9, 677-684; Fraisl et al. (2009) *Dev Cell* 16, 167-179). The concerted action of hypoxia-regulated pathways allows tumor cells to sprout new vessels, co-opt host vessels and/or recruit angio-competent bone marrow-derived cells to generate functionally abnormal tumor vasculatures (Ferrara et al. (2005) *Nature* 438, 967-974). In spite of the well-established roles of hypoxia-inducible factor (HIF)-1α and vascular endothelial growth factor (VEGF), increasing evidence suggests the contribution of alternative 'non-canonical' pathways to hypoxia-driven neovascularization (Ferrara, N. (2010) *Cytokine Growth Factor Rev* 21, 21-26). This proposition is firmly grounded on emerging preclinical and clinical data demonstrating 'evasive resistance' or 'intrinsic refractoriness' to VEGF-targeted therapies, which fail to produce enduring clinical benefits (Ferrara, N. (2010) *Cytokine Growth Factor Rev* 21, 21-26; Ebos et al. (2009) *Cancer Cell* 15, 232-239; Paez-Ribes et al. (2009) *Cancer Cell* 15, 220-231).

The mechanisms underlying 'evasive resistance' involve revascularization as a result of the delivery of alternative pro-angiogenic signals (Bergers et al. (2008) *Nat Rev Cancer* 8, 592-603) and/or mobilization of bone marrow-derived inflammatory cells, which together with endothelial and pericyte progenitors, are recruited to the tumor vasculature (Shojaei et al. (2007) *Nat Biotechnol* 25, 911-920; Bergers et al. (2008) *Nat Rev Cancer* 8, 592-603). Future anti-angiogenic therapies might capitalize on an improved understanding of these compensatory pathways, as well as the elucidation of the molecular underpinnings of blood vessel normalization and the identification of hallmark signatures which distinguish healthy from tumor-associated endothelium (Jain, R. K. (2005) *Science* 307, 58-62). Although substantial changes in the endothelial cell (EC) surface 'glycome' were apparent under different culture conditions (Garcia-Vallejo et al. (2006) *J Cell Physiol* 206, 203-210; Willhauck-Fleckenstein et al. (2010) *Angiogenesis* 13, 25-42), suggesting a role for glycan structures in differentially regulating angiogenesis in hypoxic versus normoxic and in neoplastic versus healthy tissues, the specific glycan structures, mediating molecules, and mechanisms were not known prior to the results described herein.

Programmed remodeling of cell surface glycans can control cellular processes by displaying or masking ligands for endogenous lectins (Paulson et al. (2006) *Nat Chem Biol* 2, 238-248; van Kooyk et al. (2008) *Nat Immunol* 9, 593-601). Recent efforts involving genetic manipulation of N- and O-glycosylation pathways have revealed essential roles for multivalent lectin-glycan lattices in the control of receptor signaling (Ohtsubo, et al. (2006) *Cell* 126, 855-867; Dennis et al. (2009) *Cell* 139, 1229-1241; Dam et al. (2010) *Glycobiology* 20, 1061-1064). Regulated glycosylation can control sprouting angiogenesis by modulating binding of Notch receptor to its ligands Delta-like 4 (Dll4) or Jagged1 (Benedito et al. (2009) *Cell* 137, 1124-1135), fine-tuning neuropilin-1 (NRP-1) signaling (Shintani et al. (2006) *EMBO J* 25, 3045-3055) and facilitating CD31-mediated homophylic interactions (Kitazume et al. (2010) *J Biol Chem* 285, 6515-6521). Yet, whether differential glycosylation enables the formation of discrete lectin-glycan lattices and signaling clusters that are functionally relevant to angiogenesis remains largely unexplored.

In view of the above, it is clear that there remains a need in the art for compositions and methods to specifically boost host anti-viral (e.g., anti-EBV) immune responses, as well as inhibiting hypoxia associated angiogenesis in a number of disorders.

SUMMARY OF THE INVENTION

The present invention relates in general to a role of galectin-1 (Gal1) in diagnosing, prognosing, monitoring, treating and/or modulating PTLD, including EBV-associated PTLD and/or hypoxia associated angiogenesis disorders.

The present inventors have determined a vascular regulatory circuit involving Galectin-1 (Gal1), a member of a highly-conserved family of animal lectins, is expressed and secreted by a variety of tumors where it contributes to malignant transformation and metastasis (Paez-Ribes et al. (2009) *Cancer Cell* 15, 220-231; Liu et al. (2005) *Nature Rev Cancer*

5, 29-41), based on the differential glycosylation of ECs that promotes the formation of lectin-glycan lattices. These interactions couple tumor hypoxia to VEGFR2-mediated neovascularization through mechanisms that are independent of HIF-1α and VEGF. The 'glycosylation signature' of ECs can be selectively altered by tolerogenic, inflammatory, proliferative and hypoxic stimuli, which can either enable or hinder formation of these lattices. Targeted disruption of Gal1-glycan interactions, through Gal1 blockade or prevention of N-glycan branching, attenuated hypoxia-driven angiogenesis, while promoting extensive remodeling of vascular networks and increased influx and expansion of immune effector cells into the tumor parenchyma. These results underscore novel opportunities for targeting aberrant vascular networks, while simultaneously potentiating T cell-mediated antitumor immunity.

The present invention is also based, in part, on the identification of novel anti-Gal1 monoclonal antibodies. Accordingly, in one aspect, the present invention features a monoclonal antibody, or antigen-binding fragment thereof, wherein the monoclonal antibody comprises a heavy chain sequence with at least about 95% identity to a heavy chain sequence selected from the group consisting of the sequences listed in Table 1 or a light chain sequence with at least about 95% identity to a light chain sequence selected from the group consisting of the sequences listed in Table 1. In one embodiment, the monoclonal antibody comprises a heavy chain CDR sequence with at least about 95% identity to a heavy chain CDR sequence selected from the group consisting of the sequences listed in Table 1 or a light chain CDR sequence with at least about 95% identity to a light chain CDR sequence selected from the group consisting of the sequences listed in Table 1. In another embodiment, the monoclonal antibody, or antigen-binding fragment thereof comprises a heavy chain sequence selected from the group consisting of the sequences listed in Table 1 or a light chain sequence selected from the group consisting of the sequences listed in Table 1. In still another embodiment, the monoclonal antibody, or antigen-binding fragment thereof comprises a heavy chain CDR sequence selected from the group consisting of the sequences listed in Table 1 or a light chain CDR sequence selected from the group consisting of the sequences listed in Table 1. In yet another embodiment, the monoclonal antibody, or antigen-binding fragment thereof is chimeric, humanized, composite, or human. In another embodiment, the monoclonal antibody, or antigen-binding fragment thereof, is detectably labeled, comprises an effector domain, comprises an Fc domain, is a single-chain antibody, or is a Fab fragment. In still another embodiment, the monoclonal antibody, or antigen-binding fragment thereof, inhibits the binding of commercial antibody to Gal1. In yet another embodiment, the monoclonal antibody, or antigen-binding fragment thereof, reduces or inhibits at least one Gal1 activity (e.g., binding to beta-galacostides) relative to the absence of the monoclonal antibody or antigen-binding fragment thereof selected from the group consisting. Host cells expressing the described monoclonal antibodies, or antigen-binding fragment thereof, are also contemplated.

In another aspect, the present invention features isolated nucleic acid molecules that hybridize, under stringent conditions, with the complement of a nucleic acid encoding a polypeptide selected from the group consisting of the sequences listed in Table 1, or sequences with at least about 95% homology to a nucleic acid encoding a polypeptide selected from the group consisting of the sequences listed in Table 1. In one embodiment, the isolated nucleic acid is comprised within a vector. In another embodiment, a host cell comprises In still another aspect, the present invention features a device or kit comprising at least one monoclonal antibody or antigen-binding fragment thereof of the present invention, said device or kit optionally comprising a label to detect the at least one monoclonal antibody or antigen-binding fragment thereof of the present invention, or a complex comprising the monoclonal antibody or antigen-binding fragment thereof of the present invention.

In yet another aspect, the present invention features a pharmaceutical composition comprising the antibody or antigen-binding fragment thereof of the present invention, in a pharmaceutically acceptable carrier.

In another aspect, the present invention features a method of detecting the presence or level of a Gal1 polypeptide said method comprising obtaining a sample and detecting said polypeptide in a sample by use of at least one monoclonal antibody or antigen-binding fragment thereof of the present invention. In one embodiment, the method utilizes at least one monoclonal antibody or antigen-binding fragment thereof of the present invention to form a complex with a Gal1 polypeptide and the complex is detected in the form of an enzyme linked immunosorbent assay (ELISA), radioimmune assay (RIA), or immunochemically.

In another aspect, the present invention features a method for monitoring the progression of a disease in a subject, the method comprising detecting in a subject sample at a first point in time the level of expression of Gal1 using at least one monoclonal antibody or antigen-binding fragment thereof of the present invention; repeating the previous step at a subsequent point in time; and comparing the level of expression of said Gal1 detected in steps a) and b) to monitor the progression of the disease in the subject. In one embodiment, the subject has undergone treatment to ameliorate the disease between the first point in time and the subsequent point in time.

In still another aspect, the present invention features a method for predicting the clinical outcome of a subject afflicted with a disease, the method comprising determining the level of expression of Gal1 in a patient sample using at least one monoclonal antibody or antigen-binding fragment thereof of the present invention; determining the level of expression of Gal1 in a sample from a control subject having a good clinical outcome using at least one monoclonal antibody or antigen-binding fragment thereof of the present invention; and comparing the level of expression of Gal1 in the patient sample and in the sample from the control subject; wherein a significantly higher level of expression in the patient sample as compared to the expression level in the sample from the control subject is an indication that the patient has a poor clinical outcome.

In yet another aspect, the present invention features a method of assessing the efficacy of a therapy for a disease in a subject, the method comprising comparing the level of expression of Gal1 using at least one monoclonal antibody or antigen-binding fragment thereof of the present invention, in a first sample obtained from the subject prior to providing at least a portion of the therapy to the subject, and the level of expression of Gal1 in a second sample obtained from the subject following provision of the portion of the therapy, wherein a significantly lower level of expression of Gal1 in the second sample, relative to the first sample, is an indication that the therapy is efficacious for inhibiting the disease in the subject.

In another aspect, the present invention features a method for treating a subject afflicted with a disease comprising administering at least one monoclonal antibody or antigen-binding fragment thereof of the present invention, such that the subject afflicted with the disease is treated.

In another aspect, the present invention features a method for monitoring the progression of a viral-associated PTLD or hypoxia associated angiogenesis disorder in a subject, the method comprising detecting in a subject sample at a first point in time the level of expression of Gal1; repeating the previous step at a subsequent point in time; and comparing the level of expression of said Gal1 detected at various time points to monitor the progression of the viral-associated PTLD or hypoxia associated angiogenesis disorder in the subject. In one embodiment, the subject has undergone treatment to ameliorate the viral-associated PTLD or hypoxia associated angiogenesis disorder between the first point in time and the subsequent point in time.

In yet another aspect, the present invention features a method of assessing the efficacy of a test compound for inhibiting a viral-associated PTLD in a subject, the method comprising comparing the level of expression of Gal1 in a first sample obtained from the subject and exposed to the test compound; and the level of expression of Gal1 in a second sample obtained from the subject, wherein the second sample is not exposed to the test compound, and a significantly lower level of expression of Gal1, relative to the second sample, is an indication that the test compound is efficacious for inhibiting the viral-associated PTLD in the subject. In one embodiment, the first and second samples are portions of a single sample obtained from the subject or portions of pooled samples obtained from the subject.

In another aspect, the present invention features a method for predicting the clinical outcome of a subject afflicted with a viral-associated PTLD or hypoxia associated angiogenesis disorder patient, the method comprising determining the level of expression of Gal1 in a patient sample; determining the level of expression of Gal1 in a sample from a control subject having a good clinical outcome; and comparing the level of expression of Gal1 in the patient sample and in the sample from the control subject; wherein a significantly higher level of expression in the patient sample as compared to the expression level in the sample from the control subject is an indication that the patient has a poor clinical outcome.

In another aspect, the present invention features a method of assessing the efficacy of a therapy for a viral-associated PTLD or hypoxia associated angiogenesis disorder in a subject, the method comprising comparing the level of expression of Gal1 in a first sample obtained from the subject prior to providing at least a portion of the therapy to the subject, and the level of expression of Gal1 in a second sample obtained from the subject following provision of the portion of the therapy, wherein a significantly lower level of expression of Gal1 in the second sample, relative to the first sample, is an indication that the therapy is efficacious for inhibiting the viral-associated PTLD or hypoxia associated angiogenesis disorder in the subject.

In some embodiments of the methods of the present invention, a sample comprises cells obtained from a subject. In another embodiment, cells are in a fluid selected from the group consisting of whole blood fluid, serum fluid, plasma fluid, interstitial fluid, cerebrospinal fluid, lymph fluid, saliva, stool, and urine. In still another embodiment, the level of Gal1 expression is assessed using a reagent which specifically binds with a Gal1 protein, polypeptide or protein fragment thereof (e.g., an antibody, an antibody derivative, or an antibody fragment). In yet another embodiment, the level of Gal1 expression is assessed by detecting the presence in the sample of a transcribed polynucleotide encoded by a Gal1 polynucleotide (e.g., mRNA or cDNA) or a portion of said transcribed polynucleotide. In another embodiment, the step of detecting further comprises amplifying the transcribed polynucleotide. In still another embodiment, the level of Gal1 expression is assessed by detecting the presence in the sample of a transcribed polynucleotide which anneals with a Gal1 polynucleotide or anneals with a portion of a Gal1 polynucleotide, under stringent hybridization conditions. In yet another embodiment, a significant increase comprises an at least two fold or at least five fold increase between the level of expression of Gal1 in the subject sample relative to the normal level of expression of Gal1 in the sample from the control subject.

In another aspect, the present invention features a method for modulating an immune response in a subject afflicted with a viral-associated PTLD or hypoxia associated angiogenesis disorder comprising contacting an immune cell with an agent that modulates the interaction between Gal1 or a fragment thereof and its natural binding partner(s) to thereby modulate the immune response. In one embodiment, the immune response is upregulated. In another embodiment, the immune response is downregulated. In still another embodiment, signaling via the Gal1 binding partner is inhibited using an agent selected from the group consisting of: a blocking antibody or an antigen binding fragment thereof that recognizes Gal1, a blocking antibody or an antigen binding fragment thereof that recognizes the Gal1 binding partner(s) or a fragment thereof, natural ligands, small molecules, aptamers, peptides, peptidomimetics, glycan-related compounds, glycomimetics, and RNA interference molecules. In yet another embodiment, the immune cell is further contacted (e.g., in vivo or in vitro) with an additional agent that upregulates an immune response.

In still another aspect, the present invention features a method for treating a subject afflicted with a viral-associated PTLD or hypoxia associated angiogenesis disorder comprising administering an agent that inhibits the interaction between Gal1 and its natural binding partner(s) on cells of the subject such that the subject afflicted with the viral-associated PTLD is treated. In one embodiment, the agent is selected from the group consisting of: a blocking antibody or an antigen binding fragment thereof that recognizes Gal1, a blocking antibody or an antigen binding fragment thereof that recognizes the Gal1 binding partner(s) or a fragment thereof, natural ligands, small molecules, aptamers, peptides, peptidomimetics, glycan-related compounds, glycomimetics, and RNA interference molecules. In another embodiment, a second agent that upregulates an immune response, downregulates hypoxia associated angiogenesis (e.g., VEGF-targeted therapeutic such as an anti-VEGF antibody), or combination thereof, is administered to the subject.

In yet another aspect, the present invention features a method for modulating angiogenesis in a hypoxia associated angiogenesis disorder comprising contacting a cell exhibiting hypoxia associated angiogenesis with an agent that modulates the interaction between Gal1 or a fragment thereof and its natural binding partner(s) to thereby modulate angiogenesis. In one embodiment, hypoxia associated angiogenesis is downregulated. In another embodiment, downregulation of hypoxia associated angiogenesis is determined by at least one effect selected from the group consisting of: reduction in vessel diameter, reduction in vessel distribution, reduction in tortuous vessels, increase in pericyte coverage, increase in the fraction of pericytes that are mature, and reduction in pimonidazole adduct formation. In still another embodiment, hypoxia associated angiogenesis is modulated using an agent selected from the group consisting of: a blocking antibody or an antigen binding fragment thereof that recognizes Gal1, a blocking antibody or an antigen binding fragment thereof that recognizes a Gal1 binding partner(s) or a fragment thereof, natural ligands, small molecules, aptamers, peptides, peptidomimetics, glycan-related compounds, glycomimctics, and RNA interference molecules. In yet another embodiment, the method further comprises contacting the cell (e.g., in vivo or in vitro) exhibiting hypoxia associated angiogenesis with an additional agent that downregulates hypoxia associate angiogenesis.

In another aspect, the present invention features an isolated complex comprising a Gal1 polypeptide and a VEGFR2 polypeptide. In one embodiment, the Gal1 polypeptide is a polypeptide describe herein or fragment thereof that is capable of binding to a VEGFR2 polypeptide and the VEGR2 polypeptide described herein or fragment thereof that is capable of binding to a Gal1 polypeptide. In another embodiment, at least one polypeptide or fragment is a fusion protein. In still another embodiment, at least one polypeptide or fragment is labeled. In yet another embodiment, the complex is generated within a host cell. In another embodiment, the Gal1 polypeptide or fragment thereof and said VEGFR2 polypeptide or fragment thereof are covalently linked.

In still another aspect, the present invention features an isolated antibody of the present invention has the ability to disrupt a complex comprising a Gal1 polypeptide and a VEGFR2 polypeptide.

In yet another aspect, the present invention features a method for identifying a compound that modulates a Gal1/VEGFR2 complex comprising: a) contacting the complex with a test compound; and b) assaying the amount or activity of the complex, wherein a change in the amount or activity of the complex in the presence of the test compound as compared to the amount or activity of the complex in the absence of the test compound is indicative of a compound that modulates a Gal1/VEGFR2 complex.

In another aspect, the present invention features a hybridoma, 14-19 8F4-F8-G7, deposited under accession number PTA-10535.

For any method described herein, the relevant condition, disease, or disorder can be a viral-associated PTLD, cancer, and/or a hypoxia associated angiogenesis disorder. In addition, the level of expression of a marker, such as Gal1 to be analyzed, can be determined by the amount, structure, subcellular localization, and/or activity of the marker, as described further herein. Moreover, the progress, outcome, or efficacy of any method describe herein can be measured by at least one criteria selected from the group consisting of survival until mortality, pathological complete response, clinical complete remission, clinical partial remission, clinical stable disease, recurrence-free survival, metastasis free survival, and disease free survival, according to, but not limited by, exemplary embodiments described further herein. Also, the Gal1 binding partner can be VEGFR2 for any method, composition, and/or complex of the present invention.

BRIEF DESCRIPTION OF THE DRAWINGS

FIG. 7A shows Gal1 expression in a cHL cell line (L428), a series of EBV-transformed LCLs (NOR-, RIC-, STA-, FOL-, LOV-, RIV-, WOL-, FW-, VS-, MA-, SC-, DS-, AND DW-LCL), and a DLBCL cell line (SU-DHL6). FIG. 7B shows Gal1 immunohistochemical staining of three representative primary EBV+ PTLDs (panels a, b, and c) and a DLBCL (panel d). The recently developed murine αGal1mAb, 8F4F8G7, was used at 1:20,000 in immunoblots in FIG. 7A and 1:40,000 in IHC in FIG. 7B. Original magnifications: ×1000.

FIG. 9A shows total phospho-cJun and JunB expression in a cHL cell line, L428, and two EBV-transformed LCLs, RIC and NOR-actin was used as a loading control. FIG. 9B shows results of ChIP-PCR analysis of cJun and JunB binding to Gal1 enhancer regions in the cHL cell line, L428, and two LCLs, NOR and RIC. Results are representative of triplicate experiments. FIG. 9C shows results of densitometric analyses of ChIP-PCR data from FIG. 9B. FIG. 9D shows Gal1 promoter and enhancer-driven luciferase activity in LCLs. NOR cells were cotransfected with 300 ng of the pGL3-Gal 1-promoter constructs (without or with the wild-type or mutant AP-1 dependent Gal1 enhancer) and 100 ng of the control reporter plasmid, pRL-TK, and evaluated for relative luciferase activity as described (Juszczynski et al. (2007) *Proc Natl Acad Sci USA* 104:13134-9). FIG. 9E shows IHC analysis of JunB (panels a, c, and e) and phospho-cJun (panels b, d, and f) in 3 primary PTLDs. The PTLDs had uniformly high nuclear staining of JunB and positive phospho-cJun staining of variable intensity.

FIG. 10B shows that Gal1 was 2 fold more abundant in LMP-transduced germinal center B cells ($p<0.002$).

FIG. 11A shows LMP1- and LMP2A-enhanced Gal1 promoter-driven luciferase activity. 293T cells were co-transfected with the pGL3-LGALS1 promoter (Juszczynski et al. (2007) *Proc Natl Acad Sci USA* 104: 13134-9), control reporter plasmid pRL-PGK and pFLAG-CMV2 empty vector or expression vector LMP1-FLAG or LMP2A-FLAG or LMP1-FLAG plus LMP2A-FLAG and evaluated for relative luciferase activity. FIG. 11B shows RNAi-mediated down-regulation of LMP2A in EBV-transformed LCL. NOR. β-actin was used as a loading control. FIG. 11C shows chemical inhibition of PI3K activity (25 µM Ly294002) and associated change in Gal1 expression in EBV-transformed LCLs.

FIG. 13B shows a histogram summarizing the percentage of annexin V+ cells in the absence of rGal or the presence of rGal alone or rGal1 pre-incubated with the αGal1 mAb or isotype control.

FIG. 14A shows results of EBV-specific CTLs treated with rGal1 alone or rGal1 pre-incubated with αGal1 mAb or isotype control. The percentage of viable CD8+ CTLs (7-AAD negative) is shown on the top of the gate. FIG. 14B shows a histogram summarizing the percentage of viable EBV-specific CD8+ CTLs following the indicated treatments.

FIG. 15A shows results of EBV-specific CTLs treated with rGal1 alone or rGal1 pre-incubated with anti-Gal1 mAb or isotype control IgG2b as in FIGS. 14A-14B. The percentage of viable CD8+ CTLs (7-AAD negative) is shown on the top of the gate. FIG. 15B shows a histogram summarizing the percentage of viable CD8+ CTLs following the indicated treatments.

FIGS. 16A-16S show that differential glycosylation of endothelial cells (ECs) controls the formation of lectin-glycan lattices. FIG. 16A shows the glycan repertoire of HUVEC under resting conditions (2% FCS) detected with biotinylated L-PHA, LEL, SNA, MAL II, PNA and HPA (filled histograms) or with PE-conjugated stravidin alone (open histograms). Data are representative of eight independent experiments. FIG. 16B shows the glycan repertoire of HUVEC under resting, proliferative (bFGF), tolerogenic (IL-10 and/or TGF-$β_1$) or pro-inflammatory (TNF, IFN-γ and/or IL-17) conditions. rMFI (relative mean fluorescence intensity)= (MFI with lectin−MFI without lectin)/MFI without lectin. Data are presented as the ratio relative to resting conditions (dotted line; value=1) and are the mean±SEM of four independent experiments. FIG. 16C shows binding results of 488-Gal1 to HUVEC with or without lactose or sucrose, swainsonine or benzyl-α-GalNAc. Data are the mean±SEM of three independent experiments. FIG. 16D shows binding results of 488-Gal1 to HUVEC transfected with GnT5 or GCNT1 siRNA. Cells without siRNA or transfected with scrambled (src) siRNA were used as controls. Data are the mean±SEM of at least three independent experiments. FIG. 16E shows binding results of 488-Gal1 to HUVEC exposed to tolerogenic, proliferative or inflammatory stimuli. Data are presented as the rMFI ratio relative to resting ECs (dotted line; value=1) and are the mean±SEM of four independent experiments. * P<0.05, ** P<0.01 versus control. FIGS. 16F-16H show results of [$^3$H]thymidine incorporation (FIG. 16F), migration (FIG. 16G) and tube formation (FIG. 16H) of ECs transfected or not with GnT5, GCNT1 or scr siRNA and treated or not with Gal1 (1 µM) and/or VEGF (20 ng/ml) with or without lactose. P<0.05 vs Gal1; *P<0.05 ** P<0.01 versus control. Data are the mean±SEM of at least five independent experiments. FIG. 16I shows tube formation induced by Gal1 or VEGF in HUVEC transfected with GnT5, GCNT1 or scr siRNA. * P<0.05 versus scr siRNA. Data are the mean±SEM of three independent experiments. FIG. 16J shows in vivo vascularization of Matrigel sponges containing Gal1 with or without lactose and the right panel in particular shows quantification of hemoglobin content. Data are representative of two independent experiments. FIG. 16K shows schematic representation of N- and O-glycan biosynthesis, including relevant glycosyltransferases, such as α2-6 sialyltransferase 1 (ST6Gal1), N-acetylglucosaminyltransferase 5 (GnT5), α2-3 sialyltransferase 1 (ST3Gal1) and core 2 N-acetylglucosaminyltransferase 1 (GCNT1), the coordinated actions of which lead to the generation or masking of common glycosylated ligands for galectins (N-acetyllactosamine; LacNAc) or poly-LacNAc residues in complex N-glycans or core 2 O-glycans) at the top, whereas the bottom shows schematic representation of lectin-binding sites in N- and O-glycans. Specific residues recognized by MAL II, LEL, SNA and L-PHA on complex N-glycans and by HPA, PNA and LEL on O-glycans are indicated (green). The common glycosylated ligand for Gal1 (LacNAc) is also indicated (purple). FIG. 16L shows binding results of biotinylated L-PHA to HUVEC transfected with GnT5 (filled histogram) or with scrambled (scr) (open black histogram) siRNA. Cells stained with PE-conjugated Stravidin alone were used as negative control (open grey histogram). Data are representative of four independent experiments. FIG. 16M shows results of qRT-PCR analysis of GnT5 mRNA, whereas FIG. 16N shows that for GCNT1 mRNA of HUVEC transfected with different concentrations of specific siRNA relative to RN18S1 mRNA (AU: arbitrary units). **P<0.01 versus control. Data are the mean±SEM of four independent experiments. FIGS. 16O-16Q show dose-dependent proliferation (FIG. 16O), migration (FIG. 16P) and tube formation (FIG. 16Q) of HUVEC incubated with or without different concentrations of Gal1, VEGF (20 ng/ml) or both. Gal1 effects were completely prevented by co-incubation with 30 mM lactose. * P<0.05 and ** P<0.01, versus control; $^†$ P<0.05 vs Gal1 (1 µM). Data are the mean±SEM of five experiments. FIG. 16R shows light microscopy images of capillary tube formation (upper panels) and migration (lower panels) of HUVEC incubated with Gal1 in the presence or absence of lactose. VEGF was used as positive control. Images representative of five independent experiments are shown. FIG. 16S shows dose-dependent invasion of HUVEC in the presence or absence of different concentrations of Gal1 or VEGF (20 ng/ml). Results are plotted as invasion index calculated as the number of fluorescent invasive cells relative to control. * P<0.05 and ** P<0.01. Data are the mean±SEM of five experiments.

FIG. 17A shows results of a phospho-RTK signaling array of HUVEC exposed to medium (control), VEGF or Gal1, wherein in the left panel, arrows indicate proteins with increased phosphorylation intensity. Data are representative of three independent experiments. By contrast, the right panel shows quantification of pixel intensity. * P<0.05,  P<0.01 versus control. Data are the mean±SEM of three independent experiments. FIG. 2O shows ELISA results of VEGF secretion by HUVEC after specific siRNA-mediated silencing. nd, not-detected. Data are the mean±SEM of four experiments. FIG. 17R shows ELISA results of VEGF secretion by HUVEC incubated with different concentrations of Gal1 with or without lactose. Hypoxia was used as positive control of VEGF secretion. Data are the mean±SEM of six independent experiments.

FIGS. 18A-18U show the galectin-1-glycan lattices link tumor hypoxia to VEGFR2-mediated angiogenesis. FIG. 18A shows the glycan repertoire on HUVEC incubated in hypoxia (black filled histograms) or normoxia (grey filled histograms), detected with biotinylated L-PHA, LEL, SNA, MAL II or PNA, or with PE-conjugated stravidin alone (open histograms). Data are representative of five independent experiments. FIG. 18B shows binding results of 488-Gal1 to HUVEC exposed to hypoxia or normoxia.  P<0.01. Data are the mean±SEM of five independent experiments. FIGS. 18C-18F show expression of Gal1 in KS cells transfected with or without HIF-1α siRNA or a super-repressor form of IκB-α (IκB-α-SR) and incubated under hypoxia or normoxia. FIG. 18C shows promoter activity and data are the mean±SEM of five independent experiments. FIG. 18D shows qRT-PCR results of Gal1 mRNA relative to RN18S1. AU, arbitrary units. P<0.01. Data are the mean±SEM of three independent experiments. FIG. 18E shows immunoblot results of Gal1, IκB-α and HIF-1α. Data are representative of four experiments. FIG. 18F shows ELISA results of Gal1 secretion. P<0.01. Data are the mean±SEM of three independent experiments. FIG. 18G shows ELISA results of Gal1 secretion by KS cells cultured in hypoxia or normoxia in the presence or absence of N-acetyl-cysteine (NAC; 0.5 mM). FIG. 18H shows ELISA results of Gal1 secretion by KS cells exposed to $H_2O_2$ (0.5 mM) in the presence or absence of BAY 11-7082. Data are the mean±SEM of three independent experiments. FIG. 18I shows immunoperoxidase staining results of Gal1 in non-hypoxic and hypoxic areas of KS xenografts in the upper panels, whereas the lower panels show immunofluorescence of Gal1 and Hypoxyprobe-1 staining. Images are representative of three independent experiments. FIG. 18J show tube formation results by HUVEC incubated with conditioned medium (CM) from normoxic or hypoxic KS cells transfected or not with scr or VEGF siRNA and/or Gal1 shRNA.  P<0.01. Data are the mean±SEM of four independent experiments. FIG. 18K shows hemoglobin content results of Matrigel plugs containing CM of KS cells transfected or not with Gal1 or scr shRNA, cultured under hypoxic or normoxic conditions and inoculated into wild-type or Lgals1$^{-/-}$ mice.  P<0.01. Data are the mean±SEM of four independent experiments. FIG. 18L shows tube formation results by HUVEC transfected with GnT5, GCNT1 or scr siRNA incubated with CM from normoxic or hypoxic KS cells.  P<0.01. Data are the mean±SEM of four independent experiments. FIG. 18M shows immunoblot analysis of Gal1 expression induced by hypoxia in human and mouse melanoma (A375 and B16-F0), mouse breast carcinoma (4T1) and human prostate carcinoma (LNCaP) cell lines. Right panel, quantification of band intensity relative to that of actin. Data are representative of three independent experiments. FIG. 18N shows secretion of Gal1 by KS cells cultured under hypoxic or normoxic conditions in the presence or absence of HIF-1α or NF-κB inhibitor.  P<0.01. Data are the mean±SEM of three independent experiments. FIG. 18O shows expression results of Gal1 upon treatment of KS cells with $CoCl_2$ (chemical activator of HIF-1α) evaluated by immunoblot (left panel) or promoter activity (right panel) assays. Modulation of pGL3-Gal1-Luciferase activity relative to renilla expression is shown. P<0.01. Data are the mean±SEM of three independent experiments. FIG. 18P shows putative NF-κB consensus sequences (SEQ ID NOS 28-35, respectively, in order of appearance) revealed by in silico analysis (MatInspector Software) of the regulatory sequences of human LGALS1 gene. A fragment ranging from 2400 bp upstream to 2500 bp downstream from the start site (+1) of LGALS1 coding sequence was analyzed. A relevant NF-κB consensus sequence (#3) located at the promoter sequence 341 by upstream of the start site is highlighted. A schematic representation of the LGALS1 gene fragment indicating the eight putative NF-κB consensus sequences is shown. A schematic representation of pGL3-Gal1-Luc, used in luciferase assays, which consists of LGALS1 promoter region (−473 to +67, encompassing NF-κB consensus sequence #3) ligated into the pGL3 promoterless reporter vector is shown. FIG. 18Q shows ELISA results of Gal1 secretion and immunoblot analysis of Gal1 and IκB-α expression (inset) by KS cells cultured in hypoxia or normoxia in the presence or absence of increasing concentrations of the ROS scavenger NAC. * $P<0.05$; ** $P<0.01$ versus control. Data are the mean±SEM. of three independent experiments. FIG. 18R shows ELISA results of Gal1 secretion by KS cells cultured with increasing concentrations of $H_2O_2$. Data are the mean±SEM of three independent experiments. FIG. 18S shows immunoblot results of KS cells expressing shRNA constructs that target different sequences of human Gal1 mRNA (sh-Gal1.1, sh-Gal1.2 and sh-Gal1-3) or scrambled shRNA (sh-scr) cultured under normoxic (upper panel) or hypoxic (lower panel) conditions. rGal1, recombinant Gal1. The lower right panel shows laser confocal microscopy results of sh-Gal-1.2 KS cells co-infected with GFP-encoding vector fixed and stained with anti-Gal1 antibody (red). Data are representative of five independent experiments. FIGS. 18T-18U show ELISA results of VEGF (FIG. 18T) or Gal1 (FIG. 18U) secretion by sh-scr or sh-Gal1.2 KS cells transfected with 100 nM siRNA specific for VEGF (VEGF siRNA) or scr siRNA incubated under normoxic or hypoxic conditions. Data are the mean±SEM of four independent experiments.

FIGS. 19A-19N show that targeting galectin-1-glycan lattices in vivo prevents tumor growth and angiogenesis. FIGS. 19A-19C show results of nude mice inoculated with KS clones ($5\times10^6$ cells) expressing Gal1 shRNA (sh-Gal1.1 and sh-Gal1.2), control KS cells expressing scr shRNA (sh-scr) or wild-type KS cells (KS wt). * $P<0.05$,  $P<0.01$ versus sh-scr. Data are the mean±SEM of four independent experiments with five animals per group. FIG. 19A shows results of tumor growth. FIG. 19B show results of flow cytometry of tumor-associated $CD34^+$ ECs. Dot plots are representative of four independent experiments. FIG. 19C shows results of tumor hemoglobin content. FIG. 19D shows Gal1 transcript profiles of mouse mECK36 KS tumors compared to normal skin in the left panel, whereas the right panel shows laser confocal microscopy of mECK36 stained for Gal1 and LANA. FIG. 19E shows a Gal1 transcript profile of human KS compared to normal skin. FIG. 19F shows representative images of human benign vascular lesions (n=26) and primary KS tumors (n=15) stained with H&E or with anti-Gal1 antibody, wherein quantification of Gal1 expression is shown to the right.  $P<0.01$. FIG. 19G shows results of in vitro cell growth of KS clones expressing Gal1 shRNA (sh-Gal1.1 and sh.Gal1.2), scr shRNA (sh-scr) or wild-type KS cells (KS wt). Data are the mean±SEM of four independent experiments. FIG. 19H shows flow cytometry results of tumor-associated $CD34^+$ ECs of nude mice inoculated with KS clones. Data are the mean±SEM of three independent experiments. ** $P<0.01$ versus sh-scr. FIG. 19I shows immunoblot results of KS clones generated by limited dilution of antisense transfectants (As-Gal1.1, As-Gal1.2 and As-Gal1.3) or wild type KS cells (KS wt). Data are representative of three experiments. FIG. 19J shows in vitro cell growth results of KS wt cells, control KS cells transfected with vector alone (As-control) and Gal1 knockdown KS clones. Data are the mean±SEM of three independent experiments. FIGS. 19K-19M show results of nude mice inoculated with As-Gal1.1, As-Gal1.2, As-Gal1.3, As-control or wt KS cells. FIG. 19K shows kinetics of tumor growth. $P<0.05$. Data are the mean±SEM of three independent experiments with three animals per group. FIG. 19L shows quantitative analysis of tumor microvessel density. * $P<0.05$. Data are the mean±SEM of three independent experiments with three animals per group. FIG. 19M shows qRT-PCR results of Gal1 mRNA in mECK36 KS tumors and normal skin. ** $P<0.01$. FIG. 19N shows representative images of human benign vascular lesions (n=26) and primary KS tumors (n=15) stained with H&E or with anti-Gal1 antibody.

FIGS. 20A-20F show results from B6 mice inoculated with B16 clones ($2\times10^5$ cells) expressing Gal1 shRNA (sh-Gal1.1 and sh-Gal1.2), sh-scr or wild-type B16 cells (B16 wt). For FIGS. 20A-20C, * $P<0.05$,  $P<0.01$ versus sh-scr, whereas for FIGS. 20D-20F,  $P<0.01$ versus sh-scr. Data are the mean±SEM of three independent experiments. FIG. 5A shows the kinetics of tumor growth. FIG. 20B shows the results of flow cytometry of tumor-associated $CD34^+$ ECs. FIG. 20C shows tumor hemoglobin content. FIG. 20D shows proliferation and FIG. 20E shows secretion of IFN-γ and IL-17 by TDLN cells from mice receiving B16 knockdown clones or control transfectants after ex vivo restimulation with B16 cells. nd, not detected. FIG. 20F shows flow cytometry results of $CD4^+CD25^+FoxP3^+T_{reg}$ cells in TDLN from mice receiving knockdown clones or control transfectants. FIG. 20G shows confocal microscopy results of lectin staining (green) and $CD31^+$ ECs (red) in B16 tumors and normal skin, wherein the left panel shows quantification of fluorescence intensity (10 fields per tumor, 200×). Mean represents the ratio of green versus red fluorescence. FIG. 20H shows IHC of biopsies (n=19) from patients with primary melanoma stained with anti-Gal1 or anti-CD31 antibodies, wherein representative images are shown and the right panel shows the correlation between Gal1 expression and microvascular density (MVD). FIG. 20I shows immunoblot results of B16 clones expressing Gal1 shRNA (sh-Gal1.1 and sh-Gal1.2), control B16 cells expressing scr shRNA (sh-scr) or wild-type B16 cells (B16 wt). Data are representative of three experiments. FIG. 20J shows in vitro cell growth of B16 clones expressing Gal1 shRNA (sh-Gal1.1 and sh.Gal1.2), scr shRNA (sh-scr) or wild-type B16 cells (B16 wt). Data are the mean±SEM of three independent experiments.

FIG. 21A shows results of binding of 488-Gal1 to HUVEC in the presence or absence of 8F4F8G7 mAb (0.5 µM), isotype control (Iso) or lactose. The filled histogram shows non-specific binding determined with unlabeled Gal1. Data are representative of four independent experiments. FIGS. 21B-21D show the functional activity of 8F4F8G7 mAb in vitro (** $P<0.01$ versus isotype. Data are the mean±SEM for FIGS. 6B-6D or are representative of three independent experiments for FIG. 6E.) FIG. 21B shows proliferation, FIG. 21C shows migration, and FIG. 21D shows tube formation of HUVEC incubated with Gal1 or VEGF in the presence or absence of 8F4F8G7 mAb or isotype control. FIG. 21E shows immunoblot results of VEGFR2 phosphorylation induced by Gal1 in HUVEC incubated with 8F4F8G7 mAb or isotype control or in HUVEC transfected with GnT5 siRNA. FIGS. 21F-21H show the results of nude mice inoculated with wild-type KS treated in vivo with 8F4F8G7 mAb (7.5 mg/kg) or isotype control every three days (* P<0.05 versus isotype. Data are the mean±SEM of four independent experiments with five animals per group). FIG. 21F shows the kinetics of tumor growth. FIG. 21G shows the results of flow cytometry of tumor-associated CD34$^+$ ECs. FIG. 21H shows tumor hemoglobin content. FIG. 21I shows binding results of fluorescently-labeled (488)-Gal1 to HUVEC in the presence or absence of 8F4F8G7, 8B5E6H9 or 2E52H12 anti-Gal1 mAb (all used at 0.5 µM). * P<0.05 versus control. Data are the mean±SEM of three independent experiments. FIG. 21J shows binding results of 488-Gal3 (20 µg/ml, left panel) and 488-Gal8 (20 µg/ml, right panel) to HUVEC in the presence or absence of 8F4F8G7 mAb (0.5 µM). Filled histogram show non-specific binding determined with unlabeled galectins. Data are representative of three independent experiments. FIG. 21K shows tumor growth results in nude mice inoculated with wild-type KS cells and treated in vivo every three days with different doses of 8F4F8G7 mAb or with isotype control. Data are the mean±SEM of three independent experiments. * P<0.05 versus isotype control.

FIGS. 22A-22R show that therapeutic administration of a neutralizing anti-galectin-1 mAb promotes vascular remodeling and tumor-specific immunity. FIGS. 22A-22J show the results of B6 mice inoculated with 2×10$^5$ wild type B16 cells treated in vivo with 8F4F8G7 mAb (7.5 mg/kg) or with isotype control every three days. FIG. 22A shows kinetics of tumor growth. * P<0.05,  P<0.01 versus B16. Data are the mean±SEM of four independent experiments with six animals per group. FIG. 22B shows confocal microscopy results of lectin (GLS-1$_{B4}$)-perfused vessels in sized-matched tumors. FIG. 22C shows quantification of vessel diameters (10 fields per tumor, 200×). FIG. 22D shows confocal microscopy results of lectin-perfused vessels (green) labeled with anti-αSMA antibody (red). Arrows indicate vessel-associated pericytes, wherein the right panel shows the percentage of tumor vessels with pericyte coverage (10 fields per tumor, 200×). FIG. 22E shows confocal microscopy results of tumors stained with anti-desmin (red, upper panels) or anti-RGS5 (red, lower panels). ECs were stained with anti-CD31 (green) and quantification of vessels covered by pericytes expressing RGS5, desmin, αSMA and PDGFRβ is shown to the right. For FIGS. 22C-22E, P<0.01 versus isotype control and data are the mean±SEM of three independent experiments with four animals per group. FIG. 22F shows confocal microscopy results of B16 sized-matched tumors immunostained with Hypoxyprobe-1. FIG. 22G shows proliferation results and FIG. 22H shows secretion results of IFN-γ and IL-17 (FIG. 22H) by TDLN cells from mice treated with 8F4F8G7 mAb or isotype control in response to ex vivo restimulation with B16 cells, wherein P<0.01 versus isotype control and data are the mean±SEM of four independent experiments with four mice per group for both figures. FIG. 22I shows flow cytometry results of CD25$^+$FoxP3$^+$TDLN cells from mice given 8F4F8G7 mAb or isotype control. Dot plots are representative of four independent experiments. FIG. 22K shows results of spleen T cells purified from B16 tumor-bearing mice, stained with CFSE and transferred (5×10$^6$) to mice with established syngeneic tumors treated with 8F4F8G7 mAb or with isotype control. Representative dot plots of CFSE T cells reaching tumors and spleen of recipient mice are shown. The number at the top right of the figure indicates positive events. FIG. 22L shows the number of fluorescently-labeled beads (relative to 1×10$^5$ events) reaching tumors and spleen of mice given 8F4F8G7 mAb or isotype control 15 min after inoculation. Data are the mean±SEM of two independent experiments with four animals per group. P<0.01 versus isotype control. FIG. 22M shows tumor growth results in B6-Rag1$^{-/-}$ immunodeficient mice inoculated with 2×10$^5$ wild type B16 cells treated in vivo with 8F4F8G7 mAb (7.5 mg/kg) or with isotype control every three days. * P<0.05 versus isotype control. Data are the mean±SEM of two independent experiments with four animals per group. FIG. 22N-22Q show results of immunocompetent B6 mice inoculated with 2×10$^5$ wild-typeB16 cells treated in vivo with 8F4F8G7 mAb (7.5 mg/kg) or with isotype control every three days. FIG. 22N shows flow cytometry results of tumor-associated CD34$^+$ ECs. P=N.S. at day 20 after tumor inoculation. FIG. 22O shows laser confocal microscopy results of tumors immunostained with anti-Rgs5 (red) or anti-desmin (red). ECs were stained with anti-CD31 (green). FIG. 22P shows flow cytometry results of IFN-γ-, IL-17- and IL-10-producing CD4$^+$ T cells in TDLN from mice treated with 8F4F8G7 mAb or isotype control in response to ex vivo restimulation with B16 cells. Numbers in the top right quadrants indicate percentage of double positive cells. Data are representative of three independent experiments with four mice per group. FIG. 22Q shows flow cytometry results of FoxP3 expression within CD4$^+$CD25$^+$cells in TDLN of B16 tumors from mice treated with 8F4F8G7 mAb or isotype control. Data are the mean±SEM of three independent experiments. FIG. 22R shows results of spleen T cells isolated from B16 tumor-bearing mice and stained with CFSE inoculated (5×10$^6$) in mice with established syngeneic tumors treated with the 8F4F8G7 mAb or with isotype control. The number of CFSE$^+$ cells/0.1 cm$^3$ in tumors and spleen of recipient mice is shown.

DETAILED DESCRIPTION OF THE INVENTION

Figure 1:
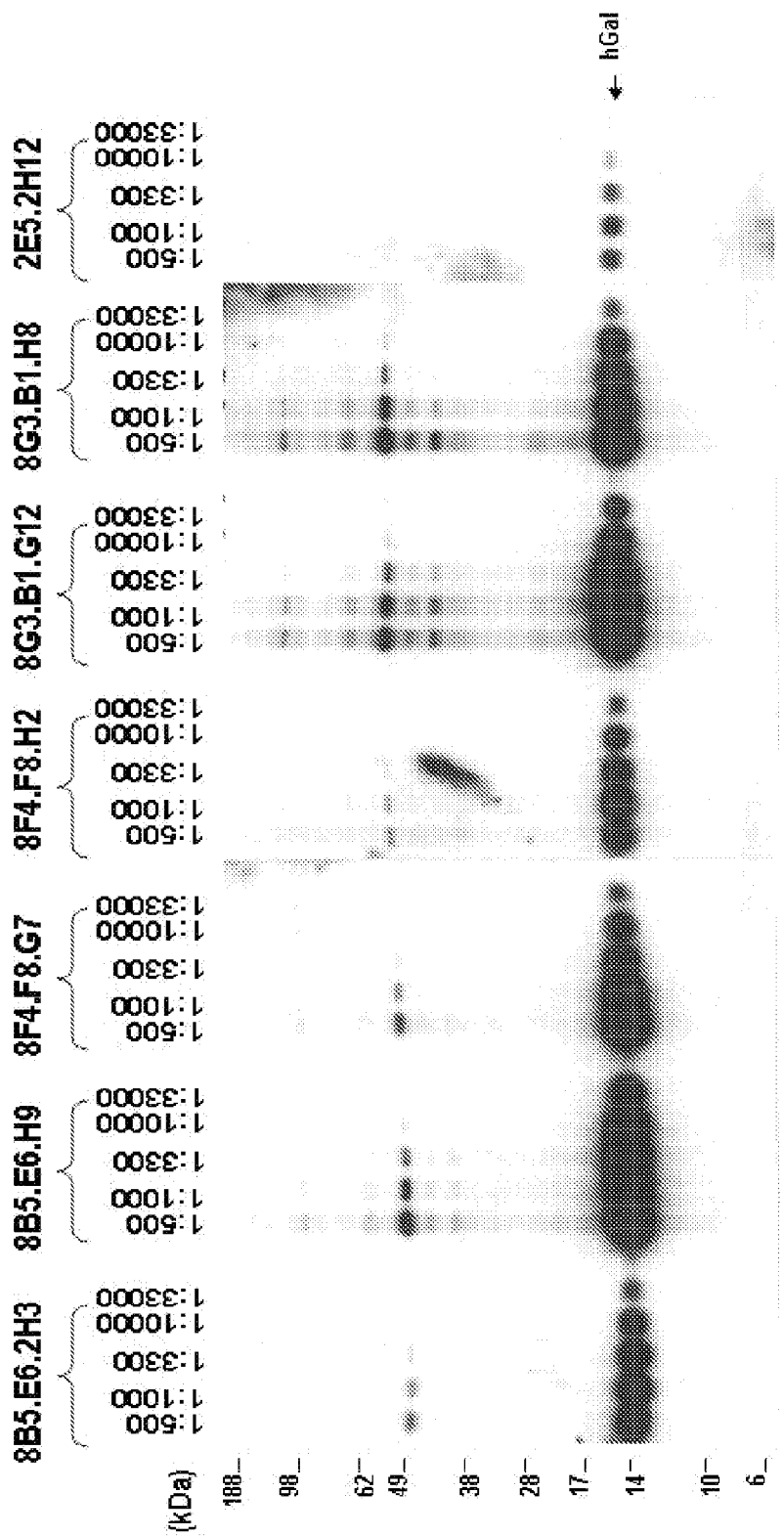
FIG. 1 shows serial dilution-based reactivity data for anti-human Gal1 monoclonal antibodies assayed against endogenous Gal1 from a Hodgkin lymphoma cell line.

The present invention is based, in part, on the discovery that galectin-1 (Gal1) is overexpressed by viral-associated post-transplantation lymphoblastoid cells and that the Gal1 overexpression by such cells is directly implicated in the development and maintenance of a tolerogenic and immunosuppressive microenvironment, leading to an ineffective host anti-proliferative immune response. The present invention is further based, in part, on the discovery that hypoxia promotes upregulation of Gal1 resulting in angiogenesis such that targeted disruption of Gal1-glycan lattices attenuates hypoxia associated angiogenesis, while promoting pericyte maturation and vacular remoding. Thus, agents such as natural ligands, derivatives of natural ligands, small molecules, RNA interference, aptamer, peptides, peptidomimetics, glycan-related compounds, glycomimetics, and antibodies that specifically bind to the Gal1 gene or gene products, or fragments thereof, can be utilized for the diagnosis, prognosis, monitoring and/or treatment of viral-associated PTLD, e.g., EBV-associated PTLD, and/or hypoxia associated angiogenesis disorders. In addition, such agents can be utilized to modulate, e.g., increase, immune surveillance in viral-associated PTLD, e.g., EBV-associated PTLD and/or downregulate hypoxia associated angiogenesis. Moreover, agents such as Gal1 gene sequences, Gal1 gene products, anti-Gal1 RNA interference molecules, anti-Gal1 antibodies (i.e., antibodies that specifically bind to Gal1 gene products or fragments thereof), or fragments thereof, can be utilized to restore immune surveillance and neutralization of viral-associated PTLD, e.g., EBV-associated PTLD, and/or down-regulate hypoxia associated angiogenesis.

Thus, it has been discovered that a higher than normal level of expression of Gal1 correlates with the presence of a viral-associated PTLD, e.g., EBV-associated PTLD, and/or hypoxia associated angiogenesis disorders in a subject. Gal1 polypeptides and fragments thereof, e.g., biologically active or antigenic fragments thereof, are provided, as reagents or targets in assays applicable to treatment and/or diagnosis of viral-associated PTLD, e.g., EBV-associated PTLD, and/or hypoxia associated angiogenesis disorders. In particular, the methods and compositions of the present invention relate to detection and/or modulation of expression and/or activity of a Gal1 gene or fragment thereof, e.g., biologically active fragments thereof, as well as to the detection and/or modulation of expression and/or activity of gene products or fragments thereof encoded by the Gal1 gene, e.g., biologically active fragments thereof. The methods of the present invention can utilize the Gal1 gene sequence or fragments thereof, as well as gene products of the Gal1 gene and/or modulators thereof or fragments thereof, e.g., antibodies which specifically bind to such Gal1 gene products. The present invention further features methods for detecting the presence, absence, stage, and other characteristics of viral-associated PTLD, e.g., EBV-associated PTLD, and/or hypoxia associated angiogenesis disorders in a sample that are relevant to prevention, diagnosis, characterization, and therapy in a patient. In addition, the present invention also features compositions of matter, including antibodies (e.g., antibodies which specifically bind to any one of the polypeptides described herein) as well as fusion polypeptides, including all or a fragment of a polypeptide described herein. Moreover, the present invention features compositions useful for the reduction of Gal1 nucleic acids (e.g., Gal1 mRNA or hnRNA or fragments thereof), including RNA interference compositions, directed against Gal1 nucleic acids or fragments thereof.

I. Definitions

The articles "a" and "an" are used herein to refer to one or to more than one (i.e. to at least one) of the grammatical object of the article. By way of example, "an element" means one element or more than one element.

The term "altered amount" of a marker of a marker refers to increased or decreased copy number of a marker and/or increased or decreased nucleic acid level of a particular marker gene or genes in a sample, as compared to that of the marker in a control sample. The term "altered amount" of a marker also includes an increased or decreased protein level of a marker in a sample, as compared to the protein level of the marker in a normal, control sample.

The term "altered activity" of a marker refers to an activity of a marker which is increased or decreased in a disease state, e.g., in a biological sample, as compared to the activity of the marker in a normal, control sample. Altered activity of a marker may be the result of, for example, altered expression of the marker, altered protein level of the marker, altered structure of the marker, or, e.g., an altered interaction with other proteins involved in the same or different pathway as the marker, or altered interaction with transcriptional activators or inhibitors.

The term "altered structure" of a marker refers to the presence of mutations or allelic variants within the marker gene or maker protein, e.g., mutations which affect expression or activity of the marker, as compared to the normal or wild-type gene or protein. For example, mutations include, but are not limited to substitutions, deletions, or addition mutations. Mutations may be present in the coding or non-coding region of the marker.

The term "altered subcellular localization" of a marker refers to the mislocalization of the marker within a cell relative to the normal localization within the cell e.g., within a healthy and/or wild-type cell. An indication of normal localization of the marker can be determined through an analysis of subcellular localization motifs known in the field that are harbored by marker polypeptides or, for example, through cellular analyses such as internalization of normally extracellular mature functional Gal1.

The term "angiogenesis" or "neovascularization" refers to the process by which new blood vessels develop from pre-existing vessels [Varner et al. (1999) Angiogen. 3(1):53-60; Mousa et al. (2000) Angiogen. Stim. & Inhib. 35-42; 44. Kim et al. (2000) Amer. J. Path. 156:1345-1362; Kim et al. (2000) J. Biol. Chem. 275:33920-33928; Kumar et al. (2000) Angiogenesis: From Molecular to Integrative Pharm. 169-180]. Endothelial cells from pre-existing blood vessels or from circulating endothelial stem cells [Takahashi et al. (1995) Nat. Med. 5:434-438; Isner et al. (1999) J. Clin. Invest. 103: 1231-1236] become activated to migrate, proliferate, and differentiate into structures with lumens, forming new blood vessels, in response to growth factor or hormonal cues, or hypoxic or ischemic conditions. During ischemia, such as occurs in cancer, the need to increase oxygenation and delivery of nutrients apparently induces the secretion of angiogenic factors by the affected tissue; these factors stimulate new blood vessel formation. Several additional terms are related to angiogenesis.

For example, the term "tissue exhibiting angiogenesis" refers to a tissue in which new blood vessels are developing from pre-existing blood vessels.

As used herein, the term "inhibiting angiogenesis," "diminishing angiogenesis," "reducing angiogenesis," and grammatical equivalents thereof refer to reducing the level of angiogenesis in a tissue to a quantity which is at least 10%, 15%, 20%, 25%, 30%, 35%, 40%, 45%, 50%, 55%, 60%, 65%, 70%, 75%, 80%, 85%, 90%, 95%, 99% or less than the quantity in a corresponding control tissue, and most preferably is at the same level which is observed in a control tissue. A reduced level of angiogenesis need not, although it may, mean an absolute absence of angiogenesis. The invention does not require, and is not limited to, methods that wholly eliminate angiogenesis. The level of angiogenesis may be determined using methods well known in the art, including, without limitation, counting the number of blood vessels and/or the number of blood vessel branch points, as discussed herein and in the examples. An alternative in vitro assay contemplated includes the tubular cord formation assay that shows growth of new blood vessels at the cellular level [D. S. Grant et al., Cell, 58: 933-943 (1989)]. Art-accepted in vivo assays are also known, and involve the use of various test animals such as chickens, rats, mice, rabbits and the like. These in vivo assays include the chicken chorioallantoic membrane (CAM) assay, which is suitable for showing anti-angiogenic activity in both normal and neoplastic tissues [D. H. Ausprunk, Amer. J. Path., 79, No. 3: 597-610 (1975) and L. Ossonowski and E. Reich, Cancer Res., 30: 2300-2309 (1980)]. Other in vivo assays include the mouse metastasis assay, which shows the ability of a compound to reduce the rate of growth of transplanted tumors in certain mice, or to inhibit the formation of tumors or preneoplastic cells in mice which are predisposed to cancer or which express chemically-induced cancer [M. J. Humphries et al., Science, 233:

467-470 (1986) and M. J. Humphries et al., J. Clin. Invest., 81: 782-790 (1988)]. Moreover, in some embodiments, angiogenesis can be measured according to such attributes as pericyte maturation and vascular remodeling as described further herein.

As used herein, the term "hypoxia associated angiogenesis" or "hypoxia-induced angiogenesis" refers generally to the process of pathological angiogenesis in non-neoplastic disease states and is typically, although not necessarily, accompanied by a transition to a neoplastic state. Hypoxia-induced transcription factors (HIFs) induce the expression of angiogeneic factors including HIF-lzlpha, VEGF, nitric oxide synthase, PDFG, Ang2, and others. As a result, hypoxia associated angiogenesis encompasses a well-known set of pathological conditions characterized by such a process Pugh et al. (2003) Nat Med 9, 677-684; Fraisl et al. (2009) Dev Cell 16, 167-179; Ferrara et al. (2005) Nature 438, 967-974; Ferrara, N. (2010) Cytokine Growth Factor Rev 21, 21-26]. In some embodiments, the set of hypoxia associate angiogenesis pathologies includes, but is not limited to, neoplasms and cancers, age-related macular degeneration, diabetes retinopathy, atherosclerosis, chronic obstructive lung disease, and psoriasis.

The term "organized vasculature" means substantially branched blood vessels, or blood vessels with a normal or increased degree of branching, so as to promote blood supply to surrounding tissue. The term "disorganized vasculature" means substantially unbranched blood vessels, or blood vessels with a reduced degree of branching, so as to impair blood supply to surrounding tissue.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody. An "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. "Inactivating antibodies" refers to antibodies that do not induce the complement system.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., Gal1 polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) Science 242:423-426; and Huston et al. (1988) Proc. Natl. Acad. Sci. USA 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab , Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) Human Antibodies and Hybridomas 6:93-101) and use of a cysteine residue, a marker peptide and a C-terminal polyhistidine tag to make bivalent and biotinylated scFv polypeptides (Kipriyanov, S. M., et al. (1994) Mol. Immunol. 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g., humanized, chimeric, etc.). Antibodies may also be fully human. In one embodiment, antibodies of the present invention bind specifically or substantially specifically to Gal1 polypeptides or fragments thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells may exist alone within an animal, or may be a non-tumorigenic cancer cell, such as a leukemia cell. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like.

The terms "CDR", and its plural "CDRs", refer to a complementarity determining region (CDR) of which three make up the binding character of a light chain variable region (CDRL1, CDRL2 and CDRL3) and three make up the binding character of a heavy chain variable region (CDRH1, CDRH2 and CDRH3). CDRs contribute to the functional activity of an antibody molecule and are separated by amino acid sequences that comprise scaffolding or framework regions. The exact definitional CDR boundaries and lengths are subject to different classification and numbering systems. CDRs may therefore be referred to by Kabat, Chothia, contact or any other boundary definitions. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat, Chothia, and/or MacCallum et al., (Kabat et al., in "Sequences of Proteins of Immunological Interest," $5^{th}$ Edition, U.S. Department of Health and Human Services, 1992; Chothia et al. (1987) J. Mol. Biol. 196, 901; and MacCallum et al., J. Mol. Biol. (1996) 262, 732, each of which is incorporated by reference in its entirety).

As used herein, the term "classifying" includes "to associate" or "to categorize" a sample with a disease state. In certain instances, "classifying" is based on statistical evidence, empirical evidence, or both. In certain embodiments, the methods and systems of classifying use of a so-called training set of samples having known disease states. Once established, the training data set serves as a basis, model, or template against which the features of an unknown sample are compared, in order to classify the unknown disease state of the sample. In certain instances, classifying the sample is akin to diagnosing the disease state of the sample. In certain other instances, classifying the sample is akin to differentiating the disease state of the sample from another disease state.

As used herein, the term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

"Complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In one embodiment, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. In another embodiment, all nucleotide residues of the first portion are capable of base pairing with nucleotide residues in the second portion.

As used herein, the term "composite antibody" refers to an antibody which has variable regions comprising germline or non-germline immunoglobulin sequences from two or more unrelated variable regions. Additionally, the term "composite, human antibody" refers to an antibody which has constant regions derived from human germline or non-germline immunoglobulin sequences and variable regions comprising human germline or non-germline sequences from two or more unrelated human variable regions. A composite, human antibody is useful as an effective component in a therapeutic agent according to the present invention since the antigenicity of the composite, human antibody in the human body is lowered.

As used herein, the term "Fc region" is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. Suitable native-sequence Fc regions for use in the antibodies of the present invention include human IgG1, IgG2 (IgG2A, IgG2B), IgG3 and IgG4.

As used herein, "Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the Fc RI, Fc RII, and Fc RII subclasses, including allelic variants and alternatively spliced forms of these receptors, Fc RII receptors include Fc RIIA (an "activating receptor") and Fc RIIB (an "inhibiting receptor"), which have similar amino acid sequences that differ primarily in the cytoplasmic domains thereof. Activating receptor Fc RIIA contains an immunoreceptor tyrosine-based activation motif (ITAM) in its cytoplasmic domain. Inhibiting receptor Fc RIIB contains an immunoreceptor tyrosine-based inhibition motif (ITIM) in its cytoplasmic domain (see M. Daëron, *Annu. Rev. Immunol.* 15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

A molecule is "fixed" or "affixed" to a substrate if it is covalently or non-covalently associated with the substrate such the substrate can be rinsed with a fluid (e.g. standard saline citrate, pH 7.4) without a substantial fraction of the molecule dissociating from the substrate.

As used herein, "Framework" or "FR" residues are those variable-domain residues other than the HVR residues as herein defined.

As used herein, the term "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

As used herein, the term "host cell" is intended to refer to a cell into which a nucleic acid of the present invention, such as a recombinant expression vector of the present invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "humanized antibody", as used herein, is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

As used herein, the term "hypervariable region," "HVR," or "HV," refers to the regions of an antibody-variable domain that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al. (2000) Immunity 13, 37-45; Johnson and Wu in Methods in Molecular Biology 248, 1-25 (Lo, ed., Human Press, Totowa, N.J., 2003)). Indeed, naturally occurring camelid antibodies consisting of a heavy chain only are functional and stable in the absence of light chain (see, e.g., Hamers-Casterman et al. (1993) Nature 363:446-448 (1993) and Sheriff et al. (1996) Nature Struct. Biol. 3, 733-736).

As used herein, the term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

As used herein, the term "immune disorder" includes immune diseases, conditions, and predispositions to, including, but not limited to, Hodgkin lymphoma (including, e.g., lymphocyte-rich classical Hodgkin lymphoma, mixed cellularity classical Hodgkin lymphoma, lymphocyte-depleted classical Hodgkin lymphoma, nodular sclerosis classical Hodgkin lymphoma, anaplastic large cell lymphoma, or MLL pre B-cell ALL), cancer, chronic inflammatory disease and disorders (including, e.g., Crohn's disease, inflammatory bowel disease, reactive arthritis, and Lyme disease), insulin-dependent diabetes, organ specific autoimmunity (including, e.g., multiple sclerosis, Hashimoto's thyroiditis, autoimmune uveitis, and Grave's disease), contact dermatitis, psoriasis, graft rejection, graft versus host disease, sarcoidosis, atopic conditions (including, e.g., asthma and allergy including, but not limited to, allergic rhinitis and gastrointestinal allergies such as food allergies), eosinophilia, conjunctivitis, glomerular nephritis, systemic lupus erythematosus, scleroderma, certain pathogen susceptibilities such as helminthic (including, e.g., leishmaniasis) and certain viral infections (including, e.g., HIV and bacterial infections such as tuberculosis and lepromatous leprosy).

As used herein, the term "immune response" includes T cell mediated and/or B cell mediated immune responses. Exemplary immune responses include T cell responses, e.g., cytokine production, and cellular cytotoxicity. In addition, the term immune response includes immune responses that are indirectly effected by T cell activation, e.g., antibody production (humoral responses) and activation of cytokine responsive cells, e.g., macrophages.

As used herein, the term "inhibit" includes the decrease, limitation, or blockage, of, for example a particular action, function, or interaction.

As used herein, the term "interaction", when referring to an interaction between two molecules, refers to the physical contact (e.g., binding) of the molecules with one another.

Generally, such an interaction results in an activity (which produces a biological effect) of one or both of said molecules. The activity may be a direct activity of one or both of the molecules, (e.g., signal transduction). Alternatively, one or both molecules in the interaction may be prevented from binding their ligand, and thus be held inactive with respect to ligand binding activity (e.g., binding its ligand and triggering or inhibiting an immune response). To inhibit such an interaction results in the disruption of the activity of one or more molecules involved in the interaction. To enhance such an interaction is to prolong or increase the likelihood of said physical contact, and prolong or increase the likelihood of said activity.

As used herein, an "antisense" nucleic acid polypeptide comprises a nucleotide sequence which is complementary to a "sense" nucleic acid encoding a protein, e.g., complementary to the coding strand of a double-stranded cDNA polypeptide, complementary to an mRNA sequence or complementary to the coding strand of a gene. Accordingly, an antisense nucleic acid polypeptide can hydrogen bond to a sense nucleic acid polypeptide.

As used herein, the term an "isolated antibody" is intended to refer to an antibody which is substantially free of other antibodies having different antigenic specificities (e.g., an isolated antibody that specifically binds to human Gal1 and is substantially free of antibodies that do not bind to Gal1). An isolated antibody that specifically binds to an epitope of human Gal1 may, however, have cross-reactivity to other Gal1 proteins, respectively, from different species. However, in some embodiments, the antibody maintains higher affinity and selectivity for human Gal1. In addition, an isolated antibody is typically substantially free of other cellular material and/or chemicals. In one embodiment of the present invention, a combination of "isolated" monoclonal antibodies having different specificities to human Gal1 are combined in a well defined composition.

As used herein, an "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of Gal1 polypeptide or fragment thereof, in which the protein is separated from cellular components of the cells from which it is isolated or recombinantly produced. In one embodiment, the language "substantially free of cellular material" includes preparations of Gal1 protein or fragment thereof, having less than about 30% (by dry weight) of non-Gal1 protein (also referred to herein as a "contaminating protein"), more preferably less than about 20% of non-Gal1 protein, still more preferably less than about 10% of non-Gal1 protein, and most preferably less than about 5% non-Gal1 protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

As used herein, the term "isotype" refers to the antibody class (e.g., IgM or IgG1) that is encoded by heavy chain constant region genes.

As used herein, the term "$K_D$" is intended to refer to the dissociation equilibrium constant of a particular antibody-antigen interaction. The binding affinity of antibodies of the disclosed invention may be measured or determined by standard antibody-antigen assays, for example, competitive assays, saturation assays, or standard immunoassays such as ELISA or RIA.

As used herein, a "kit" is any manufacture (e.g. a package or container) comprising at least one reagent, e.g. a probe, for specifically detecting or modulating the expression of a marker of the present invention. The kit may be promoted, distributed, or sold as a unit for performing the methods of the present invention.

As used herein, the term "monoclonal antibody", refers to an antibody which displays a single binding specificity and affinity for a particular epitope. Accordingly, the term "human monoclonal antibody" refers to an antibody which displays a single binding specificity and which has variable and constant regions derived from human germline or non-germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

A "post-transplantation lymphoproliferative disorder", "PTLD", and/or "viral-associated PTLD" each refers to a disorder in which lymphocytes, which are white blood cells produced in the lymphatic tissue (e.g., lymph nodes, spleen, and/or thymus), are over-produced or act abnormally and are caused by or correlated with a virus. Lymphoid cells include thymus derived lymphocytes (T cells); bone marrow-derived lymphocytes (B cells), and natural killer (NK cells), for example. Lymphocytes progress through a number of different stages, including proliferation, activation, and maturation, and lymphoma or aberrant proliferation can develop at each stage. Disorders may be malignant neoplasms (and may be classified as aggressive or indolent, or as low, intermediate or high-grade), including those associated with IFN-.gamma., or the disorders may involve non-malignant aberrant expansion of lymphoid cells. LPDs include any monoclonal or polyclonal LPD that is not resolving without treatment and/or that involves excessive cellular proliferation, such as an expanding, monoclonal, polyclonal or oligoclonal, lymphoid neoplasm. Cellular proliferation may be more rapid than normal and may continue after the stimuli that initiated the new growth cease. A neoplasm will show partial or complete lack of structural organization and functional coordination with the normal tissue, and may form a distinct mass of tissue that may be either benign (benign tumor) or malignant (cancer).

Such viral-associated PTLD may be caused by or associated with, e.g., Epstein-Barr virus (EBV), a herpes virus, HHV-8, cytomegalovirus, C-type retrovirus, human T-lymphotropic virus type 1 (C-type retrovirus), and/or human immunodeficiency virus (HIV, HIV-1, HIV-2). HIV- and/or AIDS-associated cancers include HIV-associated LPDs, such as Karposi sarcoma, non-Hodgkin's lymphoma, central nervous system (CNS) lymphoma, adult T-cell leukemia/lymphoma (HTLV-1+), and AIDS-associated lymphoma. Immune deficiency such as in AIDS patients, organ transplant recipients, and genetic immune disorders may allow latent EBV to reactivate, causing proliferation of abnormal lymphocytes and the potential to develop an EBV-associated LPD, for example. Methods to detect the presence of virus or viral infection in an aberrant cell, such as a cell involved in a PTLD, are known in the art. Viral nucleic acids or polypeptides may be detected in a cell, tissue, or organism such as an aberrant cell, for example. Also, methods to detect immune response specific for a virus are known. A delayed type-hypersensitivity (DTH) assay, such as a trans vivo DTH assay may be used to detect regulatory T cells, for example. In such an assay, human or other mammalian peripheral blood mononuclear cells (PBMC) may be mixed with a carrier control with and without viral antigen, for example, and injected into a heterologous naive recipient, such as the pinnae or footpad of naive mice. If the donor of the PBMC had previously been sensitized to the challenge antigen, DTH-like swelling responses are observed.

A "marker" is a gene whose altered level of expression in a tissue or cell from its expression level in normal or healthy tissue or cell is associated with a disease state, such as cancer. A "marker nucleic acid" is a nucleic acid (e.g., mRNA, cDNA) encoded by or corresponding to a marker of the present invention. Such marker nucleic acids include DNA (e.g., cDNA) comprising the entire or a partial sequence of any of the nucleic acid sequences set forth in the Sequence Listing or the complement of such a sequence. The marker nucleic acids also include RNA comprising the entire or a partial sequence of any of the nucleic acid sequences set forth in the Sequence Listing or the complement of such a sequence, wherein all thymidine residues are replaced with uridine residues. A "marker protein" is a protein encoded by or corresponding to a marker of the present invention. A marker protein comprises the entire or a partial sequence of any of the sequences set forth in the Sequence Listing. The terms "protein" and "polypeptide" are used interchangeably.

As used herein, the term "modulate" includes up-regulation and down-regulation, e.g., enhancing or inhibiting a response.

The "normal" level of expression of a marker is the level of expression of the marker in cells of a subject, e.g., a human patient, not afflicted with a viral-associated PTLD. An "over-expression" or "significantly higher level of expression" of a marker refers to an expression level in a test sample that is greater than the standard error of the assay employed to assess expression, and is preferably at least twice, and more preferably three, four, five or ten times the expression level of the marker in a control sample (e.g., sample from a healthy subjects not having the marker associated disease) and preferably, the average expression level of the marker in several control samples. A "significantly lower level of expression" of a marker refers to an expression level in a test sample that is at least twice, and more preferably three, four, five or ten times lower than the expression level of the marker in a control sample (e.g., sample from a healthy subject not having the marker associated disease) and preferably, the average expression level of the marker in several control samples.

As used herein, the term "nucleic acid molecule" is intended to include DNA molecules and RNA molecules. A nucleic acid molecule may be single-stranded or double-stranded, but preferably is double-stranded DNA. As used herein, the term "isolated nucleic acid molecule" in reference to nucleic acids encoding antibodies or antibody portions (e.g., $V_H$, $V_L$, CDR3) that bind to Gal1, is intended to refer to a nucleic acid molecule in which the nucleotide sequences encoding the antibody or antibody portion are free of other nucleotide sequences encoding antibodies or antibody portions that bind antigens other than Gal1, which other sequences may naturally flank the nucleic acid in human genomic DNA.

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

An "over-expression" or "significantly higher level of expression" of a marker refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the marker in a control sample (e.g., sample from a healthy subject not having the marker associated disease) and preferably, the average expression level of the marker in several control samples. A "significantly lower level of expression" of a marker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the marker in a control sample (e.g., sample from a healthy subject not having the marker associated disease) and preferably, the average expression level of the marker in several control samples.

The terms "polypeptide fragment" or "fragment", when used in reference to a reference polypeptide, refers to a polypeptide in which amino acid residues are deleted as compared to the reference polypeptide itself, but where the remaining amino acid sequence is usually identical to the corresponding positions in the reference polypeptide. Such deletions may occur at the amino-terminus, internally, or at the carboxy-terminus of the reference polypeptide, or alternatively both. Fragments typically are at least 5, 6, 8 or 10 amino acids long, at least 14 amino acids long, at least 20, 30, 40 or 50 amino acids long, at least 75 amino acids long, or at least 100, 150, 200, 300, 500 or more amino acids long. They can be, for example, at least and/or including 10, 15, 20, 25, 30, 35, 40, 45, 50, 55, 60, 65, 70, 75, 80, 85, 90, 95, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, 800, 820, 840, 860, 880, 900, 920, 940, 960, 980, 1000, 1020, 1040, 1060, 1080, 1100, 1120, 1140, 1160, 1180, 1200, 1220, 1240, 1260, 1280, 1300, 1320, 1340 or more long so long as they are less than the length of the full-length polypeptide. Alternatively, they can be no longer than and/or excluding such a range so long as they are less than the length of the full-length polypeptide. The VEGFR2-GAL1 intereaction involves N-glycosylation sites as it is prevented by treatment with swainsoninc or siRNA-mediated silencing of GnT5 glycosyltransferasem, which is responsible for generating complex N-glycans. A fragment can retain one or more of the biological activities of the reference polypeptide. In various embodiments, a fragment may comprise an enzymatic activity and/or an interaction site of the reference polypeptide. In another embodiment, a fragment may have immunogenic properties. In an exemplary embodiment the fragment comprises a binding domain. In one exemplary embodiment a Gal1 fragment is able to form a complex with a VEGFR2 polypeptide, or a fragment thereof. In another embodiment a VEGFR2 fragment is able to form a complex with a Gal1 polypeptide, or a fragment thereof.

The term "probe" refers to any molecule which is capable of selectively binding to a specifically intended target molecule, for example, a nucleotide transcript or protein encoded by or corresponding to a marker. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

As used herein, the term "rearranged" refers to a configuration of a heavy chain or light chain immunoglobulin locus wherein a V segment is positioned immediately adjacent to a D-J or J segment in a conformation encoding essentially a complete $V_H$ and $V_L$ domain, respectively. A rearranged immunoglobulin gene locus can be identified by comparison to germline DNA; a rearranged locus will have at least one recombined heptamer/nonamer homology element.

As used herein, the term "recombinant host cell" (or simply "host cell"), is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "recombinant human antibody" includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline and/or non-germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The present invention "response" is generally related to for example, determining the effects on progression, efficacy, or outcome of a clinical intervention. In some embodiments, responses relate directly to a change in tumor mass and/or volume after initiation of clinical intervention (e.g., administration of an anti-Gal1 monoclonal antibody). For example, hyperproliferative disorder responses may be assessed according to the size of a tumor after systemic intervention compared to the initial size and dimensions as measured by CT, PET, mammogram, ultrasound or palpation. Response may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment may be done early after the onset of the clinical intervention, e.g., after a few hours, days, weeks or preferably after a few months. A typical endpoint for response assessment is upon termination of the clinical intervention or upon surgical removal of residual tumor cells and/or the tumor bed.

As used herein, the term "specific binding" refers to antibody binding to a predetermined antigen. Typically, the antibody binds with an affinity ($K_D$) of approximately less than $10^{-7}$ M, such as approximately less than $10^{-8}$ M, $10^{-9}$ M or $10^{-10}$ M or even lower when determined by surface plasmon resonance (SPR) technology in a BIACORE® assay instrument using human FAS and/or USP2a as the analyte and the antibody as the ligand, and binds to the predetermined antigen with an affinity that is at least 1.1-, 1.2-, 1.3-, 1.4-, 1.5-, 1.6-, 1.7-, 1.8-, 1.9-, 2.0-, 2.5-, 3.0-, 3.5-, 4.0-, 4.5-, 5.0-, 6.0-, 7.0-, 8.0-, 9.0-, or 10.0-fold or greater than its affinity for binding to a non-specific antigen (e.g., BSA, casein) other than the predetermined antigen or a closely-related antigen. The phrases "an antibody recognizing an antigen" and "an antibody specific for an antigen" are used interchangeably herein with the term "an antibody which binds specifically to an antigen."

As used herein, "subject" refers to any healthy animal, mammal or human, or any animal, mammal or human afflicted with a viral-associated PTLD, e.g., EBV-associated PTLD. The term "subject" is interchangeable with "patient". The term "non-human animal" includes all vertebrates, e.g., mammals and non-mammals, such as non-human primates, sheep, dog, cow, chickens, amphibians, reptiles, etc.

The language "substantially free of chemical precursors or other chemicals" includes preparations of antibody, polypeptide, peptide or fusion protein in which the protein is separated from chemical precursors or other chemicals which are involved in the synthesis of the protein. In one embodiment, the language "substantially free of chemical precursors or other chemicals" includes preparations of antibody, polypeptide, peptide or fusion protein having less than about 30% (by dry weight) of chemical precursors or non-antibody, polypeptide, peptide or fusion protein chemicals, more preferably less than about 20% chemical precursors or non-antibody, polypeptide, peptide or fusion protein chemicals, still more preferably less than about 10% chemical precursors or non-antibody, polypeptide, peptide or fusion protein chemicals, and most preferably less than about 5% chemical precursors or non-antibody, polypeptide, peptide or fusion protein chemicals.

As used herein, the term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a marker of the present invention and normal post-transcriptional processing (e.g. splicing), if any, of the RNA transcript, and reverse transcription of the RNA transcript.

As used herein, the term "T cell" includes CD4+ T cells and CD8+ T cells. The term T cell also includes both T helper 1 type T cells and T helper 2 type T cells. The term "antigen presenting cell" includes professional antigen presenting cells (e.g., B lymphocytes, monocytes, dendritic cells, Langerhans cells) as well as other antigen presenting cells (e.g., keratinocytes, endothelial cells, astrocytes, fibroblasts, oligodendrocytes).

As used herein, the term "unrearranged" or "germline configuration" in reference to a V segment refers to the configuration wherein the V segment is not recombined so as to be immediately adjacent to a D or J segment.

As used herein, the term "vector" refers to a nucleic acid capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

Genetic Code

| | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 81%, 82%, 83%, 84%, 85%, 86%, 87%, 88%, 89%, 90%, 91%, 92%, 93%, 94%, 95%, 96%, or more of the nucleotides, and more preferably at least about 97%, 98%, 99% or more of the nucleotides. Alternatively, substantial homology exists when the segments will hybridize under selective hybridization conditions, to the complement of the strand.

The percent identity between two sequences is a function of the number of identical positions shared by the sequences (i.e., % identity=# of identical positions/total # of positions× 100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available on the world wide web at the GCG company website), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11 17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48): 444 453 (1970)) algorithm which has been incorporated into the GAP program in the GCG software package (available on the world wide web at the GCG company website), using either a Blosum 62 matrix or a PAM250 matrix, and a gap weight of 16, 14, 12, 10, 8, 6, or 4 and a length weight of 1, 2, 3, 4, 5, or 6.

The nucleic acid and protein sequences of the present invention can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403 10. BLAST nucleotide searches can be performed with the NBLAST program, score=100, wordlength=12 to obtain nucleotide sequences homologous to the nucleic acid molecules of the present invention. BLAST protein searches can be performed with the XBLAST program, score=50, wordlength=3 to obtain amino acid sequences homologous to the protein molecules of the present invention. To obtain gapped alignments for comparison purposes, Gapped BLAST can be utilized as described in Altschul et al., (1997) Nucleic Acids Res. 25(17): 3389 3402. When utilizing BLAST and Gapped BLAST programs, the default parameters of the respective programs (e.g., XBLAST and NBLAST) can be used (available on the world wide web at the NCBI website).

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art (see, F. Ausubel, et al., ed. Current Protocols in Molecular Biology, Greene Publishing and Wiley Interscience, New York (1987)).

The nucleic acid compositions of the present invention, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

In view of the foregoing, the nucleotide sequence of a DNA or RNA coding for a fusion protein or polypeptide of the present invention (or any portion thereof) can be used to derive the fusion protein or polypeptide amino acid sequence, using the genetic code to translate the DNA or RNA into an amino acid sequence. Likewise, for fusion protein or polypeptide amino acid sequence, corresponding nucleotide sequences that can encode the fusion protein or polypeptide can be deduced from the genetic code (which, because of its redundancy, will produce multiple nucleic acid sequences for any given amino acid sequence). Thus, description and/or disclosure herein of a nucleotide sequence which encodes a fusion protein or polypeptide should be considered to also include description and/or disclosure of the amino acid sequence encoded by the nucleotide sequence. Similarly, description and/or disclosure of a fusion protein or polypeptide amino acid sequence herein should be considered to also include description and/or disclosure of all possible nucleotide sequences that can encode the amino acid sequence.

II. Description

The present invention relates, in part, to compositions, kits, and methods for the diagnosis, prognosis, monitoring, and modulation of viral-associated PTLD and/or hypoxia associated angiogenesis of a gene referred to herein as the galectin-1 (Gal1) gene or a fragment thereof. In particular, the methods and compositions of the present invention relate to detection and/or modulation of expression and/or activity of Gal1 or a fragment thereof, e.g., a biologically active fragment thereof, as well as to the detection and/or modulation of expression and/or activity of gene products encoded by the Gal1 gene (i.e., a "Gal1 gene product") or fragments thereof, e.g., biologically active fragments thereof. The present invention can utilize the Gal1 gene sequence or fragments thereof, as well as gene products of the Gal1 gene and/or modulators thereof, e.g., antibodies which specifically bind to such Gal1 gene products, or fragments thereof.

Sequences, structures, domains, biophysical characteristics, and functions of Gal1 gene and gene products have been described in the art. See, for example, Rabinovich et al. (2002) *Trends Immunol* 23:313-320; Liu and Rabinovich (2005) *Nature Reviews Cancer* 5:29-41; Rubinstein et al. (2004) *Cancer Cell* 5:241-251; Le et al. (2005) *J Clin Oncol* 23:8932-8941; Vasta et al. (2004) *Curr Opin Struct Biol* 14:617-630; Toscano et al. (2007) *Cyt Growth Fact Rev* 18:57-71; Camby et al. (2006) *Glycobiol* 16:137R-157R, each of which is incorporated herein, by reference, in its entirety. Gal1 gene and gene products from many species are known and include, for example, chimpanzee Gal1 (NCBI Accession XM_001162066), rat Gal1 (NCBI Accession NM_019904), mouse Gal1 (NM_008495), and chicken Gal1 (NM_205495). Human Gal1 sequences include those listed below.

Gal1 coding nucleic acid sequence (SEQ ID NO: 1):

```
ATGGCTTGTG GTCTGGTCGC CAGCAACCTG AATCTCAAAC
CTGGAGAGTG CCTTCGAGTG CGAGGCGAGG TGGCTCCTGA
CGCTAAGAGC TTCGTGCTGA ACCTGGGCAA AGACAGCAAC
AACCTGTGCC TGCACTTCAA CCCTCGCTTC AACGCCCACG
```

-continued

```
GCGACGCCAA CACCATCGTG TGCAACAGCA AGGACGGCGG

GGCCTGGGGG ACCGAGCAGC GGGAGGCTGT CTTTCCCTTC

CAGCCTGGAA GTGTTGCAGA GGTGTGCATC ACCTTCGACC

AGGCCAACCT GACCGTCAAG CTGCCAGATG GATACGAATT

CAAGTTCCCC AACCGCCTCA ACCTGGAGGC CATCAACTAC

ATGGCAGCTG ACGGTGACTT CAAGATCAAA TGTGTGGCCT

TTGACTGA
```

Gal1 protein sequence (SEQ ID NO: 2):

```
MACGLVASNL NLKPGECLRV RGEVAPDAKS FVLNLGKDSN

NLCLHFNPRF NAHGDANTIV CNSKDGGAWG TEQREAVFPF

QPGSVAEVCI TFDQANLTVK LPDGYEFKFP NRLNLEAINY

MAADGDFKIK CVAFD
```

Similarly, sequences, structures, domains, biophysical characteristics, and functions of VEGFR2 gene and gene products, and glycosylated forms thereof, have been described in the art. See, for example, Terman et al. (1992) *Biochem. Biophys. Res. Commun.* 187:1579-1586; Witte et al. (1998) *Cancer Metastasis* 17:155-161; Ortega et al. (1999) *Front. Biosci.* 4:D141-D152; Shibuya (2002) *Biol. Chem.* 383:1573-1579; Olsson et al. (2006) *Nat. Rev. Mol. Cell. Biol.* 7:359-371; and Shibuya (2006) *J. Biochem. Mol. Biol.* 39:469-478; each of which is incorporated herein, by reference, in its entirety. VEGFR2 gene and gene products from many species are known and include, for example, chimpanzee VEGFR2 (NCBI Accession XM_517284.2 and XP_517284.2), dog VEGFR2 (NCBI Accession XM_539273.2 and XP_539273.2), cow VEGFR2 (NCBI Accession XM_611785.3 and XP_611785.3), mouse VEGFR2 (NCBI Accession NM_010612.2 and NP_034742.2) and chicken Gal1 (NM_001004368.1 and NP_001004368.1). Human VEGFR2 sequences include those listed below. In addition, glycosylated forms of VEGFR2 all known in the art as described, for example, by Zhang et al. (2010) *Cell Death Differ.* 17:499, which is incorporated herein, by reference, in its entirety.

VEGFR2 coding nucleic acid sequence (NM_002253.2) (SEQ ID NO: 3):

```
   1 atgcagagca aggtgctgct ggccgtcgcc ctgtggctct
     gcgtggagac ccgggccgcc 61 tctgtgggtt tgcctagtgt ttctcttgat ctgcccaggc
     tcagcataca aaaagacata 121 cttacaatta aggctaatac aactcttcaa attacttgca
     ggggacagag ggacttggac 181 tggctttggc ccaataatca gagtggcagt gagcaaaggg
     tggaggtgac tgagtgcagc 241 gatgcctct tctgtaagac actcacaatt ccaaaagtga
     tcggaaatga cactggagcc 301 tacaagtgct tctaccggga aactgacttg gcctcggtca
     tttatgtcta tgttcaagat 361 tacagatctc catttattgc ttctgttagt gaccaacatg
     gagtcgtgta cattactgag 421 aacaaaaaca aaactgtggt gattccatgt ctcgggtcca
     tttcaaatct caacgtgtca 481 ctttgtgcaa gatacccaga aaagagattt gttcctgatg
     gtaacagaat ttcctgggac 541 agcaagaagg gctttactat tcccagctac atgatcagct
     atgctggcat ggtcttctgt 601 gaagcaaaaa ttaatgatga aagttaccag tctattatgt
     acatagttgt cgttgtaggg 661 tataggattt atgatgtggt tctgagtccg tctcatggaa
     ttgaactatc tgttggagaa 721 aagcttgtct taaattgtac agcaagaact gaactaaatg
     tggggattga cttcaactgg 781 gaataccctt cttcgaagca tcagcataag aaacttgtaa
     accgagacct aaaaacccag 841 tctgggagtg agatgaagaa atttttgagc accttaacta
     tagatggtgt aaccccggagt 901 gaccaaggat tgtacacctg tgcagcatcc agtgggctga
     tgaccaagaa gaacagcaca 961 tttgtcaggg tccatgaaaa acctttttgtt gcttttggaa
     gtggcatgga atctctggtg 1021 gaagccacgg tgggggagcg tgtcagaatc cctgcgaagt
     accttggtta cccacccca 1081 gaaataaaat ggtataaaaa tggaatacc cttgagtcca
     atcacacaat taaagcgggg 1141 catgtactga cgattatgga agtgagtgaa agagacacag
     gaaattacac tgtcatcctt 1201 accaatccca tttcaaagga gaagcagagc catgtggtct
     ctctggttgt gtatgtccca 1261 ccccagattg tgagaaatc tctaatctct cctgtggatt
     cctaccagta cggcaccact 1321 caaacgctga catgtacggt ctatgccatt cctccccgc
     atcacatcca ctggtattgg 1381 cagttggagg aagagtgcgc caacgagccc agccaagctg
     tctcagtgac aaacccatac 1441 ccttgtgaag aatggagaag tgtggaggac ttccagggag
     gaaataaaat tgaagttaat 1501 aaaaatcaat ttgctctaat tgaaggaaaa aacaaaactg
     taagtaccct tgttatccaa 1561 gcggcaaatg tgtcagcttt gtacaaatgt gaagcggtca
     acaaagtcgg gagaggagag 1621 agggtgatct ccttccacgt gaccaggggt cctgaaatta
     ctttgcaacc tgacatgcag 1681 cccactgagc aggagagcgt gtctttgtgg tgcactgcag
     acagatctac gtttgagaac 1741 ctcacatggt acaagcttgg cccacagcct ctgccaatcc
     atgtgggaga gttgcccaca 1801 cctgtttgca gaacttgga tactctttgg aaattgaatg
     ccaccatgtt ctctaatagc 1861 acaaatgaca ttttgatcat ggagcttaag aatgcatcct
     tgcaggacca aggagactat 1921 gtctgccttg ctcaagacag gaagaccaag aaaagacatt
     gcgtggtcag gcagctcaca 1981 gtcctagagc gtgtggcacc cacgatcaca ggaaacctgg
     agaatcagac gacaagtatt
```

-continued 2041 ggggaaagca tcgaagtctc atgcacggca tctgggaatc
     cccctccaca gatcatgtgg 2101 tttaaagata atgagaccct tgtagaagac tcaggcattg
     tattgaagga tgggaaccgg 2161 aacctcacta tccgcagagt gaggaaggag gacgaaggcc
     tctacacctg ccaggcatgc 2221 agtgttcttg gctgtgcaaa agtggaggca tttttcataa
     tagaaggtgc ccaggaaaag 2281 acgaacttgg aaatcattat tctagtaggc acggcggtga
     ttgccatgtt cttctggcta 2341 cttcttgtca tcatcctacg gaccgttaag cgggccaatg
     gaggggaact gaagacaggc 2401 tacttgtcca tcgtcatgga tccagatgaa ctcccattgg
     atgaacattg tgaacgactg 2461 ccttatgatg ccagcaaatg ggaattcccc agagaccggc
     tgaagctagg taagcctctt 2521 ggccgtgtgt cctttgccca agtgattgaa gcagatgcct
     ttggaattga caagacagca 2581 acttgcagga cagtagcagt caaaatgttg aaagaaggag
     caacacacag tgagcatcga 2641 gctctcatgt ctgaactcaa gatcctcatt catattggtc
     accatctcaa tgtggtcaac 2701 cttctaggtg cctgtaccaa gccaggaggg ccactcatgg
     tgattgtgga attctgcaaa 2761 tttggaaacc tgtccactta cctgaggagc aagagaaatg
     aatttgtccc ctacaagacc 2821 aaaggggcac gattccgtca agggaaagac tacgttggag
     caatccctgt ggatctgaaa 2881 cggcgcttgg acagcatcac cagtagccag agctcagcca
     gctctggatt tgtggaggag 2941 aagtccctca gtgatgtaga agaagaggaa gctcctgaag
     atctgtataa ggacttcctg 3001 accttggagc atctcatctg ttacagcttc caagtggcta
     agggcatgga gttcttggca 3061 tcgcgaaagt gtatccacag ggacctggcg gcacgaaata
     tcctcttatc ggagaagaac 3121 gtggttaaaa tctgtgactt tggcttggcc cgggatattt
     ataaagatcc agattatgtc 3181 agaaaggag atgctcgcct ccctttgaaa tggatggccc
     cagaaacaat ttttgacaga 3241 gtgtacacaa tccagagtga cgtctggtct tttggtgttt
     tgctgtggga aatattttcc 3301 ttaggtgctt ctccatatcc tgggataag attgatgaag
     aattttgtag gcgattgaaa 3361 gaaggaacta aatgagggc ccctgattat actacaccag
     aaatgtacca gaccatgctg 3421 gactgctggc acggggagcc cagtcagaga cccacgtttt
     cagagttggt ggaacatttg 3481 ggaaatctct gcaagctaa tgctcagcag gatggcaaag
     actacattgt tcttccgata 3541 tcagagactt tgagcatgga agaggattct ggactctctc
     tgcctacctc acctgtttcc 3601 tgtatggagg aggaggaagt atgtgacccc aaattccatt
     atgacaacac agcaggaatc 3661 agtcagtatc tgcagaacag taagcgaaag agccggcctg
     tgagtgtaaa aacatttgaa 3721 gatatcccgt tagaagaacc agaagtaaaa gtaatcccag
     atgacaacca gacggacagt 3781 ggtatggttc ttgcctcaga agagctgaaa actttggaag
     acagaaccaa attatctcca 3841 tcttttggtg gaatggtgcc cagcaaaagc agggagtctg
     tggcatctga aggctcaaac 3901 cagacaagcg gctaccagtc cggatatcac tccgatgaca
     cagacaccac cgtgtactcc 3961 agtgaggaag cagaactttt aaagctgata gagattggag
     tgcaaaccgg tagcacagcc 4021 cagattctcc agcctgactc ggggaccaca ctgagctctc
     ctcctgttta a VEGFR2 protein sequence (NP_002244.1) (SEQ ID NO: 4):

1 mqskvllava lwlcvetraa svglpsysld lprlsiqkdi
     ltikanttlq itcrgqrdld 61 wlwpnnqsgs eqrvevtecs dglfcktlti pkvigndtga
     ykcfyretdl asviyvyvqd 121 yrspfiasys dqhgvvyite nknktvvipc lgsisnlnvs
     lcarypekrf vpdgnriswd 181 skkgftipsy misyagmvfc eakindesyq simyivvvvg
     yriydvvlsp shgielsvge 241 klvlnctart elnvgidfnw eypsskhqhk klvnrdlktq
     sgsemkkfls tltidgvtrs 301 dqglytcaas sglmtkknst fvrvhekpfv afgsgmeslv
     eatvgervri pakylgyppp 361 eikwykngip lesnhtikag hvltimevse rdtgnytvil
     tnpiskekqs hvvslvvyvp 421 pqigekslis pvdsyqygtt qtltctvyai ppphhihwyw
     qleeecanep sqavsvtnpy 481 pceewrsved fqggnkievn knqfaliegk nktvstlviq
     aanvsalykc eavnkvgrge 541 rvisfhvtrg peitlqpdmq pteqesyslw ctadrstfen
     ltwyklgpqp lpihvgelpt 601 pvcknldtlw klnatmfsns tndilimelk naslqdqgdy
     vclaqdrktk krhcvvrqlt 661 vlervaptit gnlenqttsi gesievscta sgnpppqimw
     fkdnetlved sgivlkdgnr 721 nltirrvrke deglytcqac svlgcakvea ffiiegaqek
     tnleiiilvg taviamffwl 781 llviilrtvk ranggelktg ylsivmdpde lpldehcerl
     pydaskwefp rdrlklgkpl 841 grgafgqvie adafgidkta tcrtvavkml kegathsehr
     almselkili highhlnvvn 901 llgactkpgg plmvivefck fgnlstylrs krnefvpykt
     kgarfrqgkd yvgaipvdlk 961 rrldsitssq ssassgfvee kslsdveeee apedlykdfl
     tlehlicysf qvakgmefla 1021 srkcihrdla arnillsekn vvkicdfgla rdiykdpdyv
     rkgdarlplk wmapetifdr

```
1081    vytiqsdvws  fgvllweifs  lgaspypgvk  ideefcrrlk
        egtrmrapdy  ttpemyqtml 1141    dcwhgepsqr  ptfselvehl  gnllqanaqq  dgkdyivlpi
        setlsmeeds  glslptspvs 1201    cmeeeevcdp  kfhydntagi  sqylqnskrk  srpvsvktfe
        dipleepevk  vipddnqtds 1261    gmvlaseelk  tledrtklsp  sfggmvpsks  resvasegsn
        qtsgyqsgyh  sddtdttvys 1321    seeaellkli  eigvqtgsta  qilqpdsgtt  lssppv
```

The present invention is based, in part, on the discovery that Gal1 is overexpressed by viral-associated post-transplantation lymphoblastoid cells and that the Gal1 overexpression by such cells is directly implicated in the development and maintenance of a tolerogenic and immunosuppressive microenvironment, leading to an ineffective host anti-proliferative immune response. The present invention is further based, in part, on the discovery that hypoxia promotes upregulation of Gal1, which results in angiogenesis mediated by VEGFR2 signaling and whose targeted disruption downregulates hypoxia-driven angiogenesis, while promoint pericyte maturation and vascular remodeling, Thus, agents such as natural ligands, derivatives of natural ligands, and small molecules, RNA interference, aptamer, peptides, peptidomimetics, glycan-related compounds, glycomimetics, and antibodies that specifically bind to the Gal1 gene or gene products or fragments thereof can be utilized to modulate (e.g., increase) immune surveillance in viral-associated PTLD, e.g., EBV-associated PTLD, and/or hypoxia associated angiogenesis disorders. Additionally, agents such as Gal1 gene sequences, Gal1 gene products, anti-Gal1 RNA interference molecules, anti-Gal1 antibodies (i.e., antibodies that specifically bind to Gal1 gene products), or fragments thereof, can be utilized to reduce the level of TH2 cell activity and/or increase the level of TH1 cell activity to restore immune surveillance in viral-associated PTLD, e.g., EBV-associated PTLD, and/or down-regulate hypoxia associated angiogenesis associated.

The Gal1 gene is also expressed in other cells known in the art. See, for example, Gottschalk et al. (2005) *Annu. Rev. Med.* 56, 29-44; Nalesnik et al. (1999) *Clin. Transplant.* 13, 39-44; Toscano et al. (2007) *Nat. Immunol.* 8, 825-834; Ilarregui et al. (2009) *Nat. Immunol.* 10, 981-991; Re et al. (2005) *J. Clin. Oncol.* 23, 6379-6386; Marshall et al. (2004) *Blood* 103, 1755-1762; Gandhi et al. (2006) *Blood* 108, 2280-2289; Juszczynski et al. (2007) *Proc. Natl. Acad. Sci. U.S.A.* 104, 13134-13139; Rodig et al. (2008) *Clin. Cancer Res.* 14, 3338-3344; Rabinovich et al. (2002) *Trends Immunol* 23:313-320; Liu and Rabinovich (2005) *Nature Reviews Cancer* 5:29-41; Rubinstein et al. (2004) *Cancer Cell* 5:241-251; Le et al. (2005) *J Clin Oncol* 23:8932-8941; Vasta et al. (2004)*Curr Opin Struct Biol* 14:617-630; Toscano et al. (2007) *Cyt Growth Fact Rev* 18:57-71; Camby et al. (2006) *Glycobiol* 16:137 R-157R, each of which is incorporated herein, by reference, in its entirety. Thus, the above-described compositions (e.g., natural ligands, derivatives of natural ligands, and small molecules, RNA interference, aptamer, peptides, peptidomimetics, glycan-related compounds, glycomimetics, antibodies that specifically bind to the Gal1 gene or gene products, or fragments thereof) can also be utilized to modulate immune responses in these immune-related cells.

III. Agents that Modulate Immune Cell Activation

The agents of the invention can modulate, e.g., up or down regulate, expression and/or activity of gene products or fragments thereof encoded by the Gal1 gene or fragment thereof and, thereby, modulate, e.g., up or downregulate, an immune response. The interaction between a Gal1 polypeptide or a fragment thereof and its natural binding partner(s) or a fragment(s) thereof in the context of cHL results in a tolerogenic and/or immunosuppressive microenvironment. Thus, in one embodiment, agents which block the interactions between a Gal1 polypeptide or a fragment thereof and its natural binding partner(s) or a fragment(s) thereof can enhance an immune response (e.g., restore immune surveillance in viral-associated PTLD, e.g., EBV-associated PTLD), and/or down-regulate hypoxia associated angiogenesis. In another embodiment, agents that increase the interactions between a Gal1 polypeptide or a fragment thereof and its natural binding partner(s) or a fragment(s) thereof can decrease an immune response (e.g., immunosuppression). Exemplary agents for modulating a Gal1-mediated immune response include antibodies against Gal1 which inhibit the interactions between a Gal1 polypeptide or a fragment thereof and its natural binding partner(s) or a fragment(s) thereof; small molecules, peptides, peptidomimetics, glycan-related compounds, glycomimetics, natural ligands, and derivatives of natural ligands, which inhibit the interactions between a Gal1 polypeptide or a fragment thereof and its natural binding partner(s) or a fragment(s) thereof; and RNA interference, antisense, and nucleic acid aptamers that reduce Gal1 nucleic acids or Gal1 expression products or fragments thereof.

1. Isolated Nucleic Acid Molecules

One aspect of the present invention pertains to isolated nucleic acid molecules that encode polypeptides of the present invention (e.g., including the sequences in Table 1) or biologically active portions thereof, as well as nucleic acid fragments sufficient for use as hybridization probes to identify nucleic acid molecules encoding these polypeptides and fragments for use as PCR primers for the amplification or mutation of the nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. In some embodiments an "isolated" nucleic acid molecule is free of sequences which naturally flank the nucleic acid (i.e., sequences located at the 5' and 3' ends of the nucleic acid molecule) in the genomic DNA of the organism from which the nucleic acid is derived. For example, an "isolated" nucleic acid molecule, such as a cDNA molecule, can be substantially free of other cellular material, or culture medium, when produced by recombinant techniques, or substantially free of chemical precursors or other chemicals when chemically synthesized.

A nucleic acid molecule of the present invention (e.g., including the sequences in Table 1), or a portion thereof, can be isolated using standard molecular biology techniques and the sequence information provided herein. For example, a nucleic acid molecule encompassing all or a portion of sequences shown in Table 1 can be isolated by the polymerase chain reaction (PCR) using synthetic oligonucleotide primers designed based upon the sequences shown in Table 1.

A nucleic acid molecule of the present invention can be amplified using cDNA, mRNA or, alternatively, genomic DNA as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to nucleic acid sequences of the present invention can be prepared by standard synthetic techniques, e.g., using an automated DNA synthesizer.

In another embodiment, an isolated nucleic acid molecule of the present invention comprises a nucleic acid molecule which is a complement of a nucleic acid molecule of the present invention (e.g., including the sequences in Table 1), or a portion thereof. A nucleic acid molecule which is complementary to a nucleic acid molecule of the present invention (e.g., including the sequences in Table 1), or a portion thereof, is one which is sufficiently complementary to the nucleotide sequence shown in Table 1, such that it can hybridize to the respective nucleotide sequence shown in Table 1, thereby forming a stable duplex.

In still another embodiment, an isolated nucleic acid molecule of the present invention comprises a nucleotide sequence which is at least about 70%, 75%, 80%, 85%, 90%, 91%, 92%, 93%, 94%, 95%, 96%, 97%, 98%, 99% or more identical to the entire length of the nucleotide sequence shown in Table 1, or a portion of any of these nucleotide sequences.

Moreover, the nucleic acid molecule of the present invention can comprise only a portion of a nucleic acid molecule of the present invention (e.g., including the sequences in Table 1), or a portion thereof, for example, a fragment which can be used as a probe or primer or a fragment which encodes a portion of a polypeptide of the present invention, e.g., those in Table 1. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a nucleic acid molecule of the present invention (e.g., including the sequences in Table 1); of an anti-sense sequence of a nucleic acid molecule of the present invention (e.g., including the sequences in Table 1); or of a mutant of a nucleic acid molecule of the present invention (e.g., including the sequences in Table 1).

Probes based on a nucleic acid molecule of the present invention (e.g., including the sequences in Table 1) can be used to detect transcripts or genomic sequences encoding the same or homologous polypeptides. In one embodiment, the probe further comprises a label group attached thereto, e.g., the label group can be a radioisotope, a fluorescent compound, an enzyme, or an enzyme co-factor.

A nucleic acid fragment encoding a "biologically active portion of a polypeptide of the present invention" can be prepared by isolating a portion of the nucleotide sequence of a nucleic acid molecule of the present invention (e.g., including the sequences in Table 1) which encodes a polypeptide having a biological activity of a polypeptide of the present invention (e.g., the ability to bind to its antigenic target, such as human Gal1), expressing the encoded portion of the polypeptide of the present invention (e.g., by recombinant expression in vitro) and assessing the activity of the encoded portion of the polypeptide of the present invention.

In other embodiments, a nucleic acid fragment encoding a "peptide epitope of the present invention" can be prepared by isolating a portion of the nucleotide sequence of a nucleic acid molecule of the present invention (e.g., including the sequences in Table 1) which encodes a polypeptide for which antibodies raised against the polypeptide are specific (e.g., a human Gal1 peptide epitopes shown in Table 1).

The invention further encompasses nucleic acid molecules that differ from nucleotide sequence(s) shown in Table 1 due to degeneracy of the genetic code and thus encode the same polypeptides as those encoded by the respective nucleotide sequence shown in Table 1. In another embodiment, an isolated nucleic acid molecule of the present invention has a nucleotide sequence encoding a polypeptide of the present invention (e.g., including the sequences in Table 1).

Nucleic acid molecules corresponding to homologues of a nucleic acid molecule of the present invention (e.g., including the sequences in Table 1) can be isolated based on their homology to the nucleic acids disclosed herein using the cDNAs disclosed herein, or a portion thereof, as a hybridization probe according to standard hybridization techniques under stringent hybridization conditions.

Accordingly, in another embodiment, an isolated nucleic acid molecule of the present invention is at least 15, 20, 25, 30 or more nucleotides in length and hybridizes under stringent conditions to the nucleic acid molecule comprising a nucleic acid molecule of the present invention (e.g., including the sequences in Table 1).

As used herein, the term "hybridizes under stringent conditions" is intended to describe conditions for hybridization and washing under which nucleotide sequences that are significantly identical or homologous to each other remain hybridized to each other. Preferably, the conditions are such that sequences at least about 70%, more preferably at least about 80%, even more preferably at least about 85% or 90% identical to each other remain hybridized to each other. Such stringent conditions are known to those skilled in the art and can be found in Current Protocols in Molecular Biology, Ausubel et al., eds., John Wiley & Sons, Inc. (1995), sections 2, 4 and 6. Additional stringent conditions can be found in Molecular Cloning: A Laboratory Manual, Sambrook et al., Cold Spring Harbor Press, Cold Spring Harbor, N.Y. (1989), chapters 7, 9 and 11. A non-limiting example of stringent hybridization conditions includes hybridization in 4× or 6× sodium chloride/sodium citrate (SSC), at about 65-70° C. (or hybridization in 4×SSC plus 50% formamide at about 42-50° C.) followed by one or more washes in 1×SSC, at about 65-70° C. A further non-limiting example of stringent hybridization conditions includes hybridization at 6×SSC at 45° C., followed by one or more washes in 0.2×SSC, 0.1% SDS at 65° C. A non-limiting example of highly stringent hybridization conditions includes hybridization in 1×SSC, at about 65-70° C. (or hybridization in 1×SSC plus 50% formamide at about 42-50° C.) followed by one or more washes in 0.3× SSC, at about 65-70° C. A non-limiting example of reduced stringency hybridization conditions includes hybridization in 4× or 6×SSC, at about 50-60° C. (or alternatively hybridization in 6×SSC plus 50% formamide at about 40-45° C.) followed by one or more washes in 2×, at about 50-60° C. Ranges intermediate to the above-recited values, e.g., at 65-70° C. or at 42-50° C. are also intended to be encompassed by the present invention. SSPE (1×SSPE is 0.15M NaCl, 10 mM NaH$_2$PO$_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete. The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m$ (° C.)=2(# of A+T bases)+4(# of G+C bases). For hybrids between 18 and 49 base pairs in length, $T_m$ (° C.)=81.5+16.6($\log_{10}$ [Na$^+$])+0.41(% G+C)−(600/N), where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, PVP and the like. When using nylon membranes, in particular, an additional non-limiting example of stringent hybridization conditions is hybridization in 0.25-0.5M NaH$_2$PO$_4$, 7% SDS at about 65° C., followed by one or more washes at 0.02M NaH$_2$PO$_4$, 1% SDS at 65° C., see e.g., Church and Gilbert (1984) Proc. Natl. Acad. Sci. USA 81:1991-1995 (or alternatively 0.2×SSC, 1% SDS).

The skilled artisan will further appreciate that changes can be introduced by mutation into a nucleic acid molecule of the present invention (e.g., including the sequences in Table 1), thereby leading to changes in the amino acid sequence of the encoded polypeptides of the present invention, without altering the functional ability of the polypeptides. For example, nucleotide substitutions leading to amino acid substitutions at "non-essential" amino acid residues can be made in a nucleic acid molecule of the present invention (e.g., including the sequences in Table 1). A "non-essential" amino acid residue is a residue that can be altered from a nucleic acid molecule of the present invention (e.g., including the sequences in Table 1) without altering the biological activity, whereas an "essential" amino acid residue is required for biological activity. For example, amino acid residues that are conserved among the polypeptides of the present invention, e.g., those required for binding of the polypeptides to its target antigen, are predicted to be particularly unamenable to alteration.

Accordingly, another aspect of the present invention pertains to nucleic acid molecules encoding polypeptides of the present invention (e.g., including the sequences in Table 1) that contain changes in amino acid residues that are not essential for activity. Such polypeptides differ in amino acid sequence from the sequences in Table 1, or portions thereof, yet retain biological activity. In one embodiment, the isolated nucleic acid molecule comprises a nucleotide sequence encoding a polypeptide, wherein the polypeptide comprises an amino acid sequence at least about 71%, 75%, 80%, 85%, 90%, 91%, 92%, 93%, 94%, 95%, 96%, 97%, 98%, 99% or more identical to the sequences in Table 1, or portions thereof.

An isolated nucleic acid molecule encoding a polypeptide identical to the polypeptides of the sequences in Table 1, or portions thereof, can be created by introducing one or more nucleotide substitutions, additions or deletions into the nucleotide sequence of the sequences in Table 1, or portions thereof, such that one or more amino acid substitutions, additions or deletions are introduced into the encoded polypeptide. Mutations can be introduced into nucleic acid molecules of the present invention (e.g., including the sequences in Table 1) by standard techniques, such as site-directed mutagenesis and PCR-mediated mutagenesis. In one embodiment, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a polypeptide of the present invention (e.g., including the sequences in Table 1) can be replaced with another amino acid residue from the same side chain family. Alternatively, in another embodiment, mutations can be introduced randomly along all or part of a nucleic acid molecule(s) of the present invention (e.g., including the sequences in Table 1), such as by saturation mutagenesis, and the resultant mutants can be screened for biological activity to identify mutants that retain activity. Following mutagenesis of a nucleic acid molecule of the present invention (e.g., including the sequences in Table 1), the encoded polypeptide can be expressed recombinantly and the activity of the polypeptide can be determined.

In one embodiment, a mutant polypeptide of the present invention can be assayed for the ability to bind to and/or modulate the activity of Gal1.

Yet another aspect of the present invention pertains to isolated nucleic acid molecules encoding fusion proteins. Such nucleic acid molecules, comprising at least a first nucleotide sequence encoding a polypeptide of the present invention (e.g., including the sequences in Table 1) operatively linked to a second nucleotide sequence encoding a polypeptide of the present invention (e.g., including the sequences in Table 1) can be prepared by standard recombinant DNA techniques.

The expression characteristics of a nucleic acid molecules of the present invention (e.g., including the sequences in Table 1) within a cell line or microorganism may be modified by inserting a heterologous DNA regulatory element into the genome of a stable cell line or cloned microorganism such that the inserted regulatory element is operatively linked with a nucleic acid molecule of the present invention (e.g., including the sequences in Table 1). For example, a heterologous regulatory element may be inserted into a stable cell line or cloned microorganism, such that it is operatively linked with a nucleic acid molecule of the present invention (e.g., including the sequences in Table 1), using techniques, such as targeted homologous recombination, which are well known to those of skill in the art, and described, e.g., in Chappel, U.S. Pat. No. 5,272,071; PCT publication No. WO 91/06667, published May 16, 1991.

2. Isolated Polypeptide Molecules

Another aspect of the present invention pertains to isolated polypeptides of the present invention (e.g., including the sequences in Table 1) and biologically active portions thereof. In one embodiment, polypeptides of the present invention (e.g., including the sequences in Table 1), and biologically active portions thereof can be isolated from cells or tissue sources by an appropriate purification scheme using standard protein purification techniques. In another embodiment, polypeptides of the present invention (e.g., including the sequences in Table 1), and biologically active portions thereof are produced by recombinant DNA techniques. Alternatively, polypeptides of the present invention (e.g., including the sequences in Table 1), and biologically active portions thereof can be chemically synthesized using standard peptide synthesis techniques.

As used herein, a "biologically active portion" of polypeptide(s) of the present invention (e.g., including the sequences in Table 1) include polypeptides which participate in an interaction between Gal1 and a non-Gal1 molecule. Biologically active portions of a polypeptide(s) of the present invention (e.g., including the sequences in Table 1) include peptides comprising amino acid sequences sufficiently identical to or derived from the amino acid sequence of polypeptide(s) of the present invention (e.g., including the sequences in Table 1), which include fewer amino acids than the respective, full length polypeptide(s) of the present invention (e.g., including the sequences in Table 1), and exhibit at least one activity of the respective polypeptide(s) of the present invention (e.g., including the sequences in Table 1). In one embodiment, biologically active portions comprise a domain or motif with the ability to specifically bind Gal1 according to the antigen, respectively, to which it was raised or designed to bind.

In another embodiment, polypeptide(s) of the present invention (e.g., including the sequences in Table 1) has an amino acid sequence shown in Table 1. In other embodiments, the polypeptide is substantially identical to polypeptide(s) shown in Table 1, and retains the functional activity of the respective polypeptide(s) shown in Table 1, yet differs in amino acid sequence due to mutagenesis, as described in detail herein. Accordingly, in another embodiment, a polypeptide(s) of the present invention is a polypeptide which comprises an amino acid sequence at least about 71%, 75%, 80%, 85%, 90%, 91%, 92%, 93%, 94%, 95%, 96% 97%, 98%, 99%, 99.5%, or 99.9% or more identical to a polypeptide(s) shown in Table 1.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-identical sequences can be disregarded for comparison purposes). In one embodiment, the length of a reference sequence aligned for comparison purposes is at least 30%, preferably at least 40%, more preferably at least 50%, even more preferably at least 60%, and even more preferably at least 70%, 80%, 90%, 95%, 96%, 97%, 98%, 99%, 99.5%, or 99.9% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The invention also provides chimeric or fusion proteins. As used herein, a "chimeric protein" or "fusion protein" comprises a polypeptide(s) of the present invention (e.g., including the sequences in Table 1) operatively linked to a polypeptide not of the present invention. A "polypeptide(s) of the present invention" refers to a polypeptide having an amino acid sequence corresponding to a polypeptide shown in Table 1, whereas a "polypeptide not of the present invention" refers to a polypeptide not having an amino acid sequence corresponding to a polypeptide which is not substantially homologous to a polypeptide shown in Table 1, e.g., a polypeptide which is different from a polypeptide shown in Table 1 and which is derived from the same or a different organism. Within the fusion protein, the term "operatively linked" is intended to indicate that the polypeptide(s) of the present invention and the polypeptide(s) not of the present invention are fused in-frame to each other. The polypeptide(s) not of the present invention can be fused to the N-terminus or C-terminus of the polypeptide(s) of the present invention and corresponds to a moiety that alters the solubility, binding affinity, stability, or valency of the polypeptide(s) of the present invention. In a preferred embodiment, the fusion protein comprises at least one biologically active portion of a Gal1 molecule, e.g., the carbohydrate recognition domain (CRD).

A chimeric or fusion polypeptide(s) of the present invention (e.g., including the sequences in Table 1) can be produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, Current Protocols in Molecular Biology, Ausubel et al., eds., John Wiley & Sons: 1992). Moreover, many expression vectors are commercially available that already encode a fusion moiety (e.g., a GST polypeptide).

In one embodiment, the second peptide may optionally correspond to a moiety that alters the solubility, affinity, stability or valency of the first peptide, for example, an immunoglobulin constant region. Preferably, the first peptide consists of a portion of Gal1 that comprises at least one biologically active portion of a Gal1 molecule, e.g., the carbohydrate recognition domain (CRD). In another preferred embodiment, the first peptide consists of a portion of a biologically active molecule (e.g. the extracellular portion of the polypeptide or the ligand binding portion). The second peptide can include an immunoglobulin constant region, for example, a human Cγ1 domain or Cγ4 domain (e.g., the hinge, CH2 and CH3 regions of human IgCγ1, or human IgCγ4, see e.g., Capon et al. U.S. Pat. Nos. 5,116,964; 5,580,756; 5,844,095 and the like, incorporated herein by reference). Such constant regions may retain regions which mediate effector function (e.g. Fc receptor binding) or may be altered to reduce effector function. A resulting fusion protein may have altered solubility, binding affinity, stability and/or valency (i.e., the number of binding sites available per polypeptide) as compared to the independently expressed first peptide, and may increase the efficiency of protein purification. Fusion proteins and peptides produced by recombinant techniques can be secreted and isolated from a mixture of cells and medium containing the protein or peptide. Alternatively, the protein or peptide can be retained cytoplasmically and the cells harvested, lysed and the protein isolated. A cell culture typically includes host cells, media and other byproducts. Suitable media for cell culture are well known in the art. Protein and peptides can be isolated from cell culture media, host cells, or both using techniques known in the art for purifying proteins and peptides. Techniques for transfecting host cells and purifying proteins and peptides are known in the art.

In another embodiment, the fusion protein is a GST fusion protein with a polypeptide(s) of the present invention. Such fusion proteins can facilitate the purification of recombinant polypeptides of the present invention. In another embodiment, the fusion protein contains a heterologous signal sequence at its N-terminus. In yet another embodiment, the fusion protein contains a cytotoxic moiety (e.g., toxin). In certain host cells (e.g., mammalian host cells), expression and/or secretion of polypeptide(s) of the present invention can be increased through use of a heterologous signal sequence.

The fusion proteins of the present invention can be used as immunogens to produce antibodies in a subject. Such antibodies may be used to purify the respective natural polypeptides from which the fusion proteins were generated, or in screening assays to identify polypeptides which inhibit the interactions between a Gal1 polypeptide or a fragment thereof and its natural binding partner(s) or a fragment(s) thereof.

The amino acid sequences of polypeptide(s) of the present invention (e.g., including the sequences in Table 1) identified herein will enable those of skill in the art to produce polypeptides corresponding to polypeptide(s) of the present invention (e.g., including the sequences in Table 1). Such polypeptides can be produced in prokaryotic or eukaryotic host cells by expression of polynucleotides encoding a polypeptide(s) of the present invention (e.g., including the sequences in Table 1). Alternatively, such peptides can be synthesized by chemical methods. Methods for expression of heterologous polypeptides in recombinant hosts, chemical synthesis of polypeptides, and in vitro translation are well known in the art and are described further in Maniatis et al., Molecular Cloning: A Laboratory Manual (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) J. Am. Chem. Soc. 91:501; Chaiken I. M. (1981) CRC Crit. Rev. Biochem. 11:255; Kaiser et al. (1989) Science 243:187; Merrifield, B. (1986) Science 232:342; Kent, S. B. H. (1988) Annu Rev. Biochem. 57:957; and Offord, R. E. (1980) Semisynthetic Proteins, Wiley Publishing, which are incorporated herein by reference).

In another aspect of this invention, peptides or peptide mimetics can be used to antagonize or promote the interactions between a Gal1 polypeptide or a fragment thereof and its natural binding partner(s) or a fragment(s) thereof. In one embodiment, variants of Gal1 which function as a modulating agent for the respective full length protein, can be identified by screening combinatorial libraries of mutants, e.g., truncation mutants, for antagonist activity. In one embodiment, a variegated library of Gal1 variants is generated by combinatorial mutagenesis at the nucleic acid level and is encoded by a variegated gene library. A variegated library of Gal1 variants can be produced, for instance, by enzymatically ligating a mixture of synthetic oligonucleotides into gene sequences such that a degenerate set of potential polypeptide sequences is expressible as individual polypeptides containing the set of polypeptide sequences therein. There are a variety of methods which can be used to produce libraries of polypeptide variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential polypeptide sequences. Methods for synthesizing degenerate oligonucleotides are known in the art (see, e.g., Narang, S. A. (1983) Tetrahedron 39:3; Itakura et al. (1984) Annu. Rev. Biochem. 53:323; Itakura et al. (1984) Science 198:1056; Ike et al. (1983) Nucleic Acid Res. 11:477.

In addition, libraries of fragments of a polypeptide coding sequence can be used to generate a variegated population of polypeptide fragments for screening and subsequent selection of variants of a given polypeptide. In one embodiment, a library of coding sequence fragments can be generated by treating a double stranded PCR fragment of a polypeptide coding sequence with a nuclease under conditions wherein nicking occurs only about once per polypeptide, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the polypeptide.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of polypeptides. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of Gal1 (Arkin and Youvan (1992) Proc. Natl. Acad. Sci. USA 89:7811-7815; Delagrave et al. (1993) Protein Eng. 6(3):327-331). In one embodiment, cell based assays can be exploited to analyze a variegated polypeptide library. For example, a library of expression vectors can be transfected into a cell line which ordinarily synthesizes Gal1. The transfected cells are then cultured such that the full length polypeptide and a particular mutant polypeptide are produced and the effect of expression of the mutant on the full length polypeptide activity in cell supernatants can be detected, e.g., by any of a number of functional assays. Plasmid DNA can then be recovered from the cells which score for inhibition, or alternatively, potentiation of full length polypeptide activity, and the individual clones further characterized.

Systematic substitution of one or more amino acids of a polypeptide amino acid sequence with a D-amino acid of the same type (e.g., D-lysine in place of L-lysine) can be used to generate more stable peptides. In addition, constrained peptides comprising a polypeptide amino acid sequence of interest or a substantially identical sequence variation can be generated by methods known in the art (Rizo and Gierasch (1992) Annu. Rev. Biochem. 61:387, incorporated herein by reference); for example, by adding internal cysteine residues capable of forming intramolecular disulfide bridges which cyclize the peptide.

The amino acid sequences disclosed herein will enable those of skill in the art to produce polypeptides corresponding peptide sequences and sequence variants thereof. Such polypeptides can be produced in prokaryotic or eukaryotic host cells by expression of polynucleotides encoding the peptide sequence, frequently as part of a larger polypeptide. Alternatively, such peptides can be synthesized by chemical methods. Methods for expression of heterologous proteins in recombinant hosts, chemical synthesis of polypeptides, and in vitro translation are well known in the art and are described further in Maniatis et al. *Molecular Cloning: A Laboratory Manual* (1989), 2nd Ed., Cold Spring Harbor, N.Y.; Berger and Kimmel, Methods in Enzymology, Volume 152, Guide to Molecular Cloning Techniques (1987), Academic Press, Inc., San Diego, Calif.; Merrifield, J. (1969) *J. Am. Chem. Soc.* 91:501; Chaiken I. M. (1981) *CRC Crit. Rev. Biochem.* 11: 255; Kaiser et al. (1989) *Science* 243:187; Merrifield, B. (1986) *Science* 232:342; Kent, S. B. H. (1988) *Annu. Rev. Biochem.* 57:957; and Offord, R. E. (1980) *Semisynthetic Proteins*, Wiley Publishing, which are incorporated herein by reference).

In another aspect of the present invention, peptides are provided in which the peptides have an amino acid sequence identical or similar to the Gal1 binding site of its natural binding partner(s) or a fragment(s) thereof. In one embodiment, the peptide competes with a Gal1 polypeptide or a fragment thereof for binding its natural binding partner(s) or a fragment(s) thereof. In a preferred embodiment, the peptide carries carbohydrate moieties recognized by a Gal1 polypeptide or a fragment thereof and said peptide competes with the Gal1 polypeptide or a fragment thereof for binding the Gal1 natural binding partner(s) or a fragment(s) thereof.

Peptides can be produced, typically by direct chemical synthesis, and used e.g., as antagonists of the interactions between a Gal1 polypeptide or a fragment thereof and its natural binding partner(s) or a fragment(s) thereof. Peptides can be produced as modified peptides, with nonpeptide moieties attached by covalent linkage to the N-terminus and/or C-terminus. In certain preferred embodiments, either the carboxy-terminus or the amino-terminus, or both, are chemically modified. The most common modifications of the terminal amino and carboxyl groups are acetylation and amidation, respectively. Amino-terminal modifications such as acylation (e.g., acetylation) or alkylation (e.g., methylation) and carboxy-terminal-modifications such as amidation, as well as other terminal modifications, including cyclization, can be incorporated into various embodiments of the present invention. Certain amino-terminal and/or carboxy-terminal modifications and/or peptide extensions to the core sequence can provide advantageous physical, chemical, biochemical, and pharmacological properties, such as: enhanced stability, increased potency and/or efficacy, resistance to serum proteases, desirable pharmacokinetic properties, and others. Peptides disclosed herein can be used therapeutically to treat disease, e.g., by altering costimulation in a patient.

Peptidomimetics (Fauchere, J. (1986) *Adv. Drug Res.* 15:29; Veber and Freidinger (1985) TINS p. 392; and Evans et al. (1987) *J. Med. Chem.* 30:1229, which are incorporated herein by reference) are usually developed with the aid of computerized molecular modeling. Peptide mimetics that are structurally similar to therapeutically useful peptides can be used to produce an equivalent therapeutic or prophylactic effect. Generally, peptidomimetics are structurally similar to a paradigm polypeptide (i.e., a polypeptide that has a biological or pharmacological activity), such as a human Gal1 polypeptide or a fragment thereof, but have one or more peptide linkages optionally replaced by a linkage selected from the group consisting of: —CH2NH—, —CH2S—, —CH2-CH2-, —CH=CH— (cis and trans), —COCH2-, —CH(OH)CH2-, and —CH2SO—, by methods known in the art and further described in the following references: Spatola, A. F. in "*Chemistry and Biochemistry of Amino Acids, Peptides, and Proteins*" Weinstein, B., ed., Marcel Dekker, New York, p. 267 (1983); Spatola, A. F., Vega Data (March 1983), Vol. 1, Issue 3, "Peptide Backbone Modifications" (general review); Morley, J. S. (1980) *Trends Pharm. Sci. pp.* 463-468 (general review); Hudson, D. et al. (1979) *Int. J. Pept. Prot. Res.* 14:177-185 (—CH2NH—, CH2CH2-); Spatola, A. F. et al. (1986) *Life Sci.* 38:1243-1249 (—CH2-S); Hann, M. M. (1982) *J. Chem. Soc. Perkin Trans. I.* 307-314 (—CH═CH—, cis and trans); Almquist, R. G. et al. (190) *J. Med. Chem.* 23:1392-1398 (—COCH$_2$—); Jennings-White, C. et al. (1982) *Tetrahedron Lett.* 23:2533 (—COCH2-); Szelke, M. et al. European Appln. EP 45665 (1982) CA: 97:39405 (1982) (—CH(OH)CH2-); Holladay, M. W. et al. (1983) *Tetrahedron Lett.* (1983) 24:4401-4404 (—C(OH)CH2-); and Hruby, V. J. (1982) *Lift Sci.* (1982) 31:189-199 (—CH2-S—); each of which is incorporated herein by reference. In one embodiment, the non-peptide linkage is —CH2NH—. Such peptide mimetics may have significant advantages over polypeptide embodiments, including, for example: more economical production, greater chemical stability, enhanced pharmacological properties (half-life, absorption, potency, efficacy, etc.), altered specificity (e.g., a broad-spectrum of biological activities), reduced antigenicity, and others. Labeling of peptidomimetics usually involves covalent attachment of one or more labels, directly or through a spacer (e.g., an amide group), to non-interfering position(s) on the peptidomimetic that are predicted by quantitative structure-activity data and/or molecular modeling. Such non-interfering positions generally are positions that do not form direct contacts with the macropolypeptides(s) to which the peptidomimetic binds to produce the therapeutic effect. Derivitization (e.g., labeling) of peptidomimetics should not substantially interfere with the desired biological or pharmacological activity of the peptidomimetic.

Similarly, glycan-related compounds and/or glycomimetics can be used according to the methods of the present invention and according to well known methods in the art (see, e.g., U.S. Pat. Pub. 20080200406, 20080112955, and 2004092015). For example, glycan-related compounds or glycomimetic analogs of proteins or peptides described herein can be used to modulate immune responses and/or hypoxia associated angiogenesis. The terms related to any glycosidic structure, disaccharide, trisaccharide, tetrasaccharide, pentasaccharide or higher order saccharide structure, branched or linear, substituted or unsubstituted by other chemical groups. In some embodiments, proteins, peptides, and antibodies may be glycosylated such that the glycosidic structure are recognized by glycosidic and/or glycoylated protein antibodies.

For example, the glycan can be a glycoaminoacid, a glycopeptide, a glycolipid, a glycoaminoglycan (GAG), a glycoprotein, a whole cell, a cellular component, a glycoconjugate, a glycomimetic, a glycophospholipid anchor (GPI), glycosyl phosphatidylinositol (GPI)-linked glycoconjugates, bacterial lipopolysaccharides and endotoxins. The glycans can also include N-glycans, O-glycans, glycolipids and glycoproteins. The glycans can also include 2 or more sugar units. Any type of sugar unit can be present in the glycans of the invention, including, for example, allose, altrose, arabinose, glucose, galactose, gulose, fucose, fructose, idose, lyxose, mannose, ribose, talose, xylose, or other sugar units. The figures provided herein list other examples of sugar units that can be used in the glycans of the invention. Such sugar units can have a variety of modifications and substituents. Some examples of the types of modifications and substituents contemplated are provided in the figures herein. For example, sugar units can have a variety of substituents in place of the hydroxy (—OH), carboxylate (—COO$^-$), and methylenehydroxy (—CH$_2$—OH) substituents. Thus, lower alkyl moieties can replace any of the hydrogen atoms from the hydroxy (—OH), carboxylic acid (—COOH) and methylenehydroxy (—CH$_2$—OH) substituents of the sugar units in the glycans of the invention. For example, amino acetyl (—NH—CO—CH$_3$) can replace any of the hydroxy or hydrogen atoms from the hydroxy (—OH), carboxylic acid (—COOH) and methylenehydroxy (—CH$_2$—OH) substituents of the sugar units in the glycans of the invention. N-acetylneuraminic acid can replace any of the hydrogen atoms from the hydroxy (—OH), carboxylic acid (—COOH) and methylenehydroxy (—CH$_2$—OH) substituents of the sugar units in the glycans of the invention. Sialic acid can replace any of the hydrogen atoms from the hydroxy (—OH), carboxylic acid (—COOH) and methylenehydroxy (—CH$_2$—OH) substituents of the sugar units in the glycans of the invention. Amino or lower alkyl amino groups can replace any of the OH groups on the hydroxy (—OH), carboxylic acid (—COOH) and methylenehydroxy (—CH$_2$—OH) substituents of the sugar units in the glycans of the invention. Sulfate (—SO$_4^-$) or phosphate (—PO$_4^-$) can replace any of the OH groups on the hydroxy (—OH), carboxylic acid (—COON) and methylenehydroxy (—CH$_2$—OH) substituents of the sugar units in the glycans of the invention. Hence, substituents that can be present instead of, or in addition to, the substituents typically present on the sugar units include N-acetyl, N-acetylneuraminic acid, oxy (O), sialic acid, sulfate (—SO$_4^-$), phosphate (—PO$_4^-$), lower alkoxy, lower alkanoyloxy, lower acyl, and/or lower alkanoylaminoalkyl.

The following definitions are used, unless otherwise described: Alkyl, alkoxy, alkenyl, alkynyl, etc. denote both straight and branched groups; but reference to an individual radical such as "propyl" embraces only the straight chain radical, when a branched chain isomer such as "isopropyl" has been specifically referred to. Halo is fluoro, chloro, bromo, or iodo.

Specifically, lower alkyl refers to (C$_1$-C$_6$)alkyl, which can be methyl, ethyl, propyl, isopropyl, butyl, iso-butyl, sec-butyl, pentyl, 3-pentyl, or hexyl; (C$_3$-C$_6$)cycloalkyl can be cyclopropyl, cyclobutyl, cyclopentyl, or cyclohexyl; (C$_3$-C$_6$) cycloalkyl(C$_1$-C$_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; (C$_1$-C$_6$)alkoxy can be methoxy, ethoxy, propoxy, isopropoxy, butoxy, iso-butoxy, sec-butoxy, pentoxy, 3-pentoxy, or hexyloxy.

It will be appreciated by those skilled in the art that the glycans of the invention having one or more chiral centers may exist in and be isolated in optically active and racemic forms. Some compounds may exhibit polymorphism. It is to be understood that the present invention encompasses any racemic, optically-active, polymorphic, or stereoisomeric form, or mixtures thereof, of a glycan of the invention, it being well known in the art how to prepare optically active forms (for example, by resolution of the racemic form by recrystallization techniques, by synthesis from optically-active starting materials, by chiral synthesis, or by chromatographic separation using a chiral stationary phase).

3. Anti-Gal1 Antibodies

Without being bound by theory, and offered to improve the understanding of the disclosed invention, it is believed that the antibodies of the present invention are unique relative to known Gal1 binding antibodies within at least one of the CDRs (complementarity determining regions) which participate in binding to the Gal1 polypeptide. This belief is based in part on the well known structural arrangement of elements, including the CDR containing hypervariable regions, of an antibody's structure. Antibodies of the present invention may also differ from known Gal1 binding antibodies at more than one CDR and/or at more than one amino acid position within one or more CDR. These differences may provide the antibodies of the disclosed invention with the characteristic of binding to a different epitope than previous antibodies against Gal1 so as, for example, to be specific to human Gal1 (i.e., not cross-reactive with Gal1 molecules in other species). Accordingly, the anti-human GAL1 antibodies of the present invention recognize human GAL1 with higher specificity and sensitivity relative to known GAL1 antibodies. Such antibodies are suitable for, among other uses, Western blotting (or immunoblotting), immunohistochemistry (IHC), detection of denatured or fixed forms of Gal1, ELISA assays, and RIA assays.

The antibodies of the present invention and antigen-binding fragments thereof may also inhibit Gal1 activity and so act as Gal1 inhibitors. Such antibodies, and fragments, may be used to both detect the presence of Gal1 and to inhibit Gal1 activity without the need for introduction of an additional Gal1 inhibitor. Alternatively, a Gal1 inhibitory antibody or antigen-binding fragment thereof may be used in combination with another Gal1 inhibitor, such as in a composition for inhibiting Gal1 activity or as administered, separately or in combination, to a subject as part of a method to inhibit Gal1 activity.

Monoclonal antibodies of the present invention can be produced using a variety of known techniques, such as the standard somatic cell hybridization technique described by Kohler and Milstein, Nature 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

One method for generating hybridomas which produce monoclonal antibodies of the present invention is the murine system. Hybridoma production in the mouse is well known in the art, including immunization protocols and techniques for isolating and fusing immunized splenocytes.

Polyclonal antibodies can be prepared as described above by immunizing a suitable subject with a polypeptide immunogen. An antigenic peptide of Gal1 comprises at least 8 amino acid residues and encompasses an epitope present in the respective full length molecule such that an antibody raised against the peptide forms a specific immune complex with the respective full length molecule. Preferably, the antigenic peptide comprises at least 10 amino acid residues. Preferred epitopes encompassed by the antigenic peptides are regions of Gal1 that mediate ligand specific carbohydrate binding, e.g., the Gal1 carbohydrate recognition domain, amino acids 30 to 90 of human Gal1, and amino acids 62 to 86 of human Gal1. In one embodiment such epitopes can be specific for a given polypeptide molecule from one species, such as mouse or human (i.e., an antigenic peptide that spans a region of the polypeptide molecule that is not conserved across species is used as immunogen; such non conserved residues can be determined using an alignment such as that provided herein). The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well known techniques, such as protein A chromatography to obtain the IgG fraction. At an appropriate time after immunization, e.g., when the antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

Any of the many well known protocols used for fusing lymphocytes and immortalized cell lines can be applied for the purpose of generating an anti-Gal1 monoclonal antibody (see, e.g., Galfre, G. et al. (1977) *Nature* 266:55052; Gefter et al. (1977) supra; Lerner (1981) supra; Kenneth (1980) supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of mycloma cell lines can be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the present invention are detected by screening the hybridoma culture supernatants for antibodies that bind a given polypeptide, e.g., using a standard ELISA assay.

As an alternative to preparing monoclonal antibody-secreting hybridomas, a monoclonal specific for one of the above described polypeptides can be identified and isolated by screening a recombinant combinatorial immunoglobulin library (e.g., an antibody phage display library) with the appropriate polypeptide to thereby isolate immunoglobulin library members that bind the polypeptide. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening an antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Biotechnology* (NY) 9:1369-1372; Hay et al. (1992) *Hum. Antibod. Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clarkson et al. (1991) *Nature* 352:624-628; Gram et al. (1992) *Proc. Natl. Acad. Sci. USA* 89:3576-3580; Garrard et al. (1991) *Biotechnology* (NY) 9:1373-1377; Hoogenboom et al. (1991) *Nucleic Acids Res.* 19:4133-4137; Barbas et al. (1991) *Proc. Natl. Acad. Sci. USA* 88:7978-7982; and McCafferty et al. (1990) *Nature* 348:552-554.

Additionally, recombinant anti-Gal1 antibodies, such as chimeric, composite, and humanized monoclonal antibodies, which can be made using standard recombinant DNA techniques, can be generated. Such chimeric, composite, and humanized monoclonal antibodies can be produced by recombinant DNA techniques known in the art, for example using methods described in Robinson et al. International Patent Publication PCT/US86/02269; Akira et al. European Patent Application 184,187; Taniguchi, M. European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *Biotechniques* 4:214; Winter U.S. Pat. No. 5,225,539; Jones et al. (1986) *Nature* 321:552-525; Verhoeyan et al. (1988) *Science* 239:1534; and Beidler et al. (1988) *J. Immunol.* 141:4053-4060.

In addition, humanized antibodies can be made according to standard protocols such as those disclosed in U.S. Pat. No. 5,565,332. In another embodiment, antibody chains or specific binding pair members can be produced by recombination between vectors comprising nucleic acid molecules encoding a fusion of a polypeptide chain of a specific binding pair member and a component of a replicable generic display package and vectors containing nucleic acid molecules encoding a second polypeptide chain of a single binding pair member using techniques known in the art, e.g., as described in U.S. Pat. Nos. 5,565,332, 5,871,907, or 5,733,743. The use of intracellular antibodies to inhibit protein function in a cell is also known in the art (see e.g., Carlson, J. R. (1988) *Mol. Cell. Biol.* 8:2638-2646; Biocca, S. et al. (1990) *EMBO J.* 9:101-108; Werge, T. M. et al. (1990) *FEBS Lett.* 274:193-198; Carlson, J. R. (1993) *Proc. Natl. Acad. Sci. USA* 90:7427-7428; Marasco, W. A. et al. (1993) *Proc. Natl. Acad. Sci. USA* 90:7889-7893; Biocca, S. et al. (1994) *Biotechnology* (NY) 12:396-399; Chen, S-Y. et al. (1994) *Hum. Gene Ther.* 5:595-601; Duan, L et al. (1994) *Proc. Natl. Acad. Sci. USA* 91:5075-5079; Chen, S-Y. et al. (1994) *Proc. Natl. Acad. Sci. USA* 91:5932-5936; Beerli, R. R. et al. (1994) *J. Biol. Chem.* 269:23931-23936; Beerli, R. R. et al. (1994) *Biochem. Biophys. Res. Commun.* 204:666-672; Mhashilkar, A. M. et al. (1995) *EMBO J.* 14:1542-1551; Richardson, J. H. et al. (1995) *Proc. Natl. Acad. Sci. USA* 92:3137-3141; PCT Publication No. WO 94/02610 by Marasco et al.; and PCT Publication No. WO 95/03832 by Duan et al.).

In another embodiment, human monoclonal antibodies directed against Gal1 can be generated using transgenic or transchromosomal mice carrying parts of the human immune system rather than the mouse system. In one embodiment, transgenic mice, referred to herein as "HuMAb mice" which contain a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. (1994) Nature 368(6474): 856 859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) Handbook of Experimental Pharmacology 113:49 101; Lonberg, N. and Huszar, D. (1995) Intern. Rev. Immunol. Vol. 13: 65 93, and Harding, F. and Lonberg, N. (1995) Ann. N.Y. Acad. Sci. 764:536 546). The preparation of HuMAb mice is described in Taylor, L. et al. (1992) Nucleic Acids Research 20:6287 6295; Chen, J. et al. (1993) International Immunology 5: 647 656; Tuaillon et al. (1993) Proc. Natl. Acad. Sci. USA 90:3720 3724; Choi et al. (1993) Nature Genetics 4:117 123; Chen, J. et al. (1993) EMBO J. 12: 821 830; Tuaillon et al. (1994) J. Immunol. 152:2912 2920; Lonberg et al., (1994) Nature 368(6474): 856 859; Lonberg, N. (1994) Handbook of Experimental Pharmacology 113:49 101; Taylor, L. et al. (1994) International Immunology 6: 579 591; Lonberg, N. and Huszar, D. (1995) Intern. Rev. Immunol. Vol. 13: 65 93; Harding, F. and Lonberg, N. (1995) Ann. N.Y. Acad. Sci. 764:536 546; Fishwild, D. et al. (1996) Nature Biotechnology 14: 845 851. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992.

In another embodiment, an antibody for use in the invention is a bispecific antibody. A bispecific antibody has binding sites for two different antigens within a single antibody polypeptide. Antigen binding may be simultaneous or sequential. Triomas and hybrid hybridomas are two examples of cell lines that can secrete bispecific antibodies. Examples of bispecific antibodies produced by a hybrid hybridoma or a trioma are disclosed in U.S. Pat. No. 4,474,893. Bispecific antibodies have been constructed by chemical means (Staerz et al. (1985) Nature 314:628, and Perez et al. (1985) Nature 316:354) and hybridoma technology (Staerz and Bevan (1986) Proc. Natl. Acad. Sci. USA, 83:1453, and Staerz and Bevan (1986) Immunol. Today 7:241). Bispecific antibodies are also described in U.S. Pat. No. 5,959,084. Fragments of bispecific antibodies are described in U.S. Pat. No. 5,798,229.

Bispecific agents can also be generated by making heterohybridomas by fusing hybridomas or other cells making different antibodies, followed by identification of clones producing and co-assembling both antibodies. They can also be generated by chemical or genetic conjugation of complete immunoglobulin chains or portions thereof such as Fab and Fv sequences. The antibody component can bind to Gal1. In one embodiment, the bispecific antibody could specifically bind to both Gal1 and a non-Gal1 molecule.

Yet another aspect of the present invention pertains to anti-Gal1 polypeptide antibodies that are obtainable by a process comprising, immunizing an animal with an immunogenic Gal1 polypeptide or an immunogenic portion thereof (e.g., Gal1 polypeptides shown in Table 1), and then isolating from the animal antibodies that specifically bind to the polypeptide.

In still another aspect of the present invention, partial or known antibody sequences can be used to generate and/or express new antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, Nature 332:323 327; Jones, P. et al., 1986, Nature 321:522 525; and Queen, C. et al., 1989, Proc. Natl. Acad. See. U.S.A. 86:10029 10033). Such framework sequences can be obtained from public DNA databases that include germline or non-germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region. For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody. Partial heavy and light chain sequence spanning the CDR regions is typically sufficient for this purpose. The partial sequence is used to determine which germline and/or non-germline variable and joining gene segments contributed to the recombined antibody variable genes. The germline and/or non-germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons. The process can also be used to screen libraries of particular immunoglobulin encoding sequences in one species (e.g., human) to design cognate immunoglobulin encoding sequences from known antibody sequence in another species (e.g., mouse).

The nucleotide sequences of heavy and light chain transcripts from a hybridoma are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266L19867019870); and, HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assembled into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region in the PCR amplification to generate fragments that can easily be cloned into the expression vector constructs.

The reconstructed heavy and light chain variable regions are then combined with cloned promoter, leader sequence, translation initiation, leader sequence, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains. Plasmids for this use are known in the art. Fully human and chimeric antibodies of the present invention also include IgG2, IgG3, IgE, IgA, IgM, and IgD antibodies. Similar plasmids can be constructed for expression of other heavy chain isotypes, or for expression of antibodies comprising lambda light chains.

Thus, in another aspect of the present invention, the structural features of known, non-human or human antibodies (e.g., a mouse anti-human Gal1 antibody) can be used to create structurally related human anti-human Gal1 antibodies that retain at least one functional property of the antibodies of the present invention, such as binding to Gal1. Another functional property includes inhibiting binding of the original known, non-human or human antibodies in a competition ELISA assay. In addition, one or more CDR or variable regions of the present invention (e.g., including the sequences of Table 1, or portions thereof) can be combined recombinantly with known human framework regions and CDRs to create additional, recombinantly-engineered, human anti-Gal1 antibodies of the present invention.

Since it is well known in the art that antibody heavy and light chain CDR3 domains play a particularly important role in the binding specificity/affinity of an antibody for an antigen, the recombinant antibodies of the present invention prepared as set forth above preferably comprise the heavy and light chain CDR3s of variable regions of the present invention (e.g., including the sequences of Table 1, or portions thereof). The antibodies further can comprise the CDR2s of variable regions of the present invention (e.g., including the sequences of Table 1, or portions thereof). The antibodies further can comprise the CDR1s of variable regions of the present invention (e.g., including the sequences of Table 1, or portions thereof). In other embodiments, the antibodies can comprise any combinations of the CDRs.

The CDR1, 2, and/or 3 regions of the engineered antibodies described above can comprise the exact amino acid sequence(s) as those of variable regions of the present invention (e.g., including the sequences of Table 1, or portions thereof) disclosed herein. However, the ordinarily skilled artisan will appreciate that some deviation from the exact CDR sequences may be possible while still retaining the ability of the antibody to bind Gal1 effectively (e.g., conservative sequence modifications). Accordingly, in another embodiment, the engineered antibody may be composed of one or more CDRs that are, for example, 50%, 60%, 70%, 80%, 85%, 90%, 91%, 92%, 93%, 94%, 95%, 96%, 97%, 98%, 99%, or 99.5% identical to one or more CDRs of the present invention (e.g., including the sequences of Table 1, or portions thereof).

In another aspect, the present invention features anti-Gal1 antibodies conjugated to a therapeutic moiety, such as a cytotoxin, a drug, and/or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention can be conjugated to a radioisotope, e.g., radioactive iodine, to generate cytotoxic radiopharmaceuticals for treating a related disorder, such as a cancer.

Conjugated anti-Gal1 antibodies can be used diagnostically or prognostically to monitor polypeptide levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, P-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

The antibody conjugates of the present invention can be used to modify a given biological response. The therapeutic moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-.gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other cytokines or growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243 56 (Alan R. Liss, Inc. 1985); Hellstrom et al., "Antibodies For Drug Delivery", in Controlled Drug Delivery (2nd Ed.), Robinson et al. (eds.), pp. 623 53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475 506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303 16 (Academic Press 1985), and Thorpe et al., "The Preparation And Cytotoxic Properties Of Antibody-Toxin Conjugates", Immunol. Rev., 62:119 58 (1982).

4. Recombinant Expression Vectors and Host Cells

Another aspect of the present invention pertains to vectors, preferably expression vectors, containing a nucleic acid molecule encoding a polypeptide of the present invention (e.g., including the sequences of Table 1, or portions thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the present invention comprise a nucleic acid of the present invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel (1990) Methods Enzymol. 185:3-7. Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the present invention can be introduced into host cells to thereby produce proteins or peptides, including fusion proteins or peptides, encoded by nucleic acids as described herein.

The recombinant expression vectors of the present invention can be designed for expression of polypeptides of the present invention (e.g., including the sequences of Table 1, or portions thereof) in prokaryotic or eukaryotic cells. For example, the polypeptides can be expressed in bacterial cells such as E. coli, insect cells (using baculovirus expression vectors), yeast cells, or mammalian cells. Suitable host cells are discussed further in Goeddel (1990) supra. Alternatively, the recombinant expression vector can be transcribed and translated in vitro, for example using T7 promoter regulatory sequences and T7 polymerase.

Expression of polypeptides in prokaryotes is most often carried out in E. coli with vectors containing constitutive or inducible promoters directing the expression of either fusion or non-fusion proteins. Fusion vectors add a number of amino acids to a polypeptide encoded therein, usually to the amino terminus of the recombinant polypeptide. Such fusion vectors typically serve three purposes: 1) to increase expression of recombinant polypeptide; 2) to increase the solubility of the recombinant polypeptide; and 3) to aid in the purification of the recombinant polypeptide by acting as a ligand in affinity purification. Often, in fusion expression vectors, a proteolytic cleavage site is introduced at the junction of the fusion moiety and the recombinant polypeptide to enable separation of the recombinant polypeptide from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant polypeptide.

Examples of suitable inducible non-fusion E. coli expression vectors include pTrc (Amann et al. (1988) Gene 69:301-315) and pET 1 Id (Studier et al. (1990) Methods Enzymol. 185:60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174(DE3) from a resident prophage harboring a T7 gn1 gene under the transcriptional control of the lacUV 5 promoter.

One strategy to maximize recombinant polypeptide expression in E. coli is to express the polypeptide in host bacteria with impaired capacity to proteolytically cleave the recombinant polypeptide (Gottesman, S. (1990) Methods Enzymol. 185:119-128). Another strategy is to alter the nucleic acid sequence of the nucleic acid to be inserted into an expression vector so that the individual codons for each amino acid are those preferentially utilized in E. coli (Wada et al. (1992) Nucleic Acids Res. 20:2111-2118). Such alteration of nucleic acid sequences of the present invention can be carried out by standard DNA synthesis techniques.

In another embodiment, the expression vector is a yeast expression vector. Examples of vectors for expression in yeast *S. cerevisiae* include pYepSec1 (Baldari et al. (1987) EMBO J. 6:229-234), pMFa (Kurjan and Herskowitz (1982) Cell 30:933-943), pJRY88 (Schultz et al. (1987) Gene 54:113-123), pYES2 (Invitrogen Corporation, San Diego, Calif.), and picZ (Invitrogen Corp, San Diego, Calif.).

Alternatively, polypeptides of the present invention (e.g., including the sequences of Table 1, or portions thereof) can be expressed in insect cells using baculovirus expression vectors. Baculovirus vectors available for expression of polypeptides in cultured insect cells (e.g., Sf 9 cells) include the pAc'series (Smith et al. (1983) Mol. Cell Biol. 3:2156-2165) and the pVL series (Lucklow and Summers (1989) Virology 170: 31-39).

In yet another embodiment, a nucleic acid of the present invention (e.g., including the sequences of Table 1, or portions thereof) is expressed in mammalian cells using a mammalian expression vector. Examples of mammalian expression vectors include pCDM8 (Seed, B. (1987) Nature 329: 840) and pMT2PC (Kaufman et al. (1987) EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J. et al., Molecular Cloning: A Laboratory Manual. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev. 1:268-277), lymphoid-specific promoters (Calame and Eaton (1988) Adv. Immunol. 43:235-275), particular promoters of T cell receptors (Winoto and Baltimore (1989) EMBO J. 8:729-733) and immunoglobulins (Banerji et al. (1983) Cell 33:729-740; Queen and Baltimore (1983) Cell 33:741-748), neuron-specific promoters (e.g., the neurofilament promoter; Byrne and Ruddle (1989) Proc. Natl. Acad. Sci. USA 86:5473-5477), pancreas-specific promoters (Edlund et al. (1985) Science 230:912-916), and mammary gland-specific promoters (e.g., milk whey promoter; U.S. Pat. No. 4,873,316 and European Application Publication No. 264,166). Developmentally-regulated promoters are also encompassed, for example by the murine hox promoters (Kessel and Gruss (1990) Science 249:374-379) and the .alpha.-fetoprotein promoter (Campes and Tilghman (1989) Genes Dev. 3:537-546).

Another aspect of the present invention pertains to host cells into which a nucleic acid molecule of the present invention (e.g., Table 1) is introduced within a recombinant expression vector or a nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a polypeptide of the present invention (e.g., including the sequences of Table 1, or portions thereof) can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (Molecular Cloning: A Laboratory Manual. 2nd, ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a Gal1 polypeptide or anti-Gal1 antibody polypeptide or can be introduced on a separate vector. Cells stably transfected with the introduced nucleic acid can be identified by drug selection (e.g., cells that have incorporated the selectable marker gene will survive, while the other cells die).

A host cell of the present invention, such as a prokaryotic or eukaryotic host cell in culture, can be used to produce (i.e., express) a polypeptide of the present invention (e.g., including the sequences of Table 1, or portions thereof). Accordingly, the invention further provides methods for producing a polypeptide of the present invention (e.g., including the sequences of Table 1, or portions thereof) using the host cells of the present invention. In one embodiment, the method comprises culturing the host cell of the present invention (into which a recombinant expression vector encoding a polypeptide of the present invention (e.g., including the sequences of Table 1, or portions thereof) has been introduced) in a suitable medium such that a polypeptide of the present invention (e.g., including the sequences of Table 1, or portions thereof) is produced. In another embodiment, the method further comprises isolating a polypeptide of the present invention (e.g., including the sequences of Table 1, or portions thereof) from the medium or the host cell.

The host cells of the present invention can also be used to produce non-human transgenic animals, as described below.

5. Other Agents

Also encompassed by the present invention are small molecules which can modulate (either enhance or inhibit) interactions, e.g., the interactions between a Gal1 polypeptide or a fragment thereof and its natural binding partner(s) or a fragment(s) thereof. The small molecules of the present invention can be obtained using any of the numerous approaches in combinatorial library methods known in the art, including: spatially addressable parallel solid phase or solution phase libraries; synthetic library methods requiring deconvolution; the 'one-bead one-compound' library method; and synthetic library methods using affinity chromatography selection. (Lam, K. S. (1997) Anticancer Drug Des. 12:145).

Examples of methods for the synthesis of molecular libraries can be found in the art, for example in: DeWitt et al. (1993) Proc. Natl. Acad. Sci. USA 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds can be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc. Natl. Acad. Sci. USA 89:1865-1869) or on phage (Scott and Smith (1990) Science 249:386-390); (Devlin (1990) Science 249:404-406); (Cwirla et al. (1990) Proc. Natl. Acad. Sci. USA 87:6378-6382); (Felici (1991) J. Mol. Biol. 222:301-310); (Ladner supra.). Compounds can be screened in cell based or non-cell based assays. Compounds can be screened in pools (e.g. multiple compounds in each testing sample) or as individual compounds. In one embodiment, the small molecule binds to the binding site involved in interactions between a Gal1 polypeptide or a fragment thereof and its natural binding partner(s) or a fragment(s) thereof.

Also provided herein are compositions comprising one or more nucleic acids comprising or capable of expressing at least 1, 2, 3, 4, 5, 10, 20 or more small nucleic acids or antisense oligonucleotides or derivatives thereof, wherein said small nucleic acids or antisense oligonucleotides or derivatives thereof in a cell specifically hybridize (e.g., bind) under cellular conditions, with cellular nucleic acids (e.g., Gal1 mRNA or a fragment thereof). In one embodiment, expression of the small nucleic acids or antisense oligonucleotides or derivatives thereof in a cell can enhance or upregulate one or more biological activities associated with the corresponding wild-type, naturally occurring, or synthetic small nucleic acids. In another embodiment, expression of the small nucleic acids or antisense oligonucleotides or derivatives thereof in a cell can inhibit expression or biological activity of cellular nucleic acids and/or proteins, e.g., by inhibiting transcription, translation and/or small nucleic acid processing of, for example, the Gal1 gene or gene products or fragment(s) thereof. In one embodiment, the small nucleic acids or antisense oligonucleotides or derivatives thereof are small RNAs (e.g., microRNAs) or complements of small RNAs. In another embodiment, the small nucleic acids or antisense oligonucleotides or derivatives thereof can be single or double stranded and are at least six nucleotides in length and are less than about 1000, 900, 800, 700, 600, 500, 400, 300, 200, 100, 50, 40, 30, 25, 24, 23, 22, 21, 20, 19, 18, 17, 16, 15, or 10 nucleotides in length. In another embodiment, a composition may comprise a library of nucleic acids comprising or capable of expressing small nucleic acids or antisense oligonucleotides or derivatives thereof, or pools of said small nucleic acids or antisense oligonucleotides or derivatives thereof A pool of nucleic acids may comprise about 2-5, 5-10, 10-20, 10-30 or more nucleic acids comprising or capable of expressing small nucleic acids or antisense oligonucleotides or derivatives thereof.

In one embodiment, binding may be by conventional base pair complementarity, or, for example, in the case of binding to DNA duplexes, through specific interactions in the major groove of the double helix. In general, "antisense" refers to the range of techniques generally employed in the art, and includes any process that relies on specific binding to oligonucleotide sequences.

Small nucleic acid and/or antisense constructs of the methods and compositions presented herein can be delivered, for example, as an expression plasmid which, when transcribed in the cell, produces RNA which is complementary to at least a unique portion of cellular nucleic acids (e.g., small RNAs, mRNA, and/or genomic DNA). Alternatively, small nucleic acids and/or antisense constructs are oligonucleotide probes that are generated ex vivo and which, when introduced into the cell, results in hybridization with cellular nucleic acids (e.g., Gal1 mRNA or a fragment thereof). Such oligonucleotide probes are preferably modified oligonucleotides that are resistant to endogenous nucleases, e.g., exonucleases and/or endonucleases, and are therefore stable in vivo. Exemplary nucleic acid molecules for use as small nucleic acids and/or antisense oligonucleotides are phosphoramidate, phosphothioate and methylphosphonate analogs of DNA (see also U.S. Pat Nos. 5,176,996; 5,264,564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches may involve the design of oligonucleotides (either DNA or RNA) that are complementary to cellular nucleic acids (e.g., Gal1 mRNA or a fragment thereof). Absolute complementarity is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with a nucleic acid (e.g., RNA) it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the mRNA, e.g., the 5' untranslated sequence up to and including the AUG initiation codon, should work most efficiently at inhibiting translation. However, sequences complementary to the 3' untranslated sequences of mRNAs have recently been shown to be effective at inhibiting translation of mRNAs as well. (Wagner, R. (1994) Nature 372:333). Therefore, oligonucleotides complementary to either the 5' or 3' untranslated, non-coding regions of genes could be used in an antisense approach to inhibit translation of endogenous mRNAs. Oligonucleotides complementary to the 5' untranslated region of the mRNA may include the complement of the AUG start codon. Antisense oligonucleotides complementary to mRNA coding regions are less efficient inhibitors of translation but could also be used in accordance with the methods and compositions presented herein. Whether designed to hybridize to the 5', 3' or coding region of cellular mRNAs, small nucleic acids and/or antisense nucleic acids should be at least six nucleotides in length, and can be less than about 1000, 900, 800, 700, 600, 500, 400, 300, 200, 100, 50, 40, 30, 25, 24, 23, 22, 21, 20, 19, 18, 17, 16, 15, or 10 nucleotides in length.

Regardless of the choice of target sequence, in vitro studies may be performed to quantitate the ability of the antisense oligonucleotide to inhibit gene expression. In one embodiment these studies utilize controls that distinguish between antisense gene inhibition and nonspecific biological effects of oligonucleotides. In another embodiment these studies compare levels of the target nucleic acid or protein with that of an internal control nucleic acid or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Small nucleic acids and/or antisense oligonucleotides can be DNA or RNA or chimeric mixtures or derivatives or modified versions thereof, single-stranded or double-stranded. Small nucleic acids and/or antisense oligonucleotides can be modified at the base moiety, sugar moiety, or phosphate backbone, for example, to improve stability of the molecule, hybridization, etc., and may include other appended groups such as peptides (e.g., for targeting host cell receptors), or agents facilitating transport across the cell membrane (see, e.g., Letsinger et al. (1989) Proc. Natl. Acad. Sci. U.S.A. 86:6553-6556; Lemaitre et al. (1987) Proc. Natl. Acad. Sci. 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al. (1988) BioTechniques 6:958-976) or intercalating agents. (See, e.g., Zon (1988), Pharm. Res. 5:539-549). To this end, small nucleic acids and/or antisense oligonucleotides may be conjugated to another molecule, e.g., a peptide, hybridization triggered cross-linking agent, transport agent, hybridization-triggered cleavage agent, etc.

Small nucleic acids and/or antisense oligonucleotides may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxytiethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-me-thylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Small nucleic acids and/or antisense oligonucleotides may also comprise at least one modified sugar moiety selected from the group including but not limited to arabinose, 2-fluoroarabinose, xylulose, and hexose.

Small nucleic acids and/or antisense oligonucleotides can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, small nucleic acids and/or antisense oligonucleotides comprises at least one modified phosphate backbone selected from the group consisting of a phosphorothioatc, a phosphorodithioate, a phosphoramidothioate, a phosphoramidate, a phosphordiamidate, a methylphosphonate, an alkyl phosphotriester, and a formacetal or analog thereof.

In a further embodiment, small nucleic acids and/or antisense oligonucleotides are α-anomeric oligonucleotides. An α-anomeric oligonucleotide forms specific double-stranded hybrids with complementary RNA in which, contrary to the usual b-units, the strands run parallel to each other (Gautier et al. (1987) Nucl. Acids Res. 15:6625-6641). The oligonucleotide is a 2'-0-methylribonucleotide (Inoue et al. (1987) Nucl. Acids Res. 15:6131-6148), or a chimeric RNA-DNA analogue (Inoue et al. (1987) FEBS Lett. 215:327-330).

Small nucleic acids and/or antisense oligonucleotides of the methods and compositions presented herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (1988) Nucl. Acids Res. 16:3209, methylphosphonate oligonucleotides can be prepared by use of controlled pore glass polymer supports (Sarin et al. (1988) Proc. Natl. Acad. Sci. U.S.A. 85:7448-7451), etc.

Small nucleic acids and/or antisense oligonucleotides can be delivered to cells in vivo. A number of methods have been developed for delivering small nucleic acids and/or antisense oligonucleotides DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

In one embodiment, small nucleic acids and/or antisense oligonucleotides may comprise or be generated from double stranded small interfering RNAs (siRNAs), in which sequences fully complementary to cellular nucleic acids (e.g. mRNAs) sequences mediate degradation or in which sequences incompletely complementary to cellular nucleic acids (e.g., mRNAs) mediate translational repression when expressed within cells. In another embodiment, double stranded siRNAs can be processed into single stranded antisense RNAs that bind single stranded cellular RNAs (e.g., microRNAs) and inhibit their expression. RNA interference (RNAi) is the process of sequence-specific, post-transcriptional gene silencing in animals and plants, initiated by double-stranded RNA (dsRNA) that is homologous in sequence to the silenced gene. In vivo, long dsRNA is cleaved by ribonuclease III to generate 21- and 22-nucleotide siRNAs. It has been shown that 21-nucleotide siRNA duplexes specifically suppress expression of endogenous and heterologous genes in different mammalian cell lines, including human embryonic kidney (293) and HeLa cells (Elbashir et al. (2001) *Nature* 411:494-498). Accordingly, translation of a gene in a cell can be inhibited by contacting the cell with short double stranded RNAs having a length of about 15 to 30 nucleotides or of about 18 to 21 nucleotides or of about 19 to 21 nucleotides. Alternatively, a vector encoding for such siRNAs or short hairpin RNAs (shRNAs) that are metabolized into siRNAs can be introduced into a target cell (see, e.g., McManus et al. (2002) RNA 8:842; Xia et al. (2002) Nature Biotechnology 20:1006; and Brummelkamp et al. (2002) Science 296:550). Vectors that can be used are commercially available, e.g., from OligoEngine under the name PSUPER RNAI SYSTEM™. An exemplary Gal1 shRNA target sequence is GCTGCCAGATGGATACGAA (SEQ ID NO: 5).

Ribozyme molecules designed to catalytically cleave cellular mRNA transcripts can also be used to prevent translation of cellular mRNAs (e.g., Gal1 mRNA or a fragment thereof) and expression of cellular polypeptides, or both (See, e.g., PCT International Publication WO90/11364, published Oct. 4, 1990; Sarver et al. (1990) Science 247:1222-1225 and U.S. Pat. No. 5,093,246). While ribozymes that cleave mRNA at site specific recognition sequences can be used to destroy cellular mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach (1988) Nature 334:585-591. The ribozyme may be engineered so that the cleavage recognition site is located near the 5' end of cellular mRNAs; i.e., to increase efficiency and minimize the intracellular accumulation of non-functional mRNA transcripts.

The ribozymes of the methods and compositions presented herein also include RNA endoribonucleases (hereinafter "Cech-type ribozymes") such as the one which occurs naturally in *Tetrahymena thermophile* (known as the IVS, or L-19 IVS RNA) and which has been extensively described by Thomas Cech and collaborators (Zaug, et al. (1984) Science 224:574-578; Zaug, et al. (1986) Science 231:470-475; Zaug, et al. (1986) Nature 324:429-433; published International patent application No. WO88/04300 by University Patents Inc.; Been, et al. (1986) Cell 47:207-216). The Cech-type ribozymes have an eight base pair active site which hybridizes to a target RNA sequence whereafter cleavage of the target RNA takes place. The methods and compositions presented herein encompasses those Cech-type ribozymes which target eight base-pair active site sequences that are present in cellular genes.

As in the antisense approach, the ribozymes can be composed of modified oligonucleotides (e.g., for improved stability, targeting, etc.) and should be delivered to cells which express Gal1 genes or a fragment thereof in vivo. A preferred method of delivery involves using a DNA construct "encoding" the ribozyme under the control of a strong constitutive pol III or pol II promoter, so that transfected cells will produce sufficient quantities of the ribozyme to destroy endogenous cellular messages and inhibit translation. Because ribozymes unlike antisense molecules, are catalytic, a lower intracellular concentration is required for efficiency.

Nucleic acid molecules to be used in triple helix formation for the inhibition of transcription of cellular genes (e.g., the Gal1 gene or a fragment thereof) are preferably single stranded and composed of deoxyribonucleotides. The base composition of these oligonucleotides should promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, containing a stretch of G residues. These molecules will form a triple helix with a DNA duplex that is rich in GC pairs, in which the majority of the purine residues are located on a single strand of the targeted duplex, resulting in CGC triplets across the three strands in the triplex.

Alternatively, the potential sequences that can be targeted for triple helix formation may be increased by creating a so called "switchback" nucleic acid molecule. Switchback molecules are synthesized in an alternating 5'-3',3'-5' manner, such that they base pair with first one strand of a duplex and then the other, eliminating the necessity for a sizable stretch of either purines or pyrimidines to be present on one strand of a duplex.

Small nucleic acids, antisense oligonucleotides, ribozymes, and triple helix molecules of the methods and compositions presented herein may be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone. One of skill in the art will readily understand that regulatable proteins, inhibitory mutants, small nucleic acids, and antisense oligonucleotides can be further linked to another peptide or polypeptide (e.g., a heterologous peptide), e.g., that serves as a means of protein detection. Non-limiting examples of label peptide or polypeptide moieties useful for detection in the invention include, without limitation, suitable enzymes such as horseradish peroxidase, alkaline phosphatase, beta-galactosidase, or acetylcholinesterase; epitope tags, such as FLAG, MYC, HA, or HIS tags; fluorophores such as green fluorescent protein; dyes; radioisotopes; digoxygenin; biotin; antibodies; polymers; as well as others known in the art, for example, in Principles of Fluorescence Spectroscopy, Joseph R. Lakowicz (Editor), Plenum Pub Corp, 2nd edition (July 1999).

The modulatory agents described herein (e.g. antibodies, small molecules, peptides, fusion proteins, or small nucleic acids) can be incorporated into pharmaceutical compositions and administered to a subject in vivo. The compositions may contain a single such molecule or agent or any combination of modulatory agents described herein.

IV. Methods of Selecting Agents that Modulate Immune Cell Activation and/or Hypoxia Associated Angiogenesis Another aspect of the present invention relates to methods of selecting agents (e.g., antibodies, fusion proteins, peptides, small molecules, or small nucleic acids) which modulate an immune response by modulating the interactions between a Gal1 polypeptide or a fragment thereof and its natural binding partner(s) or a fragment(s) thereof. Such methods utilize screening assays, including cell based and non-cell based assays.

In one embodiment, the invention relates to assays for screening candidate or test compounds which bind to, or modulate the activity of, a Gal1 polypeptide or a fragment thereof, e.g., modulate the ability of a Gal1 polypeptide or a fragment thereof to interact with, e.g., bind to, its natural binding partner(s) or a fragment(s) thereof. In one embodiment, a method for identifying an agent to modulate an immune response and/or hypoxia associated angiogenesis entails determining the ability of the agent to modulate, e.g., enhance or inhibit, the interactions between a Gal1 polypeptide or a fragment thereof and its natural binding partner(s) or a fragment(s) thereof. Such agents include, without limitation, antibodies, proteins, fusion proteins and small molecules.

In one embodiment, a method for identifying an agent which enhances an immune response entails determining the ability of the candidate agent to inhibit the interactions between a Gal1 polypeptide or a fragment thereof and its natural binding partner(s) or a fragment(s) thereof. In another embodiment, a method for identifying an agent to decrease an immune response entails determining the ability of a candidate agent to enhance the interactions between a Gal1 polypeptide or a fragment thereof and its natural binding partner(s) or a fragment(s) thereof. In still another embodiment, a method for identifying an agent which decreases hypoxia associated angiogenesis entails determining the ability of the candidate agent of inhibit the interactions between a Gal1 polypeptide or a fragment thereof and its natural binding partner(s) or a fragment(s) thereof.

In one embodiment, an assay is a cell-based assay, comprising contacting a cell expressing a Gal1 polypeptide or a fragment thereof, with a test compound and determining the ability of the test compound to modulate (e.g. stimulate or inhibit) the binding between a Gal1 polypeptide or a fragment thereof and its natural binding partner(s) or a fragment(s) thereof. Determining the ability of a Gal1 polypeptide or a fragment thereof to bind to, or interact with, a binding partner or a fragment thereof, can be accomplished, e.g., by measuring direct binding or by measuring a parameter of immune cell activation and/or hypoxia associated angiogenesis.

For example, in a direct binding assay, a Gal1 polypeptide, a Gal1 binding partner(s), or a fragment(s) thereof, can be coupled with a radioisotope or enzymatic label such that binding of the Gal1 polypeptide or a fragment thereof to its natural binding partner(s) or a fragment(s) thereof can be determined by detecting the labeled molecule in a complex. For example, a Gal1 polypeptide, a Gal1 binding partner(s), or a fragment(s) thereof, can be labeled with $^{125}I$, $^{35}S$, $^{14}C$, or $^{3}H$, either directly or indirectly, and the radioisotope detected by direct counting of radioemmission or by scintillation counting. Alternatively, a Gal1 polypeptide, a Gal1 binding partner(s), or a fragment(s) thereof, can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound to modulate the interactions between a Gal1 polypeptide or a fragment thereof and its natural binding partner(s) or a fragment(s) thereof, without the labeling of any of the interactants. For example, a microphysiometer can be used to detect the interactions between a Gal1 polypeptide or a fragment thereof and its natural binding partner(s) or a fragment(s) thereof without the labeling of either a Gal1 polypeptide or a fragment thereof and its natural binding partner(s) or a fragment(s) thereof (McConnell, H. M. et al. (1992) *Science* 257:1906-1912). As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between compound and receptor.

In a preferred embodiment, determining the ability of the blocking agents (e.g. antibodies, fusion proteins, peptides, or small molecules) to antagonize the interaction between a given set of polypeptides can be accomplished by determining the activity of one or more members of the set of interacting molecules. For example, the activity of Gal1 can be determined by detecting induction of a cellular second messenger (e.g., H-Ras), detecting catalytic/enzymatic activity of an appropriate substrate, detecting the induction of a reporter gene (comprising a target-responsive regulatory element operatively linked to a nucleic acid encoding a detectable marker, e.g., chloramphenicol acetyl transferase), or detecting a cellular response regulated by a Gal1 polypeptide or a fragment thereof. Determining the ability of the blocking agent to bind to or interact with said polypeptide can be accomplished by measuring the ability of an agent to modulate immune responses, for example, by detecting changes in type and amount of cytokine secretion, changes in apoptosis or proliferation, changes in gene expression or activity associated with cellular identity, or by interfering with the ability of said polypeptide to bind to antibodies that recognize a portion thereof.

Agents that block or inhibit interactions between a Gal1 polypeptide or a fragment thereof and its natural binding partner(s) or a fragment(s) thereof (e.g., blocking antibodies to a Gal1 polypeptide or a fragment thereof) can be identified by their ability to inhibit immune cell proliferation, and/or effector function, induce apoptosis, or to induce anergy when added to an in vitro assay. For example, cells can be cultured in the presence of an agent that stimulates signal transduction via an activating receptor. A number of recognized readouts of cell activation can be employed to measure, cell proliferation, apoptosis, or effector function (e.g., antibody production, cytokine production, phagocytosis) in the presence of the activating agent. The ability of a test agent to block this activation can be readily determined by measuring the ability of the agent to effect a decrease in proliferation, increase apoptosis, or effector function being measured, using techniques known in the art.

A number of art-recognized methods are further known to determine whether a candidate agent can reduce hypoxia associated angiogenesis. For example, endothelial cell adhesion and migration are known to regulate endothelial cell survival, proliferation, and motility during new blood vessel growth in normal and pathologic conditions that involve angiogenesis. The term "endothelial cell adhesion" as used herein refers to the adhesion of an endothelial cell to one or more components of the extracellular matrix (e.g., fibronectin, collagens I-XVIII, laminin, vitronectin, fibrinogen, osteopontin, Del 1, tenascin, von Willebrands's factor, etc.), to a ligand which is expressed on the cell surface (e.g., VCAM, ICAM, LI-CAM, VE-cadherin, integrin a2, integrin a3, etc.) and/or to another cell (e.g., another endothelial cell, to a fibroblast cell, stromal cell, tumor cell, etc.) The terms "inhibiting endothelial cell adhesion" and "reducing endothelial cell adhesion" refer to reducing the level of adhesion of an endothelial cell to one or more components of the extracellular matrix (e.g., fibronectin, collagens I-XVIII, laminin, vitronectin, fibrinogen, osteopontin, Del 1, tenascin, von Willebrands's factor, etc.), and/or to another cell (e.g., another endothelial cell, fibroblast cell, stromal cell, tumor cell, etc.) to a quantity which is preferably 10% less than, more preferably 50% less than, yet more preferably 75% than, even more preferably 90% less than, the quantity in a corresponding control endothelial cell, and most preferably is at the same level which is observed in a control endothelial cell. A reduced level of endothelial cell adhesion need not, although it may, mean an absolute absence of cell adhesion. The invention does not require, and is not limited to, methods that wholly eliminate cell adhesion. The level of endothelial cells adhesion may be determined using methods well known in the art. The term "endothelial cell migration" as used herein refers to the translocation of an endothelial cell across one or more components of the extracellular matrix (e.g., fibronectin, collagens I-XVIII, laminin, vitronectin, fibrinogen, osteopontin, Del 1, tenascin, von Willebrands's factor, etc.), or along the surface of another cell (e.g., another endothelial cell, fibroblast cell, stromal cell, tumor cell, etc.).

The terms "inhibiting endothelial cell migration" and "reducing endothelial cell migration" refer to reducing the level of migration of an endothelial cell to a quantity which is preferably 10% less than, more preferably 50% less than, yet more preferably 75% less than, and even more preferably 90% less than, the quantity in a corresponding control endothelial cells, and most preferably is at the same level which is observed in a control endothelial cell. A reduced level of endothelial cell migration need not, although it may, mean an absolute absence of cell migration. The invention does not require, and is not limited to, methods that wholly eliminate cell migration. The level of endothelial cells migration may be determined using methods well known in the art, such as time lapse video microscopy, scratch type wound assay.

For hypoxia associated angiogenesis involving ischemia, several art-recognized models for studying ischemia are known. These include, but are not limited to, experimentally induced rat hindlimb ischemia (see, e.g., Takeshita, S. et al., Circulation (1998) 98: 1261-63; and Takeshita, S. et al. (1994) Circulation 90(#5; part II):228-234), a partially ischemic hindlimb rabbit model (see, e.g., Hopkins, S. et al., J. Vasc. Surg. (1998) 27: 886-894), and a chronic porcine myocardial ischemia model (see, e.g., Harada, K. et al., Am. J. Physiol. (1996) 270: 886-94; and Hariawala, M. et al., 1996, J. Surg. Res. 63: 77-82). Another assay includes a rabbit model of hindlimb ischemia (see, e.g., Takeshita, S. et al., 1994, Circulation 90(#5; part II):228-234).

In yet another embodiment, an assay of the present invention is a cell-free assay in which a Gal1 polypeptide or a fragment thereof, e.g. a biologically active fragment thereof, is contacted with a test compound, and the ability of the test compound to bind to the polypeptide, or biologically active portion thereof, is determined. Binding of the test compound to a Gal1 polypeptide or a fragment thereof, can be determined either directly or indirectly as described above. In a preferred embodiment, the assay includes contacting the Gal1 polypeptide or fragment thereof, with a Gal1 natural binding partner(s) or fragment(s) thereof, to form an assay mixture, contacting the assay mixture with a test compound, and determining the ability of the test compound to interact with the polypeptide in the assay mixture, wherein determining the ability of the test compound to interact with the polypeptide comprises determining the ability of the test compound to preferentially bind to the polypeptide or fragment thereof, as compared to the binding partner.

For example, a Gal1 polypeptide or a fragment thereof and its natural binding partner(s) or a fragment(s) thereof can be used to form an assay mixture and the ability of a polypeptide to block this interaction can be tested by determining the ability of a Gal1 polypeptide or a fragment thereof to bind to the Gal1 natural binding partner(s) or a fragment(s) thereof, by one of the methods described above for determining direct binding. Determining the ability of a Gal1 polypeptide or a fragment thereof and its natural binding partner(s) or a fragment(s) thereof can also be accomplished using a technology such as real-time Biomolecular Interaction Analysis (BIA) (Sjolander, S, and Urbaniczky, C. (1991) *Anal. Chem.* 63:2338-2345 and Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological polypeptides. A Gal1 polypeptide or a fragment thereof can be immobilized on a BIAcore chip and multiple agents, e.g., blocking antibodies, fusion proteins, peptides, or small molecules, can be tested for binding to the immobilized Gal1 polypeptide or fragment thereof. An example of using the BIA technology is described by Fitz et al. (1997) *Oncogene* 15:613.

The cell-free assays of the present invention are amenable to use of both soluble and/or membrane-bound forms of proteins (e.g., Gal1 polypeptides, Gal1 binding partner(s) polypeptides, and fragments thereof). In the case of cell-free assays in which a membrane-bound form protein is used (e.g., a cell surface Gal1 polypeptide or a fragment thereof or Gal1 natural binding partner(s) or a fragment(s) thereof) it may be desirable to utilize a solubilizing agent such that the membrane-bound form of the protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, TRITON X-100 (4-(1,1,3,3-Tetramethylbutyl)phenyl-polyethylene glycol), TRITON X-114 (1,1,3,3-Tetramethylbutyl)phenyl-polyethylene glycol, THESIT® (hydroxypolyethoxydodecane), Isotridecylpoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In one or more embodiments of the above described assay methods, it may be desirable to immobilize either the Gal1 polypeptide, the Gal1 natural binding partner(s) polypeptide, or fragments thereof, to facilitate separation of complexed from uncomplexed forms of one or both of the proteins, as well as to accommodate automation of the assay. Binding of a test compound to a Gal1 polypeptide, a Gal1 natural binding partner(s) polypeptide, or fragments thereof, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/Gal1 or glutathione-S-transferase/Gal1 natural binding partner(s) fusion proteins, can be adsorbed onto glutathione SEPHAROSE® (cross-linked agarose) beads (Sigma Chemical, St. Louis, Mo.) or glutathione derivatized microtiter plates, which are then combined with the test compound, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of Gal1 binding or activity determined using standard techniques.

In an alternative embodiment, determining the ability of the test compound to modulate the activity of a Gal1 or Gal1 natural binding partner(s) can be accomplished by determining the ability of the test compound to modulate the expression or activity of a gene, e.g., nucleic acid, or gene product, e.g., polypeptide, that functions downstream of Gal1 or a Gal1 natural binding partner(s), e.g., a polypeptide that functions downstream of the Gal1 natural binding partner(s). For example, levels of second messengers can be determined, the activity of the interactor polypeptide on an appropriate target can be determined, or the binding of the interactor to an appropriate target can be determined as previously described.

In another embodiment, modulators of Gal1 expression are identified in a method wherein a cell is contacted with a candidate compound and the expression of Gal1 mRNA or polypeptide or fragments thereof in the cell is determined. The level of expression of Gal1 mRNA or polypeptide or fragments thereof in the presence of the candidate compound is compared to the level of expression of Gal1 mRNA or polypeptide or fragments thereof in the absence of the candidate compound. The candidate compound can then be identified as a modulator of Gal1 expression based on this comparison. For example, when expression of Gal1 mRNA or polypeptide or fragments thereof is greater (statistically significantly greater) in the presence of the candidate compound than in its absence, the candidate compound is identified as a stimulator of Gal1 expression. Alternatively, when expression of Gal1 mRNA or polypeptide or fragments thereof is reduced (statistically significantly less) in the presence of the candidate compound rather than in its absence, the candidate compound is identified as an inhibitor of Gal1 expression. The expression level of Gal1 mRNA or polypeptide or fragments thereof in the cells can be determined by methods described herein for detecting Gal1 mRNA or polypeptide or fragments thereof.

In yet another aspect of the present invention, Gal1 polypeptides or fragments thereof can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other polypeptides which bind to or interact with Gal1 or fragments thereof ("Gal1-binding proteins", "Gal1 binding partners", or "Gal1-bp") and are involved in Gal1 activity. Such Gal1-binding proteins are also likely to be involved in the propagation of signals by the Gal1 polypeptides or Gal1 natural binding partner(s) as, for example, downstream elements of a Gal1-mediated signaling pathway. Alternatively, such Gal1-binding polypeptides may be Gal1 inhibitors.

The two-hybrid system is based on the modular nature of most transcription factors, which consist of separable DNA-binding and activation domains. Briefly, the assay utilizes two different DNA constructs. In one construct, the gene that codes for a Gal1 polypeptide is fused to a gene encoding the DNA binding domain of a known transcription factor (e.g., GAL-4). In the other construct, a DNA sequence, from a library of DNA sequences, that encodes an unidentified polypeptide ("prey" or "sample") is fused to a gene that codes for the activation domain of the known transcription factor. If the "bait" and the "prey" polypeptides are able to interact, in vivo, forming a Gal1-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the polypeptide which interacts with the Gal1 polypeptide.

In another aspect, the invention pertains to a combination of two or more of the assays described herein. For example, a modulating agent can be identified using a cell-based or a cell-free assay, and the ability of the agent to modulate the activity of a Gal1 polypeptide or a fragment thereof can be confirmed in vivo, e.g., in an animal such as an animal model for cellular transformation and/or tumorigenesis.

This invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

V. Pharmaceutical Compositions

Gal1 modulating agents (e.g., agents that inhibit or promote the interactions between a Gal1 polypeptide or a fragment thereof and its natural binding partner(s) or a fragment thereof, including, e.g., blocking antibodies, peptides, fusion proteins, or small molecules) can be incorporated into pharmaceutical compositions suitable for administration to a subject. Such compositions typically comprise the antibody, peptide, fusion protein or small molecule and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the present invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (macrogolglycerol ricinoleate) (BASF, Parsippany, N.J.) or phosphate buffered saline (PBS). In all cases, the composition should be sterile and should be fluid to the extent that easy syringeability exists. It must be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., blocking antibodies, peptides, fusion proteins, or small molecules that inhibit the interactions between a Gal1 polypeptide or a fragment thereof and its natural binding partner(s) or a fragment(s) thereof) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, modulatory agents are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations should be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the present invention are dictated by, and directly dependent on, the unique characteristics of the active compound, the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the present invention, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity of Gal1 nucleic acid, polypeptide, or fragments thereof. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e., including heterorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds. It is understood that appropriate doses of small molecule agents depends upon a number of factors within the scope of knowledge of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the present invention.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the present invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the present invention can be used for modifying a given biological response, the drug moiety is not to be construed as limited to classical chemical therapeutic agents. For example, the drug moiety may be a protein or polypeptide possessing a desired biological activity. Such polypeptides may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator; or biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985); and Thorpe et al.

"The Preparation And Cytotoxic Properties Of Antibody-Toxin Conjugates", Immunol. Rev. 62:119-58 (1982). Alternatively, an antibody can be conjugated to a second antibody to form an antibody heteroconjugate as described by Segal in U.S. Pat. No. 4,676,980.

The above described modulating agents may be administered it the form of expressible nucleic acids which encode said agents. Such nucleic acids and compositions in which they are contained, are also encompassed by the present invention. For instance, the nucleic acid molecules of the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

VI. Uses and Methods of the Invention

The Gal1 molecules, e.g., the Gal1 nucleic acid molecules, polypeptides, polypeptide homologues, antibodies, and fragments thereof, described herein can be used in one or more of the following methods: a) screening assays; b) predictive medicine (e.g., diagnostic assays, prognostic assays, and monitoring clinical trials); and c) methods of treatment (e.g., therapeutic and prophylactic, e.g., by up- or down-modulating the immune response and/or downregulating hypoxia associated angiogenesis). As described herein, a Gal1 polypeptide or fragment thereof of the present invention has one or more of the following activities: 1) binds to and/or modulates the activity of its natural binding partner(s), 2) modulates intra- or intercellular signaling, 3) modulates activation and/or proliferation of lymphocytes, 4) modulates the immune response of an organism, e.g., a mammalian organism, such as a mouse or human, and 5) modulates hypoxia associated angiogenesis. See, for example, Toscano et al. (2007) *Cyt Growth Fact Rev* 18:57-71; Camby et al. (2006) *Glycobiol* 16:137 R-157R, each of which is incorporated herein, by reference, in its entirety.

The isolated nucleic acid molecules of the present invention can be used, for example, to express a Gal1 polypeptide or a fragment thereof (e.g., via a recombinant expression vector in a host cell in gene therapy applications), to detect Gal1 mRNA or a fragment thereof (e.g., in a biological sample) or a genetic alteration in a Gal1 gene, and to modulate Gal1 activity, as described further below. The Gal1 polypeptides or fragments thereof can be used to treat viral-associated PTLD, e.g., EBV-associated PTLD, and/or hypoxia associated angiogenesis disorders.

In addition, the Gal1 polypeptides or fragments thereof can be used to screen for naturally occurring Gal1 binding partner(s), to screen for drugs or compounds which modulate Gal1 activity, as well as to treat hypoxia associated angiogenesis disorders and/or viral-associated PTLD, e.g., EBV-associated PTLD, characterized by insufficient or excessive production of Gal1 polypeptide or a fragment thereof or production of Gal1 polypeptide forms which have decreased, aberrant or unwanted activity compared to Gal1 wild-type polypeptides or fragments thereof (e.g., viral-associated PTLD, e.g., EBV-associated PTLD). Moreover, the anti-Gal1 antibodies or fragments thereof of the present invention can be used to detect and isolate Gal1 polypeptides or fragments thereof, regulate the bioavailability of Gal1 polypeptides or fragments thereof, and modulate Gal1 activity, e.g., by modulating the interaction between a Gal1 polypeptide or a fragment thereof and its natural binding partner(s) or a fragment(s) thereof.

A. Screening Assays

In one aspect, the invention relates to a method for preventing in a subject, a disease or condition associated with an unwanted or less than desirable immune response. Subjects at risk for a disease that would benefit from treatment with the claimed agents and/or methods can be identified, for example, by any of a combination of diagnostic or prognostic assays known in the art and described herein (see, for example, agents and assays described in IV. Methods of Selecting Agents that Modulate Immune Cell Activation).

B. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining Gal1 polypeptide and/or nucleic acid expression as well as Gal1 activity, in the context of a biological sample (e.g., blood, serum, cells, or tissue) to thereby determine whether an individual is afflicted with a hypoxia associated angiogenesis disorder and/or a viral-associated PTLD, e.g., EBV-associated PTLD, or is at risk of developing a hypoxia associated angiogenesis disorder and/or a viral-associated PTLD, e.g., EBV-associated PTLD, associated with aberrant or unwanted Gal1 expression or activity. The invention also provides for prognostic (or predictive) assays for determining whether an individual is at risk of developing a hypoxia associated angiogenesis disorder and/or a viral-associated PTLD, e.g., EBV-associated PTLD, associated with Gal1 polypeptide, nucleic acid expression or activity. For example, mutations in a Gal1 gene can be assayed in a biological sample.

Such assays can be used for prognostic or predictive purpose to thereby prophylactically treat an individual prior to the onset of a hypoxia associated angiogenesis disorder and/or a viral-associated PTLD, e.g., EBV-associated PTLD, characterized by or associated with Gal1 polypeptide, nucleic acid expression or activity.

Another aspect of the present invention pertains to monitoring the influence of agents (e.g., drugs, compounds) on the expression or activity of Gal1 in clinical trials. These and other agents are described in further detail in the following sections.

1. Diagnostic Assays

The present invention provides, in part, methods, systems, and code for accurately classifying whether a biological sample is associated with a hypoxia associated angiogenesis disorder and/or a viral-associated PTLD, e.g., EBV-associated PTLD, associated with aberrant expression or activity of by Gal1. In some embodiments, the present invention is useful for classifying a sample (e.g., from a subject) as associated with or at risk for a hypoxia associated angiogenesis disorder and/or a viral-associated PTLD, e.g., EBV-associated PTLD, mediated by Gal1 (known as a GAL1 sample and/or Gal1 sample) using a statistical algorithm and/or empirical data (e.g., the presence or level of an Gal1).

An exemplary method for detecting the level of expression or activity of Gal1 or fragments thereof, and thus useful for classifying whether a sample is associated with a disease or disorder mediated by Gal1 or a clinical subtype thereof involves obtaining a biological sample from a test subject and contacting the biological sample with an antibody or antigen-binding fragment thereof of the present invention capable of detecting Gal1 such that the level of expression or activity of Gal1 is detected in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a GAL1 sample based upon a prediction or probability value and the presence or level of Gal1. The use of a single learning statistical classifier system typically classifies the sample as a Gal1 sample (e.g., ulcerative colitis) sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the Gal1 sample classification results to a clinician, e.g., a gastroenterologist or a general practitioner.

In another embodiment, the method of the present invention further provides a diagnosis in the form of a probability that the individual has a condition or disorder associated with aberrant expression or activity of Gal1. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having the condition or disorder. In yet another embodiment, the method of the present invention further provides a prognosis of the condition or disorder in the individual. In some instances, the method of classifying a sample as a Gal1 sample is further based on the symptoms (e.g., clinical factors) of the individual from which the sample is obtained. The symptoms or group of symptoms can be, for example, diarrhea, abdominal pain, cramping, fever, anemia, weight loss, anxiety, depression, and combinations thereof. In some embodiments, the diagnosis of an individual as having a condition or disorder associated with aberrant expression or activity of Gal1 is followed by administering to the individual a therapeutically effective amount of a drug useful for treating one or more symptoms associated with the condition or disorder (e.g., chemotherapeutic agents).

In one embodiment, the methods further involve obtaining a control biological sample (e.g., biological sample from a subject who does not have a condition or disorder mediated by Gal1), a biological sample from the subject during remission or before developing a condition or disorder mediated by Gal1, or a biological sample from the subject during treatment for developing a condition or disorder mediated by Gal1.

An exemplary method for detecting the presence or absence of Gal1 polypeptide or nucleic acid or fragments thereof in a biological sample involves obtaining a biological sample from a test subject and contacting the biological sample with a compound or an agent capable of detecting Gal1 polypeptide or nucleic acid that encodes Gal1 polypeptide (e.g., mRNA or genomic DNA) or fragments thereof such that the presence of Gal1 polypeptide or nucleic acid or fragments thereof is detected in the biological sample. A preferred agent for detecting Gal1 mRNA, genomic DNA, or fragments thereof is a labeled nucleic acid probe capable of hybridizing to Gal1 mRNA, genomic DNA, or fragments thereof. The nucleic acid probe can be, for example, full length Gal1 nucleic acid, or a portion thereof, such as an oligonucleotide of at least 15, 30, 50, 100, 250 or 500 nucleotides in length and sufficient to specifically hybridize under stringent conditions to Gal1 mRNA or genomic DNA. Other suitable probes for use in the diagnostic assays of the present invention are described herein.

A preferred agent for detecting a Gal1 polypeptide or a fragment thereof is an antibody capable of binding to a Gal1 polypeptide, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells, and biological fluids isolated from a subject, as well as tissues, cells, and fluids present within a subject. That is, the detection method of the present invention can be used to detect Gal1 mRNA, polypeptide, genomic DNA, or fragments thereof, in a biological sample in vitro as well as in vivo. For example, in vitro techniques for detection of Gal1 mRNA or a fragment thereof include Northern hybridizations and in situ hybridizations. In vitro techniques for detection of Gal1 polypeptide include enzyme linked immunosorbent assays (ELISAs), Western blots, immunoprecipitations and immunofluorescence. In vitro techniques for detection of Gal1 genomic DNA or a fragment thereof include Southern hybridizations. Furthermore, in vivo techniques for detection of a Gal1 polypeptide or a fragment thereof include introducing into a subject a labeled anti-Gal1 antibody. For example, the antibody can be labeled with a radioactive marker whose presence and location in a subject can be detected by standard imaging techniques.

In one embodiment, the biological sample contains polypeptide molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting Gal1 polypeptide, mRNA, genomic DNA, or fragments thereof, such that the presence of Gal1 polypeptide, mRNA, genomic DNA, or fragments thereof, is detected in the biological sample, and comparing the presence of Gal1 polypeptide, mRNA, genomic DNA, or fragments thereof, in the control sample with the presence of Gal1 polypeptide, mRNA, genomic DNA, or fragments thereof in the test sample.

In still other embodiments, the antibodies can be associated with a component or device for the use of the antibodies in an ELISA or RIA. Non-limiting examples include antibodies immobilized on solid surfaces for use in these assays (e.g., linked and/or conjugated to a detectable label based on light or radiation emission as described above). In other embodiments, the antibodies are associated with a device or strip for detection of Gal1 by use of an immunochromatographic or immunochemical assay such as in a "sandwich" or competitive assay. Additional examples of such devices or strips are those designed for home testing or rapid point of care testing. Further examples include those that are designed for the simultaneous analysis of multiple analytes in a single sample. For example, an unlabeled antibody of the invention may be applied to a "capture" Gal1 polypeptides in a biological sample and the captured (or immobilized) Gal1 polypeptides may be bound to a labeled form of an anti-Gal1 antibody of the invention for detection. Other standard embodiments of immunoassays are well known the skilled artisan, including assays based on, for example, immunodiffusion, immunoelectrophoresis, immunohistopathology, immunohistochemistry, and histopathology.

The invention also encompasses kits for detecting the presence of a Gal1 nucleic acid, polypeptide, or fragments thereof, in a biological sample. For example, the kit can comprise a labeled compound or agent capable of detecting a Gal1 nucleic acid, polypeptide, or fragments thereof in a biological sample; means for determining the amount of the Gal1 nucleic acid, polypeptide, or fragments thereof in the sample; and means for comparing the amount of the Gal1 nucleic acid, polypeptide, or fragments thereof in the sample with a standard. The compound or agent can be packaged in a suitable container. The kit can further comprise instructions for using the kit to detect the Gal1 nucleic acid, polypeptide, or fragments thereof.

2. Prognostic Assays

The diagnostic methods described herein can furthermore be utilized to identify subjects having or at risk of developing a hypoxia associated angiogenesis disorder and/or a viral-associated PTLD, e.g., EBV-associated PTLD, associated with aberrant or unwanted Gal1 expression or activity. As used herein, the term "aberrant" includes a Gal1 expression or activity which deviates from the wild type Gal1 expression or activity. Aberrant expression or activity includes increased or decreased expression or activity, as well as expression or activity which does not follow the wild type developmental pattern of expression or the subcellular pattern of expression. For example, aberrant Gal1 expression or activity is intended to include the cases in which a mutation in the Gal1 gene or regulatory sequence thereof causes the Gal1 gene to be underexpressed or over-expressed and situations in which such mutations result in a non-functional Gal1 polypeptide or a polypeptide which does not function in a wild-type fashion, e.g., a polypeptide which does not interact with a Gal1 binding partner(s) or one which interacts with a non-Gal1 binding partner(s). As used herein, the term "unwanted" includes an unwanted phenomenon involved in a biological response such as immune cell activation. For example, the term unwanted includes a Gal1 expression or activity which is undesirable in a subject.

The assays described herein, such as the preceding diagnostic assays or the following assays, can be utilized to identify a subject having or at risk of developing a hypoxia associated angiogenesis disorder and/or a viral-associated PTLD, e.g., EBV-associated PTLD, associated with a misregulation in Gal1 polypeptide activity or nucleic acid expression. Thus, the present invention provides a method for identifying a hypoxia associated angiogenesis disorder and/or a viral-associated PTLD, e.g., EBV-associated PTLD, associated with aberrant or unwanted Gal1 expression or activity in which a test sample is obtained from a subject and Gal1 polypeptide or nucleic acid (e.g., mRNA or genomic DNA) is detected, wherein the presence of Gal1 polypeptide or nucleic acid is diagnostic for a subject having or at risk of developing a hypoxia associated angiogenesis disorder and/or a viral-associated PTLD, e.g., EBV-associated PTLD, associated with aberrant or unwanted Gal1 expression or activity. As used herein, a "test sample" refers to a biological sample obtained from a subject of interest. For example, a test sample can be a biological fluid (e.g., cerebrospinal fluid or serum), cell sample, or tissue.

Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a hypoxia associated angiogenesis disorder and/or a viral-associated PTLD, e.g., EBV-associated PTLD, associated with aberrant or unwanted Gal1 expression or activity. For example, such methods can be used to determine whether a subject can be effectively treated with an agent for a hypoxia associated angiogenesis disorder and/or a viral-associated PTLD, e.g., EBV-associated PTLD. Thus, the present invention provides methods for determining whether a subject can be effectively treated with an agent for a hypoxia associated angiogenesis disorder and/or a viral-associated PTLD, e.g., EBV-associated PTLD, associated with aberrant or unwanted Gal1 expression or activity in which a test sample is obtained and Gal1 polypeptide or nucleic acid expression or activity is detected (e.g., wherein the abundance of Gal1 polypeptide or nucleic acid expression or activity is diagnostic for a subject that can be administered the agent to treat a hypoxia associated angiogenesis disorder and/or a viral-associated PTLD, e.g., EBV-associated PTLD, associated with aberrant or unwanted Gal1 expression or activity).

The methods of the present invention can also be used to detect genetic alterations in a Gal1 gene, thereby determining if a subject with the altered gene is at risk for a hypoxia associated angiogenesis disorder and/or a viral-associated PTLD, e.g., EBV-associated PTLD, characterized by misregulation in Gal1 polypeptide activity or nucleic acid expression. In preferred embodiments, the methods include detecting, in a sample of cells from the subject, the presence or absence of a genetic alteration characterized by at least one alteration affecting the integrity of a gene encoding a Gal1 polypeptide, or the mis-expression of the Gal1 gene. For example, such genetic alterations can be detected by ascertaining the existence of at least one of 1) a deletion of one or more nucleotides from a Gal1 gene, 2) an addition of one or more nucleotides to a Gal1 gene, 3) a substitution of one or more nucleotides of a Gal1 gene, 4) a chromosomal rearrangement of a Gal1 gene, 5) an alteration in the level of a messenger RNA transcript of a Gal1 gene, 6) aberrant modification of a Gal1 gene, such as of the methylation pattern of the genomic DNA, 7) the presence of a non-wild type splicing pattern of a messenger RNA transcript of a Gal1 gene, 8) a non-wild type level of a Gal1 polypeptide, 9) allelic loss of a Gal1 gene, and 10) inappropriate post-translational modification of a Gal1 polypeptide. As described herein, there are a large number of assays known in the art which can be used for detecting alterations in a Gal1 gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683, 202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a Gal1 gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a Gal1 gene under conditions such that hybridization and amplification of the Gal1 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a Gal1 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in Gal1 can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, genetic mutations in Gal1 can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the Gal1 gene and detect mutations by comparing the sequence of the sample Gal1 with the corresponding wild-type (control) sequence. Examples of sequencing reactions include those based on techniques developed by Maxam and Gilbert (1977) Proc. Natl. Acad. Sci. USA 74:560 or Sanger (1977) Proc. Natl. Acad. Sci. USA 74:5463. It is also contemplated that any of a variety of automated sequencing procedures can be utilized when performing the diagnostic assays (Naeve, C. W. (1995) Biotechniques 19:448-53), including sequencing by mass spectrometry (see, e.g., PCT International Publication No. WO 94/16101; Cohen et al. (1996) Adv. Chromatogr. 36:127-162; and Griffin et al. (1993) Appl. Biochem. Biotechnol. 38:147-159).

Other methods for detecting mutations in the Gal1 gene include methods in which protection from cleavage agents is used to detect mismatched bases in RNA/RNA or RNA/DNA heteroduplexes (Myers et al. (1985) Science 230:1242). In general, the art technique of "mismatch cleavage" starts by providing heteroduplexes formed by hybridizing (labeled) RNA or DNA containing the wild-type Gal1 sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) Proc. Natl. Acad. Sci. USA 85:4397 and Saleeba et al. (1992) Methods Enzymol. 217: 286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in Gal1 cDNAs obtained from samples of cells. For example, the mutY enzyme of E. coli cleaves A at G/A mismatches and the thymidine DNA glycosylase from HeLa cells cleaves T at G/T mismatches (Hsu et al. (1994) Carcinogenesis 15:1657-1662). According to an exemplary embodiment, a probe based on a Gal1 sequence, e.g., a wild-type Gal1 sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility may be used to identify mutations in Gal1 genes. For example, single strand conformation polymorphism (SSCP) may be used to detect differences in electrophoretic mobility between mutant and wild type nucleic acids (Orita et al. (1989) Proc Natl. Acad. Sci. USA 86:2766; see also Cotton (1993) Mutat. Res. 285:125-144 and Hayashi (1992) Genet. Anal. Tech. Appl. 9:73-79). Single-stranded DNA fragments of sample and control Gal1 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) Trends Genet. 7:5).

In yet another embodiment the movement of mutant or wild-type fragments in polyacrylamide gels containing a gradient of denaturant is assayed using denaturing gradient gel electrophoresis (DGGE) (Myers et al. (1985) Nature 313: 495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) Biophys. Chem. 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) Nature 324:163; Saiki et al. (1989) Proc. Natl. Acad. Sci. USA 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) Nucleic Acids Res. 17:2437-2448) or at the extreme 3' end of one primer where, under appropriate conditions, mismatch can prevent, or reduce polymerase extension (Prossner (1993) Tibtech 11:238). In addition it may be desirable to introduce a novel restriction site in the region of the mutation to create cleavage-based detection (Gasparini et al. (1992) Mol. Cell Probes 6:1). It is anticipated that in certain embodiments amplification may also be performed using Taq ligase for amplification (Barany (1991) Proc. Natl. Acad. Sci USA 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a Gal1 gene.

Furthermore, any cell type or tissue in which Gal1 is expressed may be utilized in the prognostic assays described herein.

Another aspect of the present invention includes uses of the compositions and methods described herein for association and/or stratification analyses in which the expression level and/or activity of Gal1 in biological samples from individuals with a hypoxia associated angiogenesis disorder and/or a viral-associated PTLD, e.g., EBV-associated PTLD, are analyzed and the information is compared to that of controls (e.g., individuals who do not have the disorder; controls may be also referred to as "healthy" or "normal" individuals or at early timepoints in a given time lapse study) who are preferably of similar age and race. The appropriate selection of patients and controls is important to the success of association and/or stratification studies. Therefore, a pool of individuals with well-characterized phenotypes is extremely desirable. Criteria for disease diagnosis, disease predisposition screening, disease prognosis, determining drug responsiveness (pharmacogenomics), drug toxicity screening, etc. are described herein.

Different study designs may be used for genetic association and/or stratification studies (Modern Epidemiology, Lippincott Williams & Wilkins (1998), 609-622). Observational studies are most frequently carried out in which the response of the patients is not interfered with. The first type of observational study identifies a sample of persons in whom the suspected cause of the disease is present and another sample of persons in whom the suspected cause is absent, and then the frequency of development of disease in the two samples is compared. These sampled populations are called cohorts, and the study is a prospective study. The other type of observational study is case-control or a retrospective study. In typical case-control studies, samples are collected from individuals with the phenotype of interest (cases) such as certain manifestations of a disease, and from individuals without the phenotype (controls) in a population (target population) that conclusions are to be drawn from. Then the possible causes of the disease are investigated retrospectively. As the time and costs of collecting samples in case-control studies are considerably less than those for prospective studies, case-control studies are the more commonly used study design in genetic association studies, at least during the exploration and discovery stage.

After all relevant phenotypic and/or genotypic information has been obtained, statistical analyses are carried out to determine if there is any significant correlation between the presence of an allele or a genotype with the phenotypic characteristics of an individual. Preferably, data inspection and cleaning are first performed before carrying out statistical tests for genetic association. Epidemiological and clinical data of the samples can be summarized by descriptive statistics with tables and graphs well known in the art. Data validation is preferably performed to check for data completion, inconsistent entries, and outliers. Chi-squared tests and t-tests (Wilcoxon rank-sum tests if distributions are not normal) may then be used to check for significant differences between cases and controls for discrete and continuous variables, respectively.

An important decision in the performance of genetic association tests is the determination of the significance level at which significant association can be declared when the p-value of the tests reaches that level. In an exploratory analysis where positive hits will be followed up in subsequent confirmatory testing, an unadjusted p-value <0.2 (a significance level on the lenient side), for example, may be used for generating hypotheses for significant association of a SNP with certain phenotypic characteristics of a disease. It is preferred that a p-value <0.05 (a significance level traditionally used in the art) is achieved in order for a SNP to be considered to have an association with a disease. When hits are followed up in confirmatory analyses in more samples of the same source or in different samples from different sources, adjustment for multiple testing will be performed as to avoid excess number of hits while maintaining the experiment-wise error rates at 0.05. While there are different methods to adjust for multiple testing to control for different kinds of error rates, a commonly used but rather conservative method is Bonferroni correction to control the experiment-wise or family-wise error rate (Multiple comparisons and multiple tests, Westfall et al, SAS Institute (1999)). Permutation tests to control for the false discovery rates, FDR, can be more powerful (Benjamini and Hochberg, Journal of the Royal Statistical Society, Series B 57, 1289-1300, 1995, Resampling-based Multiple Testing, Westfall and Young, Wiley (1993)). Such methods to control for multiplicity would be preferred when the tests are dependent and controlling for false discovery rates is sufficient as opposed to controlling for the experiment-wise error rates.

Once individual risk factors, genetic or non-genetic, have been found for the predisposition to disease, a classification/prediction scheme can be set up to predict the category (for instance, disease or no-disease) that an individual will be in depending on his phenotype and/or genotype and other non-genetic risk factors. Logistic regression for discrete trait and linear regression for continuous trait are standard techniques for such tasks (Applied Regression Analysis, Draper and Smith, Wiley (1998)). Moreover, other techniques can also be used for setting up classification. Such techniques include, but are not limited to, MART, CART, neural network, and discriminant analyses that are suitable for use in comparing the performance of different methods (The Elements of Statistical Learning, Hastie, Tibshirani & Friedman, Springer (2002)).

In addition, the present invention also encompasses kits for detecting the presence of a Gal1 nucleic acid, polypeptide, or fragments thereof, in a biological sample. For example, the kit can comprise a labeled compound or agent capable of detecting a Gal1 nucleic acid, polypeptide, or fragments thereof in a biological sample; means for determining the amount of the Gal1 nucleic acid, polypeptide, or fragments thereof in the sample; and means for comparing the amount of the Gal1 nucleic acid, polypeptide, or fragments thereof in the sample with a standard. The compound or agent can be packaged in a suitable container.

A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or Gal1 protein standards). A kit may additionally include buffers and other reagents recognized for use in a method of the disclosed invention. Non-limiting examples include agents to reduce non-specific binding, such as a carrier protein or a detergent.

3. Monitoring of Effects During Clinical Trials

Monitoring the influence of agents (e.g., compounds, drugs or small molecules) on the expression or activity of a Gal1 polypeptide or a fragment thereof (e.g., the modulation of cell proliferation and/or migration) can be applied not only in basic drug screening, but also in clinical trials. For example, the effectiveness of an agent determined by a screening assay as described herein to increase Gal1 gene expression, polypeptide levels, or upregulate Gal1 activity, can be monitored in clinical trials of subjects exhibiting decreased Gal1 gene expression, polypeptide levels, or downregulated Gal1 activity. Alternatively, the effectiveness of an agent determined by a screening assay to decrease Gal1 gene expression, polypeptide levels, or downregulate Gal1 activity, can be monitored in clinical trials of subjects exhibiting increased Gal1 gene expression, polypeptide levels, or Gal1 activity. In such clinical trials, the expression or activity of a Gal1 gene, and preferably, other genes that have been implicated in, for example, a hypoxia associated angiogenesis disorder and/or a viral-associated PTLD, e.g., EBV-associated PTLD, can be used as a "read out" or marker of the phenotype of a particular cell.

For example, and not by way of limitation, genes, including Gal1, that are modulated in cells by treatment with an agent (e.g., compound, drug or small molecule) which modulates Gal1 activity (e.g., identified in a screening assay as described herein) can be identified. Thus, to study the effect of agents on a hypoxia associated angiogenesis disorder and/or a viral-associated PTLD, e.g., EBV-associated PTLD, for example, in a clinical trial, cells can be isolated and RNA prepared and analyzed for the levels of expression of Gal1 and other genes implicated in the hypoxia associated angiogenesis disorder and/or viral-associated PTLD, e.g., EBV-associated PTLD, respectively. The levels of gene expression (e.g., a gene expression pattern) can be quantified by Northern blot analysis or RT-PCR, as described herein, or alternatively by measuring the amount of polypeptide produced, by one of the methods as described herein, or by measuring the levels of activity of Gal1 or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, polypeptide, peptide, nucleic acid, small molecule, or other drug candidate identified by the screening assays described herein) including the steps of (i) obtaining a pre-administration sample from a subject prior to administration of the agent; (ii) detecting the level of expression of a Gal1 polypeptide, mRNA, genomic DNA, or fragments thereof in the preadministration sample; (iii) obtaining one or more post-administration samples from the subject; (iv) detecting the level of expression or activity of the Gal1 polypeptide, mRNA, genomic DNA, or fragments thereof in the post-administration samples; (v) comparing the level of expression or activity of the Gal1 polypeptide, mRNA, genomic DNA, or fragments thereof in the pre-administration sample with the Gal1 polypeptide, mRNA, or genomic DNA in the post administration sample or samples; and (vi) altering the administration of the agent to the subject accordingly. For example, increased administration of the agent may be desirable to increase the expression or activity of Gal1 to higher levels than detected, i.e., to increase the effectiveness of the agent. Alternatively, decreased administration of the agent may be desirable to decrease expression or activity of Gal1 to lower levels than detected, i.e., to decrease the effectiveness of the agent. According to such an embodiment, Gal1 expression or activity may be used as an indicator of the effectiveness of an agent, even in the absence of an observable phenotypic response.

D. Methods of Treatment

The present invention provides for both prophylactic and therapeutic methods of treating a subject at risk of (or susceptible to) a hypoxia associated angiogenesis disorder and/or a viral-associated PTLD, e.g., EBV-associated PTLD, characterized by insufficient or excessive production of Gal1 polypeptides or production of Gal1 protein forms which have decreased or aberrant activity compared to Gal1 wild type protein. Moreover, the anti-Gal1 antibodies of the present invention can be used to detect and isolate Gal1 polypeptides or fragments thereof, regulate the bioavailability of Gal1 polypeptides or fragments thereof, and modulate Gal1 activity e.g., by modulating the interaction of a Gal1 polypeptide or a fragment thereof with its natural binding partner(s) or fragments(s) thereof.

1. Prophylactic Methods

In one aspect, the invention provides a method for preventing in a subject, a disease or condition associated with an aberrant or unwanted Gal1 expression or activity, by administering to the subject a Gal1 polypeptide or a fragment thereof or an agent which modulates Gal1 expression or at least one Gal1 activity. Subjects at risk for a hypoxia associated angiogenesis disorder and/or a viral-associated PTLD, e.g., EBV-associated PTLD associated with aberrant or unwanted Gal1 expression or activity can be identified by, for example, any or a combination of diagnostic or prognostic assays as described herein. Administration of a prophylactic agent can occur prior to the manifestation of symptoms characteristic of the Gal1 aberrancy, such that a hypoxia associated angiogenesis disorder and/or a viral-associated PTLD, e.g., EBV-associated PTLD, is prevented or, alternatively, delayed in its progression. Depending on the type of Gal1 aberrancy, for example, a Gal1 polypeptide, Gal1 agonist or Gal1 antagonist (e.g., an anti-Gal1 antibody or a combination of anti-Gal1 and antibodies against other immune related targets) agent can be used for treating the subject. The appropriate agent can be determined based on screening assays described herein.

2. Therapeutic Methods

Another aspect of the present invention pertains to methods of modulating Gal1 expression or activity or interaction with its natural binding partner(s), for therapeutic purposes. The activity and/or expression of Gal1, as well as the interaction between a Gal1 polypeptide or a fragment thereof and its natural binding partner(s) or a fragment(s) thereof can be modulated in order to modulate the immune response.

Modulatory methods of the present invention involve contacting a cell with a Gal1 polypeptide or a fragment thereof or agent that modulates one or more of the activities of Gal1 polypeptide activity associated with the cell, e.g., an agent that modulates expression or activity of Gal1 and/or modulates the interaction of a Gal1 polypeptide or a fragment thereof and its natural binding partner(s) or a fragment(s) thereof. An agent that modulates Gal1 polypeptide activity can be an agent as described herein, such as a nucleic acid or a polypeptide, a naturally-occurring binding partner of a Gal1 polypeptide, a Gal1 antibody, a combination of Gal1 antibodies and antibodies against other immune related targets, a Gal1 agonist or antagonist, a peptidomimetic of a Gal1 agonist or antagonist, a Gal1 peptidomimetic, other small molecule, or small RNA directed against a Gal1 nucleic acid gene expression product.

An agent that modulates the expression of Gal1 is, e.g., an antisense nucleic acid molecule, RNAi molecule, shRNA or other small RNA molecule, triplex oligonucleotide, ribozyme, or recombinant vector for expression of a Gal1 polypeptide. For example, an oligonucleotide complementary to the area around a Gal1 polypeptide translation initiation site can be synthesized. One or more antisense oligonucleotides can be added to cell media, typically at 200 μg/ml, or administered to a patient to prevent the synthesis of a Gal1 polypeptide. The antisense oligonucleotide is taken up by cells and hybridizes to a Gal1 mRNA to prevent translation. Alternatively, an oligonucleotide which binds double-stranded DNA to form a triplex construct to prevent DNA unwinding and transcription can be used. As a result of either, synthesis of Gal1 polypeptide is blocked. When Gal1 expression is modulated, preferably, such modulation occurs by a means other than by knocking out the Gal1 gene.

Agents which modulate expression, by virtue of the fact that they control the amount of Gal1 in a cell, also modulate the total amount of Gal1 activity in a cell.

In one embodiment, the agent the modulates Gal1 stimulates one or more Gal1 activities. Examples of such stimulatory agents include active Gal1 polypeptide or a fragment thereof and a nucleic acid molecule encoding Gal1 or a fragment thereof that has been introduced into the cell. In another embodiment, the agent inhibits one or more Gal1 activities. In a preferred embodiment, the agent inhibits or enhances the interaction of Gal1 with its natural binding partner(s). Examples of such inhibitory agents include antisense Gal1 nucleic acid molecules, anti-Gal1 antibodies, Gal1 inhibitors, and compounds identified in the subject screening assays.

These modulatory methods can be performed in vitro (e.g., by contacting the cell with the agent) or, alternatively, by contacting an agent with cells in vivo (e.g., by administering the agent to a subject). As such, the present invention provides methods of treating an individual afflicted with a viral-associated PTLD, e.g., EBV-associated PTLD, that would benefit from up- or down-modulation of a Gal1 polypeptide or a fragment thereof. In one embodiment, the method involves administering an agent (e.g., an agent identified by a screening assay described herein), or combination of agents that modulates (e.g., upregulates or downregulates) Gal1 expression or activity. In another embodiment, the method involves administering a Gal1 polypeptide or nucleic acid molecule as therapy to compensate for reduced, aberrant, or unwanted Gal1 expression or activity.

Stimulation of Gal1 activity is desirable in situations in which Gal1 is abnormally downregulated and/or in which increased Gal1 activity is likely to have a beneficial effect. Likewise, inhibition of Gal1 activity is desirable in situations in which Gal1 is abnormally upregulated and/or in which decreased Gal1 activity is likely to have a beneficial effect.

Exemplary agents for use in downmodulating Gal1 (i.e., Gal1 antagonists) include, e.g., antisense nucleic acid molecules, antibodies that recognize and block Gal1, combinations of antibodies that recognize and block Gal1 and antibodies that recognize and block other immune related targets, and compounds that block the interaction of a Gal1 polypeptide or a fragment thereof with its naturally occurring binding partner(s) or fragment(s) thereof on an immune cell. Exemplary agents for use in upmodulating Gal1 (i.e., Gal1 agonists) include, e.g., nucleic acid molecules encoding Gal1 polypeptides, multivalent forms of Gal1, compounds that increase the expression of Gal1, compounds that enhance the interaction of Gal1 with its naturally occurring binding partner(s) and cells that express Gal1.

In addition, these modulatory agents can also be administered in combination therapy with, e.g., chemotherapeutic agents, hormones, antiangiogens, radiolabelled, compounds, or with surgery, cryotherapy, and/or radiotherapy. The preceding treatment methods can be administered in conjunction with other forms of conventional therapy, either consecutively with, pre- or post-conventional therapy. For example, these modulatory agents can be administered with a therapeutically effective dose of chemotherapeutic agent. In another embodiment, these modulatory agents are administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regiment and dosages of these aforementioned chemotherapeutic drugs that are therapeutically effective will depend on the particular viral-associated PTLD, e.g., EBV-associated PTLD, being treated, the extent of the disease and other factors familiar to the physician of skill in the art and can be determined by the physician.

3. Upregulation of Immune Responses and/or Downregulation of Hypoxia Associated Angiogenesis Also useful therapeutically is the inhibition of interactions between a Gal1 polypeptide or a fragment thereof and its natural binding partner(s) or a fragment(s) thereof to thereby upregulate immune responses and/or downregulate hypoxia associated angiogenesis. Upregulation of immune responses and/or downregulation of hypoxia associated angiogenesis can be in the form of enhancing an existing or eliciting an initial immune response and/or anti-hypoxia associated angiogenesis response. In one embodiment, an agent that blocks interactions between a Gal1 polypeptide or a fragment thereof and its natural binding partner(s) or a fragment(s) thereof is used to enhance the immune response and/or downregulate hypoxia associated angiogenesis. Such an agent (e.g., a Gal1 blocking antibody) is therapeutically useful in situations where upregulation of antibody and cell-mediated responses would be beneficial.

Alternatively, immune responses and/or anti-hypoxia associated angiogenesis can be enhanced in an infected patient through an ex vivo approach, for instance, by removing cells, such as immune cells, from the patient, contacting immune cells in vitro with an agent that blocks interactions between a Gal1 polypeptide or a fragment thereof and its natural binding partner(s) or a fragment(s) thereof, and reintroducing the in vitro stimulated immune cells into the patient.

In certain instances, it may be desirable to further administer other agents that upregulate immune responses, for example, forms of B7 family members that transduce signals via costimulatory receptors, in order to further augment the immune response. In other embodiments, such additional agents can comprise anti-angiogenesis agents such as anti-VEGF therapies well known in the art.

An agent that inhibits Gal1 activity or interactions between a Gal1 polypeptide or a fragment thereof and its natural binding partner(s) or a fragment(s) thereof, can be used prophylactically in vaccines against various polypeptides, e.g., polypeptides derived from pathogens. Immunity against a pathogen, e.g., a virus, can be induced by vaccinating with a viral polypeptide along with an agent that inhibits Gal1 activity or interactions between a Gal1 polypeptide or a fragment thereof and its natural binding partner(s) or a fragment(s) thereof, in an appropriate adjuvant. Alternately, a vector comprising genes which encode for both a pathogenic antigen and a form of Gal1 that blocks interactions between a Gal1 polypeptide or a fragment thereof and its natural binding partner(s) or a fragment(s) thereof can be used for vaccination. Nucleic acid vaccines can be administered by a variety of means, for example, by injection (e.g., intramuscular, intradermal, or the biolistic injection of DNA-coated gold particles into the epidermis with a gene gun that uses a particle accelerator or a compressed gas to inject the particles into the skin (Haynes et al. (1996) J. Biotechnol. 44:37)). Alternatively, nucleic acid vaccines can be administered by non-invasive means. For example, pure or lipid-formulated DNA can be delivered to the respiratory system or targeted elsewhere, e.g., Peyers patches by oral delivery of DNA (Schubbert (1997) Proc. Natl. Acad. Sci. USA 94:961). Attenuated microorganisms can be used for delivery to mucosal surfaces (Sizemore et al. (1995) Science 270:29).

In another embodiment, the antigen in the vaccine is a self-antigen. Such a vaccine is useful in the modulation of tolerance in an organism. Immunization with a self antigen and an agent that blocks Gal1 activity or interactions between a Gal1 polypeptide or a fragment thereof and its natural binding partner(s) or a fragment(s) thereof can break tolerance (i.e., interfere with tolerance of a self antigen). Such a vaccine may also include adjuvants such as alum or cytokines (e.g., GM-CSF, IL-12, B7-1, or B7-2).

In another embodiment, upregulation or enhancement of an immune response function and/or downregulation of hypoxia associated angiogenesis, as described herein, is useful in the induction of tumor immunity (e.g., restoration of immune surveillance in viral-associated PTLD, e.g., EBV-associated PTLD). Viral-associated PTLD cells can be transfected with a nucleic acid molecule that inhibits Gal1 activity or interactions between a Gal1 polypeptide or a fragment thereof and its natural binding partner(s) or a fragment(s) thereof. These molecules can be, e.g., nucleic acid molecules which are antisense to Gal1, or can encode non-activating anti-Gal1 antibodies or combinations of anti-Gal1 antibodies and antibodies against other immune related targets. These molecules can also be the variable region of an anti-Gal1 antibody and/or an anti-Gal1 antibody. If desired, the tumor cells can also be transfected with other polypeptides which enhance an immune response. The transfected tumor cells are returned to the patient, which results in inhibition (e.g., local inhibition) of Gal1 activity or interactions between a Gal1 polypeptide or a fragment thereof and its natural binding partner(s) or a fragment(s) thereof. Alternatively, gene therapy techniques can be used to target a tumor cell for transfection in vivo.

Stimulation of an immune response to tumor cells and/or downregulation of hypoxia associated angiogenesis can also be achieved by inhibiting Gal1 activity or interactions between a Gal1 polypeptide or a fragment thereof and its natural binding partner(s) or a fragment(s) thereof, by treating a patient with an agent that inhibits Gal1 activity or interactions between a Gal1 polypeptide or a fragment thereof and its natural binding partner(s) or a fragment(s) thereof. Examples of such agents include, e.g., antisense nucleic acid molecules, small RNAs, antibodies that recognize and block Gal1, a combination of antibodies that recognize and block Gal1 and antibodies that recognize and block other immune- and/or angiogenesis-related targets, compounds that block the interactions between a Gal1 polypeptide or a fragment thereof and its natural binding partner(s) or a fragment(s) thereof on an immune cell, and compounds identified in the subject screening assays).

In another embodiment, the immune response can be stimulated by the methods described herein, such that preexisting tolerance and/or immunosuppression is overcome. For example, immune responses against antigens to which a subject cannot mount a significant immune response, e.g., to an autologous antigen, such as a tumor specific antigens can be induced by administering an agent that blocks interactions between a Gal1 polypeptide or a fragment thereof and its natural binding partner(s) or a fragment(s) thereof.

In one embodiment, a blocking antibody that inhibits interactions between a Gal1 polypeptide or a fragment thereof and its natural binding partner(s) or a fragment(s) thereof can be used to enhance an immune response (e.g., to a tumor cell). In one embodiment, an autologous antigen, such as a tumor-specific antigen can be coadministered. In another embodiment, an immune response can be stimulated against an antigen (e.g., an autologous antigen) to treat a viral-associated PTLD, e.g., EBV-associated PTLD. In another embodiment, the subject agents can be used as adjuvants to boost responses to foreign antigens in the process of active immunization.

In one embodiment, immune cells are obtained from a subject and cultured ex vivo in the presence of an agent as described herein, to expand the population of immune cells and/or to enhance immune cell activation. In a further embodiment the immune cells are then administered to a subject. Immune cells can be stimulated in vitro by, for example, providing to the immune cells a primary activation signal and a costimulatory signal, as is known in the art. Various agents can also be used to costimulate proliferation of immune cells. In one embodiment immune cells are cultured ex vivo according to the method described in PCT Application No. WO 94/29436. The costimulatory polypeptide can be soluble, attached to a cell membrane, or attached to a solid surface, such as a bead.

In an additional embodiment, in performing any of the methods described herein, it is within the scope of the present invention to upregulate an immune response by administering one or more additional agents. For example, the use of other agents known to stimulate the immune response, such as cytokines, adjuvants, or stimulatory forms of costimulatory molecules or their ligands can be used in conjunction with an agent that inhibits Gal1 activity or a Gal1 polypeptide or a fragment thereof and its natural binding partner(s) or a fragment(s) thereof.

V. Administration of Agents

The immune modulating agents of the present invention are administered to subjects in a biologically compatible form suitable for pharmaceutical administration in vivo, to either enhance or suppress immune cell mediated immune responses. By "biologically compatible form suitable for administration in vivo" is meant a form of the protein to be administered in which any toxic effects are outweighed by the therapeutic effects of the protein. The term "subject" is intended to include living organisms in which an immune response can be elicited, e.g., mammals. Examples of subjects include humans, dogs, cats, mice, rats, and transgenic species thereof. Administration of an agent as described herein can be in any pharmacological form including a therapeutically active amount of an agent alone or in combination with a pharmaceutically acceptable carrier.

Administration of a therapeutically active amount of the therapeutic composition of the present invention is defined as an amount effective, at dosages and for periods of time necessary, to achieve the desired result. For example, a therapeutically active amount of a Gal1 blocking antibody may vary according to factors such as the disease state, age, sex, and weight of the individual, and the ability of peptide to elicit a desired response in the individual. Dosage regimens can be adjusted to provide the optimum therapeutic response. For example, several divided doses can be administered daily or the dose can be proportionally reduced as indicated by the exigencies of the therapeutic situation.

The agents or the invention described herein can be administered in a convenient manner such as by injection (subcutaneous, intravenous, etc.), oral administration, inhalation, transdermal application, or rectal administration. Depending on the route of administration, the active compound can be coated in a material to protect the compound from the action of enzymes, acids and other natural conditions which may inactivate the compound. For example, for administration of agents, by other than parenteral administration, it may be desirable to coat the agent with, or co-administer the agent with, a material to prevent its inactivation.

An agent can be administered to an individual in an appropriate carrier, diluent or adjuvant, co-administered with enzyme inhibitors or in an appropriate carrier such as liposomes. Pharmaceutically acceptable diluents include saline and aqueous buffer solutions. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEEP) and trasylol. Liposomes include water-in-oil-in-water emulsions as well as conventional liposomes (Sterna et al. (1984) *J. Neuroimmunol.* 7:27).

The agent may also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions of agents suitable for injectable use include sterile aqueous solutions (where water soluble) or dispersions and sterile powders for the extemporaneous preparation of sterile injectable solutions or dispersion. In all cases the composition will preferably be sterile and must be fluid to the extent that easy syringeability exists. It will preferably be stable under the conditions of manufacture and storage and preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating an agent of the present invention (e.g., an antibody, peptide, fusion protein or small molecule) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the agent plus any additional desired ingredient from a previously sterile-filtered solution thereof.

When the agent is suitably protected, as described above, the protein can be orally administered, for example, with an inert diluent or an assimilable edible carrier. As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

It is especially advantageous to formulate parenteral compositions in dosage unit form for ease of administration and uniformity of dosage. "Dosage unit form", as used herein, refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the present invention are dictated by, and directly dependent on, (a) the unique characteristics of the active compound and the particular therapeutic effect to be achieved, and (b) the limitations inherent in the art of compounding such an active compound for the treatment of sensitivity in individuals.

In one embodiment, an agent of the present invention is an antibody. As defined herein, a therapeutically effective amount of antibody (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an antibody can include a single treatment or, preferably, can include a series of treatments. In a preferred example, a subject is treated with antibody in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody used for treatment may increase or decrease over the course of a particular treatment. Changes in dosage may result from the results of diagnostic assays. In addition, an antibody of the present invention can also be administered in combination therapy with, e.g., chemotherapeutic agents, hormones, anti-angiogens, radiolabelled, compounds, or with surgery, cryotherapy, and/or radiotherapy. An antibody of the present invention can also be administered in conjunction with other forms of conventional therapy, either consecutively with, pre- or post-conventional therapy. For example, the antibody can be administered with a therapeutically effective dose of chemotherapeutic agent. In another embodiment, the antibody can be administered in conjunction with chemotherapy to enhance the activity and efficacy of the chemotherapeutic agent. The Physicians' Desk Reference (PDR) discloses dosages of chemotherapeutic agents that have been used in the treatment of various cancers. The dosing regiment and dosages of these aforementioned chemotherapeutic drugs that are therapeutically effective will depend on the particular viral-associated PTLD, e.g., EBV-associated PTLD, being treated, the extent of the disease and other factors familiar to the physician of skill in the art and can be determined by the physician.

This invention is further illustrated by the following examples which should not be construed as limiting. The contents of all references, patents and published patent applications cited throughout this application, as well as the Figures, are incorporated herein by reference.

EXAMPLES

Example 1

Anti-Gal1 Monoclonal Antibodies

Figure 2:
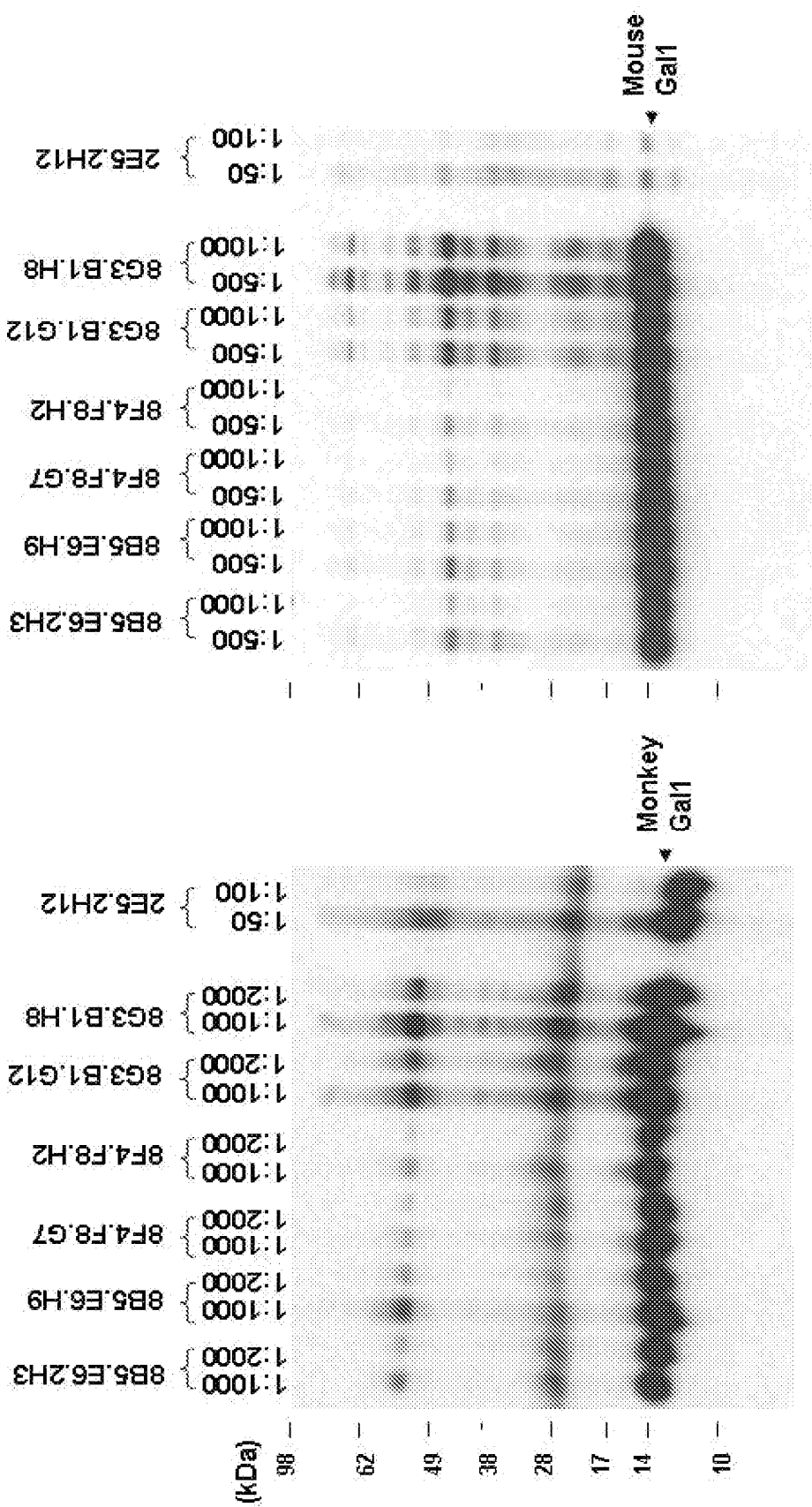
FIG. 2 shows cross-reactivity data for anti-human Gal1 monoclonal antibodies assayed against endogenous cynomologous monkey and mouse Gal1.
Figure 3:
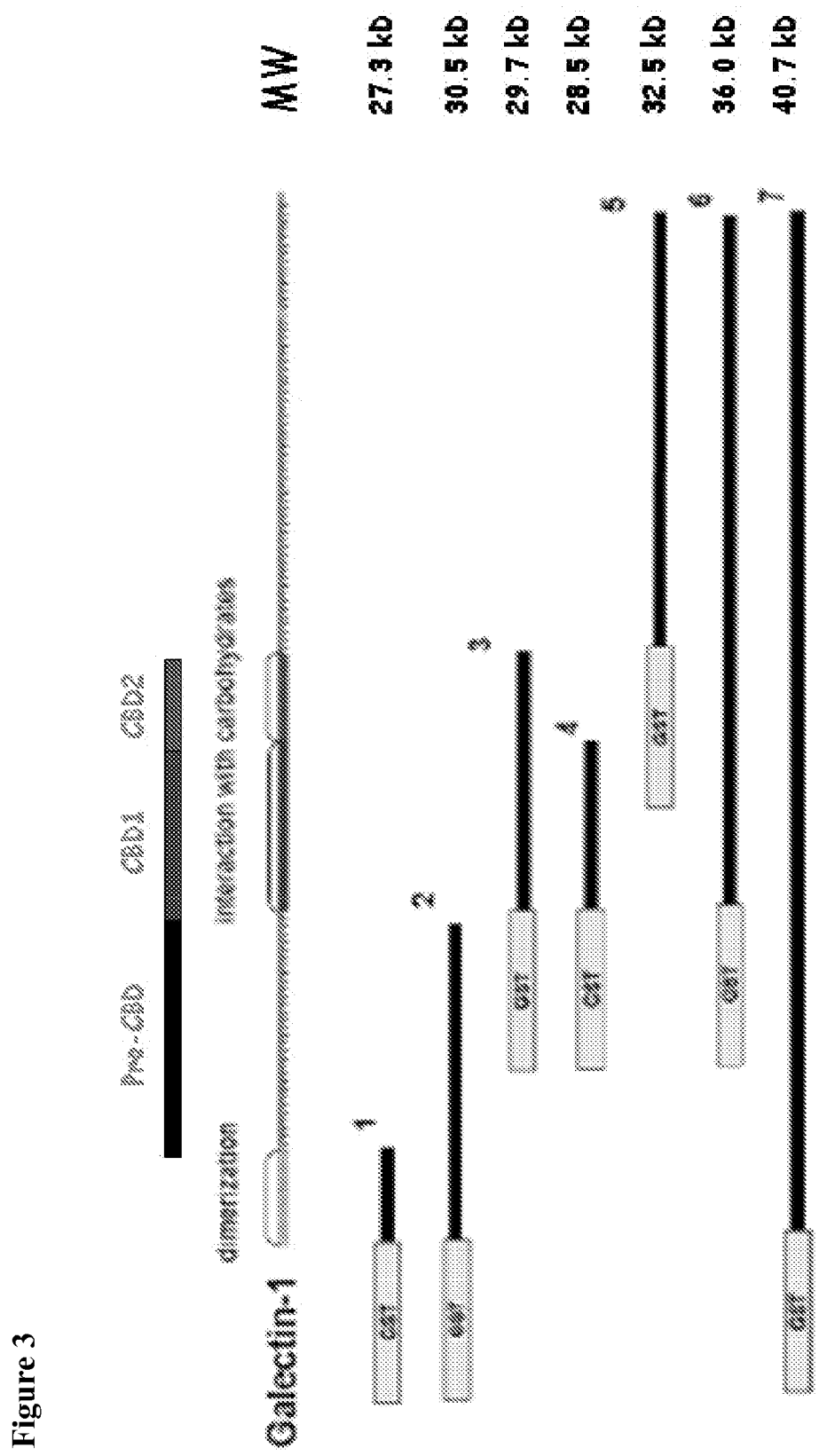
FIG. 3 shows a schematic diagram of GST-tagged human Gal1 (hGal1) fragments utilized in epitope mapping analyses of the anti-human Gal1 monoclonal antibodies.
Figure 4:
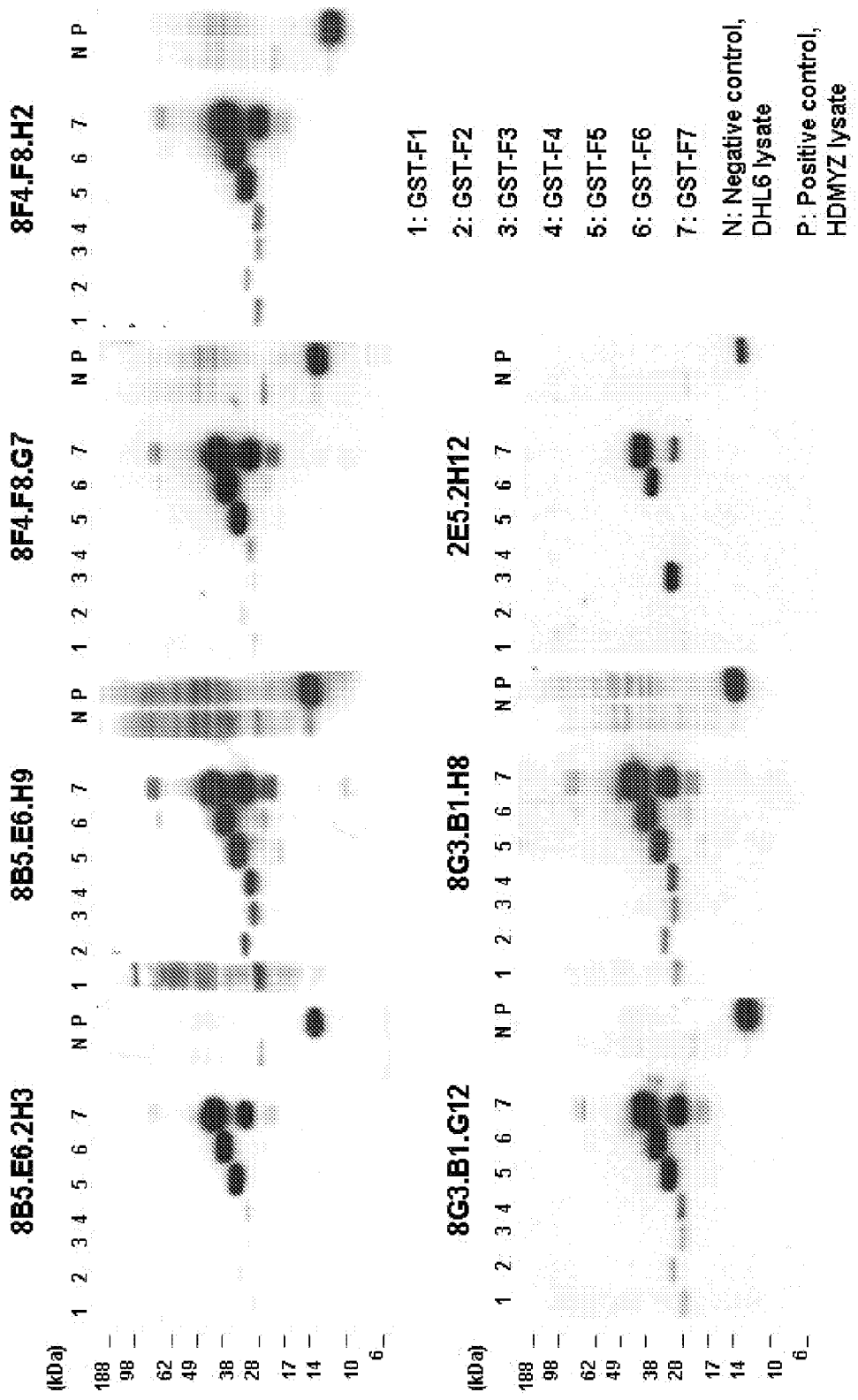
FIG. 4 shows epitope mapping data for anti-human Gal1 monoclonal antibodies.

Anti-Gal1 monoclonal antibodies were generated and reacted with human recombinant Gal1 and endogenous Gal1 in biochemical assays (FIG. 1) and in immunohistochemical analyses of primary tumors. In addition, several of the newly developed Gal1 monoclonal antibodies also cross-reacted well with endogenous Gal1 from cynomologous monkey and mouse (FIG. 2). Epitope mapping indicated that the 8B5, 8F4 and 8G3 Gal1 monoclonal antibodies all recognized a domain distal to the previously described carbohydrate-binding domain (FIGS. 3-4 and Table 1).

These antibodies (i.e., 8B5, 8F4, and 8G3) were subsequently sequenced and determined to each have the same sequence, with the light chain being lambda. Briefly, total RNA was extracted from each hybridoma and subjected to RT-PCR using constant region specific 3' primers and pools of degenerate signal sequence specific 5' primers. Amplified products were cloned and sequenced. For the heavy chain, a total of 36 clones were sequenced; and for the light chain, a total of 19 clones were sequenced. Sequence alignments yielded the same heavy and light chain sequences for all clones across all three antibodies. These sequences are presented in Table 1 below and analysis of the sequences obtained from the hybridomas is summarized in Table 2 below. In addition, hybridoma cell line 14-19 8F4-F8-G7 was deposited with the American Type Culture Collection having an address of 10801 University Boulevard, Manassas, Va. 20110-2209 U.S.A. and was received on Dec. 17, 2009 in accordance with the provisions of the Budapest Treaty on the International Recognition of the Deposit of Microorganisms for the Purposes of Patent Procedure under deposit number PTA-10535. In accordance with the United States Code Of Federal Regulations (see 37 CFR 1.808) and the United States Patent And Trademark Office's *Manual Of Patent Examination* ("MPEP") (see §2410.01), all restrictions imposed by the depositor on the availability to the public of the deposited material (except as permitted by the MPEP) will be irrevocably removed upon the granting of any patent issuing from this application or from any continuing application based thereon.

TABLE 1

Epitope mapping and sequences of anti-human Gal1 monoclonal antibodies

| mAbs | Mapping | Domain recognition |
| --- | --- | --- |
| 8B5.E6.2H3 | GST-F5; GST-F6; GST-F7 | Post-CBD |
| 8B5.E6.H9 | GST-F5; GST-F6; GST-F7 | Post-CBD |
| 8F4.F8.G7 | GST-F5; GST-F6; GST-F7 | Post-CBD |
| 8F4.F8.H2 | GST-F5; GST-F6; GST-F7 | Post-CBD |
| 8G3.B1.G12 | GST-F5; GST-F6; GST-F7 | Post-CBD |
| 8G3.B1.H8 | GST-F5; GST-F6; GST-F7 | Post-CBD |
| 2E5.2H12 | GST-F3; GST-F6; GST-F7 | CBD2 |

8B5, 8F4, and 8G3 Heavy Chain Variable (vH) DNA (SEQ ID NO: 6) and Amino Acid (SEQ ID NO: 7) Sequences*

```
          10        20        30        40        50        60        70        80        90       100
GAGGTTCAGCTGCAGCAGTCTGTGGCAGAGTTTGTGAGGCCAGGGGCCTCAGTCAGGTTGTCCTGCACAGCTTCTGGCTTCAACATTAAAAACACCTATA
  E  V  Q  L  Q  Q  S  V  A  E  F  V  R  P  G  A  S  V  R  L  S  C  T  A  S  G  F  N  I  K  N  Y  Y
                 10                      20                                    30

110       120       130       140       150       160       170       180       190       200
TACACTGGGTGAGGCAGAGGCCTGAACAGGGCCTGGAGTGGATTGGAAAGATTGATCCTGCGAATGGTAATACTAAATATTTCCCGGAGTTCCAGGGCAA
  I  H  W  V  R  Q  R  P  E  Q  G  L  E  W  I  G  K  I  D  P  A  N  G  N  I  N  K  V  P  E  F  Q  G  K
           40                               50  52 a                     60

210       220       230       240       250       260       270       280       290       300
GGCCACTATGACTGCGACACATCCTCCAACACAGTCTACCTGCACCTCAGCAGCCTGACATCTGAGGACACTGCCATCTATTACTGTGTCGATGGTTAC
  A  T  N  I  A  D  T  S  S  N  T  V  Y  L  N  L  S  S  L  T  S  E  D  T  A  T  Y  Y  Q  V  D  G  Y
        70                                  80  82 a  b  c                       90

310       320       330       340       350
TACGGCTGGTATTTCGCTGTCTGGGGCACAGGGACCACGGTCACCGTCTCCTCA
  Y  G  K  Y  F  A  V  W  G  T  G  T  T  V  T  V  S  S
           100 a                   110
```

8B5, 8F4, and 8G3, including 8F4F8G7, Light Chain Variable (vL) DNA (SEQ ID NO: 8) and Amino Acid (SEQ ID NO: 9) Sequences*

```
          10        20        30        40        50        60        70        80        90       100
CAGGCTGTTGTGACTCAGGAATCTGCACTCACCACATCACCTGGTGAAACAGTCACACTCACTTGTCGCTCAAGCACTGGGGCTGTTACAACTAGTAACT
  Q  A  V  V  T  Q  E  S  A  L  T  T  S  P  G  E  T  V  T  L  T  C  R  S  S  T  G  A  V  T  T  S  S
           9 11                           20                        27 a  b        30

110       120       130       140       150       160       170       180       190       200
ATGCCAACTGGGTCCAAGAAAAACCAGATCATTTATTCACTGGTCTAATAGGTGCTACCAACAACCGAGCTCCAGGTGTTCCTGCCAGATTCTCAGGCTC
  Y  A  N  W  V  Q  E  K  P  D  H  L  F  T  G  L  I  G  A  T  N  N  R  A  P  G  V  P  A  R  F  S  G  S
                 40                               50                              60

210       220       230       240       250       260       270       280       290       300
CCTGATTGGAGACAAGGCTGTCCTCACCATCACAGGGGCACAAACTGAGGATGAGGCAATATATTTCTGTGCTCTATGGTACAGAAACCATTTTATTTTC
  L  I  G  D  K  A  V  L  T  I  F  G  A  Q  T  E  D  E  A  I  Y  F  C  A  L  W  Y  R  N  H  F  I  F
        70                                  80                                    90

310       320
GGCAGTGGAACCAAGGTCACTGTCCTC
  G  S  G  T  K  V  I  V  L
  100                 106 a
```

8B5, 8F4, and 8G3, including 8F4F8G7, Heavy Chain Variable (vH) DNA Sequence (SEQ ID NO: 6)*

GAGGTTCAGCTGCAGCAGTCTGTGGCAGAGTTTGTGAGGCCAGGGGCCTCAGTC

AGGTTGTCCTGCACAGCTTCTGGCTTCAACATTAAA<u>AACACCTATATACACTGG</u>

GTGAGGCAGAGGCCTGAACAGGGCCTGGAGTGGATTGGA<u>AAGATTGATCCTGC</u>

<u>GAATGGTAATACTAAATATGTCCCGGAGTTCCAGGGC</u>AAGGCCACTATGACTGC

GGACACATCCTCCAACACAGTCTACCTGCACCTCAGCAGCCTGACATCTGAGGA

CACTGCCATCTATTACTGTGTCGAT<u>GGTTACTACGGCTGGTATTTCGCTGTCTGG</u>

GGCACAGGGACCACGGTCACCGTCTCCTCA

TABLE 1-continued

Epitope mapping and sequences of anti-human Gal1 monoclonal antibodies

8B5, 8F4, and 8G3, including 8F4F8G7, Light Chain Variable (vλ) DNA Sequence*

CAGGCTGTTGTGACTCAGGAATCTGCACTCACCACATCACCTGGTGAAACAGTC

ACACTCACTTGT<u>CGCTCAAGCACTGGGGCTGTTACAACTAGTAACTATGCCAAC</u>

TGGGTCCAAGAAAAACCAGATCATTTATTCACTGGTCTAATAGGT<u>GCTACCAAC</u>

<u>AACCGAGCTCC</u>AGGTGTTCCTGCCAGATTCTCAGGCTCCCTGATTGGAGACAAG

GCTGTCCTCACCATCACAGGGGCACAAACTGAGGATGAGGCAATATATTTCTGT

<u>GCTCTATGGTACAGAAACCATTTTATTTT</u>CGGCAGTGGAACCAAGGTCACTGTC

CTC

8B5, 8F4, and 8G3, including 8F4F8G7, Heavy Chain Variable (vH) Amino Acid Sequence (SEQ ID NO: 7)*

EVQLQQSVAEFVRPGASVRLSCTASGFNIK<u>NTYIH</u>WVRQRPEQGLEWIG<u>KIDPANG</u>

<u>NTKYVPEFQGK</u>ATMTADTSSNTVYLHLSSLTSEDTAIYYCVD<u>GYYGWYFAV</u>WGT

GTTVTVSS

8B5, 8F4, and 8G3, including 8F4F8G7, Light Chain Variable (vλ) DNA Sequence*

QAVVTQESALTTSPGETVTLTC<u>RSSTGAVTTSNYAN</u>WVQEKPDHLFTGLIG<u>ATNNR</u>

<u>APGVPARFSGSLIGDKAVLTITGAQTEDEAIYFC<u>ALWYRNHFI</u>FGSGTKVTVL

*CDR definitions and protein sequence numbering according to Kabat. CDR nucleotide and protein sequences are highlighted in red color or underlining in order of CDR1, CDR2, and CDR3, respectively.

TABLE 2

Summary of sequences of anti-human Gal1 monoclonal antibodies Antibody Sequence Analysis[a]

|  | H Chain | L Chain |
|---|---|---|
| CDR 1 Length | 5 aa | 14 aa |
| CDR 2 Length | 17 aa | 7 aa |
| CDR 3 Length | 9 aa | 9 aa |
| Closest Human Germline[b] | IGHV1-46 (62%) | IGLV7-46 (62%) |
| Closest Human FW1[b] | IGHV3-49 (67%) | IGLV7-46 (82%) |
| Closest Human FW2[b] | IGHV1-46 (79%) | IGLV7-43 (42%) |
| Closest Human FW3[b] | IGHV1-46 (70%) | IGlV7-46 (73%) |
| Closest Human J[b] | IGHJ6 (92%) | IGLJ1 (90%) |

[a]CDR definitions and sequence numbering according to Kabat
[b]Germline ID(s) indicated followed by % homology Example 2

Materials and Methods for Examples 3-8

A. Cell Lines

The L428 cHL cell line (L428), the SU-DHL6 DLBCL cell line and thirteen EBV-transformed B-lymphoblastoid cell lines (LCLs) (NOR-, RIC-, STA-, FOL-, LOV-, MV-, WOL-, FW-, VS-, MA-, SC-, DS-, AND DW-LCL) were maintained in RPMI-1640 supplemented with 10% FBS (Cellgro Media Tech, Manassas, Va.), 2 mM glutamine, 50 u/ml penicillin and 50 u/ml streptomycin. The 293T cell line was purchased from ATCC and maintained in Dulbecco's Modified Eagle's Medium supplemented with 10% FBS.

B. Analysis of Gal1 Transcript Abundance by Gene Expression Profiling

Gene expression profiling data were obtained for two previously described data sets (Vockerodt et al. (2008) *J Pathol* (2008) 216:83-92; Basso et al. (2005) *Nature Genetics* 37:382-90) from the Gene Expression Omnibus (accession numbers GSE2350 and GSE10821) and individually normalized by robust multiarray preprocessing. Data from Basso et al. (Basso et al. (2005) *Nature Genetics* 37:382-90) was utilized for evaluation of Gal-1 expression across a panel of 4 HL cell lines, 5 LCLs, 20 normal human B-cell samples and 42 additional B-cell neoplasms. Data from Vockerodt et al. (Vockerodt et al. (2008) *J Pathol* (2008) 216:83-92) was utilized for differential gene expression analysis of transcriptional changes induced by LMP1. This was performed within the space of top 10,000 most variable probes in the dataset, as ranked by median absolute deviation. Differences in probe intensity between LMP1-positive and LMP1-negative samples were assessed with a signal-to-noise ratio metric corrected for multiple hypothesis testing by 10,000 permutations using a previously described method (Storey et al. (2003) *Proc Natl Acad Sci USA* 100:9440-5).

C. Generation and Characterization of Anti-Human Gal1 Monoclonal Antibodies (mAbs)

Anti-human Gal1 mAbs were obtained by immunizing B6-Cg-Tg (BCL2)22Wehi-J mice (Jackson Labs, Bar Harbor, Me.) with recombinant human glutathione-s-transferase (GST)-Gal1, generating anti-Gal1 hybridomas with standard methods and purifying the Gal1 monoclonal antibody and class-matched IgG2bλ control by affinity chromatography. The specificity of the Gal1 monoclonal antibody was demonstrated by performing enzyme-linked immunosorbent assay (ELISA) of recombinant GST-Gal1 and His-Gal1 and immunoblotting recombinant human Gal1 (rGal1) and endogenous Gal1 from HL cell lines. A previously described anti-Gal1 polyclonal antibody (Juszczynski et al. (2007) *Proc Natl Acad Sci USA* 104:13134-9) was used as a positive control in all assays.

D. Immunoblotting

Expression of Gal1 protein in HL, LCL and DLBCL cell lines was determined by Western blot (WB) using the αGal1 monoclonal antibody (8F4F8G7) or the previously described polyclonal antiserum (Juszczynski et al. (2007) *Proc Natl Acad Sci USA* 104:13134-9). Knock-down of LMP2A was confirmed by WB using an αLMP2a antibody (Abcam, Cambridge, Mass.). Activity of the AP-1 components, cJun and JunB, in the HL cell line L428 and the LCLs RIC and NOR were interrogated by WB using αphospho(Ser63)-cJun (Cell Signaling Technology), αcJun (Cell Signaling Technology, Danvers, Mass.), aphospho(Ser259)-JunB (Santa Cruz Biotechnology, Inc. Santa Cruz, Calif.) and αJunB (Cell Signaling Technology). WBs were normalized using αβ-actin antibody (Sigma Aldrich, St. Louis, Mo.) to determine β-actin expression as a loading control.

E. Immunohistochemistry of Primary Tumor Specimens

A series of biopsies of newly diagnosed primary PTLDs and diffuse large B-cell lymphomas (DLBCLs) were obtained from the Brigham & Women's Hospital (BWH) archives with Institutional Review Board (IRB) approval. Immunohistochemistry (IHC) for Gal1, phospho-cJun and JunB was performed using 5 μm thick formalin-fixed, paraffin-embedded tissue sections. Antigen retrieval was conducted using a steam pressure cooker and 10 mM citrate buffer, pH 6.0 (Invitrogen, for JunB and Galectin1) or 1 mM EDTA, pH 8.0 (Invitrogen, for phospho-c-Jun) as described previously (Rodig et al. (2009) *Clin Cancer Res* 14:3338-44). All further steps were performed at room temperature in a hydrated chamber. Slides were initially treated with Peroxidase Block (DAKO USA, Carpinteria, Calif.) for 5 min to quench endogenous peroxidase activity and subsequently incubated with either αJunB (clone C37F9, 1:1000 dilution, Cell Signaling Technology), αc-Jun specific for phosphorylated serine at amino acid 63 (clone 54B3, 1:50 dilution, Cell Signaling Technology), and αgalectin1 (clone 8F4.8F.67, 1:40,000 dilution), or rabbit Gal1 antiserum in antibody diluent (DAKO) for 1 h. Thereafter, slides were washed in 50 mM Tris-Cl, 0.05% Tween 20, pH 7.4 and anti-mouse or rabbit horseradish peroxidase-conjugated antibody (Envision Plus, DAKO) was applied for 30 min. After further washing, immunoperoxidase staining was developed using diaminobenzidine (DAB) chromogen (DAKO) per the manufacturer. Slides were also counterstained with Harris hematoxylin.

F. Generation of LMP1 and LMP2A Constructs and Analysis of Gal1 Promoter Constructs with Luciferase Assays.

Total RNA from EBV-transformed LCLs was obtained using standard methods and reverse transcribed with Super™Script RT 111 (Invitrogen, Carlsbad, Calif.) and LMP1 and LMP2A gene-specific primers (AAGAAAGGTTAGTCATAG (SEQ ID NO: 10) and TGTAAGGCAGTAGTAG (SEQ ID NO: 11), respectively). LMP1 and LMP2A cDNAs were then PCR-amplified using following primer pairs: LMP1-F: GAAGAATTCGATGGAACACGACCTTGAG (SEQ ID NO: 12); LMP1-R: GACAGATCTAGGTTAG TCATAGTAGCTTAG (SEQ ID NO: 13); LMP2A-F: GAATTCTGCAGCTATGGGGTCCCTA (SEQ ID NO: 14); LMP2A-R: AGATCTGCGATCTGGTGGGCATTCT (SEQ ID NO: 15). PCR products were digested with EcoRI and BglII and ligated in the pFLAG-CMV2 vector (Sigma Aldrich, St. Louis, Mo.). The control reporter plasmid, pRL-TK, was modified by substituting the TK promoter for the phosphoglucokinase (PGK) promoter to avoid LMP1/LMP2A transactivation of the control reporter in luciferase assays. For luciferase assays, the 293T cell line was grown to 60-80% confluency on 6 well-plates and co-transfected with 150 ng/well of the previously described LGALS1 promoter pGL3 construct (Juszczynski et al. (2007) *Proc Natl Acad Sci USA* 104:13134-9), 100 ng/well of the control reporter plasmid, pRL-PGK, and 150 ng/well of LMP1-FLAG and/or LMP2A-FLAG or 150-300 ng of empty pFLAG-CMV2 vector (total amount of 550 ng of combined plasmids per well). Transfection was performed using FuGENE® 6 transfection reagent (Roche Applied Science, Indianapolis, Ind.) according to manufacturer's protocol. After 24 h of incubation, cells were lysed and luciferase activities were determined by chemiluminescence assay using the Dual Luciferase Assay kit (Promega, Madison, Wis.) and Luminoskan Ascent luminometer (Thermo Lab Systems, Franklin, Mass.) as previously described (Juszczynski et al. (2007) *Proc Natl Acad Sci USA* 104:13134-9).

G. RNA Interference-Mediated LMP2A Depletion

LMP2A siRNA oligos were designed using the Dharmacon siRNA design tool (available at the Dharmacon company website) and LMP2A mRNA (GenBank accession #Y00835) as a template. Two independent LMP2A siRNA oligos (oligo 1 target sequence: NNACACUUAACUUGACUACAA (SEQ ID NO: 16); oligo 2 target sequence: NNACUAGGAACCCAAGAUCAA (SEQ ID NO: 17)) were obtained from Dharmacon (Lafayette, Colo.) and a non-targeting siRNA control (SCR oligo) was obtained from AMBION (Cambridge, Mass.). For siRNA nucleofections, $4 \times 10^6$ of NOR-LCL cells transfected by electroporation using AMAXA nucleofector solution R containing 75 pmoles of LMP2A or SCR oligo and treated with V-001 program in the Nucleofector II device (AMAXA, Koeln, Germany). Transduction efficiency was confirmed to be above 90% by nucleofection of Cy3-labeled GAPDH oligo (Applied Biosystems/Ambion, Austin, Tex.) and subsequent flow cytometry analysis. After nucleofections, NOR cells were incubated for 72 h and whole-cell extracts were subsequently prepared for immunoblotting.

H. Analysis of AP-1 Activity and Binding to Gal1 Enhancer

Chromatin Immunoprecipitation-coupled Polymerase Chain Reaction (ChIP-PCR) was used to analyze the binding of cJun and JunB to the Gal1 enhancer region (Juszczynski et al. (2007) *Proc Natl Acad Sci USA* 104:13134-9) in EBV-transformed LCLs and the L428 cHL cell line. Assays were performed using $4 \times 10^7$ cells and a SIMPLECHIP® Enzymatic Immunoprecipitation Chromatin IP Kit (Cell Signaling Technology) according to the manufacturer's protocol. Chromatin was immunoprecipitated with rabbit monoclonal α-cJun (Clone 60A8), α-JunB (Clone C37F9) or control rabbit Ig (all obtained from Cell Signaling Technologies). Thereafter, chromatin immunoprecipitates were evaluated for Gal1 enhancer sequences by PCR using the primers specific for the previously described AP-1 dependent Gal1 enhancer (Juszczynski et al. (2007) *Proc Natl Acad Sci USA* 104:13134-9) and reference to 2% input DNA samples. PCRs were performed using Phusion Hot Start High Fidelity DNA Polymerase reagents (Finnzyme, Woburn, Mass.) according to the manufacturer's protocol (Primer Sequences: 5'-CCAAGCCCACATCTCCTC-3' (SEQ ID NO: 18), 5'-GAGGCTGCAGCTGGTTTAGT-3' (SEQ ID NO: 19)), amplified for 35 cycles and subsequently evaluated by agarose gel electrophoresis. Densitometric analysis of bands was performed using ImageJ software (National Institutes of Health, Bethesda, Md.). Additional assays of Gal1 promoter and enhancer-driven luciferase activity in EBV-transformed LCLs were performed as previously described (Juszczynski et al. (2007) *Proc Natl Acad Sci USA* 104:13134-9). In brief, NOR cells were cotransfected with 300 ng of the pGL3-Gal1-promoter constructs (without or with wild-type or mutant AP-1 dependent enhancer) and 100 ng of the control reporter plasmid, pRL-TK, and evaluated for relative luciferase activity as described (Juszczynski et al. (2007) *Proc Natl Acad Sci USA* 104:13134-9). Endogenous levels of total and active c-Jun and JunB were evaluated by immunoblotting.

I. Inhibition of PI3K and NFκB Activity

NFκB activity was inhibited by overexpressing of an IκBαsuper-repressor construct (cloned into MSCV-eGFP backbone) in the EBV-transformed LCL, NOR (Feuerhake et al. (2005) *Blood* 106:1392-9). SR-IκBα, which cannot be phosphorylated by IκK, remains in complex with the NFκB heterodimer, inhibiting NFκB translocation and activation of NFκB targets. Retroviral supernatants were generated by co-transfecting MSCV-based SR-IκBα with pKAT and VSV-G vectors into 293T cells as previously described (Juszczynski et al. (2006) *Mol Cell Biol* 26:5348-59). Supernatants containing retrovirus were harvested at 24 hours and used to infect EBV-transformed LCLs as previously described (Juszczynski et al. (2006) *Mol Cell Biol* 26:5348-59). Seventy-two or 96 hours after infection, eGFP+ cells were sorted using a B-D FACS Aria II sorter and lysates were prepared for immunoblotting. PI3K/Akt activity was inhibited using a PI3K chemical inhibitor, Ly294002 (Calbiochem). LCLs were treated with 25 μM Ly294002 or the equivalent volume of DMSO as a vehicle control for 72 hours and lysed thereafter for immunoblotting.

J. Anti-Gal1 mAb-Mediated Neutralization of Recombinant Gal1-Induced T-Cell Apoptosis Normal T cells were purified and activated with a combination of αCD3 (0.1 μg/ml) and αCD28 (0.5 μg/ml) as previously described (Juszczynski et al. (2007) *Proc Natl Acad Sci USA* 104:13134-9). Ten μM recombinant human Gal1 (rGal1) was pre-incubated with 5 μM anti-Gal1 mAb 8F4F8G7 or isotype control IgG2bλ (Rockland Immunochemicals Inc., Boyertown, Pa.) or medium alone at 37° C. for 30 min. Thereafter, rGal1+/− antibody was added to in vitro αCD3 and αCD28 activated T cells. After 16 h treatment, cells were harvested for apoptosis analysis using Annexin V-FITC and PI (BD Biosciences, San Jose, Calif.) flow cytometry as previously described (Juszczynski et al. (2007) *Proc Natl Acad Sci USA* 104:13134-9).

K. Generation of EBV-Transformed Lymphoblastoid Cell Lines (LCLs) and EBV-Specific Cytotoxic T Lymphocytes (CTLs)

After informed consent, 40-60 ml of peripheral blood from healthy donors was used to generate both EBV-transformed LCLs and EBV-specific CTLs (Straathof et al. (2005) *Blood* 105:1898-904). In brief, 5×10⁶ peripheral blood mononuclear cells (PBMCs) were incubated with concentrated culture supernatant from the marmoset B-lymphoblastoid cell line, B95-8, in the presence of 1 μg/ml cyclosporin A (Sandoz, Vienna, Austria) to establish a LCL. Subsequently, PBMCs (2×10⁶ per well of a 24-well plate) were stimulated with irradiated LCLs (at 4,000 rads) at an effector-stimulator (E/S) ratio of 40:1. After 10 days, viable cells were restimulated with irradiated LCLs (at 4:1 E/S ratio). CTLs were expanded by weekly stimulations with autologous irradiated LCLs (at 4:1 E/S ratio) in the presence of recombinant human interleukin-2 (rhIL-2, Proleukin; Chiron Emeryville, Calif.) at concentration of 40 U/ml. After 5 cycles of stimulation, CTLs were tested for EBV specificity and cryopreserved. Specificity was tested using CD107a upregulation as a surrogate marker for CTL degranulation (Betts et al. (2003) *J Immunol Methods* 281:65-78).

L. rGal1 Induced Killing of EBV-Specific CTLs

CTLs were thawed in AIM-V media (Invitrogen) containing 10 U/ml of DNAse I (Roche Applied Science, Indianapolis, Ind.) and rested in culture overnight. The next day, 5×10⁵ CTLs were treated with rGal1 alone or rGal that was pre-incubated with the anti-Gal 1 mAb (8F4F8G7) or the IgG2b isotype control at the indicated concentrations. After 4 hours, the viability of EBV-specific CD8⁺ T cells was measured using 7AAD and APC-Cγ7-labelled CD8 (BD Biosciences, San Jose, Calif.).

Example 3

Gal1 Expression in EBV-Transformed Lymphoblastoid Cell Lines and Primary Post-Transplant Lymphoproliferative Disorders (PTLDs)

Figure 5:
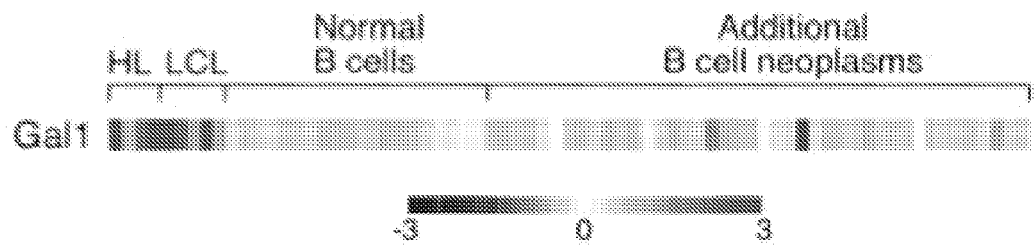
FIG. 5 shows Gal1 transcript abundance in EBV-transformed lymphoblastoid cell lines.Gal1 transcript abundance in HL lines, LCLs, normal B-cells and additional B-cell neoplasmswas assessed using publically available gene expression profiles (Kuppers R. (2009) *Nat Rev Cancer* 9:15-27). Color scale at the bottom indicates relative expression±SEM. Red connotes high-level expression; blue indicates low-level expression.
Figure 6:
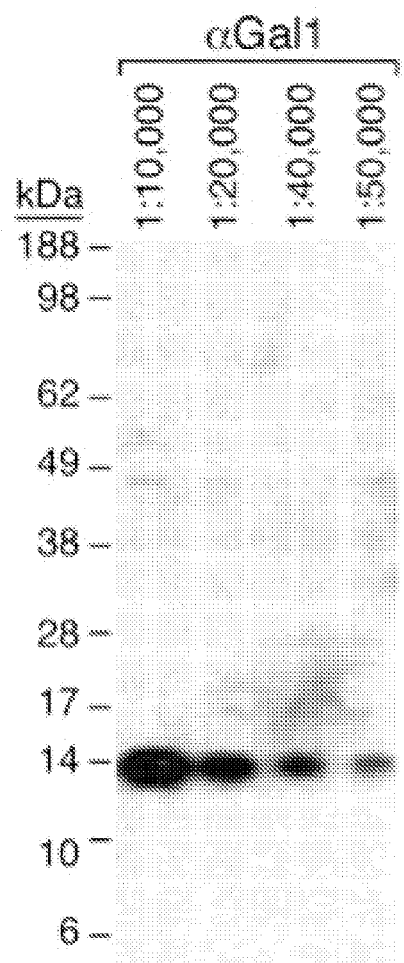
FIG. 6 shows specificity of the anti-Gal1 monoclonal antibody, 8F4F8G7, for endogenous Gal1. The newly developed Gal1 mAb specifically detected endogenous Gal1 from the cHL cell line, L428, on immunoblots.

Gal1 transcript abundance was characterized in EBV-transformed lymphoblastoid B-cell lines (LCLs), cell lines from additional B-cell malignancies including classical Hodgkin lymphoma (cHL), and additional normal B cells using publically available gene expression profiles (Basso et al. (2005) *Nature Genetics* 37:382-90). Gal1 transcripts were similarly abundant in EBV-transformed LCLs and cHL cell lines (FIG. 5). For these reasons, Gal1 protein expression was further assessed in a series of EBV-transformed LCLs using a recently developed anti-Gal1 monoclonal antibody, 8F4F8G7 (FIG. 6). All of the examined EBV-transformed LCLs expressed the ≈14 kd Gal1 protein as did the cHL cell line (FIG. 7A).

Figure 7:
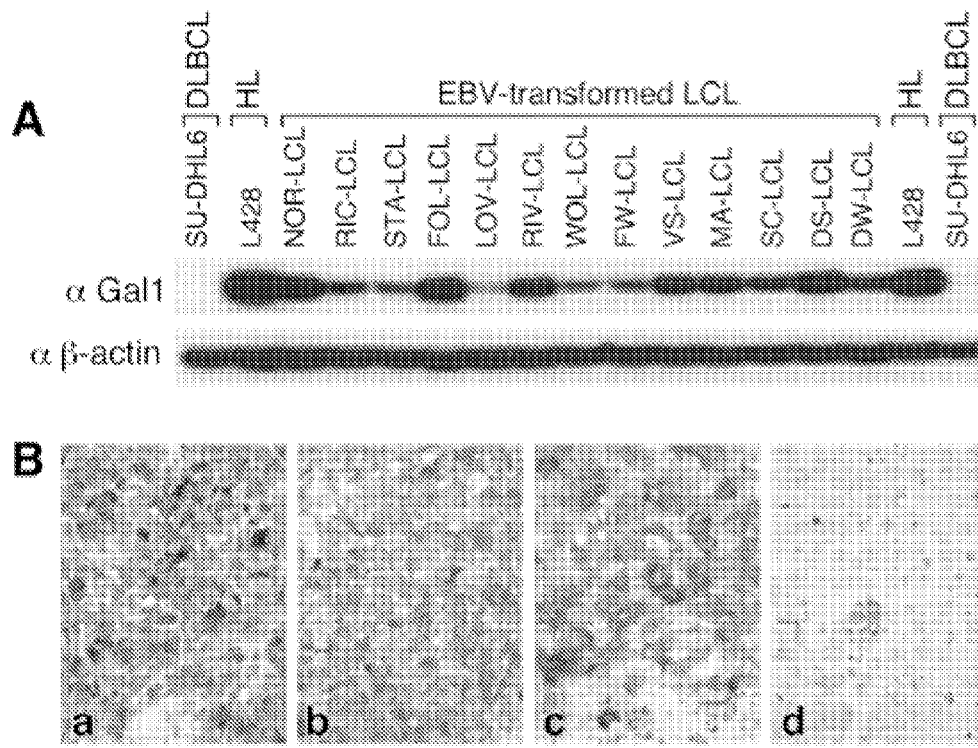
FIGS. 7A-7B shows Gal 1 expression in EBV-transformed LCLs and EBV+ primary PTLDs.
FIG. 7J shows confocal microscopy results of tumor infiltrating-CD8$^+$ T cells in the left panel, whereas the right panel shows flow cytometry results of IFN-γ-expressing tumor infiltrating-CD8$^+$ T cells. Data are the mean±SEM of three independent experiments with four mice per group.
Figure 8:
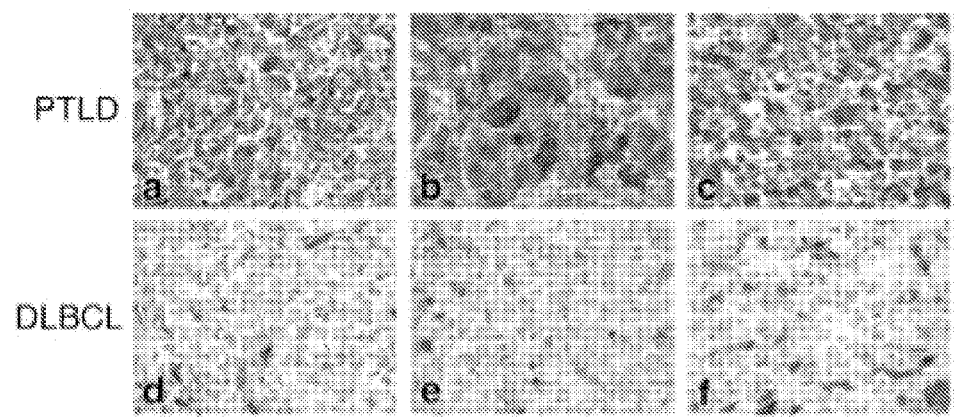
FIG. 8 shows Gal1 expression in primary post-transplant lymphoproliferative disorders (PTLDs) and DLBCLs. Gal1 immunohistochemistry (IHC) was performed with the previously described rabbit anti-Gal1 polyclonal antiserum (Juszczynski et al. (2007) *Proc Natl Acad Sci USA* 104:13134-9). Representative primary EBV+PTLDs (panels a, b, and c) and DLBCLs (panels d, c, and f) are shown. Original magnifications: ×1000.

A series of primary EBV+PTLDs was next evaluated for Gal1 expression by immunohistochemical staining; 76% (13/17) of primary EBV+PTLDs were Gal1+ whereas only 4% (3/64) of primary DLBCLs expressed Gal1 (FIG. 7B and Table 3). Similar results were obtained with the Gal1 monoclonal antibody (8F4F8G7, FIG. 7B and Table 3) and the previously described Gal1 antiserum (FIG. 8, (Juszczynski et al. (2007) *Proc Natl Acad Sci USA* 104:13134-9)).

TABLE 3

Immunohistochemical analysis of Gal1 expression in primary EBV+ PTLDs and DLBCLs. Tumors were evaluated by immunohistochemistry with the Gal1 mAb, 8F4F8G7, at 1:40,000.

|  | Gal1+ | Gal1− | % Gal1+ |
|---|---|---|---|
| EBV+ PTLD | 13 | 4 | 76 |
| DLBCL | 3 | 64 | 4 |

Example 4

AP-1 Dependent Gal1 Expression in EBV-Transformed LCLs and Primary PTLDs

Figure 9:
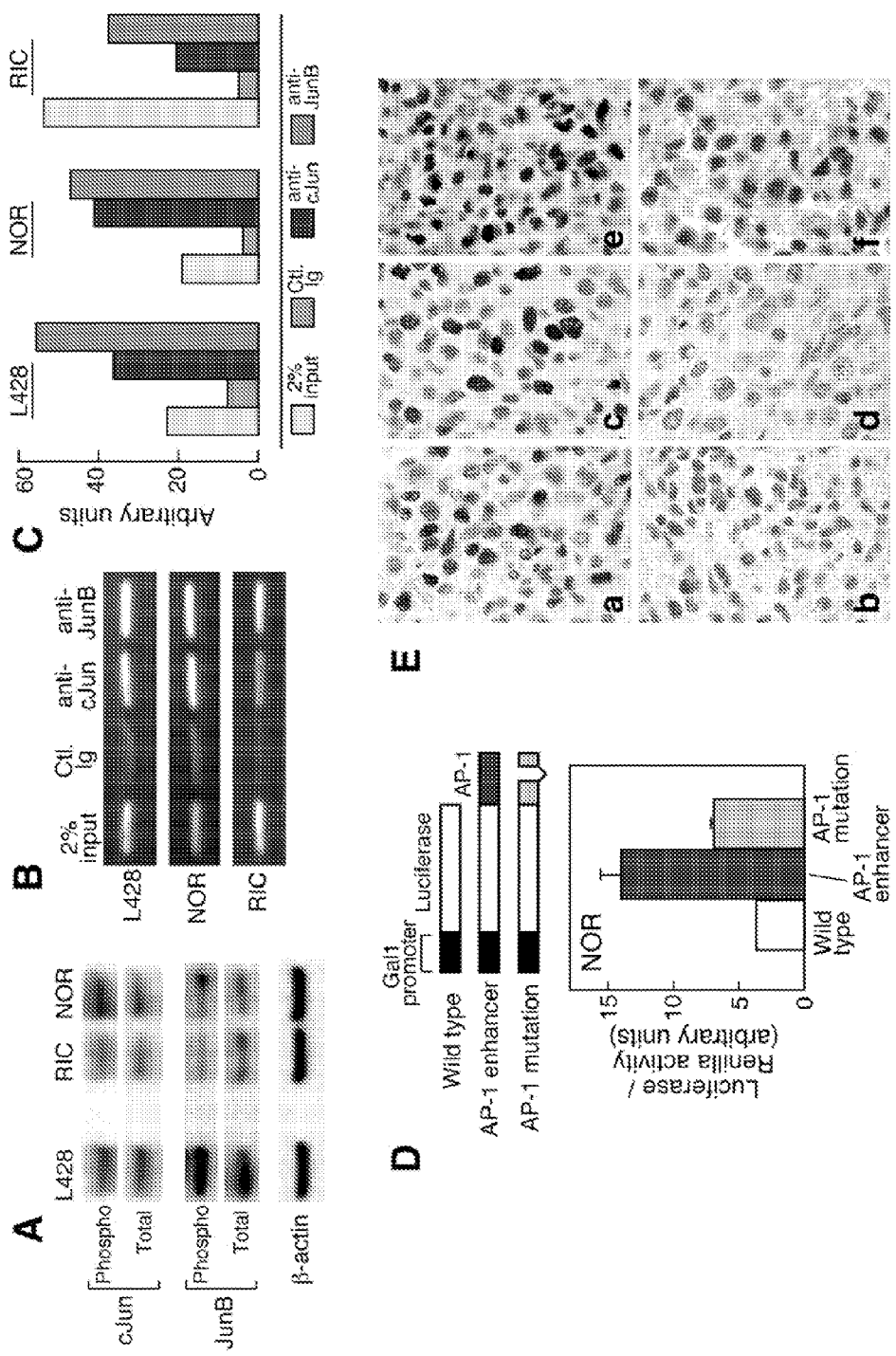
FIGS. 9A-9E show AP-1 dependent Gal1 expression in EBV-transformed LCLs and primary PTLDs.

It was previously found that Gal1 expression in classical Hodgkin lymphoma (cHL) was mediated, in part, by an AP-1 dependent Gal1 enhancer (Juszczynski et al. (2007) *Proc Natl Acad Sci USA* 104:13134-9). Because LMP1 and LMP2A both activate the AP-1 pathway and promote the formation of cJun/JunB heterodimers (Kieser et al. (1997) *Embo J* 16:6478-85; Chen et al. (2002) *J Virol* 76:9556-61; Song et al. (2004) *Cell Signal* 16:1153-62), the role of the AP-1 dependent Gal1 enhancer in EBV-transformed LCLs was assessed. The abundance and phosphorylation of the AP-1 signaling components, cJun and JunB, was first assessed in representative EBV-transformed LCLs (NOR and RIC) by immunoblotting. Total and phosphorylated cJun and JunB were readily detectable in the LCLs and the control cHL cell line (L428) (FIG. 9A). Thereafter, it was confirmed that cJun and JunB both bound to the previously described Gal1 enhancer (Juszczynski et al. (2007) *Proc Natl Acad Sci USA* 104: 13134-9) in LCLs by ChIP-PCR (FIG. 9B). Densitometric analysis of ChIP-PCRs revealed that JunB bound Gal1 enhancer regions at higher levels than cJun, highlighting the likely role of JunB as a regulator of Gal1 expression. In addition, LCL luciferase activity driven by the Gal1 promoter alone or in tandem with the Gal1 enhancer element with an intact or mutated AP-1 binding site was assessed (Juszczynski et al. (2007) *Proc Natl Acad Sci USA* 104:13134-9). Although the Gal1 promoter alone was active in the NOR LCL cell line, the AP-1-containing enhancer element increased Gal1-driven luciferase activity (≈3-fold) in an AP-1 dependent manner (FIG. 9D).

Having characterized the AP-1-dependent nature of Gal1 expression in EBV-transformed LCLs, AP-1 activity was next evaluated in a cohort of primary PTLD tumor specimens. Immunohistochemistry revealed detectable to high-level phospho-cJun expression in all PTLD tumors analyzed (15/15) (FIG. 9E, panels b, d, and f). This was in contrast to primary DLBCLs, which was previously found to be largely negative for phospho-cJun staining (Rodig et al. (2009) *Clin Cancer Res* 14:3338-44). Immunohistochemical analysis of JunB revealed uniformly strong nuclear staining in all PTLD tumors (15/15). (FIG. 9E, panels a, c, and e). Together, these data highlight the role of the AP-1 dependent Gal1 enhancer and respective AP-1 components in Gal1 expression in EBV-transformed LCLs and primary PTLDs.

Example 5

Gal1 Promoter Activity in EBV-Transformed LCLs is Driven by LMP-1 and LMP-2a

Figure 10:
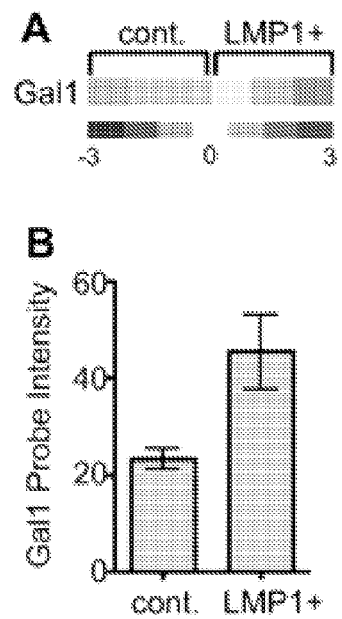
FIGS. 10A-10B show Gal1 transcript abundance in LMP1-expressing CD10+ germinal center B cells. Gal1 transcript abundance in normal CD10+ germinal center B-cells with and without LMP1 transduction was assessed using publically available gene expression profiles (Vockerodt et al. (2008) *J Pathol* (2008) 216:83-92). Gal1 induction is shown on a heat map, with red indicating high expression and blue indicating low expression in FIG. 10A.
Figure 11:
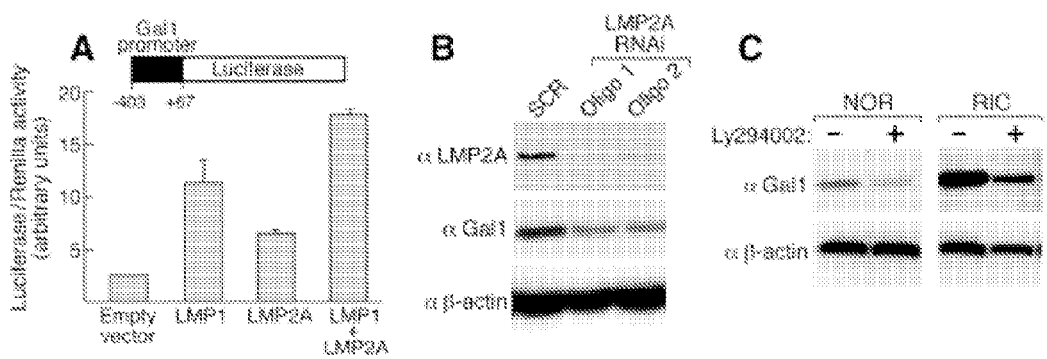
FIGS. 11A-11C show induction of Gal1 expression by LMP1 and 2A.

Given the pivotal role of the EBV latency genes, LMP-1 and LMP-2a, in EBV-induced B-cell transformation (Thorley-Lawson, D A. (2001) *Nature Reviews Immunology* 1:75-82; Kulwichit et al. (1998) *Proc Natl Acad Sci USA* 95:11963-8; Merchant et al. (2001) *Int Rev Immunol* 20:805-35), it was asked whether LMP-1 and LMP-2a modulated Gal1 expression. First, Gal1 transcript abundance in control and LMP-1-transduced normal CD10+human germinal center B (GCB) cells was compared using publically available gene expression profiles (Vockerodt et al. (2008) *J Pathol* 216:83-92) and it was found that Gal1 was ≈2-fold more abundant in LMP-1-transduced GCB cells (FIG. 10). Thereafter, the respective roles of LMP-1 and LMP-2a in Gal 1 transcriptional activation was evaluated by co-transfecting LMP-1 and/or LMP-2a and a Gal1 promoter-driven luciferase reporter into 293T cells and evaluating Gal1-driven luciferase activity. Expression of LMP1 or LMP2a increased Gal1-driven luciferase activity by ≈4.5- and 2.5-fold, respectively, and co-expression of both LMP proteins was additive (FIG. 11A). In complementary studies, siRNA-mediated LMP2a depletion markedly decreased Gal1 expression in an EBV-transformed LCL (NOR) (FIG. 11B). Taken together, the data directly implicate the EBV proteins, LMP-1 and LMP-2a, in the transcriptional activation of Gal1.

Figure 12:
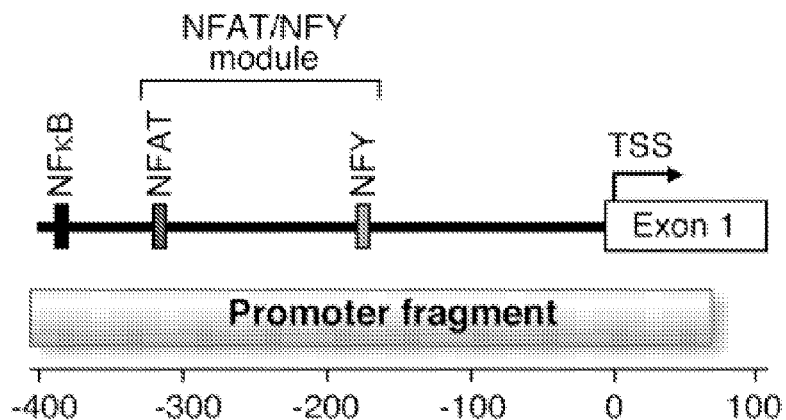
FIG. 12 shows regulatory element analysis of the Gal1 promoter. Analysis of transcription factor binding motifs and modules within the Gal1 promoter region revealed a single NFκB binding site, and a NFAT/NF-Y module. The Gal1 promoter region included in the luciferase constructs (FIGS. 11A-11C) is shown in blue relative to the transcription start site (TSS).

An analysis of the regulatory motifs and modules within the Gal1 promoter region was performed and a candidate NFκB binding sitea nd a NFAT/NFY module were identified (FIG. 12); both represent binding sites for transcription factors that can be activated by LMP/LMP2a directly (NFκB) or indirectly (NFAT and NFY activation by PI3K/Akt). Having identified these putative transcription factor binding sites in the Gal1 promoter, inhibitors of NFκB and PI3K/Akt activity were utilized to assess the potential roles of these signaling pathways in Gal 1 induction. Overexpression of an IκB super-repressor construct in an LCL cell line (NOR)decreased the abundance of known NFκB target genes, but had no effect on Gal1 expression. In contrast, treatment of two EBV-transformed LCLs (NOR and RIC) with a chemical inhibitor of PI3K activity (Ly294002) reduced Gal1 expression (FIG. 11D). Taken together, these data indicate that PI3K, but not NFκB, signaling augments Gal1 expression in EBV-transformed LCLs.

Example 6

Figure 13:
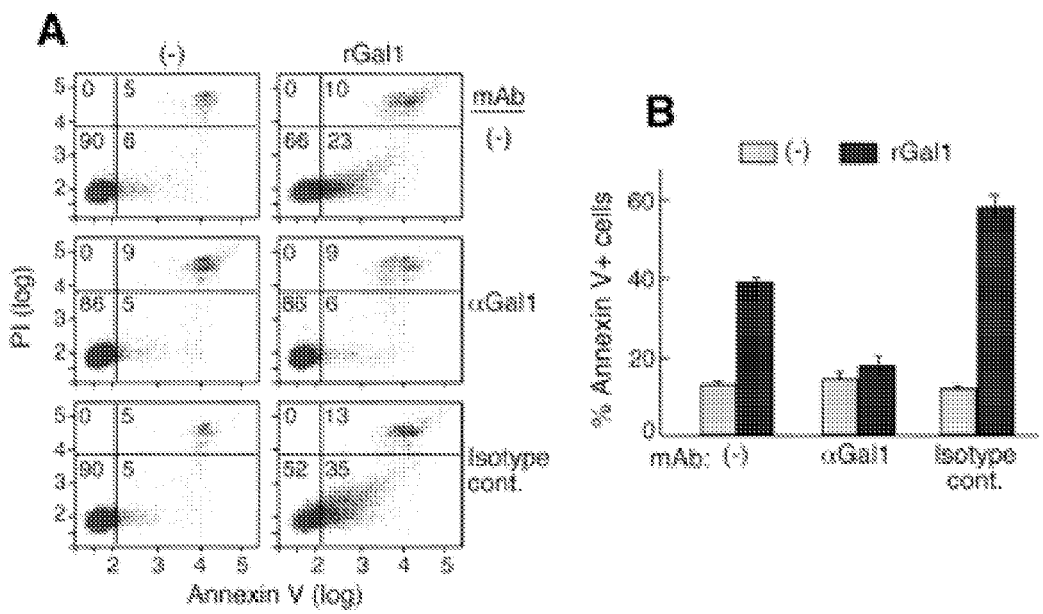
FIGS. 13A-13B show the anti-Gal1 mAb 8F4F8G7 inhibits rGal1-induced apoptosis of in vitro activated T cells. Anti-CD3/CD28 activated human T cells were treated with 10 µM of rGal1 alone or 10 µM rGal1 pre-incubated with 5 µM of anti-Gal1 mAb (8F4F8G7) or an isotype-matched IgG2b control and evaluated thereafter with a flow cytometric apoptosis assay (Annexin V-FITC and PI staining). The percentage of cells in each quadrant is indicated in FIG. 13A.

Gal1 Neutralizing mAb Inhibits rGal1-Mediated Killing of EBV-Specific Cytotoxic T Cells Given the demonstrated role of Gal1 in tumor immune escape (Rubinstein et al. (2004) *Cancer Cell* 5:241-51; Juszczynski et al. (2007) *Proc Natl Acad Sci USA* 104:13134-9), neutralization of Gal1 activity may represent a novel therapeutic strategy for Gal1-expressing tumors. For this reason, high-titer neutralizing monoclonal antibodies (mAb) directed against the Gal1 protein were developed (Example 1). These Gal1 mAbs were first screened for their capacity to inhibit recombinant-Gal1 (rGal1)-mediated apoptosis of in vitro activated T cells[6]. The Gal1 monoclonal antibody, 8F4F8G7, almost completely inhibited rGal1-induced apoptosis of normal αCD3/αCD28-activated T cells whereas an isotype-matched control antibody had no effect (FIGS. 13A and 13B).

Figure 14:
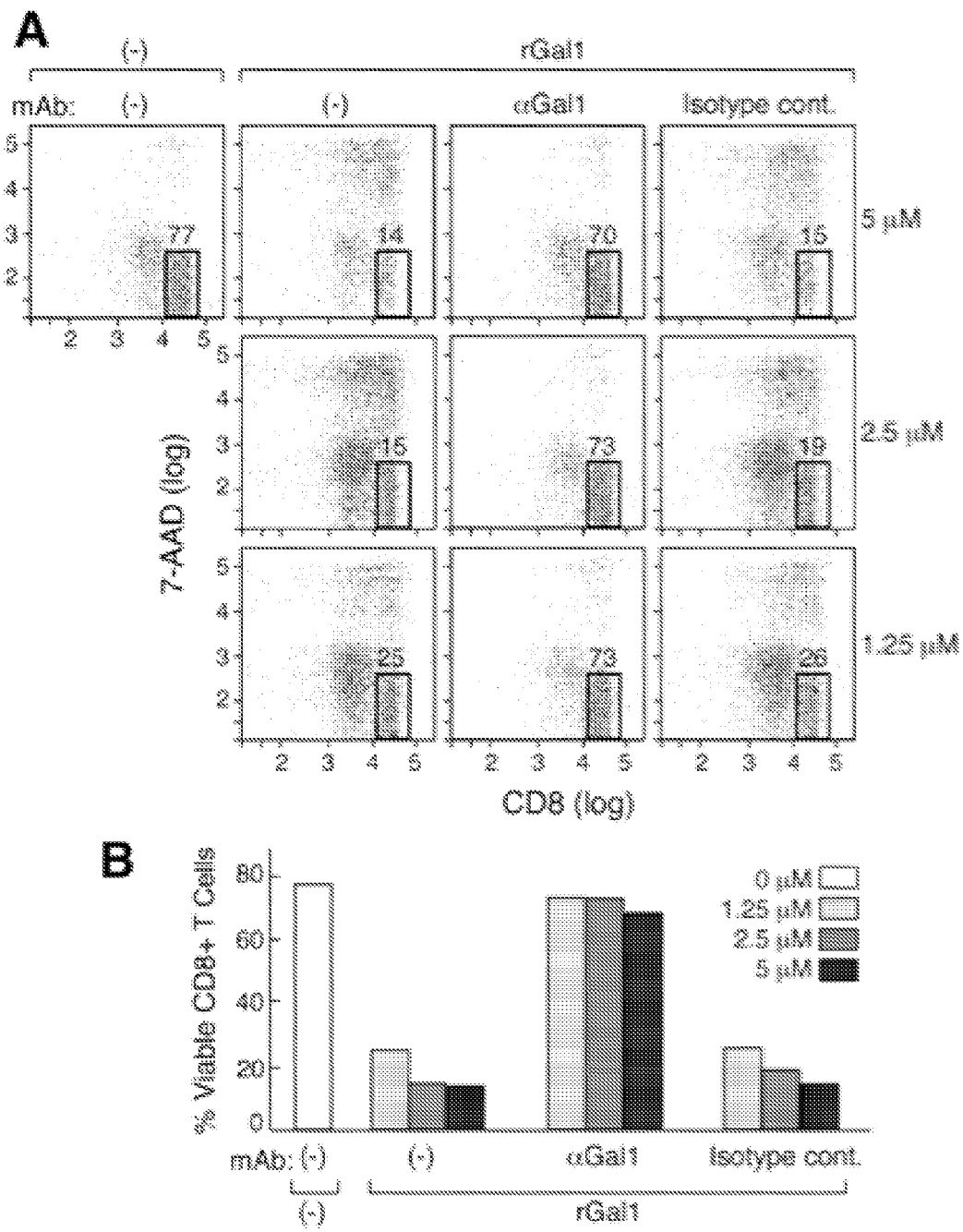
FIGS. 14A-14B show that Gal1 neutralizing mAb, 8F4F8G7, inhibits Gal1-mediated apoptosis of EBV-specific CTLs.
Figure 15:
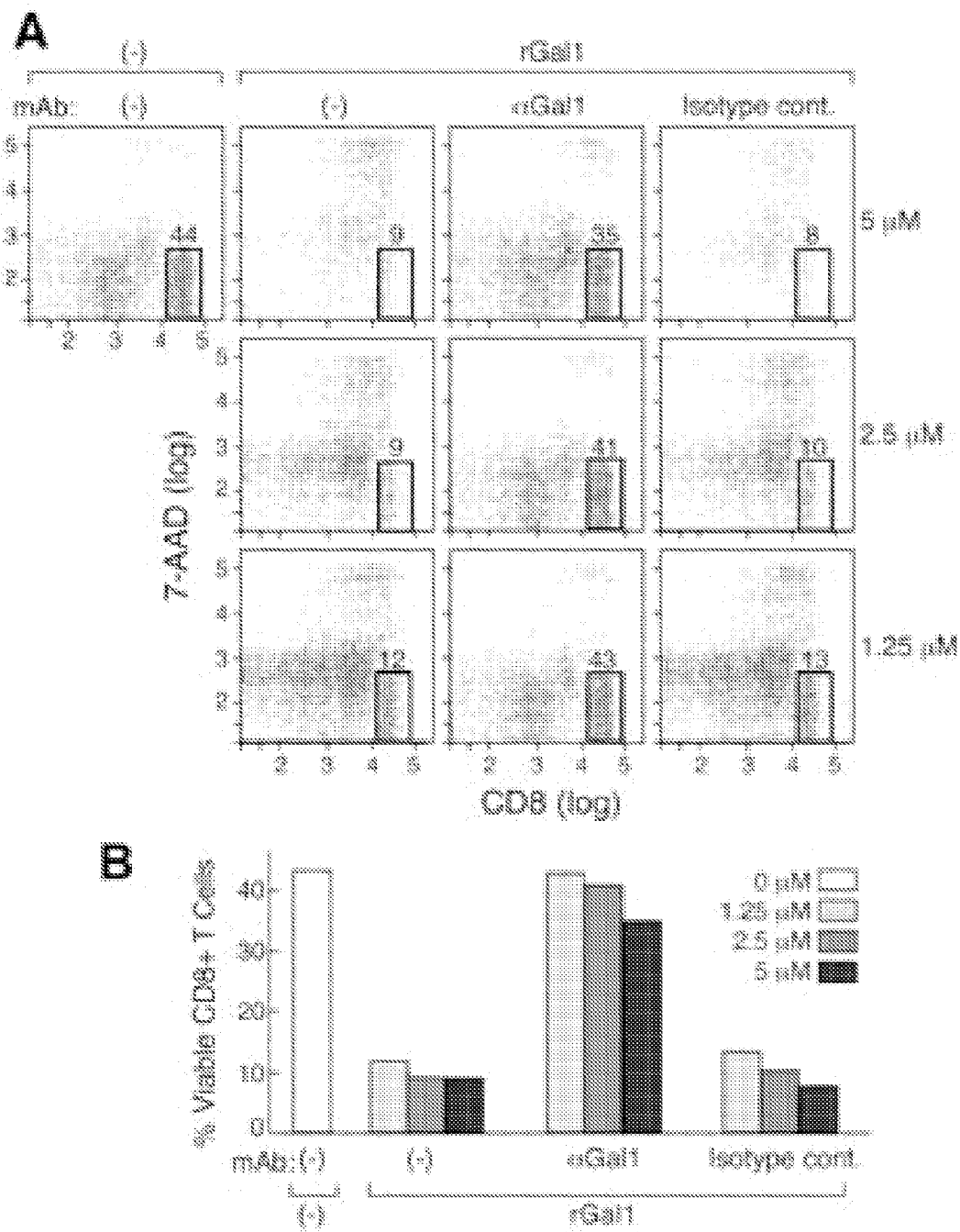
FIGS. 15A-15B show results of αGal mAb-mediated inhibition of rGal1-mediated apoptosis of EBV-specific CTLs generated from a second independent donor.

For these reasons, the effects of 8F4F8G7 on rGal 1-mediated apoptosis of EBV-specific CD8+ T cells was assessed. In these assays, rGal1 (1.25, 2.5 or 5 μM) was pre-incubated with the neutralizing Gal1 monoclonal antibody (8F4F8G7) or an isotype-matched control (IgG2bλ). Thereafter, EBV-specific, largely CD8+, T cells were cultured alone, with rGal alone, or with rGal1 pre-incubated with 8F4F8G7 or the isotype control; following treatment, the percent of viable CD8+ (7AAD−) cells was determined (FIG. 14). At all doses, rGal1 alone induced massive apoptosis of EBV-specific CD8+ T cells (FIG. 14, left panel); similar results were obtained when rGal was preincubated with isotype-matched control Ig (FIG. 14, right panel). In marked contrast, pre-incubation with the neutralizing Gal1 mAb (8F4F8G7) almost completely abrogated the cytotoxic effects of rGal1 on EBV-specific CD8+ T cells (FIG. 14, middle panel). Similar results were obtained with EBV-specific CD8+ T cells generated from additional independent donors (FIGS. 15A and 15B). Taken together, these data demonstrate that EBV-specific CD8+ T cells are exquisitely sensitive to rGal1-mediated apoptosis and that the neutralizing αGal1 monoclonal antibody, 8F4F8G7, abrogates rGal1-induced apoptosis of EBV-specific T cells. Therefore, antibody (8F4F8G7)-mediated blockade of secreted Gal1 may represent a novel immunotherapeutic strategy in EBV-associated PTLD and other Gal1 tumors.

The link between T-cell dysfunction and outgrowth of Epstein-Barr Virus (EBV)-infected B cells is well established (Tran et al. (2008) *Blood* Rev 22:261-81). Herein, it has been demonstrated that the immunomodulatory carbohydrate-binding lectin, Gal1 is selectively expressed in EBV-transformed LCLs and primary PTLDs and that Gal1 expression is enhanced by EBV-encoded latent membrane proteins and signaling via AP-1 and PI3K. Furthermore, a high-titer neutralizing Gal1 mAb has been generated that abrogates Gal1-induced apoptosis of EBV-specific cytotoxic T cells. These findings define EBV-associated Gal1 expression as a novel mechanism of viral immune evasion and highlight the potential utility of Gal1-neutralizing therapy for PTLD and other Gal1-expressing tumors.

In light of the known capacity of LMP1 and LMP2a to activate AP-1 signaling, and our previous description of the AP-1-responsiveness of Gal1 in cHL (Juszczynski et al. (2007) *Proc Natl Acad Sci USA* 104:13134-9; Rodig et al. (2009) *Clin Cancer Res* 14:3338-44), the binding of AP-1 signaling components to the Gal1 enhancer in EBV-transformed LCL cell lines aws evaluated. Both cJun and JunB bound the Gal1 enhancer in EBV-transformed LCLs, to a similar extent as in the L428 HL cell line. Luciferase assays driven by the Gal1 promoter paired with either a wild-type or mutated enhancer revealed that AP-1 binding sites were required for full enhancement of promoter activity. Furthermore, immunohistochemical investigation of AP-1 signaling components in primary PTLD tumors revealed the presence of phospho-cJun and nuclear-localized JunB in all cases, indicating constitutive AP-1 activity. These findings therefore indicate that AP-1 signaling may be a mechanism of Gal1 induction that is shared by cHL and PTLD.

Luciferase constructs containing only the Gal1 promoter were also observed to be active in an EBV-transformed cell line. As a consequence, the capacity of LMP1/LMP2a signaling to activate the Gal-1 promoter was evaluated by co-expressing LMP1 and/or LMP2a with the Gal1 promoter-driven luciferase construct in an EBV-negative cell line. LMP1 and, to a lesser extent, LMP2a increased Gal1 promoter activity and the co-expression of both antigens was additive. In order to characterize the mechanism by which LMP1/LMP2a activated Gal1 promoter activity, a detailed analysis of regulatory elements within the Gal1 promoter sequence was performed and conserved NFκB, NFAT and NFY sites were found. LMP1 and LMP2a have the potential to induce signaling through pathways that activate these transcription factors— LMP1 to activate NFκB and both LMP1 and LMP2a to activate NFAT and NFY via PI3K/Akt signaling (Toker et al. (2006) *Cancer Res* 66:3963-6; Lee et al. (2005) *J Cell Physiol* 205:270-7). Although molecular or chemical inhibition of NFκB activity had no effect on Gal1 expression, chemical inhibition of PI3K markedly decreased Gal1 abundance. Therefore, LMP1/LMP2a-associated PI3K signaling supports Gal1 expression, likely via subsequent activation of NFAT and NF-Y. Taken together, these data indicate that Gal1 may be another gene that is regulated by interactions of NFAT and AP-1 (Macian et al. (2001) *Oncogene* 20:2476-89).

Evidence presented here and in previous investigations indicate that Gal1 is an important mediator of immune evasion in PTLD, cHL (Juszczynski et al. (2007) *Proc Natl Acad Sci USA* 104:13134-9), and melanoma (Rubinstein et al. (2004) *Cancer Cell* 5:241-51) and that the lectin is also expressed at high level in additional lymphoid malignancies including anaplastic large cell lymphoma (Rodig et al. (2009) *Clin Cancer Res* 14:3338-44) and MLL-ALLs (Juszczynski et al. (2010) *Clin Cancer Res* in press). For these reasons, Gal1 represents an attractive target for directed therapy via mAb-mediated neutralization. Of note, there are ongoing clinical trials of mAb-mediated blockade of other immune-inhibitory molecules such as PD-1 (Hirano et al. (2005) *Cancer Res* 65:1089-96) and CTLA-4 (Leach et al. (1996) *Science* 271:1734-6). However, unlike neutralization of CTLA-4, which is associated with autoimmune-related side-effects in vivo (Sanderson et al. (2005) *J Clin Oncol* 23:741-50), Gal1-neutralization is expected to be well tolerated in vivo due to the lack of any observable autoimmune phenotype in Gal1 knock-out mice (Poirier et al. (1993) *Development* 119: 1229-36). Furthermore, PTLD is an excellent model system for testing the utility of a Gal1-neutralizing antibody because LMP-specific cytotoxic T-cells are sensitive to Gal1-induced apoptosis (Smith et al. (2009) *J of Virology* 83:6192-8).

Therefore, Gal1 specific mAbs were developed and screened for their ability to neutralize rGal1-induced apoptosis of EBV-specific cytotoxic T-cells. Gal1 mAbs that exhibited high affinity and specificity for recombinant and endogenous Gal1 were first evaluated for their capacity to abrogate rGal1-mediated activated T-cells in vitro. The most effective neutralizing Gal1 mAb8F4F8G7, was then assayed against highly Gal1-susceptible, EBV-specific cytotoxic T-cells. Incubation of EBV-specific donor cytotoxic T-cells with 8F4F8G7 dramatically reduced rGal1-mediated apoptosis compared to the isotype control antibody, highlighting the potential utility of this mAb in Gal1-neutralizing therapy.

In summary, it has been shown that EBV-transformed LCLs and primary PTLDs exhibit strong expression of Gal1 that is promoted by the LMP1 and LMP2a viral antigens through PI3K/Akt and AP-1 signaling. In addition, a Gal1-neutralizing mAb that protects against rGal1-induced apoptosis of EBV-specific cytotoxic T-cells was generated. Taken together, these results demonstrate a novel mechanism for EBV-induced immune evasion in PTLD and indicate an associated targeted therapeutic strategy for this disease and other Gal1-expressing malignancies.

Example 7

Materials and Methods for Examples 8-12

A. Mice

Lgals1$^{-/-}$ mice (C57BL/6) were provided by F. Poirier. Swiss N:NIH(S)nu (nude) mice were obtained from the University of La Plata and B6/Rag$^/$ mice were from Jackson Lab. Mice were bred at the animal facilities of the Institute of Biology and Experimental Medicine according to NIH guidelines. Protocols were approved by the respective Institutional Review Boards.

B. Cells

KS-1 mm is a spontaneously immortalized cell line obtained from a KS biopsy as described (Albini et al. (2001), *Cancer Res* 61, 8171-8178). All other cell lines were obtained from the ATCC. Primary HUVEC were maintained in M-199 medium supplemented with 20% FCS, EGF (10 ng/ml), bFGF (10 ng/ml), VEGF (20 ng/ml) (all from R&D) and used between passage 2 and 5. Gal1-specific shRNA was designed and cloned into the pSIREN-RetroQ vector as described in Juszczynski et al. (2007) *Proc Natl Acad Sci USA* 104, 13134-13139.

C. Glycophenotypic Analysis, Galectin Binding and Segregation Assays

For glycophenotyping, ECs were incubated with biotinylated L-PHA, LEL, SNA, MAL II, PNA and HPA (all from Vector). Recombinant Gal1 was purified as described in Ilarregui et al. (2009) *Nat Immunol* 10, 981-991. For binding assays, ECs were incubated for 1 h at 4° C. with dyLight 488-labeled galectins in the absence or presence of lactose, sucrose, anti-Gal1 or isotype control mAb or following transfection with GnTS, GCNT1 or scrambled siRNA. Cells were analyzed on a FACSAria (BD Biosciences). For segregation, ECs were treated with Gal1 for 1 h, fixed and incubated for 1 h with anti-human VEGFR2 antibody (55B11; Cell Signaling) as described in Ilarregui et al. (2009) *Nat Immunol* 10, 981-991. Cells were analyzed on a Nikon laser confocal microscope (Eclipse E800).

D. Angiogenesis Assays

HUVEC transfected or not with specific siRNA or pre-incubated with signaling pathway inhibitors were exposed to VEGF or Gal1 with or without lactose, sucrose, 8F4F8G7 mAb or control isotype (IgG1κ) or specific antibodies for VEGFR1 (AP-MAB0702; Abcam), VEGFR2 (AF357; R&D), VEGFR3 (AB89501; Abcam) or VEGF (MAB293; R&D). Cells were processed for proliferation, migration, invasion and tube formation assays. Tumor-associated blood vessels were identified by flow cytometry using Alexa Fluor 647-conjugated anti-CD34 antibody (RAM34; eBioscience).

E. Phospho-RTK Signaling Array, Co-Immunoprecipitation and Immunoblotting

Cells were lysed and analyzed by the human PathScan® RTK Signaling Antibody Array (Cell Signaling) following manufacturer's directions. For co-immunoprecipitation, 500 µg cell lysates were incubated with 2 µg of anti-VEGFR2 (55B11; Cell Signaling) or anti-NRP-1 (C-19; Santa Cruz Biotechnol) antibodies. The immunocomplexes were captured with protein G PLUS-Agarose (Santa Cruz Biotechnol) and processed for immunoblot analysis as described in Ilarregui et al. (2009) *Nat Immunol* 10, 981-991. Equal amounts of protein were resolved by SDS-PAGE, blotted onto nitrocellulose membranes (GE Healthcare) and probed with anti-IκB-α (C21), anti-Erk1/2 (C14), anti-phospho-Erk1/2 (E4) or anti-actin (I-19) (all from Santa Cruz Biotechnol) or anti-Akt (9272), anti-phospho-Akt (9271S), anti-VEGFR2 (55B11), anti-phospho-VEGFR2 (19A10) (all from Cell Signaling) or anti-HIF-1α (mgc3; ABR BioReagent) antibodies or a rabbit anti-Gal1 IgG (1.5 µg/ml) obtained as described in Tlarregui et al. (2009) *Nat Inmmunol* 10, 981-991.

F. In Vivo Tumor Models

Wild-type KS cells or shRNA clones ($5 \times 10^6$ cells) were injected subcutaneously into 6- to 8-week old nude mice. Wild-type B16 cells or shRNA clones ($2 \times 10^5$ cells) were injected into 6- to 8-week old B6 or B6/Rag$^{-/-}$ mice and tumor development was monitored as described in Rubinstein et al. (2004) *Cancer Cell* 5, 241-251. Treatments with 8F4F8G7 mAb or control isotype (2.5, 7.5 or 15 mg/kg; i.p. injections every three days) were initiated when tumors reached 100 mm$^3$. Mice were sacrificed when tumors reached a volume greater than 2 cm$^3$. At 2 weeks after tumor challenge, lymph node cells ($5 \times 10^5$ cells/well) were restimulated for 72 h with $1 \times 10^4$ irradiated (4,000 rads) B16 cells and were analyzed for proliferation and cytokine production. For adoptive transfer, splenic T cells ($5 \times 10^6$) from tumor-bearing mice were labeled with CFSE (Molecular Probes) and injected through the tail vein into tumor-bearing recipient mice treated with 8F4F8G7 or control mAb. In related studies, fluorescent beads (3 µm; BD Biosciences), rather than splenic T cells, were injected into tumor-bearing animals treated with 8F4F8G7 or control antibody. CFSE cells or PerCP-labeled beads were analyzed after 24 h or 15 min respectively by flow cytometry in tumor parenchyma and spleen.

G. Immunohistochemistry and Confocal Microscopy

For immunostaining, mice were anesthetized and cardiac-perfused with PBS and 4% paraformaldehyde and tissues were embedded in OCT. To visualize the vasculature, mice were intravenously injected with FITC-conjugated *Griffonia simplicifolia* Lectin-1 (GLS-1$_{B4}$; Vector) prior to heart perfusion and fixation. Pericyte maturation was assessed using antibodies specific for αSMA (1A4; Dako), desmin (D33; Dako), PDGFRβ (APBS; Biolegend) and Rgs5 (HPA001821; Prestige Sigma). The fraction of pericyte coverage was calculated as the ratio of αSMA area to the FITC-GLS-1$_{B4}$ or CD31 stained area using a specific anti-CD31 antibody (Mec13.3; BD Biosciences). For immunoperoxidase staining, paraffin-embedded human tumor sections were incubated with anti-CD31 (JC/70A; Dako) and anti-Gal1 antibodies as described in Juszczynski et al. (2007) *Proc Natl Acad Sci USA* 104, 13134-13139 using the Vectastain Elite ABC kit (Vector). Studies with patient biopsies were subjected to Institutional Review Boards approval (CEMIC and IBYME). Hypoxia was detected after injection of pimonidazole hydrochloride for 30 min following immunostaining with Hypoxyprobe-1 plus kit (Natural Pharmacia International).

H. Generation of Anti-Galectin-1 mAb

The neutralizing Gal-1 mAb was generated and characterized as described herein.

I. Statistical Analysis

Prism software (GraphPad) was used for statistical analysis. Two groups were compared with the Student's-t test for unpaired data. Two-way ANOVA and Dunnett's or Tukey post-tests were used for multiple comparisons. Nonparametric analysis was performed using Mann-Whitney Utest. P values of 0.05 or less were considered significant.

J. Reagents

DyLight 488-conjugated Gal1 (488-Gal1) was obtained using DyLight labeling kit (Thermo Scientific). Inhibitors of Jak2-STAT3 (AG490; 5 µM), Jnk-SAP (SP600125; 20 p38 (SB202190; 10 µM), HIF-1α (3 µM) and β-glycosylation (benzyl-α-GalNAc; 2 mM) were from Calbiochem. Inhibitors of Erk1/2 (U0126; 5 µM), PI(3)K-Akt (Ly294002; 2 µM) and NF-κB (BAY 11-7082; 1 ROS(N-acetyl-cysteine; NAC), N-glycosylation (swainsonine; 3 lactose or sucrose (30 mM) were from Sigma. PNGase F (25 U/µg protein) was from New England Biolabs. Recombinant cytokines including IL-10 (50 ng/ml), IL-17 (5 ng/ml), TGF-β$_1$ (3 ng/ml), IFN-γ (50 ng/ml), VEGF (20 ng/ml), bFGF (10 ng/ml) were from R&D. TNF (20 ng/ml) was from Sigma. Biotinylated lectins, including L-PHA (2 µg/ml), LEL (1 SNA (5 µg/ml), MAL II (10 µg/ml), PNA (10 µg/ml) and HPA (10 µg/ml) were purchased from Vector Labs and incubated in buffer containing 150 mM NaCl, 10 mM HEPES and 1% BSA (Sigma). ON-TARGETplus SMART siRNA pools against GnT5, GCNT1, VEGFR2, NRP-1, VEGF, HIF-1α and scrambled were obtained from Dharmacon. Transfections were performed by Lipofectamine-RNAiMAX (Invitrogen) following manufacturer's directions. Recombinant Gal3 and Gal8 were purified as described in Acosta-Rodriguez et al. (2004) *J Immunol* 172, 493-502 and Cardenas Delgado et al. (2010) *FASEB J* [Epub ahead of print].

K. Cells and Knockdown Clones

The A375 and LNCaP cell lines were cultured in RPMI-1640 GlutaMax complete medium supplemented with 10% FCS and the B16-F0 and 4T1 cells were cultured in DMEM supplemented with 5% FCS (all from Gibco). Retroviral shRNA delivery was performed using RetroPack PT-67 packaging cell line (BD Biosciences) according to manufacturer's instructions. After infection, cells were subjected to puromycin selection (5 µg/ml) and clones were obtained by limited dilution. For the antisense strategy, subconfluent KS cells were transfected with the pcDNA6/Gal1 antisense vector created as described in Rubinstein et al. (2004) *Cancer Cell* 5, 241-251 and cloned by limited dilution. The in vitro growth of relevant clones was measured by the MTS assay (Promega).

L. Angiogenesis Assays

The formation of capillary-like tubular structures was assessed in Matrigel-coated plates essentially as described in Albini et al. (2001), *Cancer Res* 61, 8171-8178. In brief, HUVEC ($3 \times 10^4$ cells/ml) transfected or not with specific siRNA or pre-incubated with signaling pathway inhibitors were seeded on Matrigel with our without Gal1 (0.1 to 3 µM) or VEGF (20 ng/ml) with or without lactose, sucrose, 8F4F8G7 mAb (0.5 μM) or isotype control (IgG1κ) or blocking antibodies specific for VEGFR1 (5 μg/ml), VEGFR2 (2 μg/ml), VEGFR3 (10 μg/ml) or VEGF (10 μg/ml). Cells were incubated at 37° C. for periods ranging from 0 to 24 h and were visualized by phase-contrast microscopy. In another set of experiments, conditioned medium from hypoxic or normoxic KS cells infected or not with a retroviral vector containing Gal1 shRNA was assessed on HUVEC transfected or not with GnT5, GCNT1 or scr siRNA (100 nM). Capillary-like tubular structures were scored by counting the number of tubules (closed areas) per well in a phase-contrast microscope (Nikon E-100). For migration assays, HUVEC ($4 \times 10^4$/well) transfected or not with specific siRNA were resuspended in M199 medium supplemented with 1% FCS. Cells were placed into the top chamber of the insert while the bottom well was filled with Gal1 or VEGF in the absence or presence of lactose, sucrose, 8F4F8G7 mAb or isotype control. After 24 hours, inserts were stained with crystal violet (Sigma) and analyzed in an inverted microscope. For each filter, 4 images were collected and cells were counted with the ImageJ software v1.34 (NIH).

For proliferation assays, HUVEC that were transfected or not with specific siRNA and cultured in complete M199 medium were trypsinized, harvested and seeded in 96-well microtiter plates ($1 \times 10^3$ cells/well). Cells were pre-incubated for 1 hour at 37° C. with lactose, sucrose or signaling pathway inhibitors and then exposed to Gal1. After 24 hours, cells were incubated for an additional 24 hours in the presence of 0.8 μCi [$^3$H]-thymidine (NEN Dupont). Cells were then harvested and radioactivity was measured in a 1414 Liquid Scintillation Counter (Perkin Elmer).

Invasion assays were performed using the BioCoat Angiogenesis system (BD Biosciences) following manufacturer's recommendations. For assessment of in vivo angiogenesis, growth factor-reduced Matrigel (BD Biosciences) was mixed with Gal1 (0.1 or 3 μM) with or without lactose (30 mM). In another set of experiments, serum-free CM from KS cells infected or not with a retroviral vector expressing Gal1 shRNA and cultured under hypoxic or normoxic conditions, were added to unpolymerized Matrigel and injected subcutaneously into the flanks of either wild-type or Lgals1$^{-/-}$ (B6) mice or nude mice using a cold syringe. Matrigel embedded with buffer alone was used as negative control and a cocktail containing VEGF (50 ng/ml), heparin (50 U/ml) and TNF (2 ng/ml) was used as positive control. After 6 days, Matrigel plugs were collected by surgery, photographed and weighed. Samples were minced and diluted in water to measure hemoglobin content using the Drabkin reagent kit (Sigma). Each sample was normalized to 100 mg of recovered gel and confronted with a standard curve of mouse blood hemoglobin.

M. Real-Time Quantitative RT-PCR

SYBR® Green PCR Master Mix was used with an ABI PRISM® 7500 Sequence Detection Software (all from Applied Biosystem). Primers used were: human Gal1 forward: 5'-TGAACCTGGGTAAAGACA-3' (SEQ ID NO: 20); reverse: 5'-TTGGCCTGGTCGAAGGTGAT-3' (SEQ ID NO: 21); human RN18S1 forward: 5'-CGGCCGGGGGCAT-TCGTATT-3' (SEQ ID NO: 22); reverse: 5'-TCGCTCTG-GTCCGTCTTGCG-3' (SEQ ID NO: 23); human GCNT1 forward: 5'-CCTCCTGAGACTCCGGGGTCAGA-3' (SEQ ID NO: 24); reverse: 5'-CTAGGCGGTCCGTGCCCTAGC-3' (SEQ ID NO: 25); human GnT5 forward: 5'-TGCCCCT-GCCGGGACTTCAT-3' (SEQ ID NO: 26); reverse: 5'-CAG-CAGCATGGTGCAGGGCT-3' (SEQ ID NO: 27).

N. Analysis of LGALS1 Promoter Constructs with Luciferase Assays

Cells transfected or not with HIF-1α siRNA (100 nM) or IκB-α-SR (500 ng) were grown to 60-80% confluence on 24-well plates and co-transfected with 500 ng pGL3-Gal-Luc vector containing the LGALS1 promoter region (−473 to +67) ligated into the pGL3 promoterless reporter vector (Promega) and 20 ng of the control reporter plasmid pRL-TK (Promega) using FUGENE® HD (non-liposomal lipid blend formulated in 80% ethanol) transfection reagent (Roche Applied Science) according to manufacturer's recommended protocol. After 24 hours, culture medium was replaced for M199 1% FCS and cells were incubated under normoxic or hypoxic conditions in the absence or presence of NF-κB or HIF-1α inhibitors. After 18 hours, cells were lysed and luciferase activity was determined by chemiluminiscence using the dual luciferase assay kit (Promega) in a 20/20$^n$ luminometer (Turner Biosystem).

O. Analysis of Regulatory Elements in the LGALS1 Locus

Figure 18:
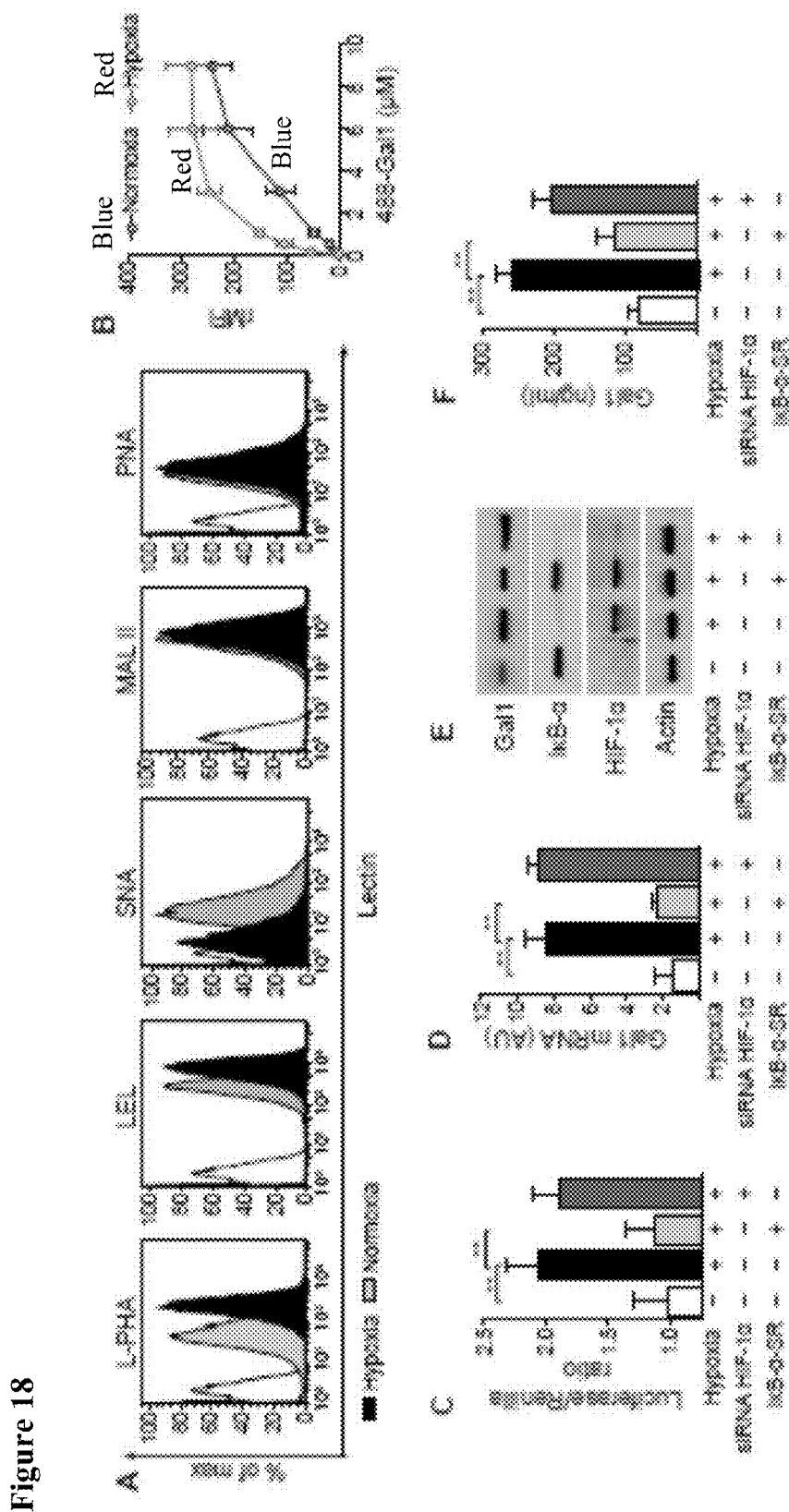
Figure 18:
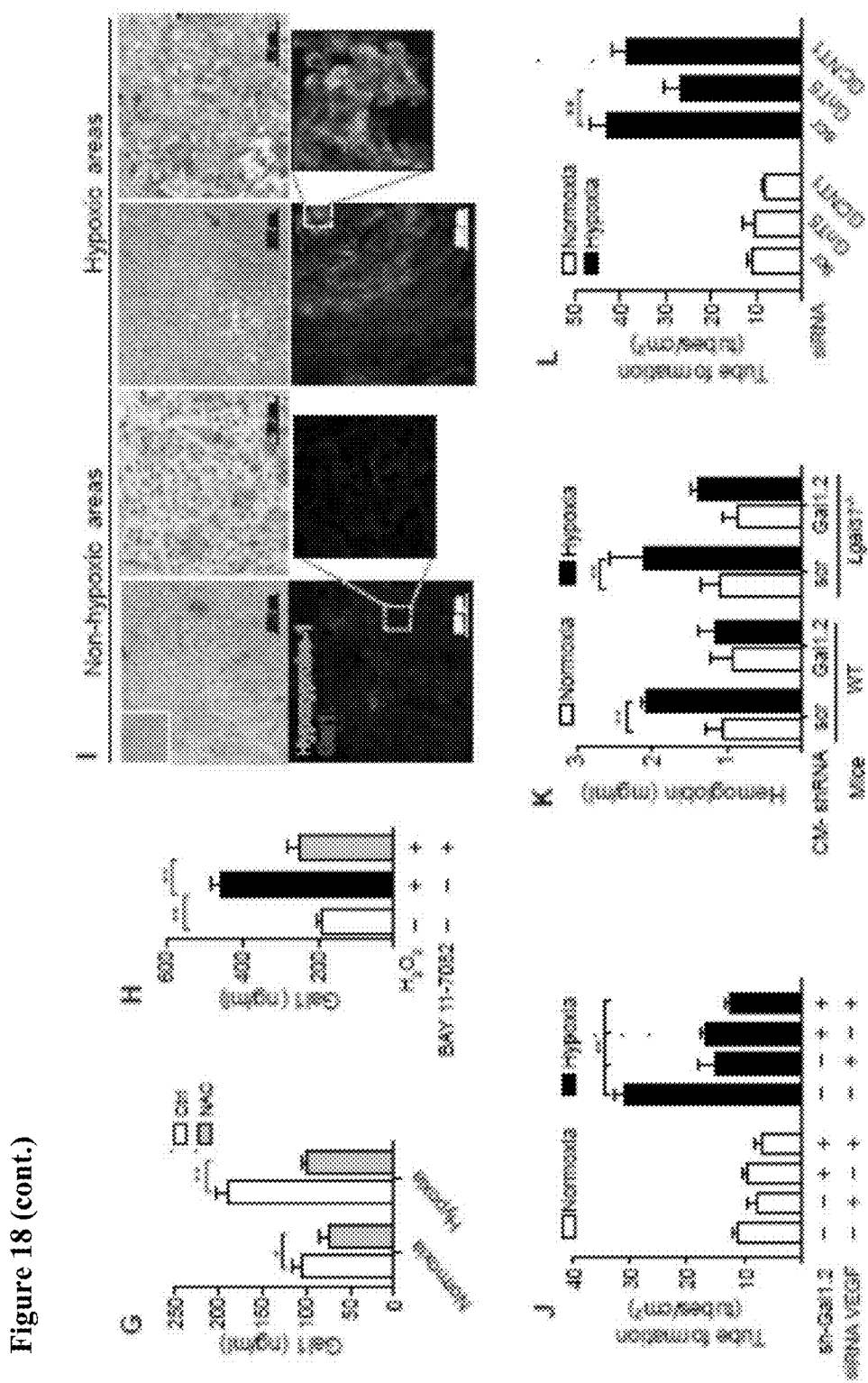
Figure 18:
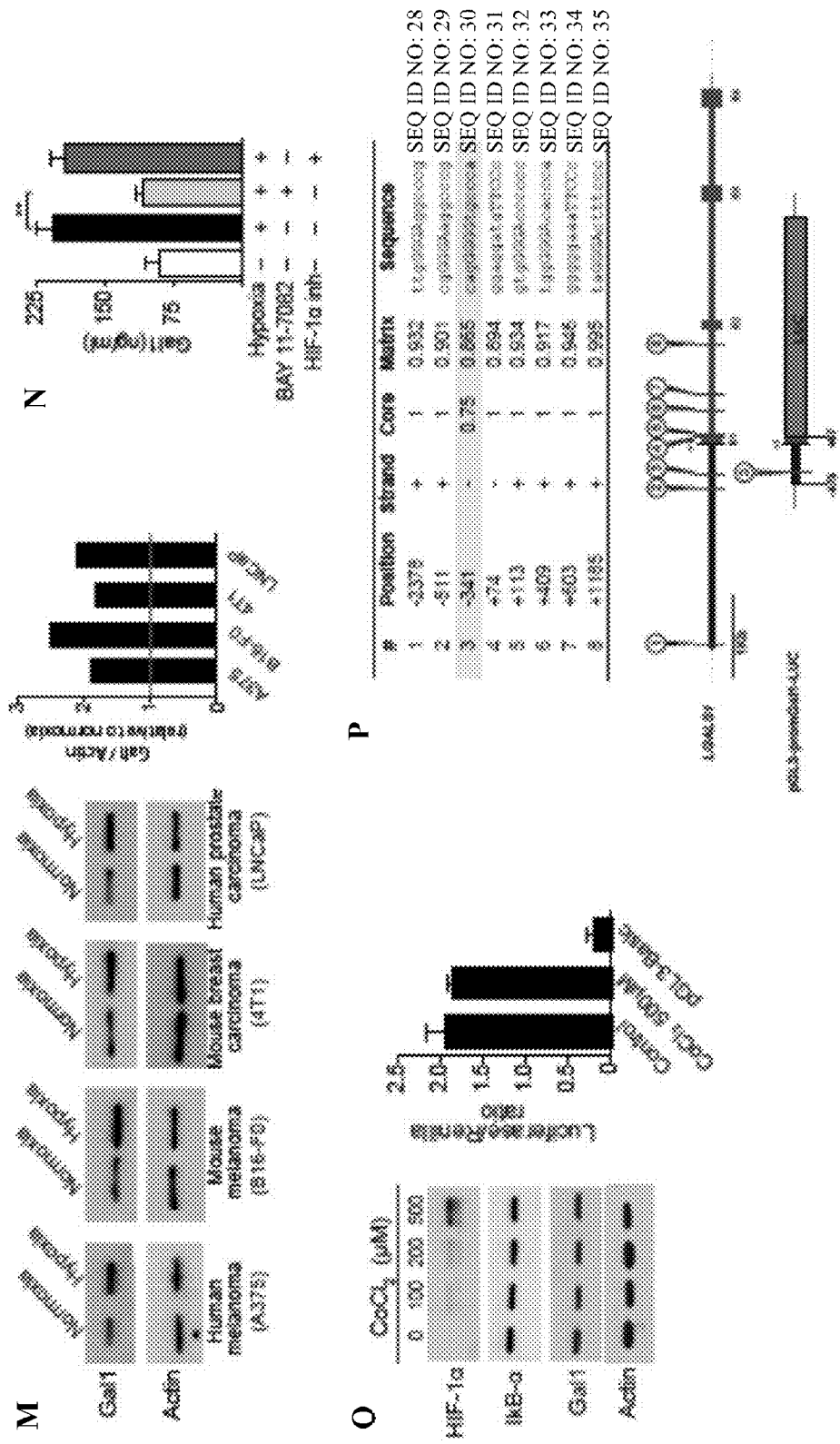
Figure 18:
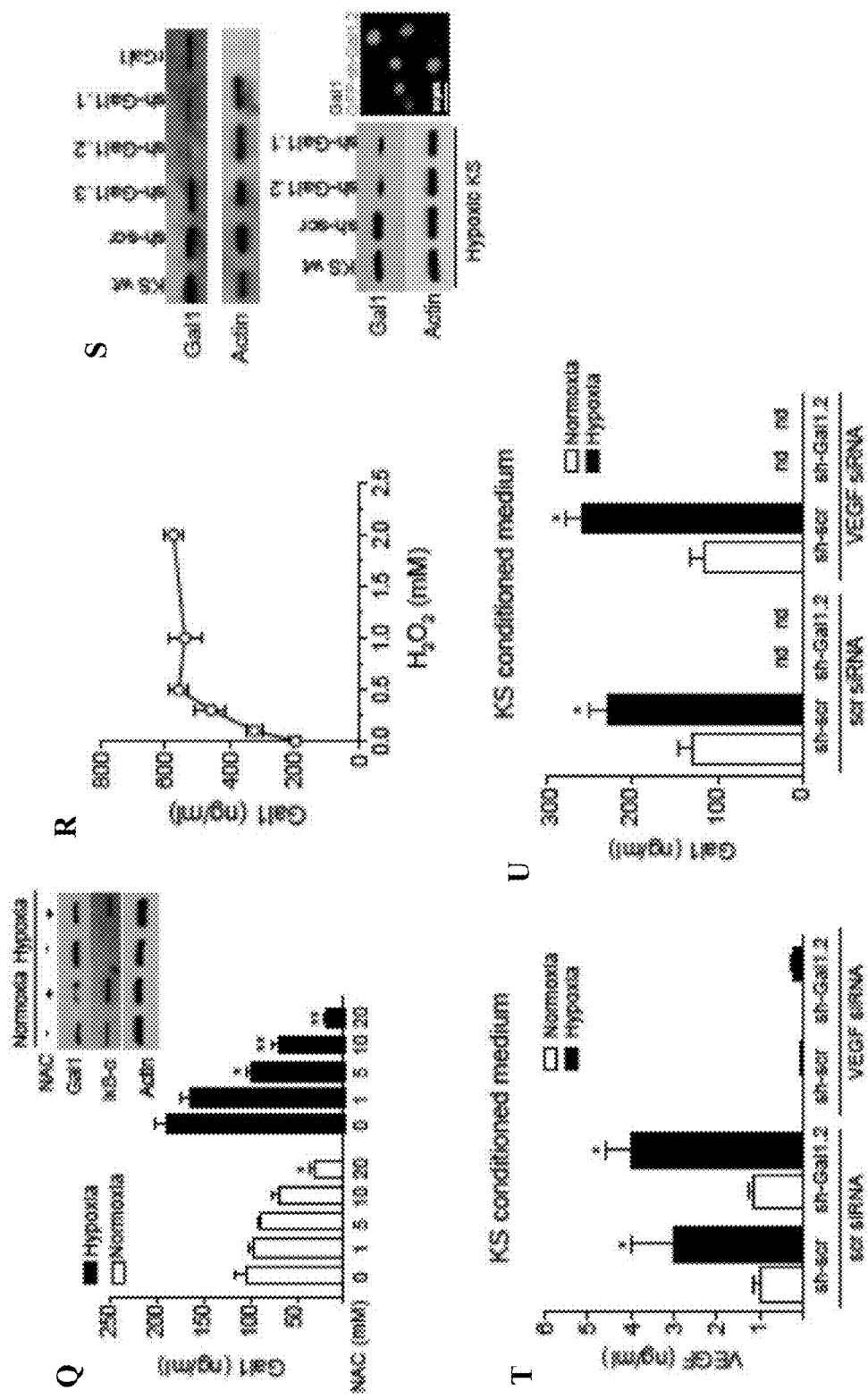

Computational analysis of the LGALS1 locus (2400 bp upstream to 2500 bp downstream to the start site) was performed with the publicly available version of MatInspector software (available on the world wide web at the Genomatix website and multiple κB binding sites were identified (FIG. 18P).

P. Induction of Hypoxia

Tumor cell lines or HUVEC were cultured in 24-well plates, placed in a modular incubator chamber (Billups-Rothenberg) and flushed at 2 psi for 10 min with a mixture of 1% $O_2$, 5% $CO_2$ and 94% $N_2$. The chamber was sealed and placed in a 37° C. incubator for 18 hours. Controls of normoxia were placed in the same incubator at 5% $O_2$. Chemical induction of HIF-1α (a condition often termed 'pseudo-hypoxia') was induced following treatment with $CoCl_2$ (Sigma).

Q. Intracellular Staining and FACS Analysis For intracellular cytokine staining, TLDN or tumor-infiltrating lymphocytes were made permeable with Perm2 solution (BD Biosciences) and were labeled with fluorescent-labeled monoclonal anti-IFN-γ (XMG1.2; BD Biosciences), anti-IL-17 (TC11-18H10; BD Biosciences), anti-IL-10 (JES5-16E3; eBioscience), anti-CD4 (GK1.5; BD Biosciences), anti-CD8 (H35-17.2; eBioscience) antibodies. $T_{reg}$ cells were determined by using the mouse $T_{reg}$ staining kit (FJK-16s, eBioscience). Cells were analyzed on a FACSAria (BD Biosciences) using a FlowJO software.

R. ELISA

Mouse IFN-γ and IL-10 ELISA sets were from BD Biosciences and mouse IL-17 kit was from R&D. Human soluble VEGF was assessed by ELISA (DY293B; R&D). Soluble Gal1 was determined using an in-house ELISA. Briefly, high binding 96-well microplates (Corning Costar) were coated with capture antibody (2 μg/ml purified rabbit anti-Gal1 polyclonal IgG) in 0.1 M sodium carbonate pH 9.5. After incubation for 18 hours at 4° C., wells were rinsed three times with wash buffer (0.05% Tween-20 in PBS) and incubated for 1 h at RT with blocking solution (2% BSA in PBS). Samples and standards (100 μl) were diluted in 1% BSA and incubated for 18 hours at 4° C. Plates were then washed and incubated with 100 ng/ml biotinylated detection antibody (purified rabbit anti-Gal1 polyclonal IgG) for 1 hour at RT. Plates were rinsed three times before adding horseradish peroxidase-labeled streptavidin (0.33 μg/ml; Sigma) for 30 min at RT. After washing, 100 μl of TMB solution (0.1 mg/ml tetramethylbenzidine and 0.06% $H_2O_2$ in citrate-phosphate buffer pH 5) was added to the plates. The reaction was stopped by adding $4NH_2SO_4$. Optical densities were determined at 450 nm in a Multiskan MS microplate reader (Thermo Electron Corporation). A standard curve ranging from 2.5 to 160 ng/ml recombinant Gal1 was run in parallel.

S. Confocal Microscopy and Immunohistochemistry

For confocal microscopy the following primary antibodies were used: mouse anti-αSMA (1A4; Dako; 1:100), mouse anti-desmin (D33; Dako; 1:100), rat anti-PDGFRβ (APB5; Biolegend; 1:50), rabbit anti-Rgs5 (Prestige Sigma; 1:50), rat anti-CD31 (Mec13.3; BD Biosciences; 1:100), rabbit anti-Gal1 IgG (1:100) generated as described in Ilarregui et al. (2009) *Nat Immunol* 10, 981-991, rabbit anti-VEGFR2 (55B11; Cell Signaling; 1:200), mouse anti-CD8 (H35-17.2; eBioscience; 1:50), rat anti-LANA (Advanced Biotechnol; 1:1000). Secondary antibodies used were: anti-mouse IgG-FITC (BD Biosciences; 1:200), anti-mouse IgG-Cy3 (Vector; 1:500), anti-rat IgG-FITC (Vector; 1:500), anti-rat IgG-Texas Red (Vector: 1:500) and anti-rabbit IgG-Alexa Fluor-555 (Cell Signaling: 1:1000).

T. Microarrays of KS and Data Analysis

The Human Genome Array Hg-U133A (Affymetrix) (Wang et al. (2004) *Nat Genet* 36, 687-693) and the Mouse Genome 430 2.0 Array (Affymetrix) were used to examine gene expression levels of KS biopsies and mECK36 tumors as described in Mutlu et al. (2007) *Cancer Cell* 11, 245-258. Raw data intensity profiles were analyzed using the Gene-Spring 7 (Agilent) to perform microarray normalization and statistical analysis.

Example 8

Figure 16:
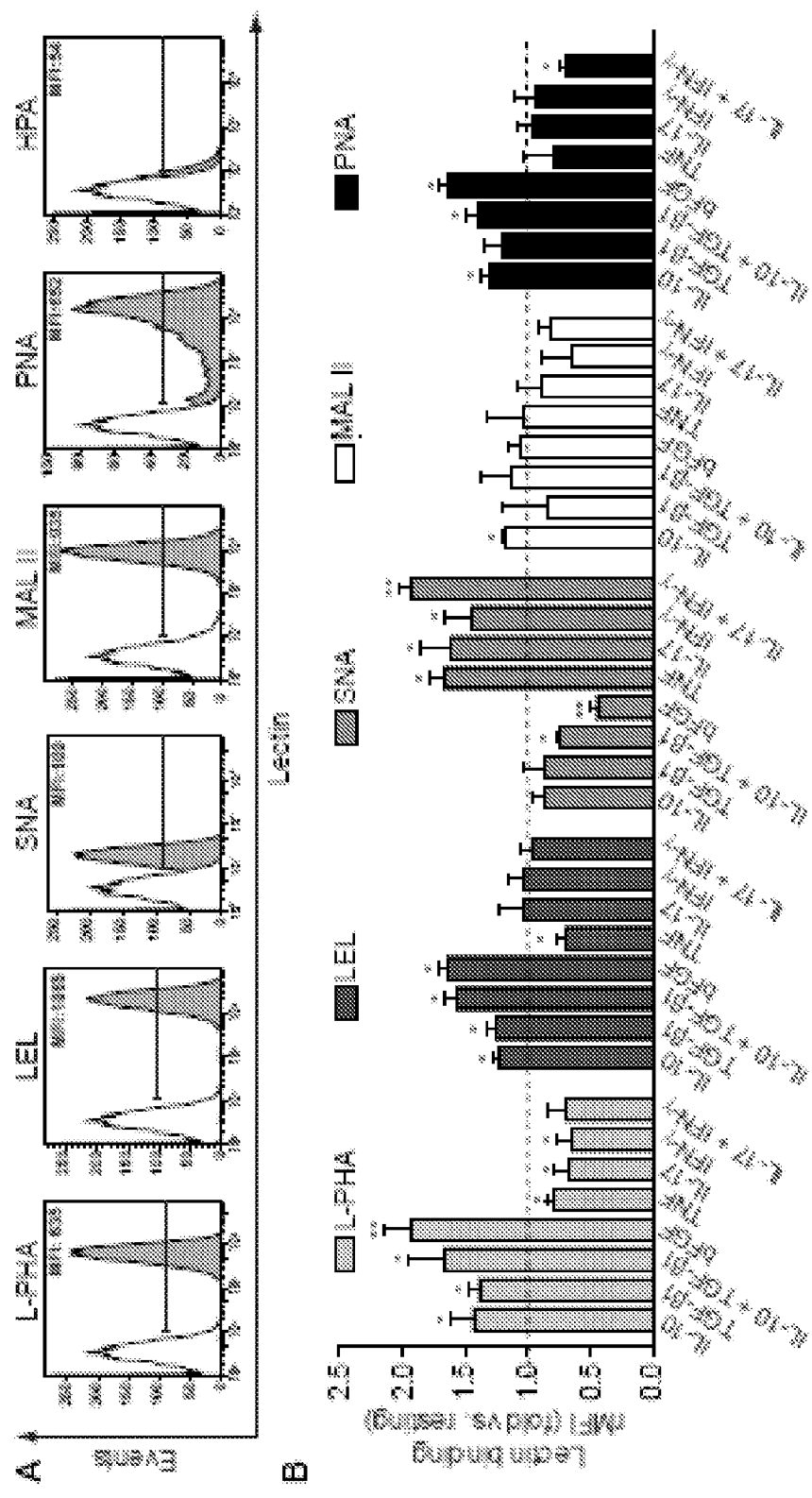
Figure 16:
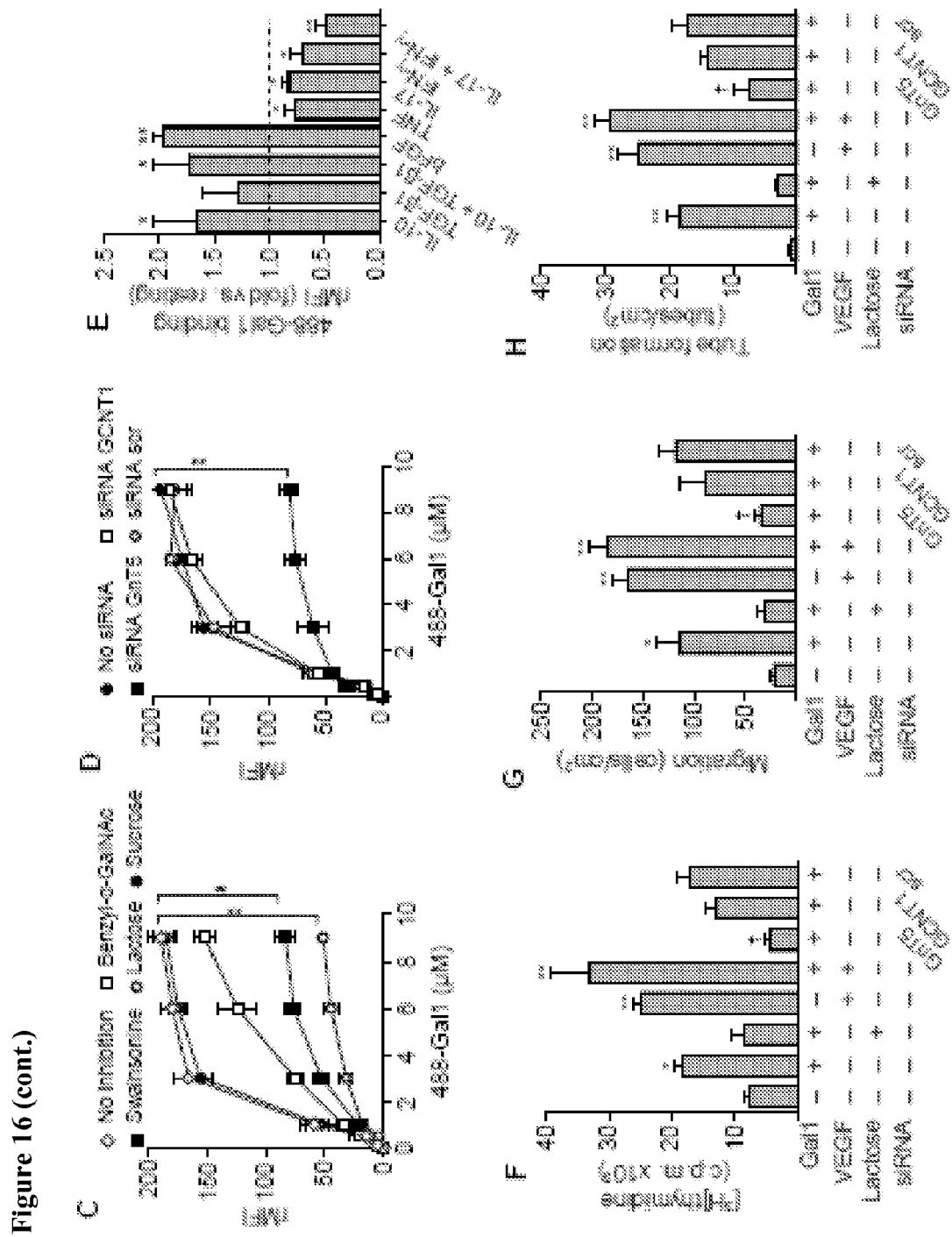
Figure 16:
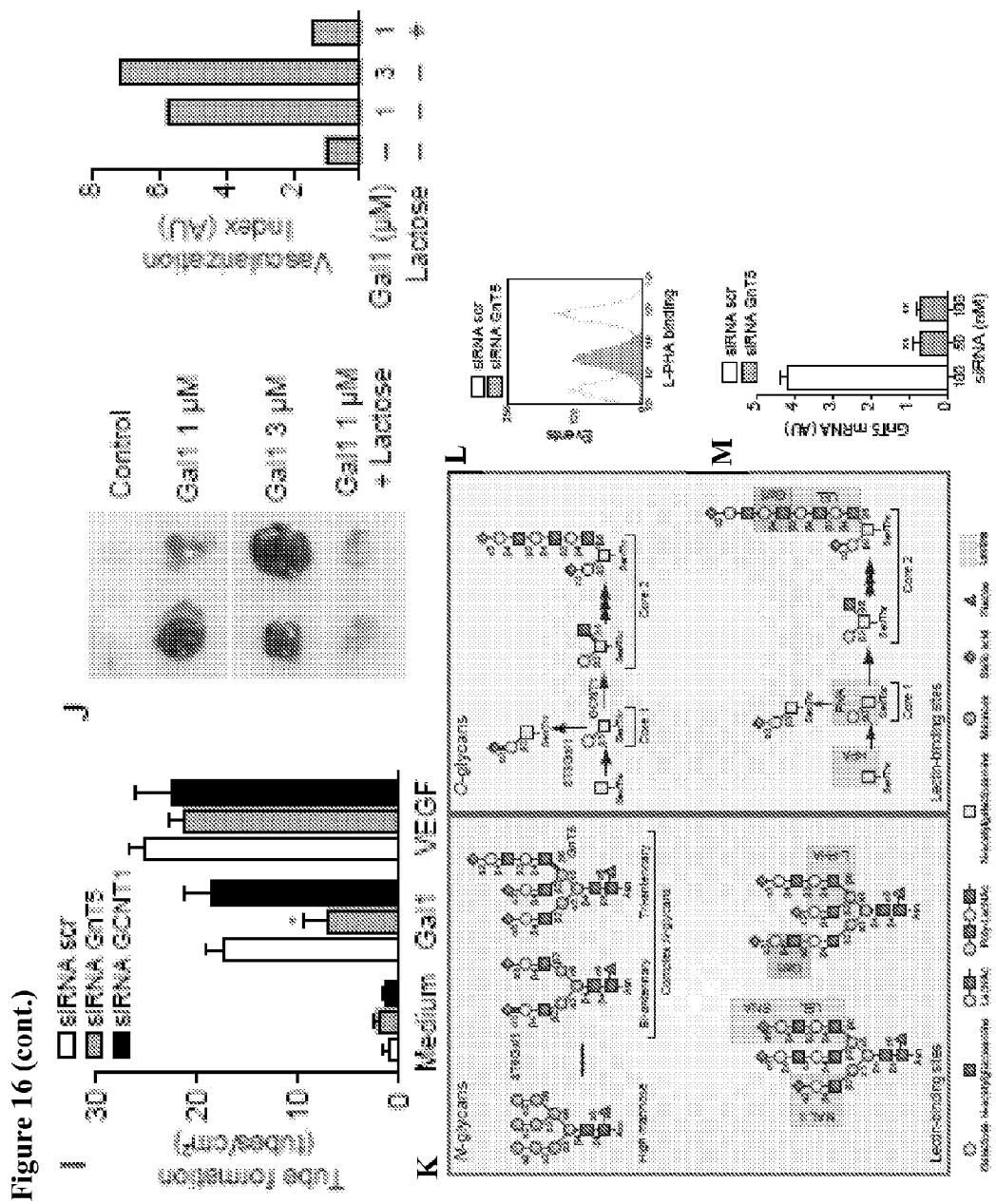
Figure 16:
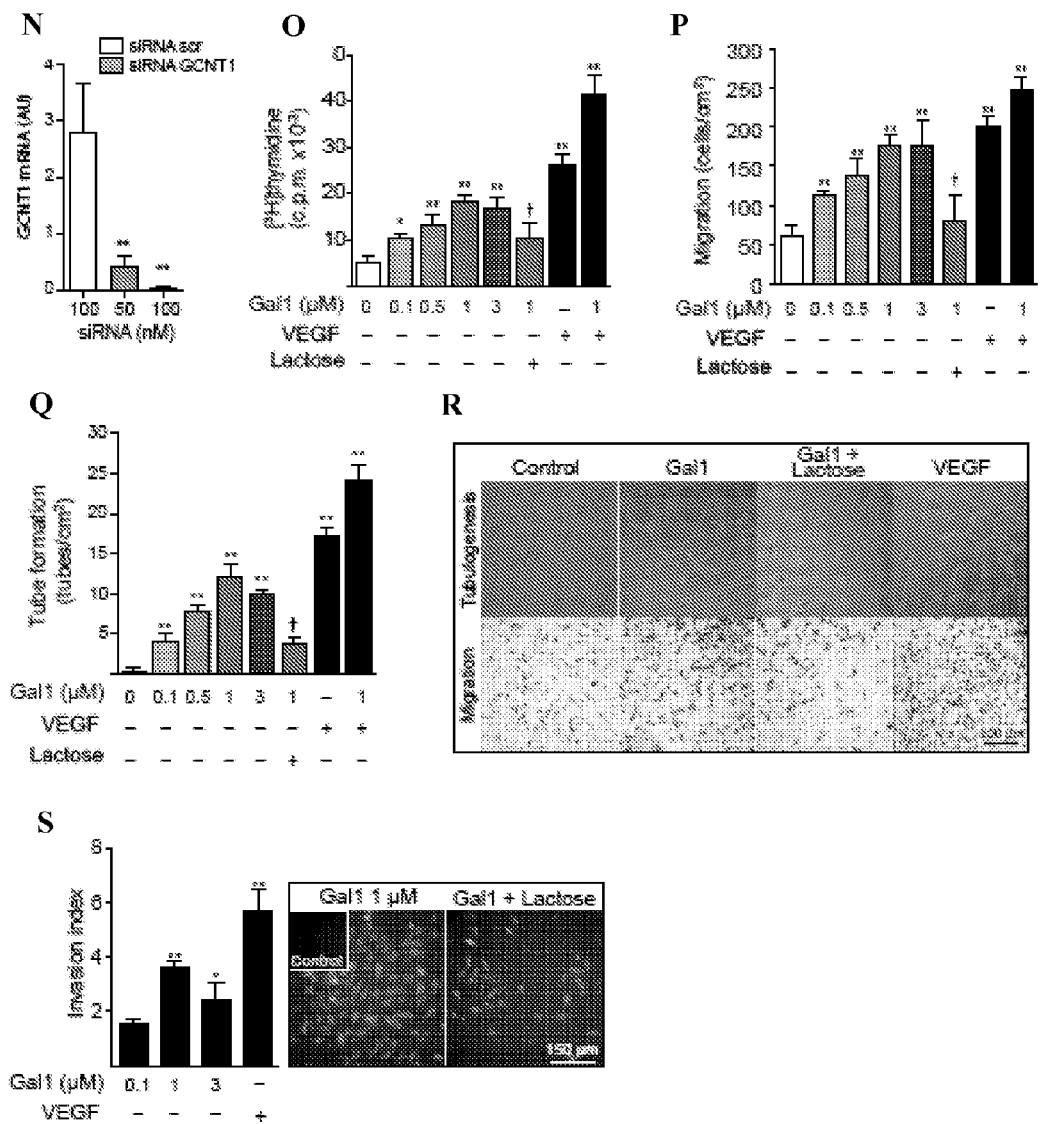

Regulated Glycosylation Modulates Vascular Biology by Allowing the Formation of Lectin-Glycan Lattices To study whether galectin-saccharide lattices contribute to formation of tumor vascular networks, the 'glycosylation signature' of human endothelial cells (ECs) was first examined both under resting conditions and when ECs are exposed to proliferative, tolerogenic or inflammatory stimuli. For this purpose, a panel of lectins was used which selectively recognize glycan structures, including those that are relevant for Gal1 binding and signaling (FIG. 16K). Gal1 recognizes multiple galactose-β1-4-N-acetylglucosamine (LacNAc) units, which may be presented on the branches of N- or O-linked glycans (Hirabayashi et al. (2002) *Biochim Biophys Acta* 1572, 232-254). Thus, regulated expression of glycosyltransferases during vascular remodeling, that serve to create poly-LacNAc ligands, may determine susceptibility to Gal1. This includes the N-acetylglucosaminyltransferase 5 (GnT5), an enzyme that generates β1,6-N-acetylglucosamine-branched complex N-glycans (Dennis et al. (2009) *Cell* 139, 1229-1241). Under resting conditions, primary human vein umbilical ECs (HUVEC) showed considerable expression of L-phytohemagglutinin (L-PHA)-reactive GnT5-modified N-glycans (FIG. 16A which substantially increased following exposure to IL-10 or TGF-$β_1$, both cytokines capable of imprinting anti-inflammatory or tolerogenic signatures (FIG. 16B). A similar tendency was observed following stimulation with a strong proliferative stimulus such as basic fibroblast growth factor (bFGF) (FIG. 16B). In contrast, ECs stimulated with pro-inflammatory (tumor necrosis factor; TNF), $T_H1$-type (IFN-γ) or $T_H17$-type (IL-17) cytokines showed a significant reduction of L-PHA-reactive glyco-epitopes (FIG. 16B). Staining with the *Lycopersicon esculentum* lectin (LEL), which recognizes poly-LacNAc ligands, revealed a substantial increase in reactive glyco-epitopes following exposure to tolerogenic and proliferative stimuli (FIGS. 16A and 16B). As α2-6 sialyltransferase (ST6Gal1) may modify LacNAc ligands and block Gal1 signaling (Toscano et al. (2007) *Nat Immunol* 8, 825-834), binding of the *Sambucus nigra* agglutinin (SNA), a lectin that recognizes α2-6-linked sialic acid (SA) sequences, was examined. ECs stimulated with bFGF or a combination of IL-10 and TGF-$β_1$ responded with diminished display of SNA-reactive glyco-epitopes, as compared to resting, TNF-, IL-17- or IFN-γ-treated ECs (FIGS. 16A and 16B), indicating that pro-inflammatory or anti-inflammatory signals may either mask or unmask poly-LacNAc sequences. In contrast, human ECs showed similar binding profiles for the *Maackia amurensis* agglutinin (MAL II), which recognizes α2-3 SA linkages, regardless of the stimuli used (FIGS. 16A and 16B); these results indicate that changes in glycosylation are specific and do not represent global loss of SA from cell surface glycoproteins.

Binding of Gal1 may also be regulated by glycosyltransferases, which compete for acceptor substrates and thus limit carbohydrate ligand synthesis. The α2-3 sialyltransferase I (ST3Gal1) competes with the core-2 β1-6-N-acetylglucosaminyltransferases (GCNTs) for core-1 O-glycan structures and may inhibit the addition of O-linked poly-LacNAc ligands (FIG. 16K). To assess the influence of this pathway, EC surface glyco-receptors were probed for the absence of sialylated core-1 O-glycans using the lectin peanut agglutinin (PNA), which binds to asialo-galactose-β1-3-N-acetylgalactosamine core-1 O-glycans. Exposure of human ECs to bFGF or IL-10 resulted in a modest but significant increase in PNA-reactive asialo core-1 O-glycans, compared to cells exposed to pro-inflammatory, $T_H1$ or $T_H17$ stimuli (FIGS. 16A and 16B). Finally, no significant binding of *Helix pomatia* (HPA), a lectin that recognizes terminal α-N-acetyl-galactosamine residues was observed (FIG. 16A). In most cases the combination of tolerogenic or anti-inflammatory stimuli had additive effects (FIG. 16B). Similar results were observed using the murine EC line, EOMA. Collectively, these results indicate that proliferative and tolerogenic stimuli, commonly found in tumor microenvironments, favor a 'Gal1 permissive' glycophenotype on ECs, while pro-inflammatory signals tend to interrupt exposure of these glyco-epitopes. These results emphasize the dynamics of the EC surface 'glycome', which may contribute to vascular biology through either masking or unmasking specific glyco-epitopes for endogenous lectins.

To determine whether the regulated glycan repertoire facilitates the formation of galectin-glycan lattices, binding of fluorescently-labeled Gal1 to ECs was analyzed under different experimental conditions. Gal1 bound to ECs in a dose- and carbohydrate-dependent fashion; the specific disaccharide lactose, but not sucrose, prevented these interactions (FIG. 16C). To dissect the contribution of N- and O-glycans to Gal1 effects, binding assays were performed in the absence or presence of glycosylation pathway inhibitors. Binding of Gal1 to ECs was almost completely abrogated by swainsonine, an early inhibitor of N-glycan biosynthesis, whereas benzyl-α-GalNAc, a metabolic competitor of O-glycan elongation, was only partially inhibitory (FIG. 16C). Moreover, interruption of complex-type N-glycan branching through short interfering RNA (siRNA)-mediated silencing of GnT5 almost completely eliminated Gal1 binding to the surface of ECs, whereas inhibition of core 2 O-glycan elongation through siRNA-mediated silencing of GCNT1 had no effect (FIGS. 16D and 16L-16N), clearly demonstrating the glycan specificity of this effect. Consistent with changes in glycosylation, binding of Gal1 was much higher in ECs exposed to proliferative or tolerogenic stimuli (either alone or in combination) compared to cells sensing inflammatory, $T_H1$ or $T_H17$ signals (FIG. 16E). Thus, highly branched cell surface N-glycans may influence vascular biology through the formation of discrete Gal1-glycan lattices, which are preferentially established under tolerogenic or proliferative settings.

To examine the functional relevance of these interactions, whether Gal1 controls vascular biology through a glycosylation-dependent mechanism was determined. Signaling through Gal1-glycan lattices elicited the typical cellular processes associated with angiogenic sprouting, including EC proliferation, migration and invasion and enabled the formation of three-dimensional tubular networks at levels similar to those attained by VEGF (FIGS. 16F-16H and 16O-16S). These effects were completely prevented by addition of the specific disaccharide lactose or by siRNA-mediated GnT5 silencing, while introduction of GCNT1 siRNA had no effect (FIGS. 16F-16H), indicating a critical role for LacNAc residues and complex N-glycan branching in angiogenic sprouting mediated by Gal1. However, the pro-angiogenic effects of VEGF were preserved regardless of the absence or presence of N- or O-glycan branching (FIG. 16I). In vivo, injection of Matrigel sponges containing recombinant Gal1 rapidly became vascularized in a manner that was dose-dependent and specifically inhibited by lactose (FIG. 16J). Thus, unlike VEGF, Gal1 endows ECs with pro-angiogenic potential through mechanisms involving regulated glycosylation of putative signaling receptors.

Example 9

Figure 17:
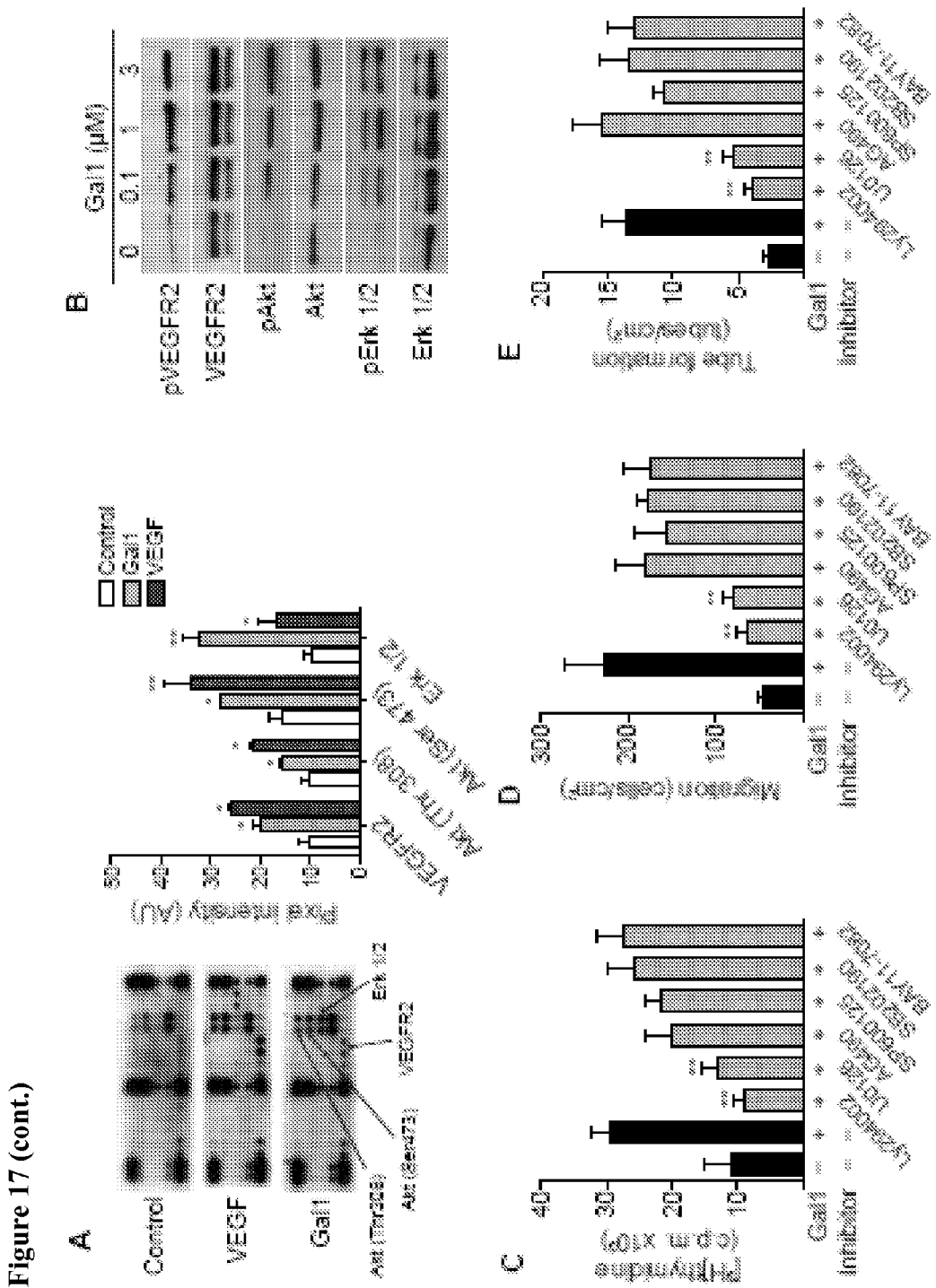
FIGS. 17A-17R show the galectin-1 co-opts VEGFR2 signaling pathways through the formation of lectin-glycan lattices on highly branched complex N-glycans.
FIG. 17B shows immunoblot results of VEGFR2, Akt and Erk1/2 phosphorylation in HUVEC treated with different concentrations of Gal1. Data are representative of six independent experiments.
FIGS. 17C-17E shows Gal1-induced proliferation (FIG. 17C), migration (FIG. 17D) and tube formation (FIG. 17E) on HUVEC pre-incubated with pharmacological inhibitors of PI(3)K/Akt (LY294002), Erk1/2 (U0126), JAK2-STAT3 (AG490), Jnk/SAP (SP600125), p38 (SB202190) or NF-κB (BAY11-7082).  P<0.01 versus Gal1. Data are the mean±SEM of five independent experiments.
FIG. 17F shows immunoblot analysis of VEGFR2, Akt and Erk1/2 phosphorylation induced by Gal1 or VEGF in HUVEC transfected with VEGFR2 or GnT5 siRNA. Data are representative of three independent experiments.
FIG. 17G shows co-immunoprecipitation results followed by immunoblot analysis of HUVEC lysates, wherein the left panel shows results from cells treated with or without Gal1 and the right panel shows results from cells transfected or not with GnT5 or GCNT1 siRNA or exposed to PNGase F and treated with Gal1. Input, whole cell lysate; IB, immunoblot; IP, immunoprecipitation. Data are representative of three independent experiments.
FIG. 17H shows laser confocal microscopy results of HUVEC transfected or not with GnT5 siRNA and treated with Gal1 or buffer control stained for VEGFR2 (red) or for nuclei (DAPI; blue). Images are representative of four independent experiments are shown.
FIG. 17I shows tube formation results of HUVEC transfected or not with VEGFR2, NRP-1, VEGF or scr siRNA treated or not with Gal1. * P<0.05 versus Gal1. Data are representative of three independent experiments.
FIG. 17J shows tube formation results of HUVEC pre-treated with lactose or blocking antibodies to VEGFR1, VEGFR2, VEGFR3 or VEGF. * P<0.05 versus Gal1. Data are representative of three independent experiments.
FIG. 17K shows fold increase results in the phosphorylation status of a panel of growth factor receptor tyrosine kinases (RTKs) and signaling nodes as determined by phospho-RTK signaling array upon exposure of HUVEC to Gal1 or VEGF. The relative signal intensity of each spot, quantified as pixel intensity is represented relative to control intensity (value=1, dotted line). * P<0.05; ** P<0.01 versus control. Data are the mean±SEM of three independent experiments.
FIG. 17L shows immunoblot analysis results of VEGFR2 and FIG. 17M shows immunoblot analysis results of NRP-1 in HUVEC transfected with specific siRNA (100 nM). Data are representative of three independent experiments.
FIG. 17N shows co-immunoprecipitation results followed by immunoblot analysis of cell lysates derived from HUVEC cultured with or without Gal1. Input, whole cell lysate; IB, immunoblot; IP, immunoprecipitation. Data are representative of three independent experiments.
FIGS. 17P-17Q show migration results of HUVEC induced by Gal1 or VEGF in transwells. Cells were transfected with 100 nM siRNA specific for VEGFR2, NRP-1 or VEGF (FIG. 17P), or were incubated with specific blocking antibodies to VEGFR2 or VEGF (FIG. 17Q). * P<0.05, ** P<0.01 versus medium, Gal1 or VEGF alone. Data are representative of three independent experiments.
Figure 17:
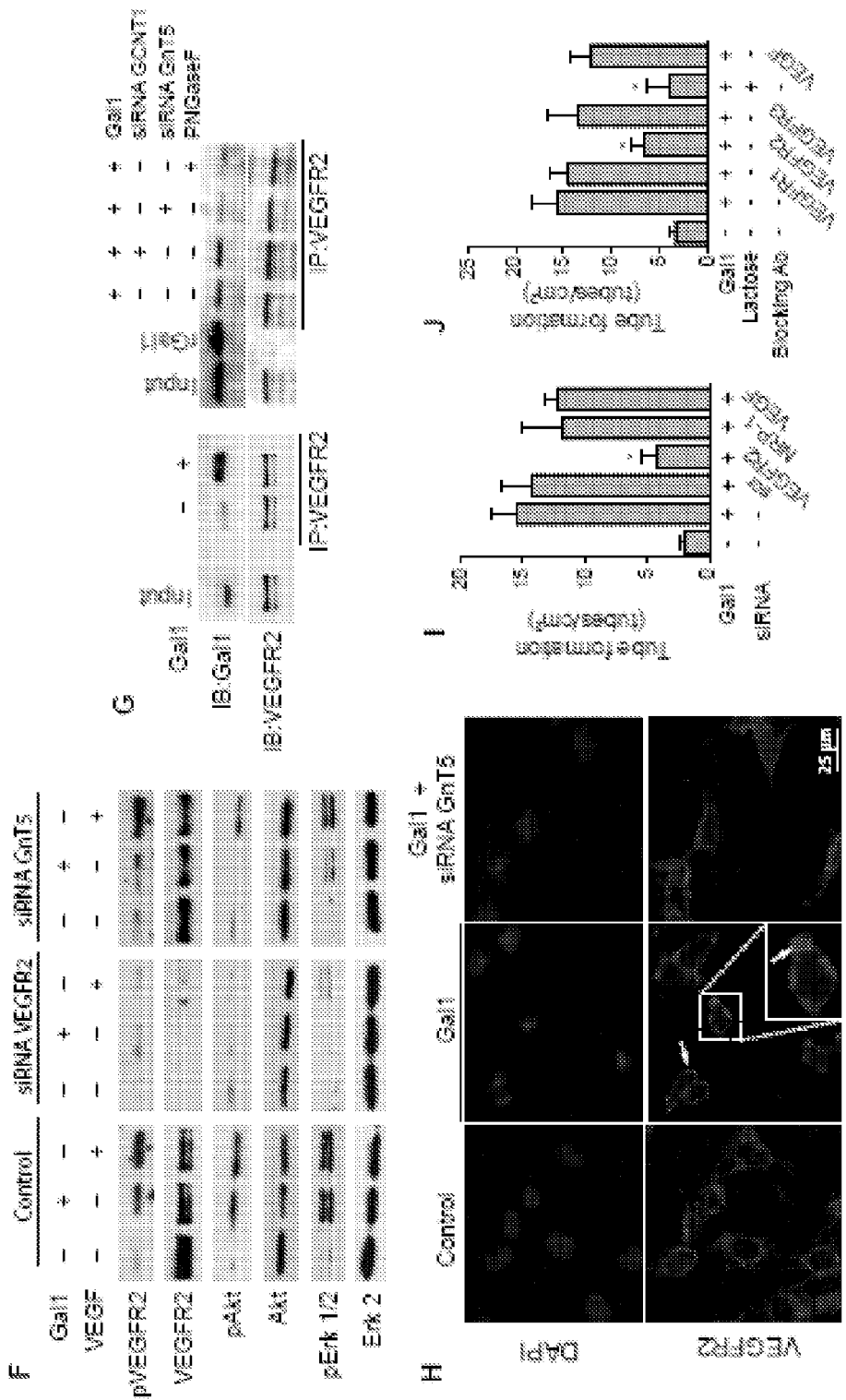
Figure 17:
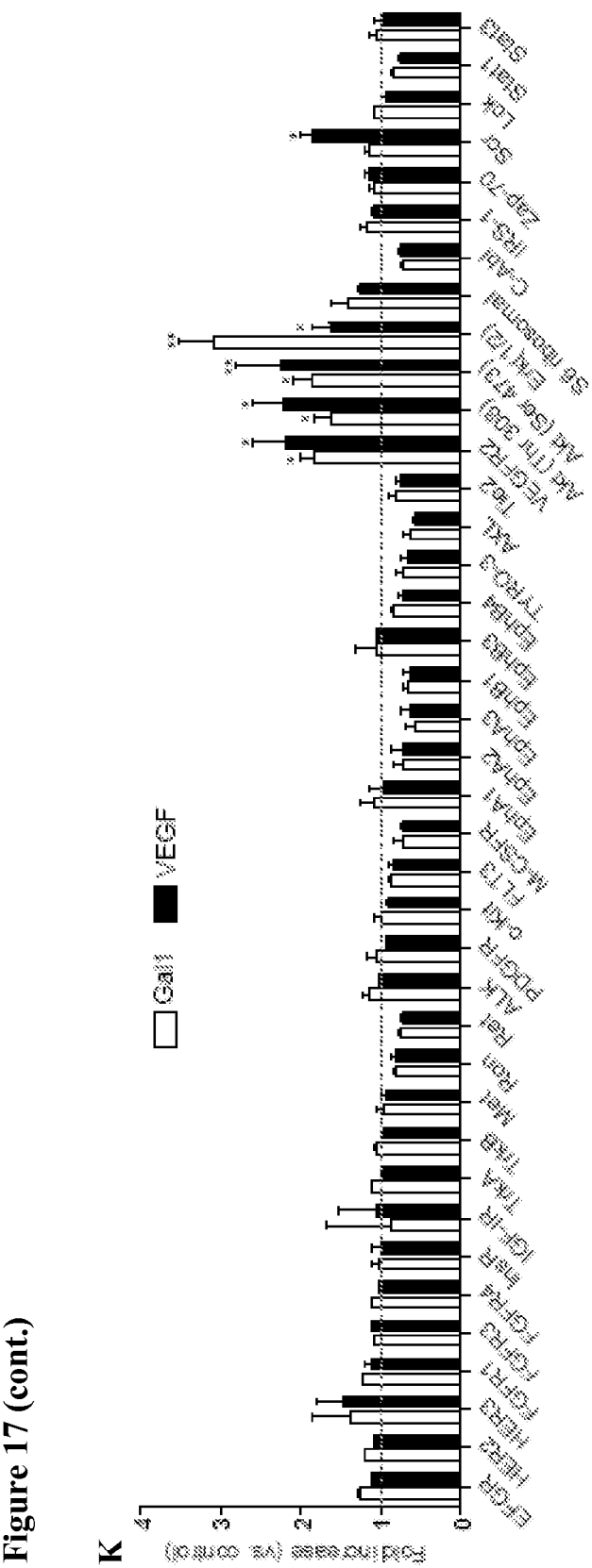
Figure 17:
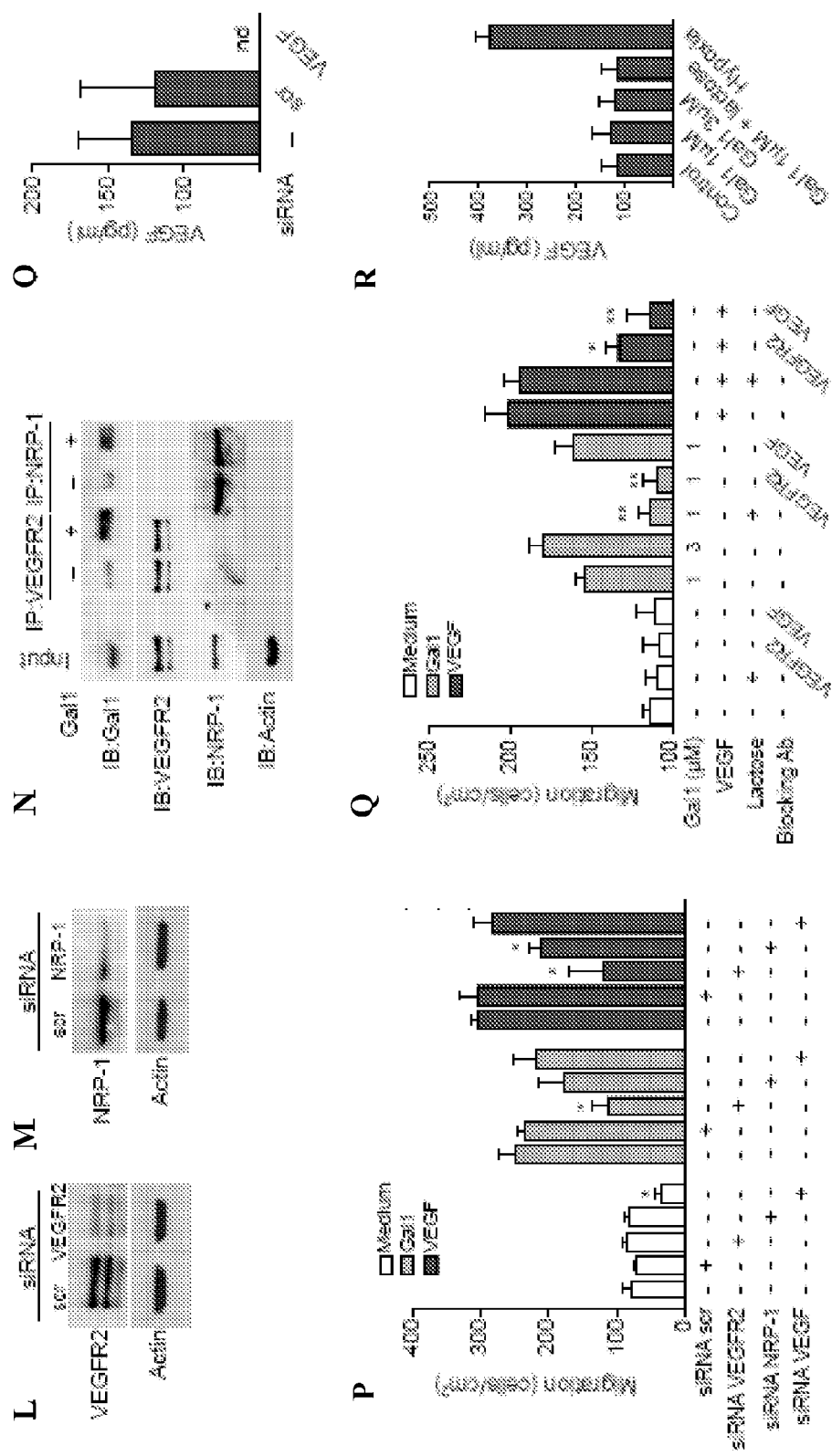

Galectin-1 Co-Opts VEGFR2 Signaling Pathways Through the Formation of Lectin-Glycan Lattices on Highly Branched Xomplex N-Glycans To elaborate further on the mechanisms associated with the pro-angiogenic functions of Gal1-glycan lattices and to identify putative glyco-receptors mediating these effects, changes in the phosphorylation status of a spectrum of growth factor receptor tyrosine kinases (RTKs) and signaling nodes were screened using a phospho-RTK signaling array. The only RTK that became phosphorylated following treatment of human ECs with Gal1 was VEGFR2 (FIGS. 17A and 17K). This phosphorylation pattern was detected as early as 15 min (FIG. 17A) and was sustained even after 60 min of exposure to this lectin. In addition, Gal1 exposure increased the phosphorylation of Akt (Thr308), Akt (Ser473) and the mitogen-activated protein kinase Erk1/2, recapitulating the phosphorylation pattern elicited by VEGF (FIG. 17A). Dose-dependent phosphorylation of VEGFR2, Akt and Erk1/2 was further validated by immunoblot analysis (FIG. 17B). Accordingly, pharmacological inhibition of PI(3)K/Akt or Erk1/2 completely suppressed Gal1-induced EC proliferation, migration and tubulogenesis, while inhibition of Jnk, p38, STAT3 or NF-κB had no effect (FIGS. 17C-17E). Furthermore, siRNA-mediated silencing of VEGFR2 completely prevented Akt and ERK1/2 phosphorylation induced by either Gal1 or VEGF (FIGS. 17F and 17L). As branching of complex N-glycans attached to growth factor receptors may fine-tune the threshold for growth factor signaling (Lau et al. (2007) Cell 129, 123-134; Song et al. (2010) Cancer Res 70, 3361-3371), analyses were conduected to determine whether fluctuations in GnT5-modified glycans can directly modulate sensitivity of VEGFR2 to its cognate ligand VEGF. Silencing of GnT5-mediated N-glycan branching selectively eliminated Gal1, but not VEGF signaling (FIG. 17F). In contrast, blockade of core-2 O-glycan elongation via GCNT1 knockdown had no substantial effect. These results indicate that Gal1 and VEGFR2 selectively associate to generate multivalent signaling clusters characterized by the presence of highly branched complex N-glycans.

To determine whether Gal1 establishes direct interactions with VEGFR2 through N-glycosylation-dependent mechanisms, co-immunoprecipitation experiments with lysates of human ECs treated with Gal1 were performed in the absence or presence of PNGase F, an endoglycosidase that releases N-linked oligosaccharides, or following transfection with GnT5 siRNA to interrupt complex N-glycan branching Gal1 associated specifically with VEGFR2 through interactions that depended on early or late stages of N-glycan elongation (FIG. 17G). Supporting these findings, exposure to Gal1 resulted in segregation of VEGFR2 to membrane patches, indicating rearrangement of signaling clusters on the surface of human ECs. Segregation was eliminated following siRNA-mediated GnT5 silencing (FIG. 17H). Hence, rather than altering VEGF signaling, Gal1 directly co-opts the VEGFR2 signaling pathway through binding to LacNAc-enriched complex N-glycan structures.

Given the contribution of various glyco-receptors to angiogenic switch (Lemmon et al. (2010) Cell 141, 1117-1134), their involvement in Gal1-mediated effects was also examined. Inhibition of VEGFR2 signaling through siRNA-mediated silencing or through antibody-mediated blockade abrogated Gal1-induced EC migration and tube formation, whereas blockade of VEGFR1 or VEGFR3 had no effect (FIGS. 17I, 17J, 17P, and 17Q), indicating that only selected glyco-receptors are amenable to the formation of signaling clusters mediated by lectin-glycan lattices. Moreover, siRNA-mediated silencing of NRP-1, a transmembrane glycoprotein responsible for amplifying VEGFR2 signaling, did not significantly affect Gal1-induced tube formation, in spite of its ability to interact with this lectin (FIGS. 17I, 17M, and 17N). While inhibition of VEGFR2 signaling abrogated EC migration induced by Gal1 or VEGF, NRP-1 silencing suppressed only VEGF effects (FIG. 17P).

Because of the active search for VEGF-independent angiogenic pathways and the autocrine effects of VEGF signaling (Lee et al. (2007) Cell 130, 691-703), it was next investigated whether Gal1-VEGFR2 signaling proceeded in the absence of VEGF. Consistent with lack of effects of Gal1 on VEGF secretion (FIG. 17R), inhibition of VEGF signaling through siRNA-mediated silencing or antibody-mediated blockade did not prevent Gal1-induced EC migration and tube formation (FIGS. 17I, 17J, and 17O-17Q). Collectively, the results indicate that signaling complexes established between endogenous lectins and specific glycan structures on selected growth factor receptors mimic 'canonical' ligands to preserve critical cellular processes, including angiogenesis.

Example 10

Galectin-1-Glycan Lattices Link Tumor Hypoxia to VEGFR2-Mediated Angiogenesis

Despite considerable progress in elucidating the signaling pathways that control hypoxia and angiogenesis, the molecular mechanisms coupling these processes are still poorly understood. To investigate whether Gal1-glycan lattices link tumor hypoxia to sprouting angiogenesis, whether exposure to hypoxic microenvironments can influence the 'glycosylation signature' of ECs was determined. As revealed by glycophenotypic analysis, hypoxia (1% $O_2$) induced a substantial increase in β1-6-branched complex-type N-oligosaccharides (L-PHA reactivity) and poly-LacNAc structures (LEL reactivity) concomitant with a considerable reduction in α2-6-linked SA (SNA binding) and slight changes in asialo-core-1 O-glycans (PNA binding), as compared to ECs cultured under normoxic conditions (FIG. 18A). In contrast, no significant differences were observed in α2-3 sialylation (MAL II reactivity) between ECs subjected to hypoxia or normoxia (FIG. 18A). These data indicate an extensive and selective remodeling of the EC surface 'glycome' in response to hypoxia, similar to that found in response to tolerogenic or proliferative stimuli, which results in increased availability of cell surface glycans essential for Gal1 signaling. Accordingly, preferential binding of this lectin to ECs exposed to hypoxia was found, as compared to those incubated under normoxic conditions (FIG. 18B).

To further delineate the functional role of Gal1-glycan lattices in hypoxic microenvironments, the regulated expression of tumor-derived Gal1 under hypoxic or normoxic conditions in immortalized Kaposi's sarcoma (KS) cells, which typically develop tumors characterized by a dense and poorly organized capillary network recruited from the host (Albini et al. (2001), Cancer Res 61, 8171-8178), was analyzed. Hypoxia induced considerable up-regulation of Gal1 in KS cells, as shown by the 2-fold induction of LGALS1 promoter activity, 4-fold induction of Gal1 mRNA and 2.5-fold induction of protein expression and secretion, as compared to KS cells grown in normoxic conditions (FIGS. 18C-18F). Hypoxia-induced Gal1 expression was also evident in human and murine melanoma (A375 and B16-F0), mouse breast carcinoma (4T1) and human prostate carcinoma (LNCaP) cell lines (FIG. 18M), indicating broad regulation of endogenous Gal1 at the transcriptional level in tumors of mesenchymal or epithelial origin. This effect was independent of the master transcription factor HIF-1α as hypoxia still induced up-regulation of Gal1 in either KS cells transfected with HIF-1α siRNA (FIGS. 18C-18F) or in KS cells incubated with a specific HIF-1α inhibitor (FIG. 18N).

Consistent with these results, chemical activation of HIF-1α (with $CoCl_2$) had no effect on Gal1 expression (FIG. 18O). As both HIF-dependent and HIF-independent oxygen-sensing mechanisms have been linked to NF-κB-regulated gene transcription (Rius et al. (2008) Nature 453, 807-811), it was next asked whether hypoxia controls Gal1 expression through NF-κB-regulated pathways. Blockade of NF-κB transcriptional activity by expression of a super-repressor form of IκB-α (IκB-α-SR) or pharmacological inhibition using BAY-117802 prevented IκB-α degradation and completely eliminated hypoxia-driven Gal1 expression and secretion without altering the levels of HIF-1α (FIGS. 18C-18F and 18N). Supporting these findings, analysis of the regulatory sequences of human LGALS1 gene revealed several putative NF-κB consensus sequences (FIG. 18P), including a specific site located at the promoter sequence -341 bp upstream of the start site, which was functionally active in transcriptional assays (FIG. 18C). As NF-κB activation may result from oxidative stress of hypoxic cells due to the generation of reactive oxygen species (ROS; Mizukami et al, 2005), whether hypoxia induces NF-κB activation and subsequent up-regulation of Gal1 through increased production of ROS was determined. Scavenging of ROS using N-acetyl-cysteine (NAC) strongly inhibited induction of Gal1 expression and secretion and prevented IκB-α degradation in KS cells cultured under hypoxic conditions (FIGS. 18G and 18Q). Moreover, exogenous administration of $H_2O_2$ stimulated the secretion of Gal1 in a dose- and NF-κB-dependent fashion (FIGS. 18H and 18R). These data indicate that ROS-dependent activation of NF-κB, but not HIF-1α, controls the induction of pro-angiogenic Gal1 in hypoxic tumor microenvironments. Supporting these findings, Gal1 preferentially localized within hypoxic regions surrounding necrotic areas in the center of KS xenografts (FIG. 18I).

Having defined the molecular pathways underlying hypoxia-regulated EC cell surface glycosylation and tumor Gal1 expression, it was next determined whether Gal1-glycan lattices could couple tumor hypoxia to angiogenesis at the tumor-EC interface. To address this question directly, a series of in vitro and in vivo experiments were performed to disrupt lattice formation either by blocking Gal1 expression or hindering N- or O-glycan elongation. Three different short hairpin RNA constructs targeting unique sequences of Gal1 (shGal1.1, shGal1.2, shGal1.3) were stably expressed in KS cells. Retroviral-mediated infection of KS cells with shGal1.1 or shGal1.2 suppressed Gal1 expression substantially under both normoxic and hypoxic conditions (FIG. 18S). Serum-free conditioned medium (CM) obtained from KS cells exposed to hypoxic conditions induced a 3-fold increase in the formation of EC tubular networks compared to KS cells incubated under normoxic conditions; this effect was eliminated when Gal1, VEGF or both were knocked down in KS cells (FIG. 18J). Additionally, CM from KS cells cultured in hypoxic microenvironments augmented angiogenesis when incorporated in vivo into Matrigel plugs (FIG. 18K). However, hypoxic KS CM failed to induce angiogenesis when cells were stably transfected with Gal1 shRNA. This effect proceeded irrespectively of whether CM from Gal1 knockdown KS clones were implanted into wild-type or Gal1-deficient (Lgals1$^{-/-}$) mice (FIG. 18K), suggesting that hypoxia-regulated, tumor-derived Gal1 contributes to angiogenesis independently of the presence or absence of the host endogenous lectin. To substantiate further the relevance of Gal1-glycan lattices as bridging partners of hypoxia-driven angiogenesis, CM from hypoxic KS cells with ECs transfected with GnT5 or GCNT1 siRNA was assayed. Interruption of complex N-glycan branching prevented full induction of tubular networks stimulated by hypoxic KS cells, whereas hampering core-2 O-glycan elongation had no effect (FIG. 18L), underscoring the critical role of complex N-glycans in coupling tumor hypoxia to HIF-1α-independent angiogenesis.

Given the critical role of VEGF in angiogenesis and vasculogenesis and the co-option of Gal1 for VEGFR2 signaling, the reciprocal regulation of these pro-angiogenic mediators by establishing single or double knockdown KS clones was further analyzed. No substantial differences could be detected in the magnitude of VEGF or Gal1 secretion among wild-type, Gal1 knockdown or VEGF knockdown KS cells incubated under normoxic or hypoxic conditions (FIGS. 18T and 18U), indicating lack of cross-regulation between these pro-angiogenic mediators. Thus, lectin-glycan lattices can form signaling clusters that bridge tumor hypoxia to angiogenesis through mechanisms that are dependent of ROS and NF-κB but are independent of HIF-1α and VEGF.

Example 11

Figure 19:
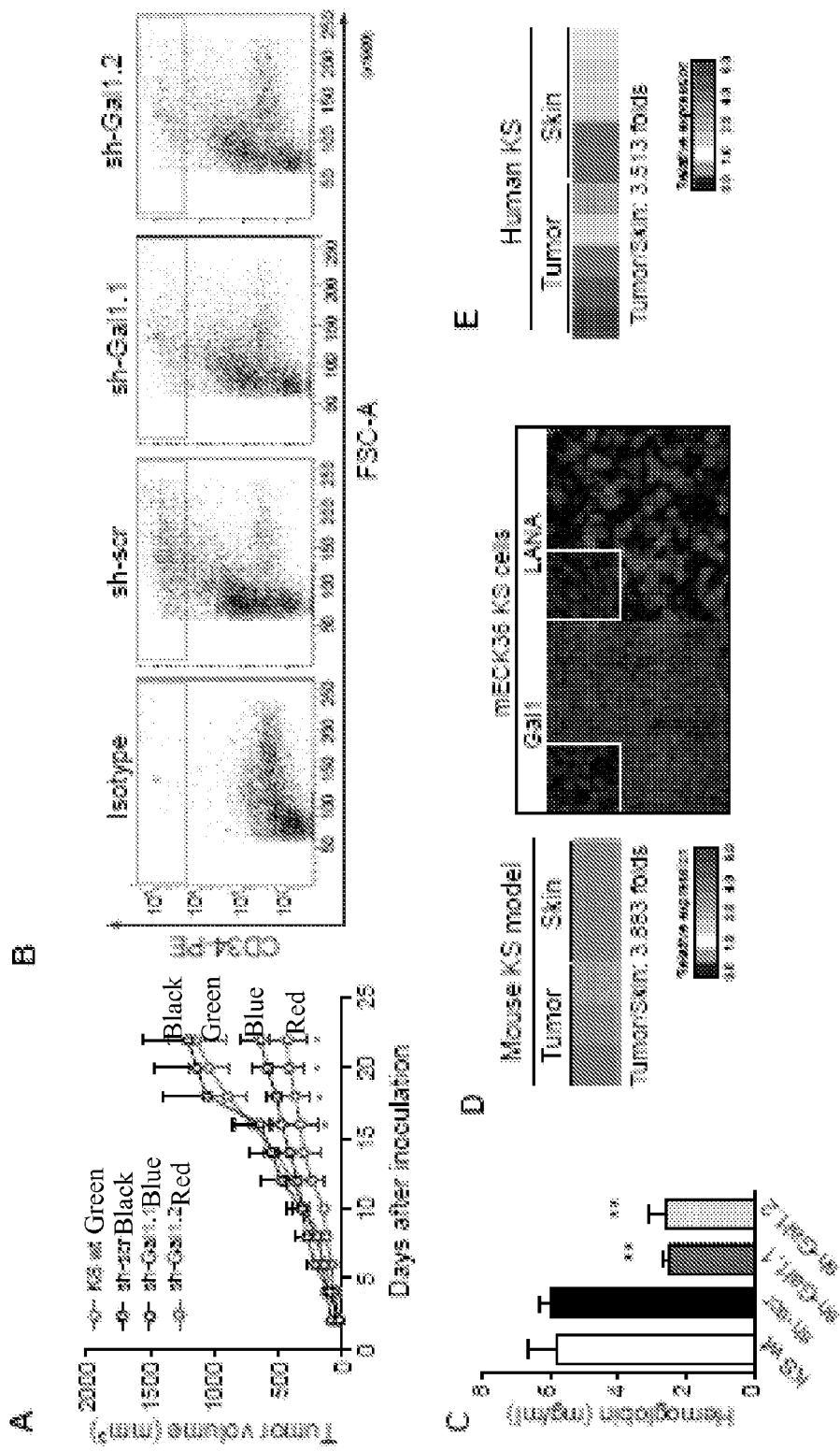
Figure 19:
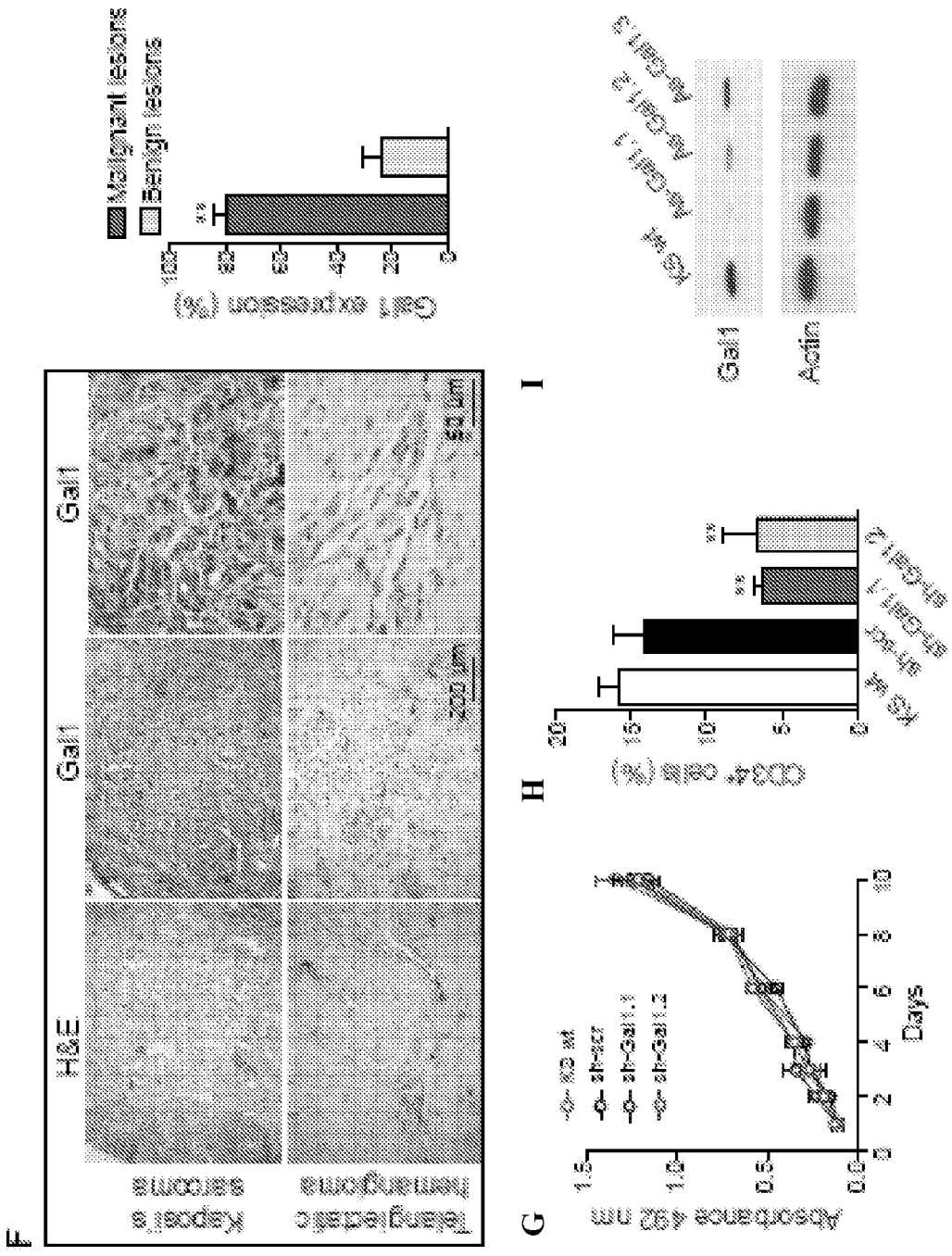
Figure 19:
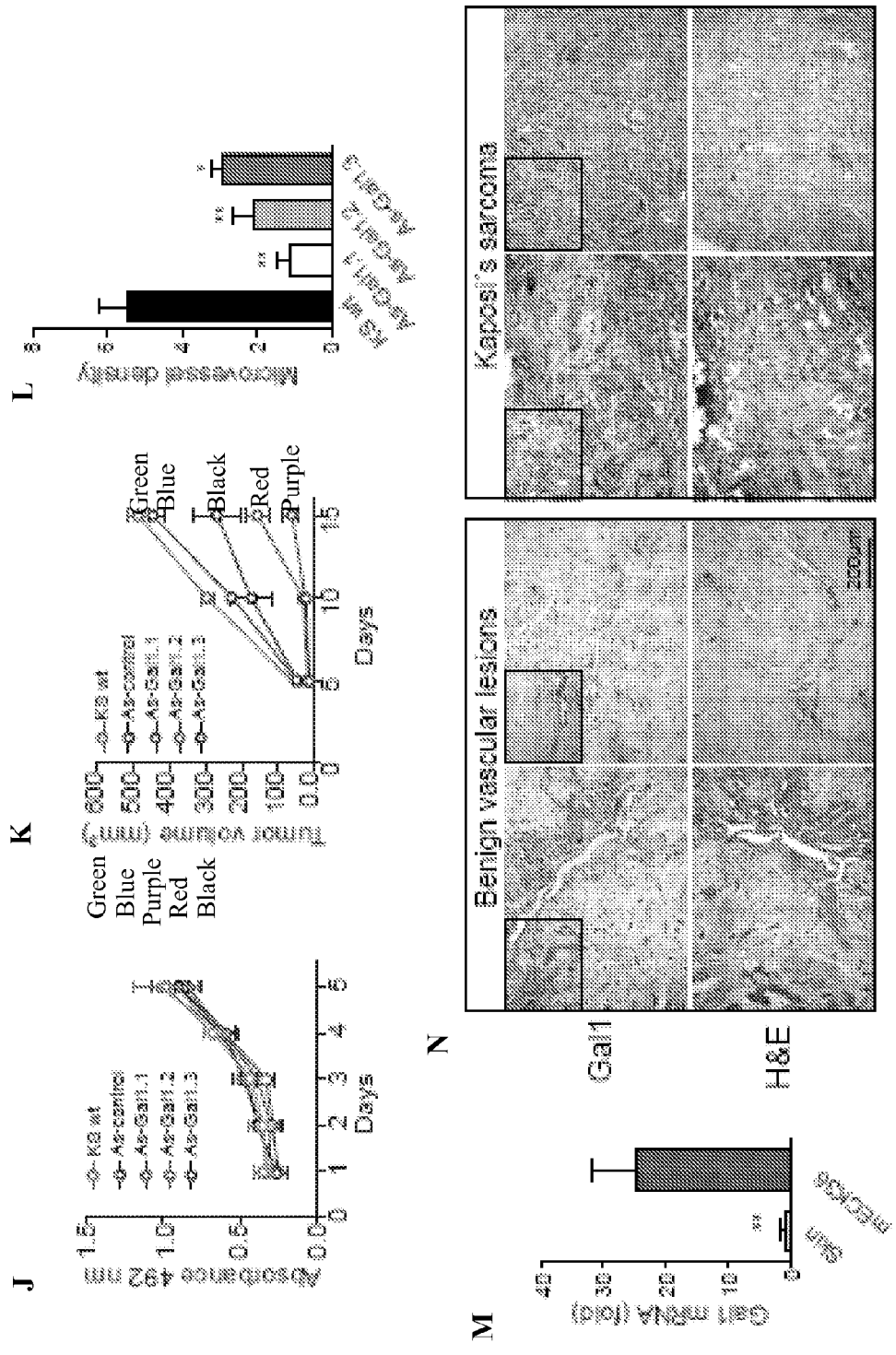

Targeted Disruption of Galectin-1-Glycan Lattices In Vivo Prevents Tumor Angiogenic Switch To delineate the pathophysiologic role of Gal1-glycan lattices, the consequences of Gal1 inhibition in a xenograft model of human KS in nude mice were assessed, which enables the examination of Gal1 function in tumor vascularization separately from its role in T cell-dependent immunity. Human knockdown KS clones expressing Gal1 shRNA, control KS cells expressing scrambled shRNA (sh-scr) or wild-type KS cells (FIG. 18S) were implanted into the flanks of nude mice. Inoculation of Gal1 knockdown KS clones led to a considerable reduction in tumor growth (sh-Gal1.1: 51.2%; sh-Gal1.2: 60.6% at day 22 post-inoculation) compared to mice receiving control KS cells (FIG. 19A). This effect was not due to intrinsic differences in proliferation rates, as control KS cells showed no growth advantage in vitro over Gal1 knockdown clones (FIG. 19G).

Gal1 silencing also attenuated the formation of a typical high density microvessel network, as reflected by a substantial decline in the levels of tumor hemoglobin content and the percentage of CD34$^+$ ECs (FIGS. 19B, 19C, and 19H). These results were verified using antisense RNA strategies (FIGS. 19I-19L). Gal1 transcript was part of the human and mouse KS molecular signature as Gal1 was overexpressed in human AIDS-KS, as well as in mECK36, a murine model of KSHV-induced KS tumors (Mutlu et al. (2007) *Cancer Cell* 11, 245-258) (FIGS. 19D, 19E, and 19M). Moreover, in patient biopsies, Gal1 was selectively expressed in KS lesions associated with vascular channels, showing robust cytoplasmic and weak membrane staining in spindle cells. In contrast, Gal1 was barely detected in all benign vascular lesions analyzed, including telangiectatic hemangioma, benign lymphangioendothelioma and pyogenic granuloma, in which only diffuse staining of the inflammatory infiltrates was detected (FIGS. 19F and 19N), indicating an additional role for Gal1 as a diagnostic biomarker capable of delineating highly angiogenic human KS from benign vascular lesions with shared morphologic and molecular features.

Figure 20:
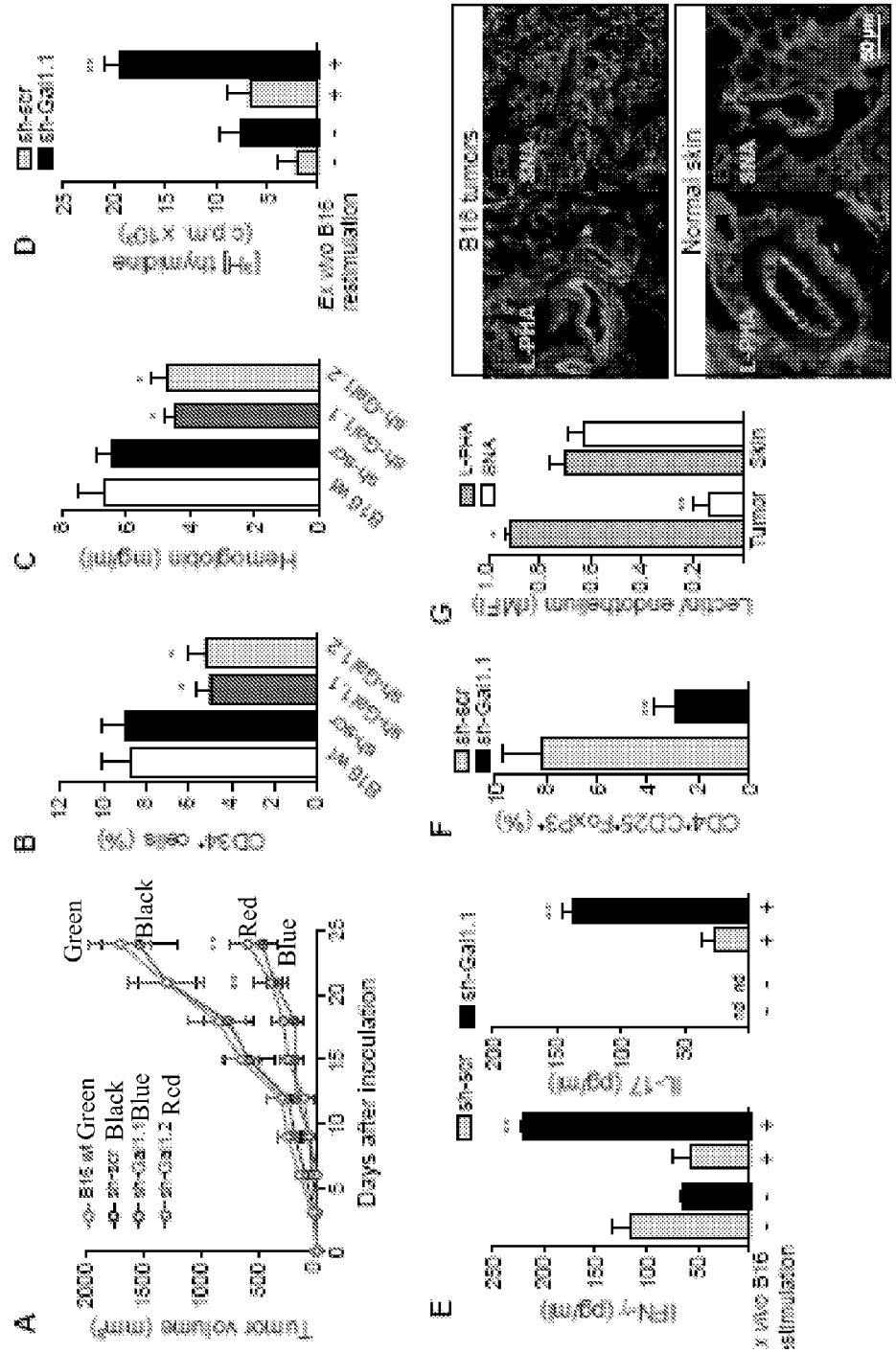
FIGS. 20A-20J show that targeted disruption of galectin-1-glycan lattices in vivo targets both vascular and immune compartments.
Figure 20:
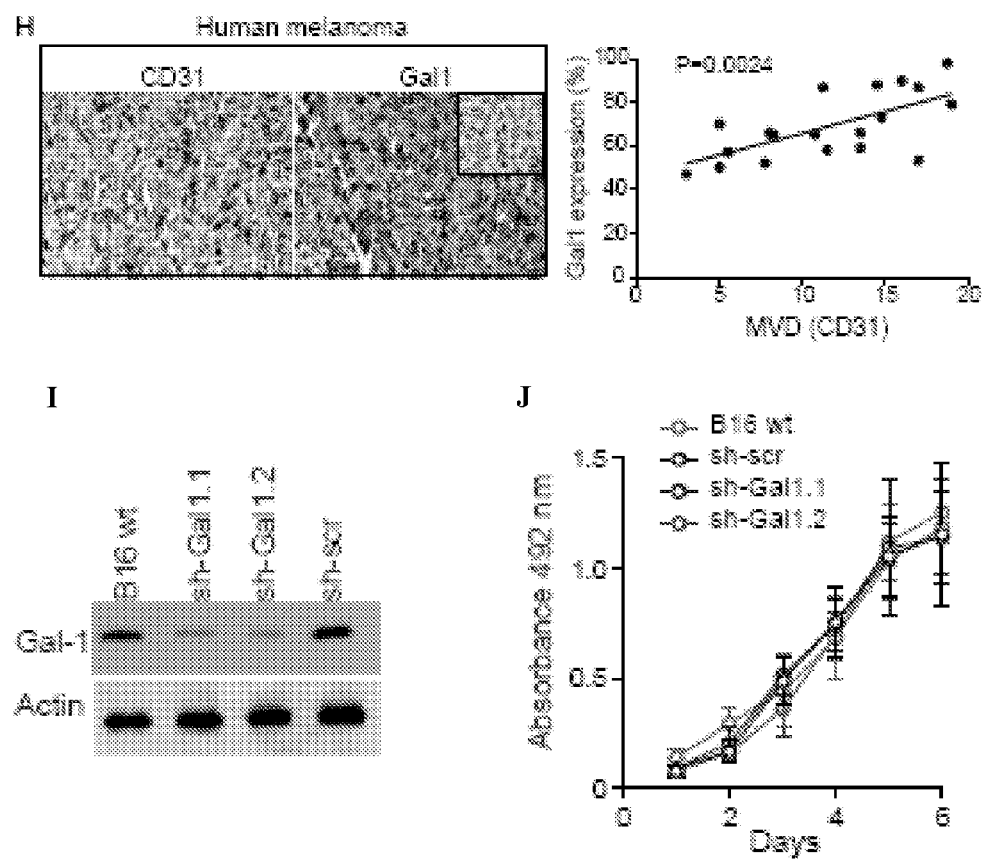

In addition, an emerging area in cancer therapy involves the identification of multi-targeted agents capable of concurrently shaping vascular and immune compartments (Jinushi et al. (2007) *Clin Cancer Res* 13, 3762-3764). In order to integrate the individual roles of Gal1-glycan lattices (i.e., remodeling vascular networks and dampening T cell immunity) and to assess directly the dual benefits of targeting these interactions, the effects of Gal1 inhibition in the B16 melanoma model in immunocompetent hosts was studied. Syngeneic mice inoculated with knockdown B16 clones expressing shRNA constructs (FIGS. 20A and 20B) showed diminished tumor burden and reduced number of tumor-associated ECs compared to mice injected with melanoma cells expressing control shRNA (FIGS. 20A-20C). Tumor-draining lymph node (TDLN) cells from mice receiving knockdown clones had increased proliferation and greater secretion of IFN-γ and IL-17 after ex vivo restimulation with B16 cells (FIGS. 20D and 20E) and showed a marked decline in the frequency of CD4 CD25 FoxP3 T regulatory ($T_{reg}$) cells (FIG. 20F), as compared to lymph node cells from mice receiving control transfectants. This effect was slightly but significantly more pronounced when shRNA B16 clones were inoculated into syngeneic Lgals1$^{-/-}$ mice, indicating a modest contribution of host-derived Gal1 to this effect. These results indicate that interruption of Gal1-glycan lattices may serve to limit tumor growth by simultaneously targeting immune and vascular compartments.

Given the extensive remodeling of EC surface glycans imprinted by proliferative, tolerogenic and hypoxic stimuli (FIGS. 16B and 18A), it was hypothesized that changes in glycosylation may selectively occur in vivo in tumor-associated versus normal vasculature. When compared to blood vessels within normal skin, tumor-associated vasculature displayed higher frequency of L-PHA-reactive glyco-epitopes and lower SNA reactivity, indicating increased β1-6 N-glycan branching and decreased α2-6-linked SA (FIG. 20G). Thus, differential glycosylation of tumor-associated versus normal vasculature may facilitate Gal1 signaling, lattice formation and promotion of angiogenic switch. Furthermore, profiling of a series of human primary melanomas established a highly significant positive correlation between tumor expression of Gal1 and microvessel density (FIG. 20H), supporting the clinical relevance of the Gal1-glycan axis in tumor vascularity and its therapeutic value in human cancer settings.

Example 12

Figure 21:
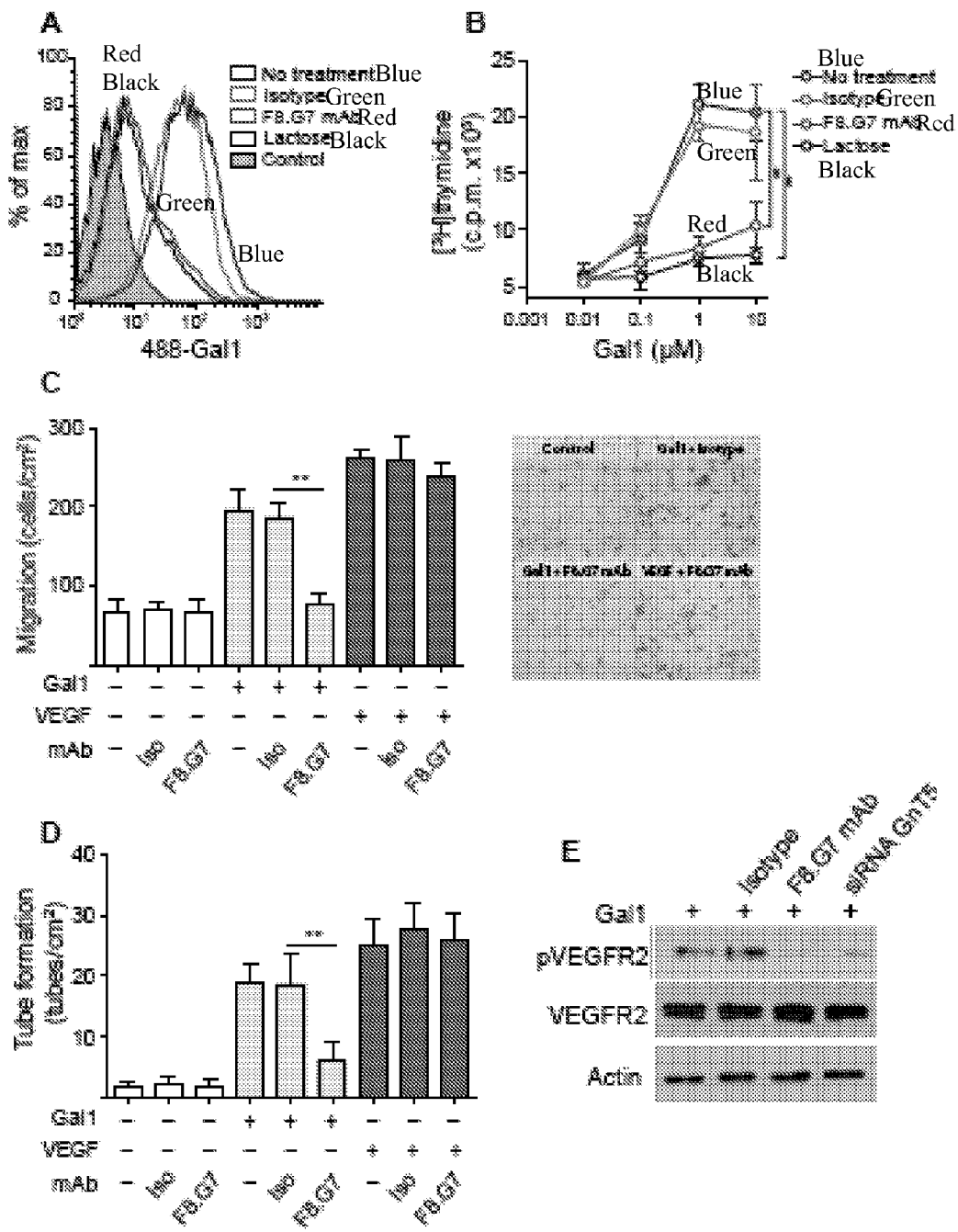
FIGS. 21A-21K show that mAb-mediated galectin-1 blockade modulates vascular biology and attenuates abnormal angiogenesis in vivo.
Figure 21:
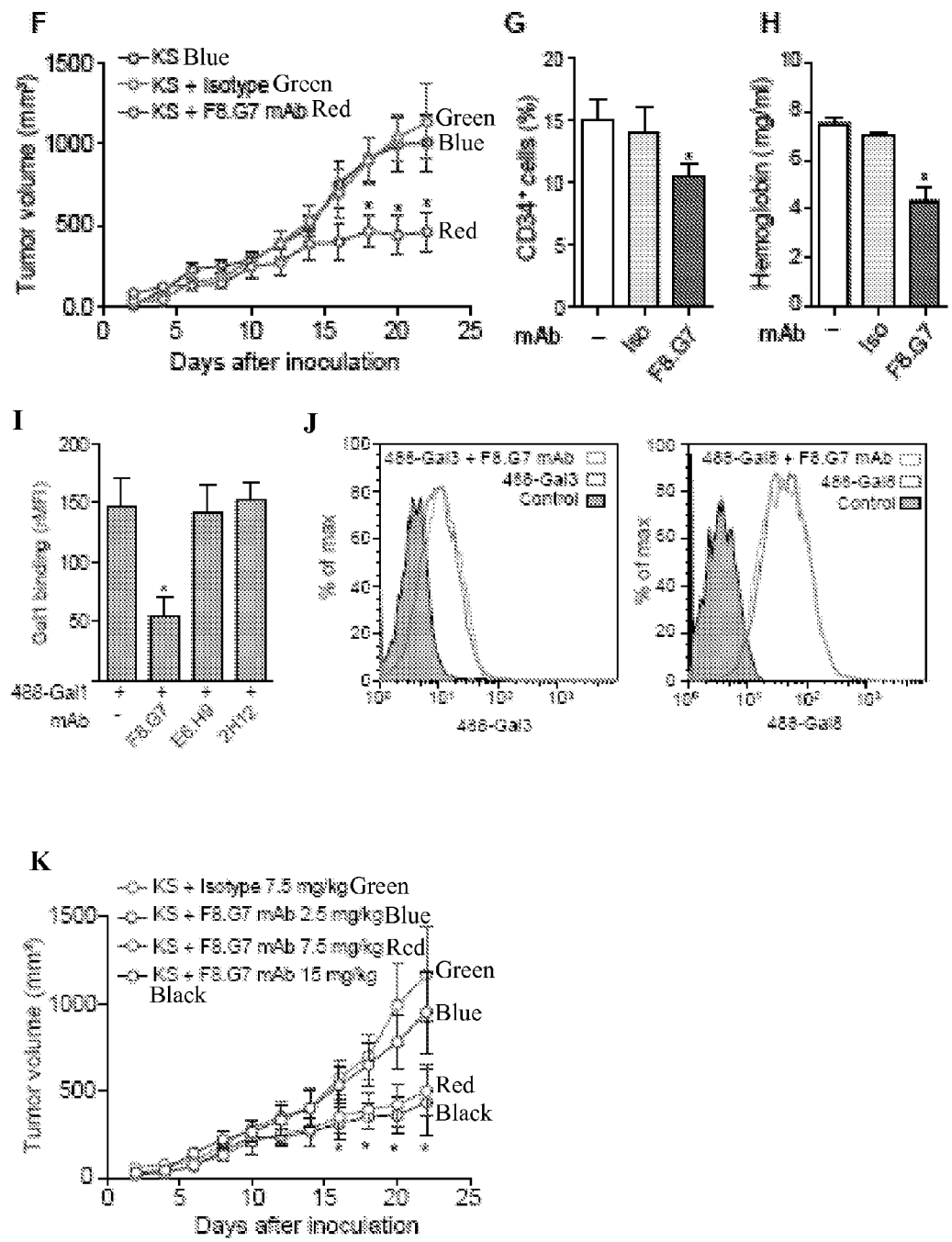

Therapeutic Administration of a Galectin-1-Specific Neutralizing mAb Promotes Vascular Remodeling and Influx of Immune Effector Cells Having established the benefits of disrupting Gal1-glycan lattices in tumor microenvironments, the effects of a recently developed neutralizing Gal1 monoclonal antibody (mAb), 8F4F8G7 (Example 1), which prevented the binding of Gal1 to human ECs, were determined (FIGS. 21A and 21I). This mAb was specific for Gal1 since it did not interfere with the binding of other members of the galectin family, such as Gal3 or Gal8, to the EC surface (FIG. 21J). The functional activity of this mAb was demonstrated in vitro through its specific capacity to prevent EC proliferation, migration and capillary tube formation induced by Gal1, but not VEGF (FIGS. 21B-21D). Notably, the 8F4F8G7 mAb did not alter EC biology in the absence of exogenous Gal1 (FIGS. 21C and 21D). Moreover, 8F4F8G7 mAb specifically inhibited VEGFR2 phosphorylation in response to Gal1 to levels comparable to those observed by GnT5 silencing (FIG. 21E); this finding further substantiates a key role for VEGFR2 in mediating Gal1 signaling, lattice formation and angiogenic sprouting.

To validate the therapeutic potential of interrupting Gal1 signaling in vivo, different doses of the 8F4F8G7 mAb (2.5 mg/kg, 7.5 mg/kg or 15 mg/kg) or the isotype control were infused into nude mice bearing established KS tumors. Treatment of nude mice with 8F4F8G7 mAb induced a dose-dependent delay in tumor growth (FIGS. 21F and 21K). Moreover, administration of 8F4F8G7 mAb, but not its isotype control, afforded a significant reduction in tumor microvasculature (FIGS. 21G and 21H), indicating that mAb-mediated Gal1 blockade attenuates aberrant neovascularization.

Figure 22:
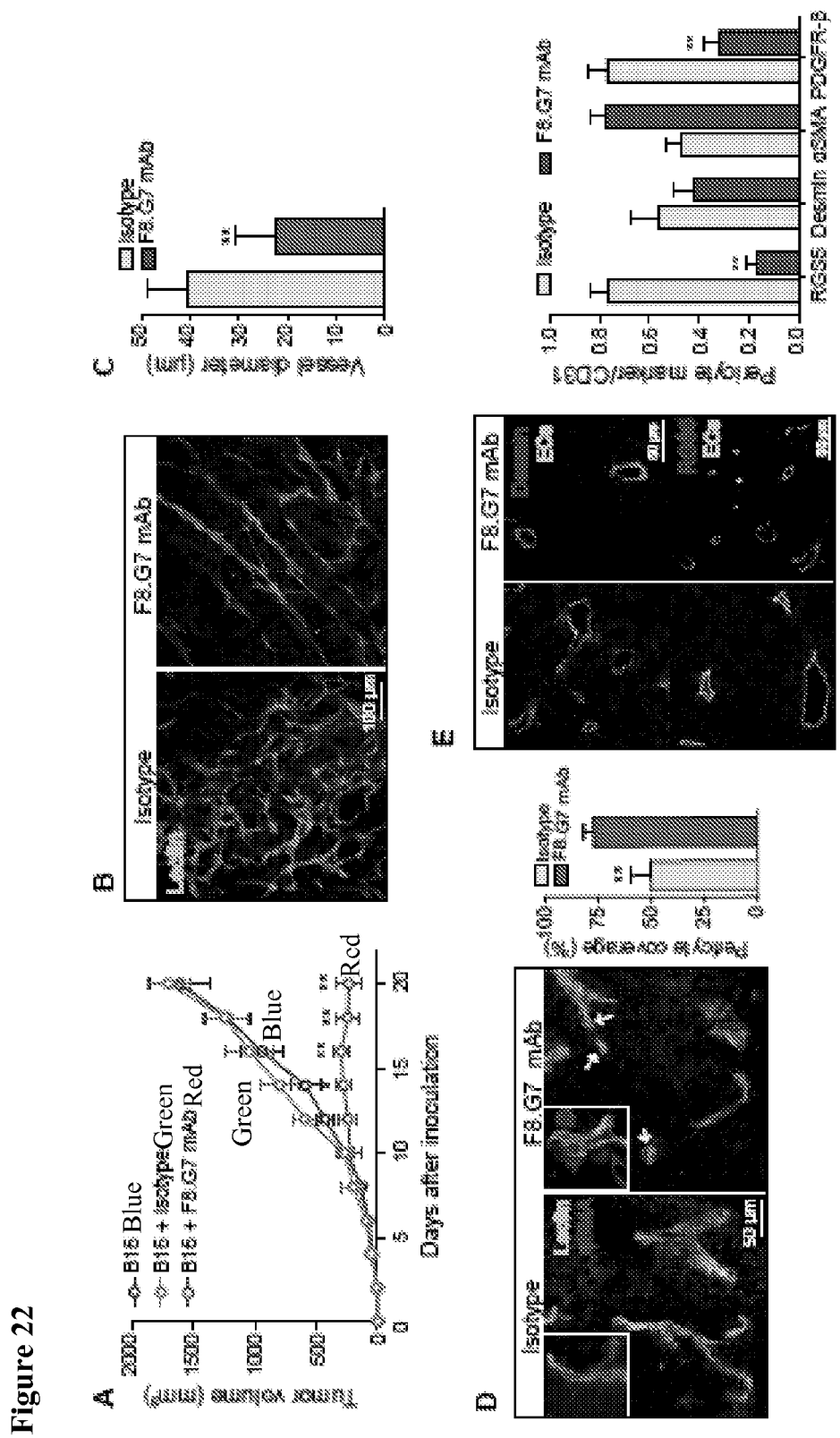
Figure 22:
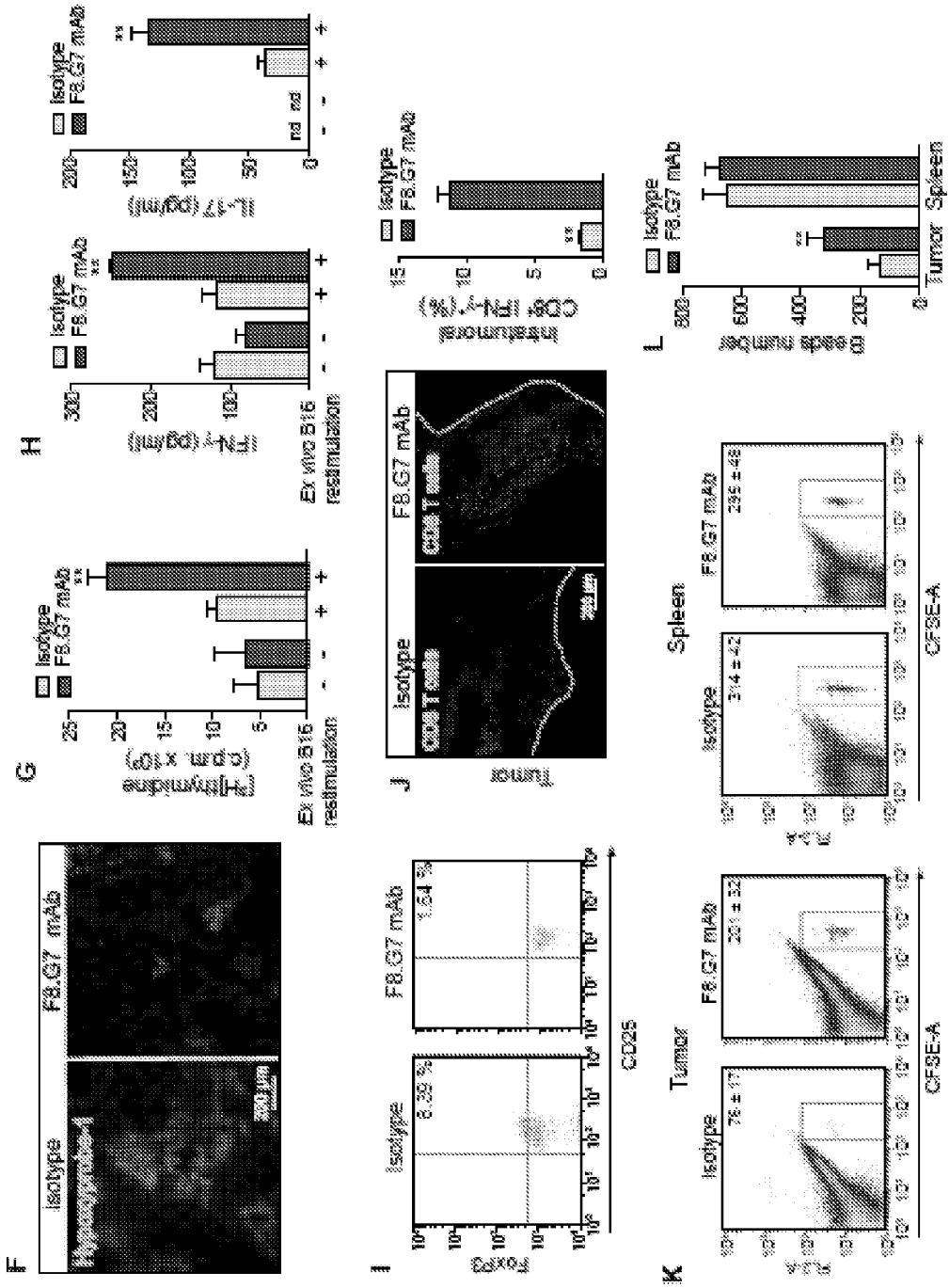
Figure 22:
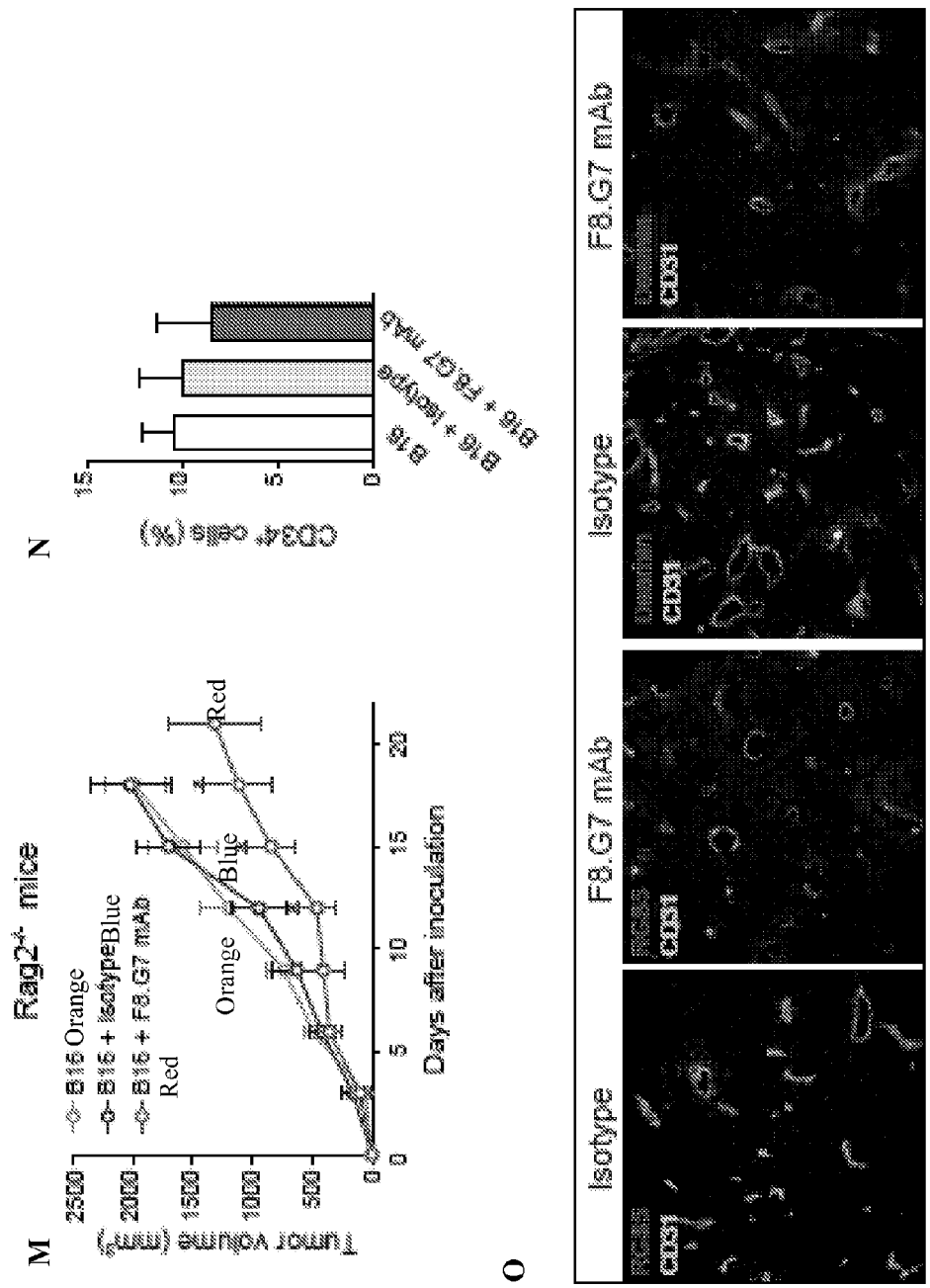
Figure 22:
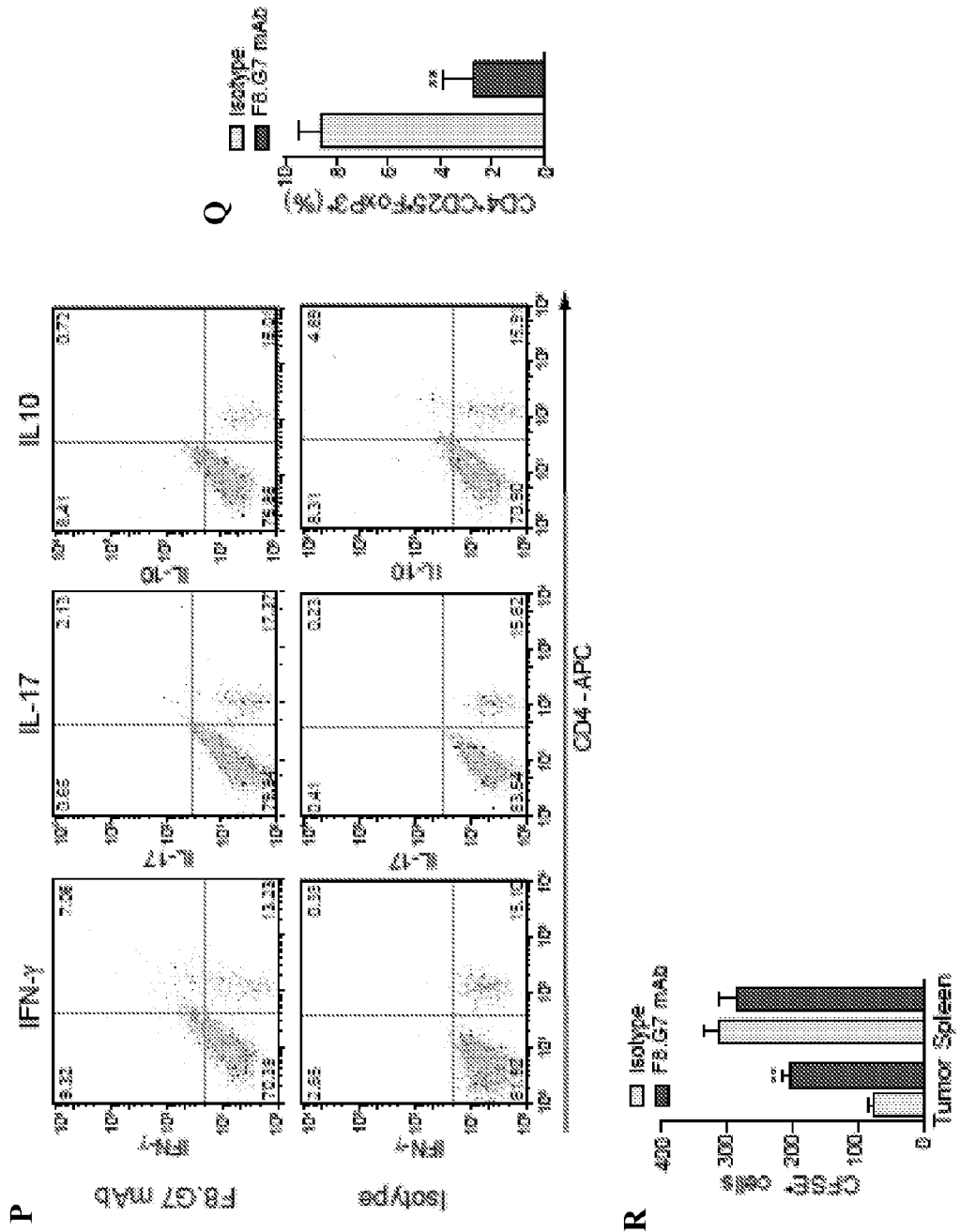

To analyze vascular and immune compartments simultaneously, the therapeutic value of 8F4F8G7 mAb in the syngeneic B16 model, in which microvessel networks are more clearly distinguishable from the tumor parenchyma, was determined. Administration of the anti-Gal1 mAb to immunocompetent mice bearing established B16 tumors resulted in markedly decreased tumor burden (−86% at day 20), while injection into immunodeficient B6/Rag$^{-/-}$ mice showed only a partial anti-tumor effect (FIGS. 22A and 22M). No significant changes in the frequency of CD34 cells at day 20 (FIG. 22N) were detected and only a slight decrease in microvessel density of tumors obtained 30 days post-inoculation was found. However, interruption of Gal1 signaling through mAb-mediated blockade resulted in substantial remodeling of tumor vasculature (FIGS. 22B-22E). While B16 tumors treated with an isotype control mAb displayed a chaotic and heterogeneous vascular architecture composed of extensive sprouting and large vessels fused to microvessels, the resultant tumor vasculature of mice treated with the 8F4F8G7 mAb resembled normal vascular networks with regard to vessel diameter and distribution (FIGS. 22B and 22C). The resultant vasculature in 8F4F8G7 mAb-treated mice included fewer dilated and tortuous vessels (FIGS. 22B and 22C) and greater coverage by pericytes (FIG. 22D). Most pericytes in 8F4F8G7 mAb-treated tumors displayed a more mature phenotype, as revealed by higher expression of α-smooth muscle actin (αSMA) and lower expression of regulator of G-protein signaling 5 (Rgs5) and platelet-derived growth factor receptor (PDGFR)β, when compared to pericytes from isotype-treated tumors (FIGS. 22D, 22E, and 22O). Yet, no significant variations were detected in the expression of desmin between 8F4F8G7-treated and isotype-treated tumors (FIG. 22E). These phenotypic changes typically delineate the transition from an immature to a mature pericyte profile (Hamzah et al. (2008) *Nature* 453, 410-414). Supporting these results, administration of 8F4F8G7 mAb, but not its isotype control, markedly alleviated tumor hypoxia as shown by reduced formation of pimonidazole adducts (FIG. 22F). Thus, blockade of Gal1 signaling counteracts the aberrant nature of tumor vasculature not only by attenuating vessel sprouting but also by modulating vascular morphology or influencing pericyte coverage and maturation early during treatment.

Given the lack of a single therapeutic agent capable of simultaneously targeting vascular and immune compartments, it was further investigated whether vascular remodeling induced by 8F4F8G7 mAb was accompanied by augmented anti-tumor immune response. Therapeutic administration of the 8F4F8G7 mAb stimulated proliferation as well as the synthesis and secretion of IFN-γ and IL-17 by tumor-draining lymph node cells restimulated ex vivo with B16 cells (FIGS. 22G, 22H, and 22P). In contrast, interruption of Gal1 signaling blunted B16-specific IL-10 production (FIG. 22O). This cytokine profile, reflecting unleashed effector responses, was further supported by a decline in the frequency of $CD4^+CD25^+FoxP3^+T_{reg}$ cells in TDLN cells from mice receiving 8F4F8G7 mAb versus those given isotype control (FIGS. 22I and 22Q). Moreover, a dramatic increase in the number of tumor-infiltrating IFN-γ-producing $CD8^+$ T cells was detected in 8F4F8G7 mAb-versus isotype-treated mice (FIGS. 22J and 22R).

To evaluate whether the augmented immune response was, at least in part, mediated by the increased influx of immune cells due to vessel remodeling, T cells obtained from mice harboring B16 tumors were labeled with the CFSE dye and adoptively transferred into tumor-bearing recipient mice treated with 8F4F8G7 mAb or isotype control. A greater number of T cells reached tumor parenchyma (3-fold increase) in mice receiving 8F4F8G7 mAb, as compared to those treated with control isotype (FIGS. 22K and 22R), indicating enhanced influx of immune cells subsequent to vessel remodeling. In contrast, there were no differences in the number of $CFSE^+$ T cells in spleens of recipient mice (FIG. 22K). To rule out the possibility that Gal1 blockade affects immune cell recruitment by influencing chemotaxis rather than vascular remodeling, similar experiments were performed using fluorescently-labeled beads as a non-cellular approach. In vivo tracking revealed increased access of fluorescently-labeled beads to the tumor parenchyma of 8F4F8G7 mAb-treated as compared to isotype-treated mice (FIG. 22L).

Taken together, these results identify the first Gal1-specific agent capable of affording therapeutic benefits by attenuating abnormal angiogenesis and facilitating vascular remodeling and influx of immune effector cells, which, in the absence of Gal1 signaling, are more competent for limiting tumor growth.

Lectin-glycan lattices are spatial arrays of glycans and endogenous multivalent lectins that organisms use to decode the biological information present in their own 'glycome' (Paulson et al. (2006) *Nat Chem Biol* 2, 238-248). Recent efforts toward deciphering this information revealed dramatic changes in the repertoire of N- and O-glycans in the transition from normal to inflamed or neoplastic tissue, providing novel opportunities for differential diagnosis and therapeutic intervention (Dube et al. (2005) *Nat Rev Drug Discov* 4, 477-488). The results described herein describe a vascular circuit, regulated by lectin-glycan lattices, which couples tumor hypoxia to abnormal neovascularization. The results demonstrate that hypoxic, proliferative, tolerogenic or inflammatory stimuli differentially regulate the glycosylation signature of ECs, allowing or preventing the formation of Gal1-glycan lattices. These signaling clusters can substitute for canonical ligands such as VEGF, modulate EC biology and preserve the angiogenic phenotype. Tumor hypoxia selectively amplifies this circuit by shaping the repertoire of N-glycans on VEGFR2 and augmenting Gal1 synthesis through mechanisms involving ROS-mediated NF-κB activation. Targeting Gal1-glycan lattices in vivo limits tumor growth by attenuating hypoxia-driven angiogenesis and favoring remodeling of tumor vascular networks, as shown by increased pericyte coverage and maturation, alleviation of tumor hypoxia and increased influx and expansion of tumor-specific immune cells.

The results described herein further demonstrate that Gal1-specific neutralizing mAbs attenuate tumor angiogenesis and promotes vascular remodeling by increasing pericyte coverage and maturation. Antibody-mediated Gal-1 blockade alleviates tumor hypoxia and fosters the influx of anti-tumor immune cells into the tumor bed. This vascular remodeling function recapitulates that observed with other anti-angiogenic agents, which can transiently normalize tumor vasculature to make it more efficient for oxygenation, drug delivery, and immune cell entry (Jain, R. K. (2005) *Science* 307, 58-62). Moreover, as bone marrow-derived myeloid cells express considerable amounts of Gal1 (Ilarregui et al. (2009) *Nat Immunol* 10, 981-991), its inhibition might also contribute to eliminate the vasculogenic potential of these cells. Although galectin inhibitors that block the carbohydrate recognition domain have been developed (Ingrassia et al. (2006) *Curr Med Chem* 13, 3513-3527; Stannard et al. (2010) *Cancer Lett*. [Epub ahead of print]), most of these inhibitors lack selectivity for individual members of the galectin family and often display weak ligand affinities and poor bioavailability. These shortcomings hinder the rapid translation of these compounds into the clinic, underscoring the advantages of a mAb that specifically neutralizes Gal1 and targets both vascular and immune compartments.

Moreover, the results described herein demonstrate a strong correlation between Gal1 expression and the extent of tumor angiogenesis in human melanoma biopsies. In addition, Gal1 expression delineated highly angiogenic KS from benign vascular lesions with shared morphologic and molecular features, indicating its potential use as a differential diagnostic biomarker in vascular malignancies. These data have additional implications as Gal1 blockade may ameliorate AIDS-related KS not only by limiting aberrant angiogenesis, but also by restoring the balance between $T_H17$ and $T_{reg}$ cell populations (Favre et al, 2009).

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the world wide web at ncbi.nlm.nih.gov.

EQUIVALENTS

Those skilled in the art will recognize, or be able to ascertain using no more than routine experimentation, many equivalents to the specific embodiments of the present invention described herein. Such equivalents are intended to be encompassed by the following claims.

What is claimed is:

1. A monoclonal antibody, or antigen-binding fragment thereof, that specifically binds galectin1 (Gal1) comprising six CDRs: CDR-H1, CDR-H2, CDR-H3, CDR-L1, CDR-L2, and CDR-L3, wherein CDR-H1 consists of residues 31-35 of SEQ ID NO: 7, CDR-H2 consists of residues 50-66 of SEQ ID NO: 7, CDR-H3 consists of residues 99-107 of SEQ ID NO: 7, CDR-L1 consists of residues 23-36 of SEQ ID NO: 9, CDR-L2 consists of residues 52-58 of SEQ ID NO: 9, and CDR-L3 consists of residues 91-99 of SEQ ID NO: 9.

2. The monoclonal antibody, or antigen-binding fragment thereof, of claim 1, comprising the heavy chain variable domain sequence of SEQ ID NO: 7.

3. The monoclonal antibody, or antigen-binding fragment thereof, of claim 1, comprising the light chain variable domain sequence of SEQ ID NO: 9.

4. The monoclonal antibody, or antigen-binding fragment thereof, of claim 1, comprising the heavy chain variable domain sequence of SEQ ID NO: 7 and the light chain variable domain sequence of SEQ ID NO: 9.

5. The monoclonal antibody, or antigen-binding fragment thereof, of claim 1, wherein the monoclonal antibody, or antigen-binding fragment thereof neutralizes Gal1.

6. The monoclonal antibody, or antigen-binding fragment thereof, of claim 5, wherein the monoclonal antibody, or antigen-binding fragment thereof neutralizes human Gal1, mouse Gal1, or cynomologous monkey Gal1.

7. The monoclonal antibody, or antigen-binding fragment thereof, of claim 1, wherein the monoclonal antibody, or antigen-binding fragment thereof blocks the interaction between Gal1 and VEGFR2.

8. The monoclonal antibody, or antigen-binding fragment thereof, of claim 1, wherein the monoclonal antibody, or antigen-binding fragment thereof inhibits Gal1-induced T cell apoptosis, stimulates IFN-γ production of lymph node cells in the presence of melanoma cells, stimulates IL-17 production of lymph node cells in the presence of melanoma cells, stimulates intratumoral CD8+ T cell influx in a melanoma tumor, inhibits endothelial cell proliferation induced by Gal1, inhibits endothelial cell migration induced by Gal1, inhibits capillary tube formation induced by Gal1, inhibits melanoma tumor hypoxia, inhibits angiogenesis, increases blood vessel pericyte coverage, or increases pericyte maturation.

9. The monoclonal antibody, or antigen-binding fragment thereof, of claim 1, wherein the monoclonal antibody, or antigen-binding fragment thereof, is a humanized antibody, a chimeric antibody, a Fab fragment, a F(ab')$_2$ fragment, or an Fv fragment.

10. The monoclonal antibody, or antigen-binding fragment thereof, of claim 1, wherein the monoclonal antibody, or antigen-binding fragment thereof, comprises an immunoglobulin heavy chain constant domain selected from the group consisting of IgG, IgG1, IgG2, IgG2A, IgG2B, IgG3, IgG4, IgA, IgM, and IgE constant domains.

11. The monoclonal antibody, or antigen-binding fragment thereof, of claim 1, wherein the monoclonal antibody, or antigen-binding fragment thereof, is conjugated to an agent selected from the group consisting of a cytotoxic agent, a drug, an enzyme, a prosthetic group, a fluorescent material, a luminescent material, a bioluminescent material, and a radioactive material.

12. A device or kit comprising at least one monoclonal antibody, or antigen-binding fragment thereof, of claim 1, said device or kit optionally comprising a label to detect the at least one monoclonal antibody or antigen-binding fragment thereof, or a complex comprising the monoclonal antibody or antigen-binding fragment thereof.

13. A pharmaceutical composition comprising the antibody, or antigen-binding fragment thereof, of claim 1, in a pharmaceutically acceptable carrier.

14. The hybridoma 14-19 8F4-F8-G7 deposited under accession number PTA-10535.

* * * * *